(12) United States Patent
Woods et al.

(10) Patent No.: US 9,718,821 B2
(45) Date of Patent: Aug. 1, 2017

(54) PYRIDOPYRIMIDINONE INHIBITORS OF KINASES

(71) Applicant: AbbVie Inc., North Chicago, IL (US)

(72) Inventors: Keith W. Woods, Libertyville, IL (US); Anthony Mastracchio, Waukegan, IL (US); Chunqiu Lai, Libertyville, IL (US); Viraj B. Gandhi, Gurnee, IL (US); Thomas D. Penning, Elmhurst, IL (US)

(73) Assignee: AbbVie Inc., North Chicago, IL (US)

( * ) Notice: Subject to any disclaimer, the term of this patent is extended or adjusted under 35 U.S.C. 154(b) by 838 days.

(21) Appl. No.: 13/773,906

(22) Filed: Feb. 22, 2013

(65) Prior Publication Data

US 2013/0225589 A1    Aug. 29, 2013

Related U.S. Application Data

(60) Provisional application No. 61/602,163, filed on Feb. 23, 2012.

(51) Int. Cl.
*A61K 31/519*    (2006.01)
*C07D 471/14*    (2006.01)
*C07D 471/04*    (2006.01)
*C07D 519/00*    (2006.01)

(52) U.S. Cl.
CPC .......... *C07D 471/14* (2013.01); *A61K 31/519* (2013.01); *C07D 471/04* (2013.01); *C07D 519/00* (2013.01)

(58) Field of Classification Search
None
See application file for complete search history.

(56) References Cited

U.S. PATENT DOCUMENTS 5,633,003 A * 5/1997 Cantor ................. A61K 31/715
424/434
8,404,677 B2 * 3/2013 Kim ..................... C07D 471/04
514/218

FOREIGN PATENT DOCUMENTS

| WO | 0170741 A1 | 9/2001 |
|---|---|---|
| WO | 2005105801 A1 | 11/2005 |
| WO | 2007088014 A1 | 8/2007 |
| WO | 2010019637 A1 | 2/2010 |
| WO | WO 2014/167347 | * 10/2014 |

OTHER PUBLICATIONS

Osol (editor)—Remington's Pharmaceutical Sciences, 1980, Philadelphia College of Pharmaceutical Science, Chapter 27: Structure-Activity Relationship and Drug Design, pp. 420-435.*

Shikhaliev et al., Annulation of a pyridine ring with vicinal ethoxycarbonyl(methyl)pyrimidines, 2009, Russian Chemical Bulletin, International Ed., vol. 58, pp. 1996-1999.*
Cross, L.C. et al., "IUPAC Commission on Nomenclature of Organic Chemistry: Rules for the Nomenclature of Organic Chemistry, Section E: Stereochemistry," Pure and Applied Chemistry, 1976, vol. 45, pp. 13-30.
Database Registry [Online] Chemical Abstracts Service, Columbus, Ohio, US, Mar. 6, 2007, XP002694819, Database Accession No. 925017-96-5.
Database Registry [Online] Chemical Abstracts Service, Columbus, Ohio, US, Jun. 25, 2008, XP002694820, Database Accession No. 1030518-03-6.
Glotzer M., et al., "Cyclin is Degraded by the Ubiquitin Pathway," Nature, 1991, vol. 349 (6305), pp. 132-138.
Hashimoto O., et al., "Cell cycle Regulation by the Wee1 Inhibitor PD0166285, Pyrido [2,3-d] Pyimidine, in the B16 Mouse Melanoma Cell Line," Bio Medical Center Cancer, 2006, 6:292.
International Search Report and Written Opinion for Application No. PCT/US2013/027265, mailed on Apr. 17, 2013, 14 pages.
Leijen S., et al., "Abrogation of the G2 Checkpoint by Inhibition of Wee-1 Kinase Results in Sensitization of p53-deficient Tumor Cells to DNA-damaging Agents," Current Clinical Pharmacology, 2010, vol. 5 (3), pp. 186-191.
Lindqvist A., et al., "The Decision to Enter Mitosis: Feedback and Redundancy in the Mitotic Entry Network," Journal of Cell Biology, 2009, vol. 185 (2), pp. 193-202.
McGowan C.H., et al., "Human Wee1 Kinase Inhibits Cell Division by Phosphorylating p34cdc2 Exclusively on Tyr15," The EMBO Journal, 1993, vol. 12 (1), pp. 75-85.
Nigro J.M., et al., "Mutations in the p53 Gene Occur in Diverse Human Tumour Types," Nature, 1989, vol. 342 (6250), pp. 705-708.
Nurse P., "Universal Control Mechanism Regulating Onset of M-Phase," Nature, 1990, vol. 344 (6266), pp. 503-508.
O'Connell M.J., et al., "Chk1 is a Wee1 Kinase in the G2 DNA Damage Checkpoint Inhibiting Cdc2 by Y15 Phosphorylation," The EMBO Journal, 1997, vol. 16 (3), pp. 545-554.
Parker L.L., et al., "Inactivation of the p34cdc2-Cyclin B Complex by the Human WEE1 Tyrosine Kinase," Science, 1992, vol. 257 (5078), pp. 1955-1957.
Sancar A., et al., "Molecular Mechanisms of Mammalian DNA Repair and the DNA Damage Checkpoints," Annual Review of Biochemistry, 2004, vol. 73, pp. 39-85.
Shikhaliev Kh.S., et al., "Annulation of a Pyridine Ring with Vicinal Ethoxycarbonyl(methyl)pyrimidines," Russian Chemical Bulletin, 2009, vol. 58 (9), pp. 1996-1999.

(Continued)

*Primary Examiner* — James D Anderson
*Assistant Examiner* — Meghan Finn
(74) *Attorney, Agent, or Firm* — Changxia Sun

(57) ABSTRACT

The present invention relates to compounds of formula (I) or pharmaceutical acceptable salts,

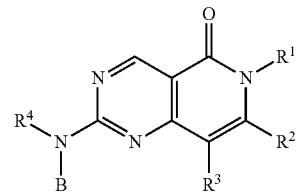

formula (I)

wherein $R^1$, $R^2$, $R^3$, $R^4$, and B are defined in the description. The present invention relates also to compositions containing said compounds which are useful for inhibiting kinases such as wee-1 and methods of treating diseases such as cancer.

1 Claim, No Drawings

(56) References Cited

OTHER PUBLICATIONS

Stumpff J., et al., "Drosophila Wee1 Kinase Regulates Cdk1 and Mitotic Entry during Embryogenesis," Current Biology, 2004, vol. 14 (23), pp. 2143-2148.

Sutton, V.R. et al., "Bcl-2 Prevents Apoptosis Induced by Perforin and Granzyme B, but Not That Mediated by Whole Cytotoxic Lymphocytes," Journal of Immunology, 1997, vol. 158 (12), pp. 5783-5790.

Wang Y., et al., "Knockdown of Chk1, Wee1 and Myt1 by RNA Interference Abrogates G2 Checkpoint and Induces Apoptosis," Cancer Biology & Therapy, 2004, vol. 3 (3), pp. 305-313.

Zhang K., et al., "Overexpression of RRM2 Decreases Thrombspondin-1 and Increases VEGF Production in Human Cancer Cells in Vitro and in Vivo: Implication of RRM2 in Angiogenesis," Molecular Cancer, 2009, 8:11.

\* cited by examiner

PYRIDOPYRIMIDINONE INHIBITORS OF KINASES

This non provisional utility patent application claims benefit of pending Provisional Application Ser. No. 61/602,163, filed Feb. 23, 2012.

FIELD OF THE INVENTION

This invention pertains to compounds which inhibit the activity of Wee-1 kinase, methods of making the compounds, compositions containing the compounds, and methods of treatment using the compounds.

BACKGROUND OF THE INVENTION

In order to undergo proper cell division, eukaryotic cells must faithfully replicate their genome and then correctly segregate their chromosomes into two daughter cells. This process of cell division, also called the cell cycle, is a step-wise process that is governed by checkpoints to ensure genomic integrity. Upon completion of DNA replication (S-phase), cells enter a growth phase (G2-phase) prior to proceeding into mitosis for chromosome segregation (M-phase). A key regulator of mitosis is the kinase Cdk1 (as called Cdc2) (Nurse, P. (1990) Universal control mechanism regulating onset of M-phase. Nature 344, 503-508). Activation of Cdk1 results in the onset of mitosis, and its subsequent inactivation initiates the exit from mitosis. Cdk1 is activated by the binding of Cyclin A or Cyclin B. Both Cyclin A-Cdk1 and Cyclin B-Cdk1 complexes function to initiate mitosis (Lindqvist, A., et. Al. (2009) The decision to enter mitosis: feedback and redundancy in the mitotic entry network. The Journal of cell biology 185, 193-202). The degradation of Cyclin B triggers the inactivation of Cdk1, resulting in the mitotic exit and entry into a growth (G1) phase prior to beginning a new round of the cell cycle (Glotzer, M., et al. (1991) Cyclin is degraded by the ubiquitin pathway. Nature 349, 132-138).

In addition to Cyclins, Cdk1 is also regulated by Wee1, an atypical tyrosine kinase that phosphorylates Cdk1 on tyrosine 15 (Y15) and inactivates Cdk1 (McGowan, C. H., et al. (1993) Human Wee1 kinase inhibits cell division by phosphorylating p34cdc2 exclusively on Tyr15. The EMBO journal 12, 75-85; Parker, L. L., et al. (1992) Inactivation of the p34cdc2-cyclin B complex by the human WEE1 tyrosine kinase. Science 257, 1955-1957). Wee1 is a critical negative regulator of Cdk1 and functions at the G2-M phase checkpoint to ensure that DNA replication has been completed and the genome is not damaged prior to entering mitosis (O'Connell, et al. (1997) Chk1 is a wee1 kinase in the G2 DNA damage checkpoint inhibiting cdc2 by Y15 phosphorylation. The EMBO journal 16, 545-554). Loss of Wee1 can result in premature entry into mitosis, resulting in mitotic catastrophe and cell death (Stumpff, J., et al. (2004) Drosophila Wee1 kinase regulates Cdk1 and mitotic entry during embryogenesis. Curr Biol 14, 2143-2148). Furthermore, many cancers are defective in their G1-phase checkpoints and are reliant on G2-M phase checkpoints (Sancar, A., et al. (2004) Molecular mechanisms of mammalian DNA repair and the DNA damage checkpoints. Annual review of biochemistry 73, 39-85). Indeed, loss of expression of Wee1 has been shown to lead to the abrogation of the G2-M phase checkpoint and sensitize tumor cells to DNA damage, especially tumors that have lost their G1-phase checkpoint due to a deficiency in the p53 protein (Wang, Y., et al. (2004) Knockdown of Chk1, Wee1 and Myt1 by RNA interference abrogates G2 checkpoint and induces apoptosis. Cancer biology & therapy 3, 305-313).

Inhibitors of Wee1 have the potential to selectively cause lethality in cancerous cells that are defective in other cell cycle checkpoints, while sparing normal tissues that can activate other cell cycle checkpoints. Thus, small molecule inhibitors of Wee1 would be beneficial for therapeutic intervention in cancer and other cell proliferative disorders.

SUMMARY OF THE INVENTION

The present invention has numerous embodiments. One embodiment of this invention, therefore, pertains to compounds that have formula (I)

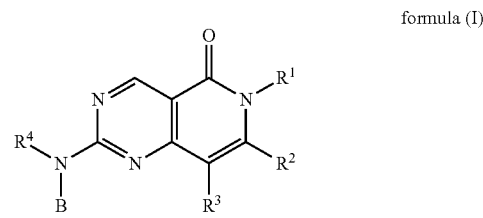

formula (I)

wherein B, $R^1$, $R^2$, $R^3$, and $R^4$ are as defined below and subsets therein.

Also provided are pharmaceutically acceptable compositions, comprising a therapeutically effective amount of a compound of formula (I) and a pharmaceutically acceptable salt in combination with a pharmaceutically suitable carrier.

One embodiment is directed to a method of treating cancer in a mammal comprising administering thereto a therapeutically acceptable amount of a compound or pharmaceutically acceptable salt of formula (I). Another embodiment pertains to a method of decreasing tumor volume in a mammal comprising administering thereto a therapeutically acceptable amount of a compound or pharmaceutically acceptable salt of formula (I).

DETAILED DESCRIPTION OF THE INVENTION

This detailed description is intended only to acquaint others skilled in the art with Applicants' invention, its principles, and its practical application so that others skilled in the art may adapt and apply the invention in its numerous forms, as they may be best suited to the requirements of a particular use. This description and its specific examples are intended for purposes of illustration only. This invention, therefore, is not limited to the embodiments described in this patent application, and may be variously modified.

Abbreviations and Definitions

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. In this application, the use of "or" means "and/or" unless stated otherwise. Furthermore, the use of the term "including", as well as other forms, such as "includes" and "included", is not limiting. With reference to the use of the words "comprise" or "comprises" or "comprising" in this patent application (including the claims), Applicants note that unless the context requires otherwise, those words are used on the basis and clear understanding that they are to be interpreted inclusively, rather than exclusively, and that Applicants intend each of those words to be so interpreted in construing this patent application, including the claims below. For a variable that occurs more than one time in any substituent or in the compound of the invention or any other formulae herein, its definition on each occurrence is independent of its definition at every other occurrence. Combinations of substituents are permissible only if such combinations result in stable compounds. Stable compounds are compounds which can be isolated in a useful degree of purity from a reaction mixture.

It is meant to be understood that proper valences are maintained for all combinations herein, that monovalent moieties having more than one atom are attached through their left ends, and that divalent moieties are drawn from left to right.

As used in the specification and the appended claims, unless specified to the contrary, the following terms have the meaning indicated:

The term "alkyl" (alone or in combination with another term(s)) means a straight- or branched-chain saturated hydrocarbyl substituent typically containing from 1 to about 10 carbon atoms; or in another embodiment, from 1 to about 8 carbon atoms; in another embodiment, from 1 to about 6 carbon atoms; and in another embodiment, from 1 to about 4 carbon atoms. Examples of such substituents include methyl, ethyl, n-propyl, isopropyl, n-butyl, isobutyl, sec-butyl, tert-butyl, pentyl, iso-amyl, and hexyl and the like.

The term "alkenyl" (alone or in combination with another term(s)) means a straight- or branched-chain hydrocarbyl substituent containing one or more double bonds and typically from 2 to about 10 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethenyl (vinyl), 2-propenyl, 3-propenyl, 1,4-pentadienyl, 1,4-butadienyl, 1-butenyl, 2-butenyl, and 3-butenyl and the like.

The term "alkynyl" (alone or in combination with another term(s)) means a straight- or branched-chain hydrocarbyl substituent containing one or more triple bonds and typically from 2 to about 10 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethynyl, 2-propynyl, 3-propynyl, 2-butynyl, and 3-butynyl and the like.

The term "carbocyclyl" (alone or in combination with another term(s)) means a saturated cyclic (i.e., "cycloalkyl"), partially saturated cyclic (i.e., "cycloalkenyl"), or completely unsaturated (i.e., "aryl") hydrocarbyl substituent containing from 3 to 14 carbon ring atoms ("ring atoms" are the atoms bound together to form the ring or rings of a cyclic substituent). A carbocyclyl may be a single-ring (monocyclic) or polycyclic ring structure.

A carbocyclyl may be a single ring structure, which typically contains from 3 to 8 ring atoms, more typically from 3 to 6 ring atoms, and even more typically 5 to 6 ring atoms. Examples of such single-ring carbocyclyls include cyclopropyl (cyclopropanyl), cyclobutyl (cyclobutanyl), cyclopentyl (cyclopentanyl), cyclopentenyl, cyclopentadienyl, cyclohexyl (cyclohexanyl), cyclohexenyl, cyclohexadienyl, and phenyl. A carbocyclyl may alternatively be polycyclic (i.e., may contain more than one ring). Examples of polycyclic carbocyclyls include bridged, fused, and spirocyclic carbocyclyls. In a spirocyclic carbocyclyl, one atom is common to two different rings. An example of a spirocyclic carbocyclyl is spiropentanyl. In a bridged carbocyclyl, the rings share at least two common non-adjacent atoms. Examples of bridged carbocyclyls include bicyclo[2.2.1]heptanyl, bicyclo[2.2.1]hept-2-enyl, and adamantanyl. In a fused-ring carbocyclyl system, two or more rings may be fused together, such that two rings share one common bond. Examples of two- or three-fused ring carbocyclyls include naphthalenyl, tetrahydronaphthalenyl (tetralinyl), indenyl, indanyl (dihydroindenyl), anthracenyl, phenanthrenyl, and decalinyl.

The term "cycloalkyl" (alone or in combination with another term(s)) means a saturated cyclic hydrocarbyl substituent containing from 3 to 14 carbon ring atoms. A cycloalkyl may be a single carbon ring, which typically contains from 3 to 8 carbon ring atoms and more typically from 3 to 6 ring atoms. Examples of single-ring cycloalkyls include cyclopropyl, cyclobutyl, cyclopentyl, and cyclohexyl. A cycloalkyl may alternatively be polycyclic or contain more than one ring. Examples of polycyclic cycloalkyls include bridged, fused, and spirocyclic carbocyclyls.

The term "aryl" (alone or in combination with another term(s)) means an aromatic carbocyclyl containing from 6 to 14 carbon ring atoms. An aryl may be monocyclic or polycyclic (i.e., may contain more than one ring). In the case of polycyclic aromatic rings, only one ring the polycyclic system is required to be unsaturated while the remaining ring(s) may be saturated, partially saturated or unsaturated. Examples of aryls include phenyl, naphthalenyl, indenyl, indanyl, and tetrahydronapthyl.

In some instances, the number of carbon atoms in a hydrocarbyl substituent (e.g., alkyl, alkenyl, alkynyl, or cycloalkyl) is indicated by the prefix "$C_x$-$C_y$-", wherein x is the minimum and y is the maximum number of carbon atoms in the substituent. Thus, for example, "$C_1$-$C_6$-alkyl" refers to an alkyl substituent containing from 1 to 6 carbon atoms. Illustrating further, $C_3$-$C_8$-cycloalkyl means a saturated hydrocarbyl ring containing from 3 to 8 carbon ring atoms.

The term "hydrogen" (alone or in combination with another term(s)) means a hydrogen radical, and may be depicted as —H.

The term "hydroxy" (alone or in combination with another term(s)) means —OH.

The term "carboxy" (alone or in combination with another term(s)) means —C(O)—OH.

The term "amino" (alone or in combination with another term(s)) means —$NH_2$.

The term "halogen" or "halo" (alone or in combination with another term(s)) means a fluorine radical (which may be depicted as —F), chlorine radical (which may be depicted as —Cl), bromine radical (which may be depicted as —Br), or iodine radical (which may be depicted as —I).

If a substituent is described as being "substituted", a non-hydrogen radical is in the place of hydrogen radical on a carbon or nitrogen of the substituent. Thus, for example, a substituted alkyl substituent is an alkyl substituent in which at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there are more than one substitution on a substituent, each non-hydrogen radical may be identical or different (unless otherwise stated).

If a substituent is described as being "optionally substituted", the substituent may be either (1) not substituted or (2) substituted. If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

This patent application uses the terms "substituent" and "radical" interchangeably.

The prefix "halo" indicates that the substituent to which the prefix is attached is substituted with one or more independently selected halogen radicals. For example, haloalkyl means an alkyl substituent in which at least one hydrogen radical is replaced with a halogen radical. Examples of haloalkyls include chloromethyl, 1-bromoethyl, fluoromethyl, difluoromethyl, trifluoromethyl, and 1,1,1-trifluoroethyl. It should be recognized that if a substituent is substituted by more than one halogen radical, those halogen radicals may be identical or different (unless otherwise stated).

The prefix "perhalo" indicates that every hydrogen radical on the substituent to which the prefix is attached is replaced with independently selected halogen radicals, i.e., each hydrogen radical on the substituent is replaced with a halogen radical. If all the halogen radicals are identical, the prefix typically will identify the halogen radical. Thus, for example, the term "perfluoro" means that every hydrogen radical on the substituent to which the prefix is attached is substituted with a fluorine radical. To illustrate, the term "perfluoroalkyl" means an alkyl substituent wherein a fluorine radical is in the place of each hydrogen radical.

The term "carbonyl" (alone or in combination with another term(s)) means —C(O)—.

The term "aminocarbonyl" (alone or in combination with another term(s)) means —C(O)—NH$_2$.

The term "oxo" (alone or in combination with another term(s)) means (=O).

The term "oxy" (alone or in combination with another term(s)) means an ether substituent, and may be depicted as —O—.

The term "alkylhydroxy" (alone or in combination with another term(s)) means—alkyl-OH.

The term "alkylamino" (alone or in combination with another term(s)) means alkyl-NH$_2$.

The term "alkyloxy" (alone or in combination with another term(s)) means an alkylether substituent, i.e., —O-alkyl. Examples of such a substituent include methoxy (—O—CH$_3$), ethoxy, n-propoxy, isopropoxy, n-butoxy, iso-butoxy, sec-butoxy, and tert-butoxy.

The term "alkylcarbonyl" (alone or in combination with another term(s)) means —C(O)-alkyl.

The term "aminoalkylcarbonyl" (alone or in combination with another term(s)) means —C(O)-alkyl-NH$_2$.

The term "alkyloxycarbonyl" (alone or in combination with another term(s)) means —C(O)—O-alkyl.

The term "carbocyclylcarbonyl" (alone or in combination with another term(s)) means —C(O)-carbocyclyl.

Similarly, the term "heterocyclylcarbonyl" (alone or in combination with another term(s)) means —C(O)-heterocyclyl.

The term "carbocyclylalkylcarbonyl" (alone or in combination with another term(s)) means —C(O)-alkyl-carbocyclyl.

Similarly, the term "heterocyclylalkylcarbonyl" (alone or in combination with another term(s)) means —C(O)-alkyl-heterocyclyl.

The term "carbocyclyloxycarbonyl" (alone or in combination with another term(s)) means —C(O)—O-carbocyclyl.

The term "carbocyclylalkyloxycarbonyl" (alone or in combination with another term(s)) means —C(O)—O-alkyl-carbocyclyl.

The term "thio" or "thia" (alone or in combination with another term(s)) means a thiaether substituent, i.e., an ether substituent wherein a divalent sulfur atom is in the place of the ether oxygen atom. Such a substituent may be depicted as —S—. This, for example, "alkyl-thio-alkyl" means alkyl-S-alkyl (alkyl-sulfanyl-alkyl).

The term "thiol" or "sulfhydryl" (alone or in combination with another term(s)) means a sulfhydryl substituent, and may be depicted as —SH.

The term "(thiocarbonyl)" (alone or in combination with another term(s)) means a carbonyl wherein the oxygen atom has been replaced with a sulfur. Such a substituent may be depicted as —C(S)—.

The term "sulfonyl" (alone or in combination with another term(s)) means —S(O)$_2$—.

The term "aminosulfonyl" (alone or in combination with another term(s)) means —S(O)$_2$—NH$_2$.

The term "sulfinyl" or "sulfoxido" (alone or in combination with another term(s)) means —S(O)—.

The term "heterocyclyl" (alone or in combination with another term(s)) means a saturated (i.e., "heterocycloalkyl"), partially saturated (i.e., "heterocycloalkenyl"), or completely unsaturated (i.e., "heteroaryl") ring structure containing a total of 3 to 14 ring atoms. At least one of the ring atoms is a heteroatom (i.e., oxygen, nitrogen, or sulfur), with the remaining ring atoms being independently selected from the group consisting of carbon, oxygen, nitrogen, and sulfur. A heterocyclyl may be a single-ring (monocyclic) or polycyclic ring structure.

A heterocyclyl may be a single ring, which typically contains from 3 to 7 ring atoms, more typically from 3 to 6 ring atoms, and even more typically 5 to 6 ring atoms. Examples of single-ring heterocyclyls include furanyl, dihydrofuranyl, tetrahydrofuranyl, thiophenyl (thiofuranyl), dihydrothiophenyl, tetrahydrothiophenyl, pyrrolyl, pyrrolinyl, pyrrolidinyl, imidazolyl, imidazolinyl, imidazolidinyl, pyrazolyl, pyrazolinyl, pyrazolidinyl, triazolyl, tetrazolyl, oxazolyl, oxazolidinyl, isoxazolidinyl, isoxazolyl, thiazolyl, isothiazolyl, thiazolinyl, isothiazolinyl, thiazolidinyl, isothiazolidinyl, thiodiazolyl, oxadiazolyl (including 1,2,3-oxadiazolyl, 1,2,4-oxadiazolyl, 1,2,5-oxadiazolyl (furazanyl), or 1,3,4-oxadiazolyl), oxatriazolyl (including 1,2,3,4-oxatriazolyl or 1,2,3,5-oxatriazolyl), dioxazolyl (including 1,2,3-dioxazolyl, 1,2,4-dioxazolyl, 1,3,2-dioxazolyl, or 1,3,4-dioxazolyl), oxathiazolyl, oxathiolyl, oxathiolanyl, pyranyl, dihydropyranyl, thiopyranyl, tetrahydrothiopyranyl, pyridinyl (azinyl), piperidinyl, diazinyl (including pyridazinyl (1,2-diazinyl), pyrimidinyl (1,3-diazinyl), or pyrazinyl (1,4-diazinyl)), piperazinyl, triazinyl (including 1,3,5-triazinyl, 1,2,4-triazinyl, and 1,2,3-triazinyl)), oxazinyl (including 1,2-oxazinyl, 1,3-oxazinyl, or 1,4-oxazinyl)), oxathiazinyl (including 1,2,3-oxathiazinyl, 1,2,4-oxathiazinyl, 1,2,5-oxathiazinyl, or 1,2,6-oxathiazinyl)), oxadiazinyl (including 1,2,3-oxadiazinyl, 1,2,4-oxadiazinyl, 1,4,2-oxadiazinyl, or 1,3,5-oxadiazinyl)), morpholinyl, azepinyl, oxepinyl, thiepinyl, and diazepinyl.

A heterocyclyl may alternatively be polycyclic (i.e., may contain more than one ring). Examples of polycyclic heterocyclyls include bridged, fused, and spirocyclic heterocyclyls. In a spirocyclic heterocyclyl, one atom is common to two different rings. In a bridged heterocyclyl, the rings share at least two common non-adjacent atoms. In a fused-ring heterocyclyl, two or more rings may be fused together, such that two rings share one common bond. Examples of fused ring heterocyclyls containing two or three rings include indolizinyl, pyranopyrrolyl, 4H-quinolizinyl, purinyl, naphthyridinyl, pyridopyridinyl (including pyrido[3,4-b]-pyridinyl, pyrido[3,2-b]-pyridinyl, or pyrido[4,3-b]-pyridinyl), and pteridinyl. Other examples of fused-ring heterocyclyls include benzo-fused heterocyclyls, such as indolyl, isoindolyl (isobenzazolyl, pseudoisoindolyl), indoleninyl (pseudoindolyl), isoindazolyl (benzpyrazolyl), benzazinyl (including quinolinyl (1-benzazinyl) or isoquinolinyl (2-benzazinyl)), phthalazinyl, quinoxalinyl, quinazolinyl, benzodiazinyl (including cinnolinyl (1,2-benzodiazinyl) or quinazolinyl (1,3-benzodiazinyl)), benzopyranyl (including chromanyl or isochromanyl), benzoxazinyl (including 1,3, 2-benzoxazinyl, 1,4,2-benzoxazinyl, 2,3,1-benzoxazinyl, or 3,1,4-benzoxazinyl), and benzisoxazinyl (including 1,2-benzisoxazinyl or 1,4-benzisoxazinyl).

The term "heterocycloalkyl" (alone or in combination with another term(s)) means a saturated heterocyclyl.

The term "heteroaryl" (alone or in combination with another term(s)) means an aromatic heterocyclyl containing from 5 to 14 ring atoms. A heteroaryl may be a single ring or 2 or 3 fused rings. Examples of heteroaryl substituents include 6-membered ring substituents such as pyridyl, pyrazyl, pyrimidinyl, pyridazinyl, and 1,3,5-, 1,2,4- or 1,2,3-triazinyl; 5-membered ring substituents such as imidazyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl; 6/5-membered fused ring substituents such as benzothiofuranyl, benzisoxazolyl, benzoxazolyl, purinyl, and anthranilyl; and 6/6-membered fused rings such as benzopyranyl, quinolinyl, isoquinolinyl, cinnolinyl, quinazolinyl, and benzoxazinyl.

A prefix attached to a multi-component substituent only applies to the first component. To illustrate, the term "alkylcycloalkyl" contains two components: alkyl and cycloalkyl. Thus, the $C_1$-$C_6$— prefix on $C_1$-$C_6$-alkylcycloalkyl means that the alkyl component of the alkylcycloalkyl contains from 1 to 6 carbon atoms; the $C_1$-$C_6$-prefix does not describe the cycloalkyl component. To illustrate further, the prefix "halo" on haloalkyloxyalkyl indicates that only the alkyloxy component of the alkyloxyalkyl substituent is substituted with one or more halogen radicals. If halogen substitution may alternatively or additionally occur on the alkyl component, the substituent would instead be described as "halogen-substituted alkyloxyalkyl" rather than "haloalkyloxyalkyl." And finally, if the halogen substitution may only occur on the alkyl component, the substituent would instead be described as "alkyloxyhaloalkyl."

The terms "treat", "treating" and "treatment" refer to a method of alleviating or abrogating a disease and/or its attendant symptoms.

The terms "prevent", "preventing" and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

The term "therapeutically effective amount" refers to that amount of the compound being administered sufficient to prevent development of or alleviate to some extent one or more of the symptoms of the condition or disorder being treated.

The term "modulate" refers to the ability of a compound to increase or decrease the function, or activity, of a kinase. "Modulation", as used herein in its various forms, is intended to encompass antagonism, agonism, partial antagonism and/or partial agonism of the activity associated with kinase. Kinase inhibitors are compounds that, e.g., bind to, partially or totally block stimulation, decrease, prevent, delay activation, inactivate, desensitize, or down regulate signal transduction. Kinase activators are compounds that, e.g., bind to, stimulate, increase, open, activate, facilitate, enhance activation, sensitize or up regulate signal transduction.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

Compounds

Embodiments of Formula (I)

In one embodiment, the present invention is directed, in part, to a class of compounds having a structure of formula (I):

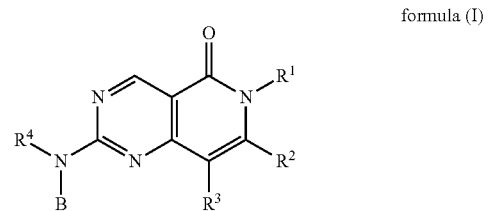

formula (I)

wherein

B is (a) $C_{3-8}$ cyloalkyl, phenyl, naphthyl, tetrahydronaphthyl, indenyl, or indanyl, wherein the $C_{3-8}$ cyloalkyl, phenyl, naphthyl, tetrahydronaphthyl, indenyl, or indanyl is optionally substituted with one or more $R^5$;

or (b) 5-16 membered monocyclic, bicyclic, or tricyclic heterocyclyl, wherein the heterocyclyl is optionally substituted with one or more $R^6$;

$R^1$ is hydrogen, $C_{1-8}$alkyl, $C_{2-8}$-alkenyl, $C_{2-8}$-alkynyl, $C_{3-8}$cycloalkyl, aryl, heteroaryl, aryl-$C_{1-6}$-alkyl-, $C_{3-8}$ cycloalkyl-$C_{1-6}$-alkyl-, or heteroaryl-$C_{1-6}$-alkyl-; wherein the $R^1C_{1-8}$alkyl, $C_{2-8}$-alkenyl, or $C_{2-8}$-alkynyl, alone or as part of another moiety, is optionally substituted with one or more substituents independently selected from the group consisting of CN, NO$_2$, halo, —OR$^a$, —C(O)R$^a$, —C(O)OR$^a$, —OC(O)R$^a$, —NR$^b$R$^c$NR$^b$C(O)R$^a$, —NHC(O)NHR$^b$, —C(O)NR$^b$R$^c$, —NHSO$_2$R$^a$, and —SO$_2$NR$^b$NR$^c$; and (b) the R$^1$C$_{3-8}$cycloalkyl, aryl, or heteroaryl, alone or as part of another moiety, is optionally substituted with one or more substituents independently selected from the group consisting of C$_{1-6}$-alkyl, C$_{1-6}$haloalkyl, C$_{2-6}$-alkenyl, heterocycloalkyl, aryl, heteroaryl, halo, oxo, CN, NO$_2$, —OR$^d$, —C(O)R$^d$, —C(O)OR$^d$, —OC(O)R$^d$, —SR$^d$, —S(O)R$^d$, —SO$_2$R$^d$, —NR$^e$R$^f$, —NHC(O)R$^e$, —NHC(O)NHR$^e$, —NHC(O)OR$^e$, —NHSO$_2$R$^d$, —C(O)NHR$^e$, and —SO$_2$NHNR$^e$;

R$^2$ is hydrogen, halo, or C$_{1-6}$-alkyl;

R$^3$ is hydrogen, halo, C$_{1-6}$-alkyl, C$_{2-6}$-alkenyl, C$_{3-8}$ cycloalkyl, C$_{3-8}$ cycloalkenyl, aryl, heteroaryl, heterocycloalkyl, aryl-C$_{1-6}$-alkyl-, cycloalkyl-C$_{1-6}$-alkyl-, heteroaryl-C$_{1-6}$-alkyl-, heterocycloalkyl-C$_{1-6}$-alkyl-, C(O)R$^7$, C(O)OR$^7$, C(O)NR$^8$R$^9$, or —C$_{1-4}$-alkyl-NR$^{10}$R$^{11}$, wherein the R$^3$C$_{1-6}$-alkyl or C$_{2-6}$-alkenyl, alone or as part of another moiety, is optionally substituted with one or more substituents independently selected from the group consisting of halo, hydroxy, and C$_{1-6}$-alkoxy, and wherein the R$^3$C$_{3-8}$ cycloalkyl, C$_{3-8}$ cycloalkenyl, aryl, heteroaryl, or heterocycloalkyl, alone or as part of another moiety, is optionally substituted with one or more substituents independently selected from the group consisting of halo, C$_{1-6}$-alkyl, C$_{1-6}$-haloalkyl, C$_{1-6}$-hydroxyalkyl, hydroxy, oxo, C$_{1-6}$-alkoxy, C$_{1-6}$-haloalkoxy, and —NR$^g$R$^h$;

or R$^2$ and R$^3$ can be joined together to form a 5-8 membered aryl or heterocyclic ring, wherein the ring is optionally substituted with one or more substituents independently selected from the group consisting of halo, C$_{1-6}$-alkyl, C$_{1-6}$-haloalkyl, C$_{1-6}$-hydroxyalkyl, hydroxy, C$_{1-6}$-alkoxy, C$_{1-6}$-haloalkoxy, —NH$_2$, —NH(C$_{1-6}$-alkyl), and N(C$_{1-6}$-alkyl)$_2$;

R$^4$ is hydrogen or C$_{1-6}$-alkyl;

R$^5$, at each occurrence, is independently CN, NO$_2$, halo, C$_{1-6}$-alkyl, C$_{1-6}$-haloalkyl, OR$^i$, SR$^i$, C(O)R$^i$, C(O)NR$^j$R$^k$, C(O)OR$^i$, NR$^j$R$^k$, NR$^j$C(O)R$^i$, S(O)$_2$R$^i$, NR$^j$S(O)$_2$R$^i$, S(O)$_2$NR$^j$R$^k$, aryl, cycloalkyl, heteroaryl, heterocycloalkyl, aryl-C$_{1-6}$-alkyl-, cycloalkyl-C$_{1-6}$-alkyl-, heteroaryl-C$_{1-6}$-alkyl-, or heterocycloalkyl-C$_{1-6}$-alkyl-; wherein the aryl, cycloalkyl, heteroaryl, or heterocycloalkyl, alone or as part of another moiety, is optionally substituted with one or more R$^{12}$;

R$^6$, at each occurrence, is independently CN, NO$_2$, halo, C$_{1-6}$-alkyl, C$_{1-6}$-haloalkyl, C$_{1-4}$-alkyl-heterocycloalkyl-, —C$_{1-6}$-alkyl-N(C$_{1-6}$-alkyl)$_2$, OR$^l$, SR$^l$, C(O)R$^l$, C(O)NR$^m$R$^n$, C(O)OR$^l$, NR$^m$R$^n$, NR$^l$C(O)R$^m$, S(O)$_2$R$^l$, NR$^m$S(O)$_2$R$^l$, or S(O)$_2$NR$^m$R$^n$;

R$^7$, at each occurrence, is independently is hydrogen, C$_{1-6}$ alkyl, C$_{1-6}$ haloalkyl, aryl, C$_{3-8}$ cycloalkyl, heteroaryl, or heterocycloalkyl;

R$^8$ and R$^9$, at each occurrence, are independently hydrogen, C$_{1-6}$ alkyl, C$_{1-6}$ haloalkyl, aryl, C$_{3-8}$ cycloalkyl, heteroaryl, or heterocycloalkyl;

R$^{10}$ and R$^{11}$, at each occurrence, are independently hydrogen, C$_{1-6}$ alkyl, C$_{1-6}$ haloalkyl, aryl, C$_{3-8}$ cycloalkyl, heteroaryl, or heterocycloalkyl;

R$^{12}$, at each occurrence, is independently is CN, NO$_2$, halo, C$_{1-6}$-alkyl, C$_{1-6}$-haloalkyl, OR$^p$, SR$^p$, C(O)R$^p$, C(O)NR$^q$R$^r$, C(O)OR$^p$, NR$^q$R$^r$, NR$^q$C(O)R$^p$, S(O)$_2$R$^p$, NR$^q$S(O)$_2$R$^p$, or S(O)$_2$NR$^q$R$^r$;

R$^a$, at each occurrence, is independently selected from the group consisting of hydrogen, C$_{1-6}$ alkyl, C$_{1-6}$ haloalkyl, aryl, C$_{3-8}$ cycloalkyl, heteroaryl, and heterocycloalkyl;

R$^b$ and R$^c$, at each occurrence, are independently selected from the group consisting of hydrogen, C$_{1-6}$ alkyl, C$_{1-6}$ haloalkyl, aryl, C$_{3-8}$ cycloalkyl, heteroaryl, and heterocycloalkyl;

R$^d$, at each occurrence, is independently selected from the group consisting of hydrogen, C$_{1-6}$ alkyl, C$_{1-6}$ haloalkyl, aryl, C$_{3-8}$ cycloalkyl, heteroaryl, and heterocycloalkyl;

R$^e$ and R$^f$, at each occurrence, are independently selected from the group consisting of hydrogen, C$_{1-6}$ alkyl, C$_{1-6}$ haloalkyl, aryl, C$_{3-8}$ cycloalkyl, heteroaryl, and heterocycloalkyl;

R$^g$ and R$^h$, at each occurrence, are independently selected from the group consisting of hydrogen, C$_{1-6}$ alkyl, C$_{1-6}$ haloalkyl, aryl, C$_{3-8}$ cycloalkyl, heteroaryl, and heterocycloalkyl;

R$^i$, at each occurrence, is independently selected from the group consisting of hydrogen, C$_{1-6}$ alkyl, aryl, C$_{3-8}$ cycloalkyl, heteroaryl, and heterocycloalkyl; wherein the C$_{1-6}$-alkyl is optionally substituted with one or more substituents independently selected from the group consisting of halo, hydroxy, C$_{1-6}$-alkoxy, —NH$_2$, —NHC$_{1-6}$-alkyl, —N(C$_{1-6}$-alkyl)$_2$, —C(O)N(C$_{1-6}$-alkyl)$_2$; and wherein the aryl, C$_{3-8}$ cycloalkyl, heteroaryl, and heterocycloalkyl are optionally substituted with one or more substituents independently selected from the group consisting of halo, C$_{1-6}$-alkyl, C$_{1-6}$-haloalkyl, C$_{1-6}$-hydroxyalkyl, hydroxy, oxo, C$_{1-6}$-alkoxy, C$_{1-6}$-haloalkoxy, —NH$_2$, —NH(C$_{1-6}$-alkyl), and N(C$_{1-6}$-alkyl)$_2$;

R$^j$ and R$^k$, at each occurrence, are independently selected from the group consisting of hydrogen, C$_{1-6}$ alkyl, aryl, C$_{3-8}$ cycloalkyl, heteroaryl, and heterocycloalkyl; wherein the C$_{1-6}$-alkyl is optionally substituted with one or more substituents independently selected from the group consisting of halo, hydroxy, C$_{1-6}$-alkoxy, —NH$_2$, —NHC$_{1-6}$-alkyl, —C(O)N(C$_{1-6}$-alkyl)$_2$, and wherein the aryl, C$_{3-8}$ cycloalkyl, heteroaryl, and heterocycloalkyl are optionally substituted with one or more substituents independently selected from the group consisting of halo, C$_{1-6}$-alkyl, C$_{1-6}$-haloalkyl, C$_{1-6}$-hydroxyalkyl, hydroxy, oxo, C$_{1-6}$-alkoxy, C$_{1-6}$-haloalkoxy, —NH$_2$, —NH(C$_{1-6}$-alkyl), and N(C$_{1-6}$-alkyl)$_2$;

R$^l$, at each occurrence, is independently selected from the group consisting of hydrogen, C$_{1-6}$ alkyl, aryl, C$_{3-8}$ cycloalkyl, heteroaryl, and heterocycloalkyl; wherein the C$_{1-6}$-alkyl is optionally substituted with one or more substituents independently selected from the group consisting of halo, hydroxy, C$_{1-6}$-alkoxy, —NH$_2$, —NHC$_{1-6}$-alkyl, and —N(C$_{1-6}$-alkyl)$_2$, and wherein the aryl, C$_{3-8}$ cycloalkyl, heteroaryl, and heterocycloalkyl are optionally substituted with one or more substituents independently selected from the group consisting of halo, C$_{1-6}$-alkyl, C$_{1-6}$-haloalkyl, C$_{1-6}$-hydroxyalkyl, hydroxy, oxo, C$_{1-6}$-alkoxy, C$_{1-6}$-haloalkoxy, —NH$_2$, —NH(C$_{1-6}$-alkyl), and N(C$_{1-6}$-alkyl)$_2$;

R$^m$ and R$^n$, at each occurrence, are independently selected from the group consisting of hydrogen, C$_{1-6}$ alkyl, aryl, C$_{3-8}$ cycloalkyl, heteroaryl, and heterocycloalkyl; wherein the C$_{1-6}$-alkyl is optionally substituted with one or more substituents independently selected from the group consisting of halo, hydroxy, C$_{1-6}$-alkoxy, —NH$_2$, —NHC$_{1-6}$-alkyl, and —N(C$_{1-6}$-alkyl)$_2$, and wherein the aryl, C$_{3-8}$ cycloalkyl, heteroaryl, and heterocycloalkyl are optionally substituted with one or more substituents independently selected from the group consisting of halo, C$_{1-6}$-alkyl, C$_{1-6}$-haloalkyl, C$_{1-6}$-hydroxyalkyl, hydroxy, oxo, C$_{1-6}$-alkoxy, C$_{1-6}$-haloalkoxy, —NH$_2$, —NH(C$_{1-6}$-alkyl), and N(C$_{1-6}$-alkyl)$_2$;

$R^p$, at each occurrence, is independently selected from the group consisting of hydrogen, $C_{1-6}$ alkyl, $C_{1-6}$ haloalkyl, aryl, $C_{3-8}$ cycloalkyl, heteroaryl, and heterocycloalkyl; and $R^q$ and $R^r$, at each occurrence, are independently selected from the group consisting of hydrogen, $C_{1-6}$ alkyl, $C_{1-6}$ haloalkyl, aryl, $C_{3-8}$ cycloalkyl, heteroaryl, and heterocycloalkyl;

or a pharmaceutically acceptable salt or solvate thereof.

In one embodiment of formula (I), $R^1$ is $C_{1-8}$-alkyl or $C_{2-8}$-alkenyl, wherein the $C_{1-8}$-alkyl or $C_{2-8}$-alkenyl is optionally substituted with one or more substituents selected from the group consisting of halo, CN, $NO_2$, —$OR^a$, —C(O)$R^a$, —C(O)O$R^a$, —OC(O)$R^a$, —$NR^bR^c$, —$NR^bC(O)R^a$, —NHC(O)NH$R^b$, —C(O)N$R^bR^c$, —NHSO$_2R^a$, and —SO$_2NR^bNR^c$. In another embodiment of formula (I), $R^1$ is $C_{1-8}$-alkyl or $C_{2-8}$-alkenyl, wherein the $C_{1-8}$-alkyl or $C_{2-8}$-alkenyl is unsubstituted. In yet another embodiment of formula (I), $R^1$ is —$CH_3$, —$CH_2CH_3$, —$CH_2CH_2CH_3$, —$CH_2CH_2CH_2CH_3$, —$CH(CH_3)_2$, —$CH_2CH(CH_3)_2$, —$CH_2CH=CH_2$, $CH_2CH=CHCH_2$, or —$CH_2CH_2CH=CH_2$.

In one embodiment of formula (I), $R^1$ is $C_{3-8}$-cycloalkyl, aryl, or heteroaryl, wherein the $C_{3-8}$-cycloalkyl, aryl, and heteroaryl are optionally substituted with one, two, or three substituents selected from the group consisting of $C_{1-6}$-alkyl, $C_{1-6}$-haloalkyl, $C_{2-6}$-alkenyl, heterocycloalkyl, aryl, heteroaryl, halo, oxo, CN, $NO_2$, —$OR^d$, —C(O)$R^d$, —C(O)O$R^d$, —OC(O)$R^d$, —$SR^d$, —S(O)$R^d$, —SO$_2R^d$, —$NR^eR^f$, —NHC(O)$R^e$, —NHC(O)NH$R^e$, —NHC(O)O$R^e$, —NHSO$_2R^d$, —C(O)NH$R^e$, and —SO$_2$NHN$R^e$.

In another embodiment of formula (I), $R^1$ is 4-8 membered monocyclic heteroaryl, wherein the heteroaryl is optionally substituted with one, two, or three substituents selected from the group consisting of $C_{1-6}$-alkyl, $C_{1-6}$-haloalkyl, $C_{2-6}$-alkenyl, heterocycloalkyl, aryl, heteroaryl, halo, oxo, CN, $NO_2$, —$OR^d$, —C(O)$R^d$, —C(O)O$R^d$, —OC(O)$R^d$, —$SR^d$, —S(O)$R^d$, —SO$_2R^d$, —$NR^eR^f$, —NHC(O)$R^e$, —NHC(O)NH$R^e$, —NHC(O)O$R^e$, —NHSO$_2R^d$, —C(O)NH$R^e$, and —SO$_2$NHN$R^e$. In another embodiment, the heteroaryl is unsubstituted. In yet another embodiment of formula (I), $R^1$ is pyridyl, pyrazyl, pyridinyl, pyrimidinyl, pyridazinyl, 1,3,5-, 1,2,4- or 1,2,3-triazinyl, imidazyl, furanyl, thiophenyl, pyrazolyl, oxazolyl, isoxazolyl, thiazolyl, 1,2,3-, 1,2,4-, 1,2,5-, or 1,3,4-oxadiazolyl, or isothiazolyl.

In another embodiment of formula (I), $R^1$ is aryl, wherein the aryl is phenyl, naphthyl, tetrahydronaphthyl, indenyl, or indanyl. In yet another embodiment, the phenyl, naphthyl, tetrahydronaphthyl, indenyl, or indanyl is unsubstituted. In yet another embodiment, the phenyl, naphthyl, tetrahydronaphthyl, indenyl, or indanyl is optionally substituted with one, two, or three substituents selected from the group consisting of $C_{1-6}$-alkyl, $C_{1-6}$-haloalkyl, $C_{2-6}$-alkenyl, heterocycloalkyl, aryl, heteroaryl, halo, oxo, CN, $NO_2$, —$OR^d$, —C(O)$R^d$, —C(O)O$R^d$, —OC(O)$R^d$, —$SR^d$, —S(O)$R^d$, —SO$_2R^d$, —$NR^eR^f$, —NHC(O)$R^e$, —NHC(O)NH$R^e$, —NHC(O)O$R^e$, —NHSO$_2R^d$, —C(O)NH$R^e$, and —SO$_2$NHN$R^e$.

In another embodiment of formula (I), $R^1$ is phenyl, wherein the phenyl is optionally substituted with one, two, or three substituents selected from the group consisting of CN, $NO_2$, $C_{1-6}$-alkyl, $C_{1-6}$-haloalkyl, halo, —$OR^a$, —C(O)$R^a$, —C(O)O$R^a$, —OC(O)$R^a$, —$NR^bR^c$, —$NR^bC(O)R^a$, —NHC(O)NH$R^b$, —C(O)N$R^bR^c$, —NHSO$_2R^a$, and —SO$_2NR^bNR^c$. In yet another embodiment, the phenyl is unsubstituted. In yet another embodiment, the phenyl is substituted with one, two, or three halo or $C_{1-6}$-haloalkyl.

In another embodiment of formula (I), $R^1$ is aryl-$C_{1-6}$-alkyl-, wherein the $R^1$aryl is optionally substituted with one or more substituents independently selected from the group consisting of $C_{1-6}$-alkyl, $C_{1-6}$-haloalkyl, $C_{2-6}$-alkenyl, heterocycloalkyl, aryl, heteroaryl, halo, oxo, CN, $NO_2$, —$OR^d$, —C(O)$R^d$, —C(O)O$R^d$, —OC(O)$R^d$, —$SR^d$, —S(O)$R^d$, —SO$_2R^d$, —$NR^eR^f$, —NHC(O)$R^e$, —NHC(O)NH$R^e$, —NHC(O)O$R^e$, —NHSO$_2R^d$, —C(O)NH$R^e$, and —SO$_2$NHN$R^e$. In another embodiment of formula (I), $R^1$ is aryl-$C_{1-6}$-alkyl-, wherein the $R^1$ aryl is phenyl. In another embodiment, $R^1$ is phenyl-$C_{1-3}$-alkyl-. In yet another embodiment, the phenyl is unsubstituted. In yet another embodiment, the phenyl is substituted with one, two, or three substituents independently selected from the group consisting of CN, $NO_2$, halo, —$OR^a$, —C(O)$R^a$, —C(O)O$R^a$, —OC(O)$R^a$, —$NR^bR^c$, —$NR^bC(O)R^a$, —NHC(O)NH$R^b$, —C(O)N$R^bR^c$, —NHSO$_2R^a$, and —SO$_2NR^bNR^c$. In yet another embodiment, the phenyl is substituted with one, two, or three halo or $C_{1-6}$-haloalkyl.

In another embodiment of formula (I), $R^1$ is $C_{3-8}$ cycloalkyl-$C_{1-6}$-alkyl-, wherein the $R^1C_{3-8}$-cycloalkyl is optionally substituted with one or more substituents independently selected from the group consisting of $C_{1-6}$-alkyl, $C_{1-6}$-haloalkyl, $C_{2-6}$-alkenyl, heterocycloalkyl, aryl, heteroaryl, halo, oxo, CN, $NO_2$, —$OR^d$, —C(O)$R^d$, —C(O)O$R^d$, —OC(O)$R^d$, —$SR^d$, —S(O)$R^d$, —SO$_2R^d$, —$NR^eR^f$, —NHC(O)$R^e$, —NHC(O)NH$R^e$, —NHC(O)O$R^e$, —NHSO$_2R^d$, —C(O)NH$R^e$, and —SO$_2$NHN$R^e$ In another embodiment of formula (I), $R^1$ is $C_{3-8}$ cycloalkyl-$C_{1-6}$-alkyl-, wherein the $R^1C_{3-8}$-cycloalkyl is unsubstituted.

In one embodiment of formula (I), $R^2$ is hydrogen.

In one embodiment of formula (I), $R^3$ is hydrogen or halo.

In another embodiment of formula (I), $R^3$ is $C_{1-6}$alkyl or $C_{2-6}$-alkenyl, wherein the $C_{1-6}$-alkyl or $C_{2-6}$-alkenyl is optionally substituted with one, two, three, four or five substituents independently selected from the group consisting of halo, hydroxy, and $C_{1-6}$-alkoxy. In another embodiment of formula (I), is $C_{1-6}$alkyl or $C_{2-6}$-alkenyl, wherein the $C_{1-6}$ alkyl or $C_{2-6}$-alkenyl is unsubstituted. In another embodiment, the $C_{1-6}$alkyl or $C_{2-6}$-alkenyl is substituted with one, two, or three halo.

In one embodiment of formula (I), $R^3$ is aryl or heteroaryl, wherein the aryl or heteroaryl is optionally substituted with one, two, or three substituents independently selected from the group consisting of halo, $C_{1-6}$alkyl, $C_{1-6}$haloalkyl, $C_{1-6}$-hydroxyalkyl, hydroxy, oxo, $C_{1-6}$-alkoxy, $C_{1-6}$-haloalkoxy, —$NH_2$, —NH($C_{1-6}$-alkyl), and N($C_{1-6}$-alkyl)$_2$.

In one embodiment of formula (I), $R^3$ is aryl, wherein the aryl is phenyl, naphthyl, tetrahydronaphthyl, indenyl, or indanyl. In yet another embodiment, the phenyl, naphthyl, tetrahydronaphthyl, indenyl, or indanyl is unsubstituted. In yet another embodiment, the phenyl, naphthyl, tetrahydronaphthyl, indenyl, or indanyl is optionally substituted with one, two, or three substituents selected from the group consisting of halo, $C_{1-6}$alkyl, $C_{1-6}$haloalkyl, $C_{1-6}$-hydroxyalkyl, hydroxy, $C_{1-6}$-alkoxy, $C_{1-6}$-haloalkoxy, —$NH_2$, —NH($C_{1-6}$-alkyl), and N($C_{1-6}$-alkyl)$_2$. In yet another embodiment of formula (I), $R^3$ is phenyl.

In another embodiment of formula (I), $R^3$ is 4-8 membered monocyclic heteroaryl or a 7-11 membered bicyclic heteroaryl, wherein the heteroaryl is optionally substituted with one, two, or three substituents selected from the group consisting of halo, $C_{1-6}$alkyl, $C_{1-6}$haloalkyl, $C_{1-6}$-hydroxyalkyl, hydroxy, oxo, $C_{1-6}$-alkoxy, $C_{1-6}$-haloalkoxy, —$NH_2$, —NH($C_{1-6}$-alkyl), and N($C_{1-6}$-alkyl)$_2$. In another embodiment, the heteroaryl is unsubstituted. In yet another embodiment of formula (I), $R^3$ is pyridyl, pyrazyl, pyridinyl, pyrimidinyl, pyridazinyl, 1,3,5-, 1,2,4- or 1,2,3-triazinyl, imidazyl, furanyl, thiophenyl, pyrazolyl, oxazolyl, isoxazolyl, thiazolyl, 1,2,3-, 1,2,4-, 1,2,5-, or 1,3,4-oxadiazolyl, or isothiazolyl. In yet another embodiment of formula (I), $R^3$ is benzothiazolyl, benzoxazolyl, benzothienyl, benzimidazolyl, benzofuryl, benzisothiazolyl, benzisoxazolyl, benzodiazinyl, benzofurazanyl, benzothiopyranyl, benzotriazolyl, or benzopyrazolyl.

In one embodiment of formula (I), $R^3$ is $C(O)R^7$, $C(O)NR^8R^9$, or $C(O)OR^7$, wherein $R^7$ at each occurrence, is independently is hydrogen, $C_{1-6}$ alkyl, $C_{1-6}$ haloalkyl, aryl, $C_{3-8}$ cycloalkyl, heteroaryl, or heterocycloalkyl; and wherein $R^8$ and $R^9$, at each occurrence, are independently hydrogen, $C_{1-6}$ alkyl, $C_{1-6}$ haloalkyl, aryl, $C_{3-8}$ cycloalkyl, heteroaryl, or heterocycloalkyl. In one embodiment of formula (I), $R^3$ is $C(O)R^7$ or $C(O)OR^7$, wherein $R^7$ is hydrogen or $C_{1-6}$-alkyl. In yet another embodiment, $R^3$ is $C(O)NR^8R^9$, wherein $R^8$ and $R^9$ are independently hydrogen or $C_{1-6}$ alkyl.

In one embodiment of formula (I), $R^3$ is or —$C_{1-4}$-alkyl-$NR^{10}R^{11}$, wherein $R^{10}$ is H and $R^{11}$ is selected from the group consisting of $C_{1-6}$ alkyl, $C_{1-6}$ haloalkyl, aryl, $C_{3-8}$ cycloalkyl, heteroaryl, and heterocycloalkyl.

In one embodiment of formula (I), $R^2$ and $R^3$ can be joined together to form a 5-8 membered aryl or heteroaryl ring, wherein the ring is optionally substituted with one, two, or three substituents selected from the group consisting of halo, $C_{1-6}$-alkyl, $C_{1-6}$-haloalkyl, $C_{1-6}$-hydroxyalkyl, hydroxy, $C_{1-6}$-alkoxy, $C_{1-6}$-haloalkoxy, —$NH_2$, —$NH(C_{1-6}$-alkyl), and $N(C_{1-6}$-alkyl)$_2$. In another embodiment, the ring is unsubstituted.

In one embodiment of formula (I), $R^2$ and $R^3$ can be joined together to form a phenyl ring, wherein the ring is optionally substituted with one, two, or three substituents selected from the group consisting of halo, $C_{1-6}$-alkyl, $C_{1-6}$-haloalkyl, $C_{1-6}$-hydroxyalkyl, hydroxy, $C_{1-6}$-alkoxy, $C_{1-6}$-haloalkoxy, —$NH_2$, —$NH(C_{1-6}$-alkyl), and $N(C_{1-6}$-alkyl)$_2$. In another embodiment, the phenyl ring is unsubstituted.

In one embodiment of formula (I), $R^2$ and $R^3$ can be joined together to form a pyridyl ring, wherein the pyridyl ring is optionally substituted with one, two, or three substituents selected from the group consisting of halo, $C_{1-6}$-alkyl, $C_{1-6}$-haloalkyl, $C_{1-6}$-hydroxyalkyl, hydroxy, $C_{1-6}$-alkoxy, $C_{1-6}$-haloalkoxy, —$NH_2$, —$NH(C_{1-6}$-alkyl), and $N(C_{1-6}$-alkyl)$_2$. In another embodiment, the pyridyl ring is unsubstituted.

In one embodiment of formula (I), $R^4$ is hydrogen.

In one embodiment of formula (I), B is $C_{3-8}$ cyloalkyl, wherein the $C_{3-8}$ cyloalkyl is unsubstituted. In another embodiment of formula (I), B is $C_{3-8}$ cyloalkyl, wherein $C_{3-8}$ cyloalkyl is substituted with one, two, or three $R^5$, wherein $R^5$ is selected from the group consisting of halo, $C_{1-6}$-alkyl, $C_{1-6}$-haloalkyl, $OR^i$, $SR^i$, $C(O)R^i$, $C(O)NR^jR^k$, $C(O)OR^i$, $NR^jR^k$, $NR^jC(O)R^i$, $S(O)_2R^i$, $NR^jS(O)_2R^i$, and $S(O)_2NR^jR^k$.

In another embodiment of formula (I), B is naphthyl, tetrahydronaphthyl, indenyl, or indanyl, wherein the naphthyl, tetrahydronaphthyl, indenyl, or indanyl is unsubstituted. In yet another embodiment of formula (I), B is naphthyl, tetrahydronaphthyl, indenyl, or indanyl, wherein the naphthyl, tetrahydronaphthyl, indenyl, or indanyl are substituted with one, two, or three $R^5$, wherein $R^5$ is selected from the group consisting of CN, $NO_2$, halo, $C_{1-6}$-alkyl, $C_{1-6}$-haloalkyl, $OR^i$, $SR^i$, $C(O)R^i$, $C(O)NR^jR^k$, $C(O)OR^i$, $NR^jR^k$, $NR^jC(O)R^i$, $S(O)_2R^i$, $NR^jS(O)_2R^i$, and $S(O)_2NR^jR^k$.

In one embodiment of formula (I), B is phenyl. In another embodiment of formula (I), B is phenyl, wherein the phenyl is unsubstituted. In another embodiment of formula (I), B is phenyl, wherein the phenyl is substituted with one, two, or three $R^5$, and $R^5$ is halo, $C_{1-6}$-alkyl, $C_{1-6}$ haloalkyl, $OR^i$, cycloalkyl, heterocycloalkyl, heterocycloalkyl-$C_{1-6}$-alkyl-, or heteroaryl, wherein the cycloalkyl, heteroaryl and heterocycloalkyl, alone or as part of another moiety, are optionally substituted with one, two, or three $R^{12}$; wherein $R^{12}$ is halo, $C_{1-6}$-alkyl, $C_{1-6}$-haloalkyl, $OR^p$, $C(O)R^p$, $C(O)NR^qR^r$, $C(O)OR^p$, $NR^qR^r$, $NR^qC(O)R^p$, $S(O)_2R^p$, or $S(O)_2NR^qR^r$. In yet another embodiment of formula (I), $R^{12}$ is $C_{1-6}$-alkyl, $C_{1-6}$ haloalkyl, or $C(O)R^p$; $R^p$ is $C_{1-6}$ alkyl, $C_{1-6}$ haloalkyl, and $C_{3-8}$ cycloalkyl.

In one embodiment of formula (I), B is phenyl, wherein the phenyl is substituted with heterocycloalkyl and optionally one or two $R^5$, wherein $R^5$ is halo, $C_{1-6}$-alkyl, $C_{1-6}$ haloalkyl, or $OR^i$, wherein the heterocycloalkyl is optionally substituted with one, two, or three $R^{12}$; wherein $R^{12}$ is halo, $C_{1-6}$-alkyl, $C_{1-6}$-haloalkyl, $OR^p$, $C(O)R^p$, $C(O)NR^qR^r$, $C(O)OR^p$, $NR^qR^r$, $NR^qC(O)R^p$, $S(O)_2R^p$, or $S(O)_2NR^qR^r$. In yet another embodiment, phenyl is substituted with heterocycloalkyl, and heterocycloalkyl is selected from the group consisting of azetidinyl, pyrrolidinyl, piperidinyl, morpholinyl, piperazinyl, azepanyl, diazepanyl, and hexahydropyrrolo[1,2-a]pyrazin-2(1H)yl.

In another embodiment of formula (I), B is

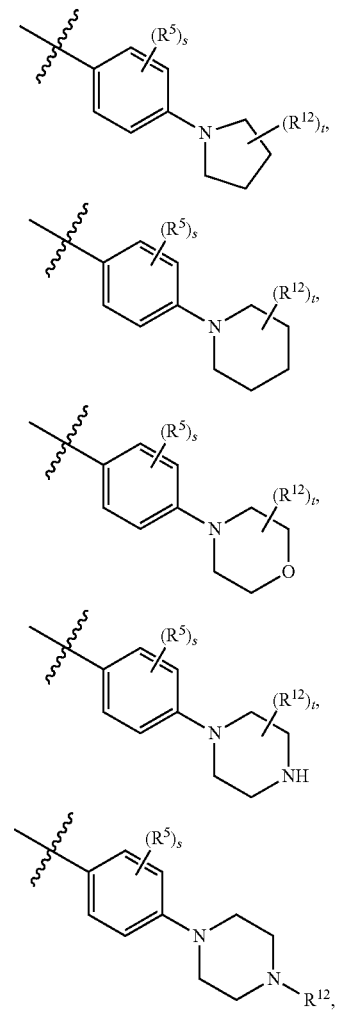

-continued

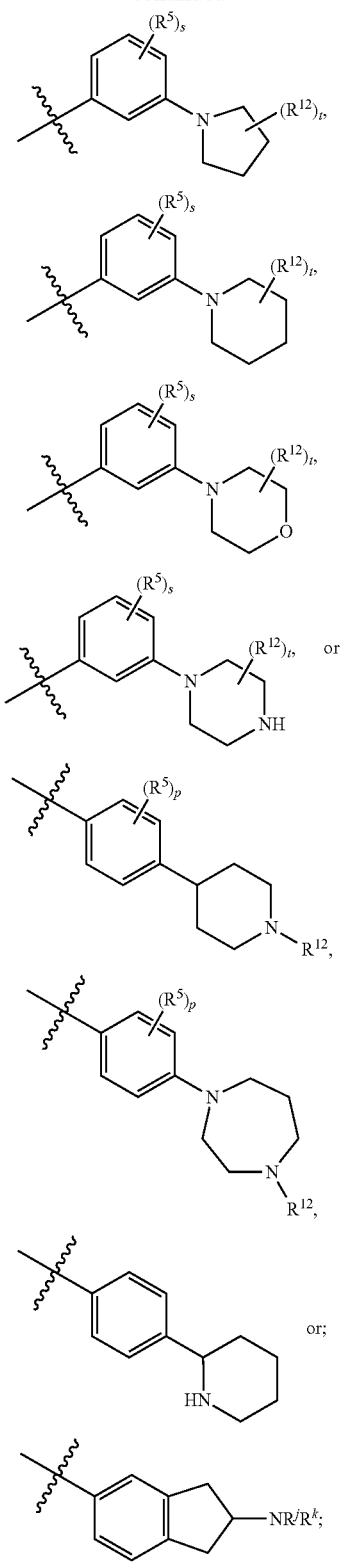

wherein $R^5$ is halo, $C_{1-6}$-alkyl, $C_{1-6}$ haloalkyl, or $OR^i$; s is 0 or 1; $R^{12}$ is $C_{1-6}$-alkyl, $C_{1-6}$-haloalkyl, $OR^p$, $C(O)R^p$, $C(O)NR^qR^r$, $C(O)OR^p$, $NR^qR^r$, $NR^qC(O)R^p$, $S(O)_2R^p$, or $S(O)_2NR^qR^r$; and t is 0 or 1.

In one embodiment of formula (I), B is

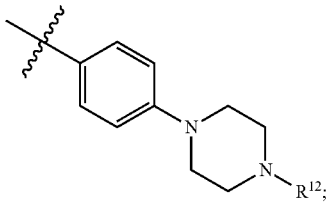

and $R^{12}$ is $C_{1-6}$-alkyl.

In one embodiment of formula (I), B is a 4-8 membered monocyclic heterocyclyl. In another embodiment, B is a 4-8 membered heterocycloalkyl or heterocycloalkenyl. In another embodiment, B is a 5-7 membered heteroaryl. In yet another embodiment of formula (I), B is pyrrolidinyl, tetrahydrofuryl, tetrahydrothienyl, imidazolidinyl, pyrazolidinyl, piperidinyl, tetrahydropyranyl, piperazinyl, dioxanyl, morpholinyl, 2-oxopyrrolidinyl, 2,5-dioxopyrrolidinyl, 2-oxopiperidinyl, 4-oxopiperidinyl, or 2,6-dioxopiperidinyl. In yet another embodiment of formula (I), B is pyridyl, pyrazyl, pyridinyl, pyrimidinyl, pyridazinyl, 1,3,5-, 1,2,4- or 1,2,3-triazinyl, imidazyl, furanyl, thiophenyl, pyrazolyl, oxazolyl, isoxazolyl, thiazolyl, 1,2,3-, 1,2,4-, 1,2,5-, or 1,3,4-oxadiazolyl, or isothiazolyl. In one embodiment, B is unsubstituted. In another embodiment, B is substituted with one, two, or three $R^6$, and $R^6$ is halo, $C_{1-6}$-alkyl, $C_{1-6}$-haloalkyl, $OR^i$, $C(O)R^i$, $C(O)OR^i$, $NR^mR^n$, or $S(O)_2R^i$.

In one embodiment of formula (I), B is a 7-11 membered bicyclic heterocyclyl. In another embodiment, B is a 7-11 membered bicyclic heterocycloalkyl or bicyclic heterocycloalkenyl. B is a 7-11 membered bicyclic heteroaryl. In yet another embodiment, B is 2,3-dihydro-2-oxo-1H-indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl, dihydroisoindolyl, dihydroquinazolinyl, 3,4-dihydro-4-oxo-quinazolinyl, benzisothiazolyl, benzisoxazolyl, benzodiazinyl, benzofurazanyl, benzothiopyranyl, benzotriazolyl, benzpyrazolyl, 1,3-benzodioxolyl, dihydrobenzofuryl, dihydrobenzothienyl, dihydrobenzothiopyranyl, dihydrobenzothiopyranyl sulfone, dihydrobenzopyranyl, dihydrobenzoxazinyl, 3-oxo-3,4-dihydro-1,4-benzoxazinyl, indolinyl, indazolyl, isochromanyl, isoindolinyl, naphthyridinyl, phthalazinyl, piperonyl, purinyl, pyridopyridyl, pyrrolotriazinyl, quinazolinyl, tetrahydroquinolinyl, thienofuryl, thienopyridyl, 3H-imidazo[4,5-c]pyridinyl, or thienothienyl. In one embodiment of formula (I), B is unsubstituted. In another embodiment of formula (I), B is substituted with one, two, or three $R^6$, and $R^6$ is halo, $C_{1-6}$-alkyl, $C_{1-6}$-haloalkyl, $OR^i$, $C(O)R^i$, $C(O)OR^i$, $NR^mR^n$, or $S(O)_2R^i$.

In one embodiment of formula (I), B is 10-15 membered tricyclic heterocyclyl. In another embodiment, B is a 10-15 membered tricyclic heterocycloalkyl or tricyclic heterocycloalkenyl. In another embodiment, B is a 10-15 membered tricyclic heteroaryl. In one embodiment of formula (I), B is unsubstituted. In another embodiment of formula (I), B is substituted with one, two, or three $R^6$, and $R^6$ is halo, $C_{1-6}$-alkyl, $C_{1-6}$-haloalkyl, $OR^i$, $C(O)R^i$, $C(O)OR^i$, $NR^mR^n$, or $S(O)_2R^i$.

In one embodiment of formula (I), B is

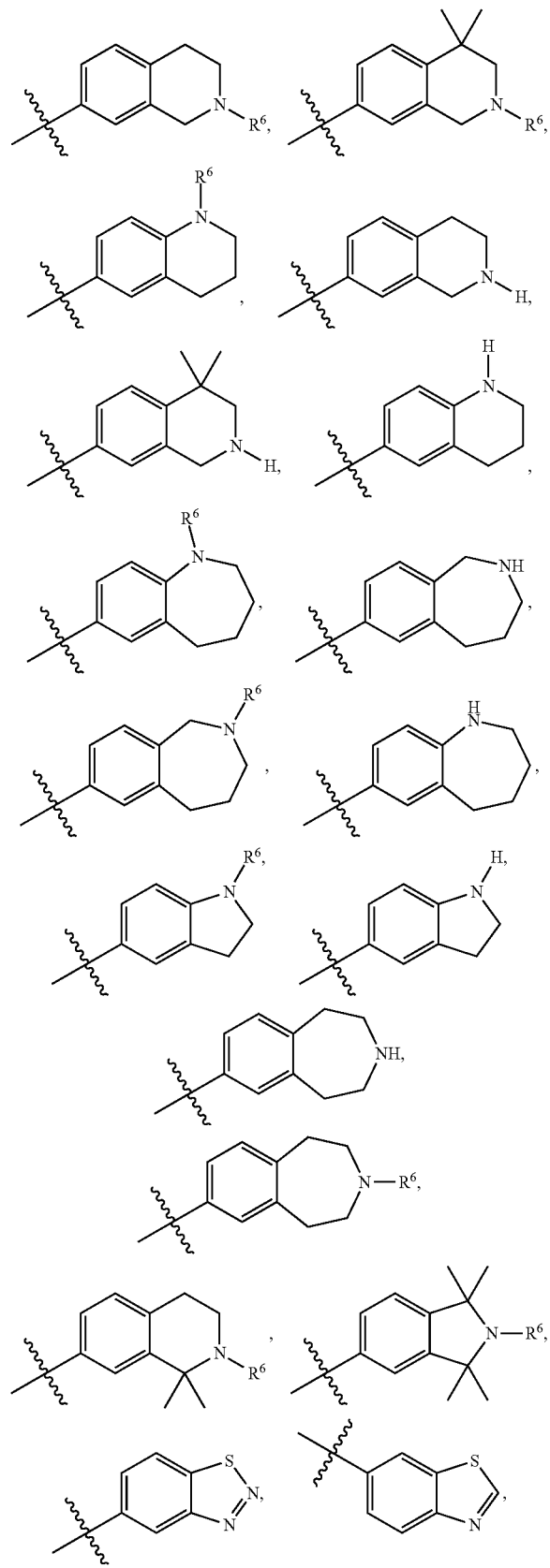

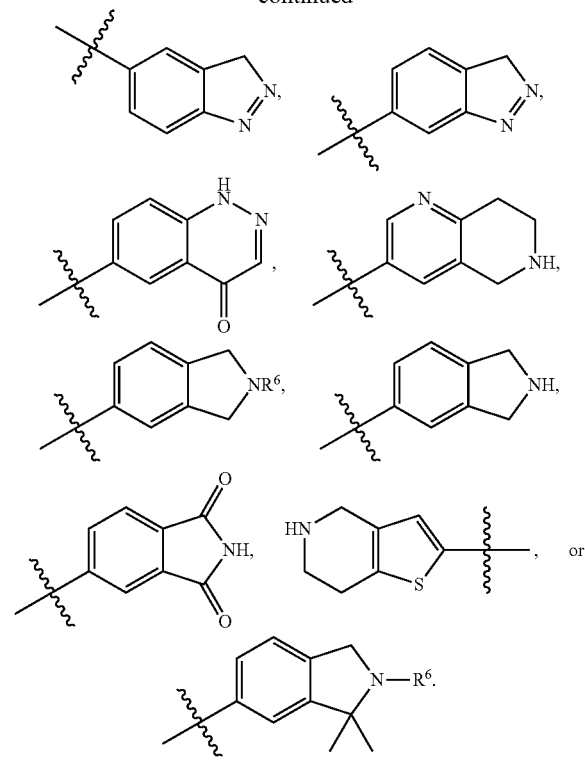

In another embodiment of formula (I), B is

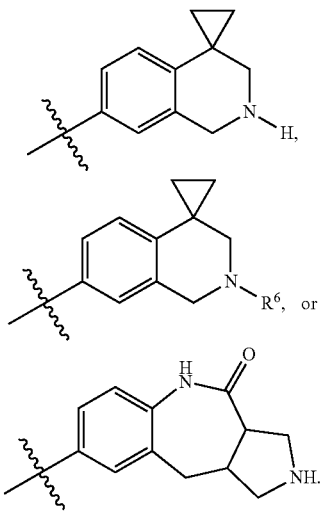

Specific embodiments contemplated as part of the invention include, but are not limited to, compounds of formula (I), for example:

ethyl 2-{[4-(4-methylpiperazin-1-yl)phenyl]amino}-5-oxo-6-(prop-2-en-1-yl)-5,6-dihydropyrido[4,3-d]pyrimidine-8-carboxylate;

ethyl 2-{[4-(4-methylpiperazin-1-yl)phenyl]amino}-5-oxo-6-phenyl-5,6-dihydropyrido[4,3-d]pyrimidine-8-carboxylate;

2-{[4-(4-methylpiperazin-1-yl)phenyl]amino}-6-phenylpyrido[4,3-d]pyrimidin-5(6H)-one;

6-benzyl-N-methyl-2-{[4-(4-methylpiperazin-1-yl)phenyl]amino}-5-oxo-5,6-dihydropyrido[4,3-d]pyrimidine-8-carboxamide;
ethyl 6-benzyl-2-{[4-(4-methylpiperazin-1-yl)phenyl]amino}-5-oxo-5,6-dihydropyrido[4,3-d]pyrimidine-8-carboxylate;
ethyl 6-(2-chlorophenyl)-2-{[4-(4-methylpiperazin-1-yl)phenyl]amino}-5-oxo-5,6-dihydropyrido[4,3-d]pyrimidine-8-carboxylate;
ethyl 2-{[4-(4-methylpiperazin-1-yl)phenyl]amino}-5-oxo-5,6-dihydropyrido[4,3-d]pyrimidine-8-carboxylate;
6-benzyl-2-{[4-(4-methylpiperazin-1-yl)phenyl]amino}-8-phenylpyrido[4,3-d]pyrimidin-5(6H)-one;
6-(2-methylbenzyl)-2-{[4-(4-methylpiperazin-1-yl)phenyl]amino}-8-phenylpyrido[4,3-d]pyrimidin-5(6H)-one;
8-bromo-6-(2,6-difluorobenzyl)-2-{[4-(4-methylpiperazin-1-yl)phenyl]amino}pyrido[4,3-d]pyrimidin-5(6H)-one;
6-(3-methylbenzyl)-2-{[4-(4-methylpiperazin-1-yl)phenyl]amino}-8-phenylpyrido[4,3-d]pyrimidin-5(6H)-one;
6-[2-fluoro-6-(trifluoromethyl)benzyl]-2-{[4-(4-methylpiperazin-1-yl)phenyl]amino}-8-phenylpyrido[4,3-d]pyrimidin-5(6H)-one;
6-(2-fluorobenzyl)-2-{[4-(4-methylpiperazin-1-yl)phenyl]amino}-8-phenylpyrido[4,3-d]pyrimidin-5(6H)-one;
2-{[2-{[4-(4-methylpiperazin-1-yl)phenyl]amino}-5-oxo-8-phenylpyrido[4,3-d]pyrimidin-6(5H)-yl]methyl}benzonitrile;
6-(2-chlorobenzyl)-2-{[4-(4-methylpiperazin-1-yl)phenyl]amino}-8-phenylpyrido[4,3-d]pyrimidin-5(6H)-one;
6-(2,6-dichlorobenzyl)-2-{[4-(4-methylpiperazin-1-yl)phenyl]amino}-8-phenylpyrido[4,3-d]pyrimidin-5(6H)-one;
6-(2-chloro-4-fluorobenzyl)-2-{[4-(4-methylpiperazin-1-yl)phenyl]amino}-8-phenylpyrido[4,3-d]pyrimidin-5(6H)-one;
6-(4-tert-butylbenzyl)-2-{[4-(4-methylpiperazin-1-yl)phenyl]amino}-8-phenylpyrido[4,3-d]pyrimidin-5(6H)-one;
6-[2-fluoro-5-(trifluoromethyl)benzyl]-2-{[4-(4-methylpiperazin-1-yl)phenyl]amino}-8-phenylpyrido[4,3-d]pyrimidin-5(6H)-one;
ethyl [2-{[4-(4-methylpiperazin-1-yl)phenyl]amino}-5-oxo-8-phenylpyrido[4,3-d]pyrimidin-6(5H)-yl]acetate;
6-(2,6-dichlorophenyl)-2-{[4-(4-methylpiperazin-1-yl)phenyl]amino}-8-[(phenylamino)methyl]pyrido[4,3-d]pyrimidin-5(6H)-one;
6-(2,6-dichlorophenyl)-2-{[4-(4-methylpiperazin-1-yl)phenyl]amino}-8-{[(2,2,2-trifluoroethyl)amino]methyl}pyrido[4,3-d]pyrimidin-5(6H)-one;
8-(1,3-benzothiazol-2-yl)-6-(2,6-dichlorophenyl)-2-{[4-(4-methylpiperazin-1-yl)phenyl]amino}pyrido[4,3-d]pyrimidin-5(6H)-one;
8-(1H-benzimidazol-2-yl)-6-(2,6-dichlorophenyl)-2-{[4-(4-methylpiperazin-1-yl)phenyl]amino}pyrido[4,3-d]pyrimidin-5(6H)-one;
6-(2,6-dichlorophenyl)-8-ethenyl-2-{[4-(4-methylpiperazin-1-yl)phenyl]amino}pyrido[4,3-d]pyrimidin-5(6H)-one;
6-(2,6-dichlorophenyl)-8-ethyl-2-{[4-(4-methylpiperazin-1-yl)phenyl]amino}pyrido[4,3-d]pyrimidin-5(6H)-one;
6-(2,6-dichlorophenyl)-2-{[4-(4-methylpiperazin-1-yl)phenyl]amino}-5-oxo-5,6-dihydropyrido[4,3-d]pyrimidine-8-carbaldehyde;
6-(2,6-dichlorophenyl)-8-methyl-2-{[4-(4-methylpiperazin-1-yl)phenyl]amino}pyrido[4,3-d]pyrimidin-5(6H)-one;
6-(2,6-dichlorophenyl)-8-methyl-2-[(2'-methyl-2',3'-dihydro-1'H-spiro[cyclopropane-1,4'-isoquinolin]-7'-yl)amino]pyrido[4,3-d]pyrimidin-5(6H)-one;
6-(2,6-dichlorophenyl)-2-(2',3'-dihydro-1'H-spiro[cyclopropane-1,4'-isoquinolin]-7'-ylamino)-8-methylpyrido[4,3-d]pyrimidin-5(6H)-one;
6-(2,6-dichlorophenyl)-2-{[2-(dimethylamino)-2,3-dihydro-1H-inden-5-yl]amino}-8-methylpyrido[4,3-d]pyrimidin-5(6H)-one;
6-(2,6-dichlorophenyl)-8-ethenyl-2-[(2'-methyl-2',3'-dihydro-1'H-spiro[cyclopropane-1,4'-isoquinolin]-7'-yl)amino]pyrido[4,3-d]pyrimidin-5(6H)-one;
6,8-dimethyl-2-{[4-(4-methylpiperazin-1-yl)phenyl]amino}pyrido[4,3-d]pyrimidin-5(6H)-one;
6-(2,6-dichlorophenyl)-8-(1H-imidazol-2-yl)-2-{[4-(4-methylpiperazin-1-yl)phenyl]amino}pyrido[4,3-d]pyrimidin-5(6H)-one;
6-(2,6-dichlorophenyl)-2-({4-[4-(dimethylamino)piperidin-1-yl]phenyl}amino)-8-methylpyrido[4,3-d]pyrimidin-5(6H)-one;
6-(2,6-dichlorophenyl)-8-(difluoromethyl)-2-{[4-(4-methylpiperazin-1-yl)phenyl]amino}pyrido[4,3-d]pyrimidin-5(6H)-one;
6-(2,6-dichlorophenyl)-8-(fluoromethyl)-2-{[4-(4-methylpiperazin-1-yl)phenyl]amino}pyrido[4,3-d]pyrimidin-5(6H)-one;
6-(2,6-dichlorophenyl)-8-(hydroxymethyl)-2-{[4-(4-methylpiperazin-1-yl)phenyl]amino}pyrido[4,3-d]pyrimidin-5(6H)-one;
8-bromo-6-(cyclopropylmethyl)-2-{[4-(4-methylpiperazin-1-yl)phenyl]amino}pyrido[4,3-d]pyrimidin-5(6H)-one;
8-(cyclohex-1-en-1-yl)-6-(cyclopropylmethyl)-2-{[4-(4-methylpiperazin-1-yl)phenyl]amino}pyrido[4,3-d]pyrimidin-5(6H)-one;
8-(cyclopent-1-en-1-yl)-6-(cyclopropylmethyl)-2-{[4-(4-methylpiperazin-1-yl)phenyl]amino}pyrido[4,3-d]pyrimidin-5(6H)-one;
8-bromo-6-ethyl-2-{[4-(4-methylpiperazin-1-yl)phenyl]amino}pyrido[4,3-d]pyrimidin-5(6H)-one;
8-(cyclohex-1-en-1-yl)-6-ethyl-2-{[4-(4-methylpiperazin-1-yl)phenyl]amino}pyrido[4,3-d]pyrimidin-5(6H)-one;
2-{[4-(4-methylpiperazin-1-yl)phenyl]amino}-6-phenylpyrimido[5,4-c]quinolin-5(6H)-one;
6-(2-chlorophenyl)-2-{[4-(4-methylpiperazin-1-yl)phenyl]amino}pyrimido[5,4-c]quinolin-5(6H)-one;
2-{[4-(4-methylpiperazin-1-yl)phenyl]amino}-6-phenylpyrimido[5,4-c][1,8]naphthyridin-5(6H)-one;
6-(2-chlorophenyl)-2-{[4-(4-methylpiperazin-1-yl)phenyl]amino}pyrimido[5,4-c][1,8]naphthyridin-5(6H)-one;
2-amino-6-(2,6-dichlorophenyl)-8-(1H-imidazol-2-yl)pyrido[4,3-d]pyrimidin-5(6H)-one;
6-(2,6-dichlorophenyl)-2-{[2-(dimethylamino)-2,3-dihydro-1H-inden-5-yl]amino}-8-ethenylpyrido[4,3-d]pyrimidin-5(6H)-one;
6-(2,6-dichlorophenyl)-2-({4-[4-(dimethylamino)piperidin-1-yl]phenyl}amino)-8-ethenylpyrido[4,3-d]pyrimidin-5(6H)-one;
6-(2,6-dichlorophenyl)-2-(2',3'-dihydro-1'H-spiro[cyclopropane-1,4'-isoquinolin]-7'-ylamino)-8-ethenylpyrido[4,3-d]pyrimidin-5(6H)-one;
6-(2,6-dichlorophenyl)-8-ethenyl-2-{[4-(hexahydropyrrolo[3,4-c]pyrrol-2(1H)-yl)phenyl]amino}pyrido[4,3-d]pyrimidin-5(6H)-one;
6-(2,6-dichlorophenyl)-8-(hydroxymethyl)-2-[(2'-methyl-2',3'-dihydro-1'H-spiro[cyclopropane-1,4'-isoquinolin]-7'-yl)amino]pyrido[4,3-d]pyrimidin-5(6H)-one;
6-(2,6-dichlorophenyl)-2-{[2-(dimethylamino)-2,3-dihydro-1H-inden-5-yl]amino}-8-(hydroxymethyl)pyrido[4,3-d]pyrimidin-5(6H)-one;

6-(2,6-dichlorophenyl)-2-({4-[4-(dimethylamino)piperidin-1-yl]phenyl}amino)-8-(hydroxymethyl)pyrido[4,3-d]pyrimidin-5(6H)-one;

6-(2,6-dichlorophenyl)-2-[(4,4-dimethyl-1,2,3,4-tetrahydroisoquinolin-7-yl)amino]-8-ethenylpyrido[4,3-d]pyrimidin-5(6H)-one;

6-(2,6-dichlorophenyl)-2-(2',3'-dihydro-1'H-spiro[cyclopropane-1,4'-isoquinolin]-7'-ylamino)-8-(hydroxymethyl)pyrido[4,3-d]pyrimidin-5(6H)-one;

6-(2,6-dichlorophenyl)-2-[(4,4-dimethyl-1,2,3,4-tetrahydroisoquinolin-7-yl)amino]-8-(hydroxymethyl)pyrido[4,3-d]pyrimidin-5(6H)-one;

6-(2,6-dichlorophenyl)-8-ethenyl-2-(1,2,3,4-tetrahydroisoquinolin-6-ylamino)pyrido[4,3-d]pyrimidin-5(6H)-one;

6-(2-chloro-6-fluorophenyl)-2-({4-[4-(dimethylamino)piperidin-1-yl]phenyl}amino)-8-ethenylpyrido[4,3-d]pyrimidin-5(6H)-one;

6-(2-chloro-6-fluorophenyl)-8-ethenyl-2-{[4-(1-methylpiperidin-4-yl)phenyl]amino}pyrido[4,3-d]pyrimidin-5(6H)-one;

6-(2-chloro-6-fluorophenyl)-8-ethenyl-2-{[4-(4-methylpiperazin-1-yl)phenyl]amino}pyrido[4,3-d]pyrimidin-5(6H)-one;

6-(2-chloro-6-fluorophenyl)-8-ethenyl-2-[(2'-methyl-2',3'-dihydro-1'H-spiro[cyclopropane-1,4'-isoquinolin]-7'-yl)amino]pyrido[4,3-d]pyrimidin-5(6H)-one;

6-(2-chloro-6-fluorophenyl)-2-{[2-(dimethylamino)-2,3-dihydro-1H-inden-5-yl]amino}-8-ethenylpyrido[4,3-d]pyrimidin-5(6H)-one;

6-(2-chloro-6-fluorophenyl)-8-methyl-2-{[4-(4-methylpiperazin-1-yl)phenyl]amino}pyrido[4,3-d]pyrimidin-5(6H)-one;

6-(2-chloro-6-fluorophenyl)-8-methyl-2-[(2'-methyl-2',3'-dihydro-1'H-spiro[cyclopropane-1,4'-isoquinolin]-7'-yl)amino]pyrido[4,3-d]pyrimidin-5(6H)-one;

6-(2-chloro-6-fluorophenyl)-2-{[2-(dimethylamino)-2,3-dihydro-1H-inden-5-yl]amino}-8-methylpyrido[4,3-d]pyrimidin-5(6H)-one;

6-(2-chloro-6-fluorophenyl)-2-({4-[4-(dimethylamino)piperidin-1-yl]phenyl}amino)-8-methylpyrido[4,3-d]pyrimidin-5(6H)-one;

6-(2-chloro-6-fluorophenyl)-8-methyl-2-[(2,4,4-trimethyl-1,2,3,4-tetrahydroisoquinolin-7-yl)amino]pyrido[4,3-d]pyrimidin-5(6H)-one;

6-(2-chloro-6-fluorophenyl)-8-methyl-2-{[4-(1-methylpiperidin-4-yl)phenyl]amino}pyrido[4,3-d]pyrimidin-5(6H)-one;

6-(2-chloro-6-fluorophenyl)-8-methyl-2-(1,2,3,4-tetrahydroisoquinolin-6-ylamino)pyrido[4,3-d]pyrimidin-5(6H)-one;

6-(2-chloro-6-fluorophenyl)-2-[(4,4-dimethyl-1,2,3,4-tetrahydroisoquinolin-7-yl)amino]-8-methylpyrido[4,3-d]pyrimidin-5(6H)-one;

6-(2-chloro-6-fluorophenyl)-2-(2',3'-dihydro-1'H-spiro[cyclopropane-1,4'-isoquinolin]-7'-ylamino)-8-methylpyrido[4,3-d]pyrimidin-5(6H)-one;

6-(2-chloro-6-fluorophenyl)-8-methyl-2-(1,2,3,4-tetrahydroisoquinolin-7-ylamino)pyrido[4,3-d]pyrimidin-5(6H)-one;

6-(2,6-dichlorophenyl)-8-methyl-2-(1,2,3,4-tetrahydroisoquinolin-6-ylamino)pyrido[4,3-d]pyrimidin-5(6H)-one;

6-(2,6-dichlorophenyl)-2-[(4,4-dimethyl-1,2,3,4-tetrahydroisoquinolin-7-yl)amino]-8-methylpyrido[4,3-d]pyrimidin-5(6H)-one;

6-(2,6-dichlorophenyl)-8-methyl-2-[(2,4,4-trimethyl-1,2,3,4-tetrahydroisoquinolin-7-yl)amino]pyrido[4,3-d]pyrimidin-5(6H)-one;

6-(2,6-dichlorophenyl)-8-methyl-2-(1,2,3,4-tetrahydroisoquinolin-7-ylamino)pyrido[4,3-d]pyrimidin-5(6H)-one;

6-(2,6-dichlorophenyl)-8-(1H-imidazol-2-yl)-2-(1,2,3,4-tetrahydroisoquinolin-6-ylamino)pyrido[4,3-d]pyrimidin-5(6H)-one;

6-(2,6-dichlorophenyl)-8-(difluoromethyl)-2-{[4-(1-methylpiperidin-4-yl)phenyl]amino}pyrido[4,3-d]pyrimidin-5(6H)-one;

6-(2,6-dichlorophenyl)-8-(difluoromethyl)-2-{[2-(dimethylamino)-2,3-dihydro-1H-inden-5-yl]amino}pyrido[4,3-d]pyrimidin-5(6H)-one;

6-(2,6-dichlorophenyl)-8-(difluoromethyl)-2-({4-[4-(dimethylamino)piperidin-1-yl]phenyl}amino)pyrido[4,3-d]pyrimidin-5(6H)-one;

6-(2,6-dichlorophenyl)-8-(difluoromethyl)-2-[(4,4-dimethyl-1,2,3,4-tetrahydroisoquinolin-7-yl)amino]pyrido[4,3-d]pyrimidin-5(6H)-one;

6-(2,6-dichlorophenyl)-8-(difluoromethyl)-2-(2',3'-dihydro-1'H-spiro[cyclopropane-1,4'-isoquinolin]-7'-ylamino)pyrido[4,3-d]pyrimidin-5(6H)-one;

6-(2,6-dichlorophenyl)-8-(difluoromethyl)-2-(1,2,3,4-tetrahydroisoquinolin-7-ylamino)pyrido[4,3-d]pyrimidin-5(6H)-one;

6-(2,6-dimethylphenyl)-8-methyl-2-[(2'-methyl-2',3'-dihydro-1'H-spiro[cyclopropane-1,4'-isoquinolin]-7'-yl)amino]pyrido[4,3-d]pyrimidin-5(6H)-one;

2-({4-[4-(dimethylamino)piperidin-1-yl]phenyl}amino)-6-(2,6-dimethylphenyl)-8-methylpyrido[4,3-d]pyrimidin-5(6H)-one;

6-(2-chloro-6-methylphenyl)-8-methyl-2-[(2'-methyl-2',3'-dihydro-1'H-spiro[cyclopropane-1,4'-isoquinolin]-7'-yl)amino]pyrido[4,3-d]pyrimidin-5(6H)-one;

6-(2-chloro-6-methylphenyl)-2-({4-[4-(dimethylamino)piperidin-1-yl]phenyl}amino)-8-methylpyrido[4,3-d]pyrimidin-5(6H)-one;

6-(2,6-dichlorophenyl)-2-[(4-{[2-(dimethylamino)ethyl]sulfanyl}phenyl)amino]-8-methylpyrido[4,3-d]pyrimidin-5(6H)-one;

6-(2,6-dichlorophenyl)-8-(difluoromethyl)-2-(1,2,3,4-tetrahydroisoquinolin-6-ylamino)pyrido[4,3-d]pyrimidin-5(6H)-one;

6-(2,6-dichlorophenyl)-8-(difluoromethyl)-2-[(2'-methyl-2',3'-dihydro-1'H-spiro[cyclopropane-1,4'-isoquinolin]-7'-yl)amino]pyrido[4,3-d]pyrimidin-5(6H)-one;

6-(2,6-dichlorophenyl)-8-(difluoromethyl)-2-{[2-(pyrrolidin-1-yl)-2,3-dihydro-1H-inden-5-yl]amino}pyrido[4,3-d]pyrimidin-5 (6H)-one;

6-(2,6-dichlorophenyl)-2-[(4-{[2-(dimethylamino)ethyl]sulfanyl}phenyl)amino]-8-methylpyrido[4,3-d]pyrimidin-5(6H)-one;

8-methyl-2-[(2'-methyl-2',3'-dihydro-1'H-spiro[cyclopropane-1,4'-isoquinolin]-7'-yl)amino]-6-(quinolin-8-yl)pyrido[4,3-d]pyrimidin-5 (6H)-one;

6-(2-chlorophenyl)-8-methyl-2-(1,2,3,4-tetrahydroisoquinolin-7-ylamino)pyrido[4,3-d]pyrimidin-5 (6H)-one;

6-(2-chlorophenyl)-2-({4-[4-(dimethylamino)piperidin-1-yl]phenyl}amino)-8-methylpyrido[4,3-d]pyrimidin-5 (6H)-one;

8-methyl-6-(naphthalen-1-yl)-2-(1,2,3,4-tetrahydroisoquinolin-7-ylamino)pyrido[4,3-d]pyrimidin-5 (6H)-one;

2-({4-[4-(dimethylamino)piperidin-1-yl]phenyl}amino)-8-methyl-6-(naphthalen-1-yl)pyrido[4,3-d]pyrimidin-5 (6H)-one;

6-(2,5-dichlorophenyl)-8-methyl-2-(1,2,3,4-tetrahydroisoquinolin-7-ylamino)pyrido[4,3-d]pyrimidin-5(6H)-one;

6-(2-fluoro-6-methylphenyl)-8-methyl-2-(1,2,3,4-tetrahydroisoquinolin-7-ylamino)pyrido[4,3-d]pyrimidin-5(6H)-one;

2-({4-[4-(dimethylamino)piperidin-1-yl]phenyl}amino)-6-(2-fluoro-6-methylphenyl)-8-methylpyrido[4,3-d]pyrimidin-5(6H)-one;

8-methyl-6-[2-(1,3-oxazol-5-yl)phenyl]-2-(1,2,3,4-tetrahydroisoquinolin-7-ylamino)pyrido[4,3-d]pyrimidin-5(6H)-one;

2-({4-[4-(dimethylamino)piperidin-1-yl]phenyl}amino)-8-methyl-6-[2-(1,3-oxazol-5-yl)phenyl]pyrido[4,3-d]pyrimidin-5(6H)-one;

methyl 4-chloro-3-[8-methyl-5-oxo-2-(1,2,3,4-tetrahydroisoquinolin-7-ylamino)pyrido[4,3-d]pyrimidin-6(5H)-yl]benzoate;

methyl 4-chloro-3-[2-({4-[4-(dimethylamino)piperidin-1-yl]phenyl}amino)-8-methyl-5-oxopyrido[4,3-d]pyrimidin-6(5H)-yl]benzoate;

6-(2,6-dichlorophenyl)-8-(fluoromethyl)-2-(1,2,3,4-tetrahydroisoquinolin-7-ylamino)pyrido[4,3-d]pyrimidin-5(6H)-one;

6-(2,6-dichlorophenyl)-8-(fluoromethyl)-2-(1,2,3,4-tetrahydroisoquinolin-6-ylamino)pyrido[4,3-d]pyrimidin-5(6H)-one;

6-(2,6-dichlorophenyl)-2-({4-[4-(dimethylamino)piperidin-1-yl]phenyl}amino)-8-(fluoromethyl)pyrido[4,3-d]pyrimidin-5(6H)-one;

6-(2,6-dichlorophenyl)-2-{[2-(dimethylamino)-2,3-dihydro-1H-inden-5-yl]amino}-8-(fluoromethyl)pyrido[4,3-d]pyrimidin-5(6H)-one;

6-(2,6-dichlorophenyl)-8-(fluoromethyl)-2-[(2'-methyl-2',3'-dihydro-1'H-spiro[cyclopropane-1,4'-isoquinolin]-7'-yl)amino]pyrido[4,3-d]pyrimidin-5(6H)-one;

2-[(4-{[6-(2,6-dichlorophenyl)-8-methyl-5-oxo-5,6-dihydropyrido[4,3-d]pyrimidin-2-yl]amino}phenyl)sulfanyl]-N-methylacetamide;

6-(2,6-dichlorophenyl)-8-methyl-2-[(1,1,2-trimethyl-2,3-dihydro-1H-isoindol-5-yl)amino]pyrido[4,3-d]pyrimidin-5(6H)-one;

6-(2,6-dichlorophenyl)-8-methyl-2-({4-[(1-methylpiperidin-4-yl)amino]phenyl}amino)pyrido[4,3-d]pyrimidin-5(6H)-one;

6-(2-hydroxyphenyl)-8-methyl-2-(1,2,3,4-tetrahydroisoquinolin-7-ylamino)pyrido[4,3-d]pyrimidin-5(6H)-one;

6-(2-hydroxy-6-methylphenyl)-8-methyl-2-(1,2,3,4-tetrahydroisoquinolin-7-ylamino)pyrido[4,3-d]pyrimidin-5(6H)-one;

8-methyl-2-(1,2,3,4-tetrahydroisoquinolin-7-ylamino)-6-(1,3,5-trimethyl-1H-pyrazol-4-yl)pyrido[4,3-d]pyrimidin-5(6H)-one;

2-[(4-{[6-(2,6-dichlorophenyl)-8-methyl-5-oxo-5,6-dihydropyrido[4,3-d]pyrimidin-2-yl]amino}phenyl)sulfonyl]-N-methylacetamide;

6-(2,6-dichlorophenyl)-2-[(1,1-dimethyl-2,3-dihydro-1H-isoindol-5-yl)amino]-8-methylpyrido[4,3-d]pyrimidin-5(6H)-one;

6-(2,6-dichlorophenyl)-8-methyl-2-({4-[(1-methylpiperidin-4-yl)oxy]phenyl}amino)pyrido[4,3-d]pyrimidin-5(6H)-one;

6-(2-hydroxyphenyl)-8-methyl-2-(1,2,3,4-tetrahydroisoquinolin-7-ylamino)pyrido[4,3-d]pyrimidin-5(6H)-one;

6-(2-hydroxy-6-methylphenyl)-8-methyl-2-(1,2,3,4-tetrahydroisoquinolin-7-ylamino)pyrido[4,3-d]pyrimidin-5(6H)-one;

8-methyl-2-(1,2,3,4-tetrahydroisoquinolin-7-ylamino)-6-(1,3,5-trimethyl-1H-pyrazol-4-yl)pyrido[4,3-d]pyrimidin-5(6H)-one;

2-[(4-{[6-(2,6-dichlorophenyl)-8-methyl-5-oxo-5,6-dihydropyrido[4,3-d]pyrimidin-2-yl]amino}phenyl)sulfonyl]-N-methylacetamide;

6-(2,6-dichlorophenyl)-2-[(1,1-dimethyl-2,3-dihydro-1H-isoindol-5-yl)amino]-8-methylpyrido[4,3-d]pyrimidin-5(6H)-one;

6-(2,6-dichlorophenyl)-8-methyl-2-({4-[(1-methylpiperidin-4-yl)oxy]phenyl}amino)pyrido[4,3-d]pyrimidin-5(6H)-one;

6-(3,5-dimethyl-1H-pyrazol-4-yl)-8-methyl-2-(1,2,3,4-tetrahydroisoquinolin-7-ylamino)pyrido[4,3-d]pyrimidin-5(6H)-one;

6-(3,5-dimethyl-1,2-oxazol-4-yl)-8-methyl-2-(1,2,3,4-tetrahydroisoquinolin-7-ylamino)pyrido[4,3-d]pyrimidin-5(6H)-one;

6-(2,6-dichlorophenyl)-8-methyl-2-({4-[(1-methylpyrrolidin-3-yl)amino]phenyl}amino)pyrido[4,3-d]pyrimidin-5(6H)-one;

6-(2,6-dimethylphenyl)-8-methyl-2-(1,2,3,4-tetrahydroisoquinolin-7-ylamino)pyrido[4,3-d]pyrimidin-5(6H)-one;

6-(2-chloro-6-methylphenyl)-8-methyl-2-(1,2,3,4-tetrahydroisoquinolin-7-ylamino)pyrido[4,3-d]pyrimidin-5(6H)-one;

6-(2,6-dichlorophenyl)-8-(1-hydroxyethyl)-2-{[4-(4-methylpiperazin-1-yl)phenyl]amino}pyrido[4,3-d]pyrimidin-5(6H)-one;

methyl 5-{[6-(2,6-dichlorophenyl)-8-methyl-5-oxo-5,6-dihydropyrido[4,3-d]pyrimidin-2-yl]amino}-2-(4-methylpiperazin-1-yl)benzoate;

6-(2,6-dichlorophenyl)-2-[(4-{[2-(dimethylamino)ethyl]amino}phenyl)amino]-8-methylpyrido[4,3-d]pyrimidin-5(6H)-one;

6-(2,6-dichlorophenyl)-2-[(4-{4-[3-(dimethylamino)propyl]piperazin-1-yl}phenyl)amino]-8-methylpyrido[4,3-d]pyrimidin-5(6H)-one;

6-(2,6-dichlorophenyl)-2-[(4-{[trans-4-(dimethylamino)cyclohexyl]amino}phenyl)amino]-8-methylpyrido[4,3-d]pyrimidin-5 (6H)-one;

6-(2,6-dichlorophenyl)-2-[(4-{[cis-4-(dimethylamino)cyclohexyl]amino}phenyl)amino]-8-methylpyrido[4,3-d]pyrimidin-5 (6H)-one;

7-(2,6-dichlorophenyl)-5-methyl-3-(1,2,3,4-tetrahydro isoquinolin-7-ylamino)pyrido[4,3-e][1,2,4]triazin-8(7H)-one;

7-(2,6-dichlorophenyl)-5-methyl-3-[(2'-methyl-2',3'-dihydro-1'H-spiro[cyclopropane-1,4'-isoquinolin]-7'-yl)amino]pyrido[4,3-e][1,2,4]triazin-8(7H)-one;

6-(2-chloro-6-hydroxyphenyl)-2-[(1,1-dimethyl-2,3-dihydro-1H-isoindol-5-yl)amino]-8-methylpyrido[4,3-d]pyrimidin-5 (6H)-one;

6-(2,6-dichlorophenyl)-8-methyl-2-{[2-(1-methylpiperidin-4-yl)-2,3-dihydro-1H-isoindol-5-yl]amino}pyrido[4,3-d]pyrimidin-5 (6H)-one;

6-(2,6-dichlorophenyl)-2-[(4-{4-[2-(dimethylamino)ethyl]piperazin-1-yl}phenyl)amino]-8-methylpyrido[4,3-d]pyrimidin-5 (6H)-one;

2-[(4-{4-[3-(dimethylamino)propyl]piperazin-1-yl}phenyl)amino]-6-(2,6-dimethylphenyl)-8-methylpyrido[4,3-d]pyrimidin-5(6H)-one;

6-(2,6-dichlorophenyl)-2-[(4-{4-[3-(dimethylamino)propyl]piperazin-1-yl}phenyl)amino]-8-(fluoromethyl)pyrido[4,3-d]pyrimidin-5(6H)-one; or 6-(2,6-dichlorophenyl)-2-({2-[2-(dimethylamino)ethyl]-2,3-dihydro-1H-isoindol-5-yl}amino)-8-methylpyrido[4,3-d]pyrimidin-5(6H)-one.

Embodiments of Formula (II)

In one embodiment, the present invention is directed, in part, to a class of compounds having a structure of formula (II),

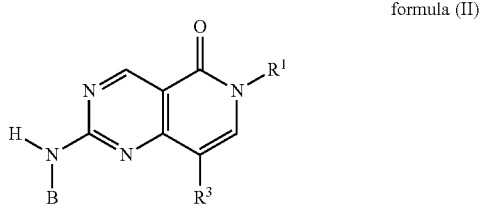

formula (II)

wherein $R^1$, $R^3$ and B are as described in formula (I).

In one embodiment of formula (II), $R^1$ is $C_{1-8}$-alkyl or $C_{2-8}$-alkenyl, wherein the $C_{1-8}$-alkyl or $C_{2-8}$-alkenyl is optionally substituted with one or more substituents selected from the group consisting of halo, CN, $NO_2$, —$OR^a$, —C(O)$R^a$, —C(O)O$R^a$, —OC(O)$R^a$, —$NR^bR^c$, —$NR^bC(O)R^a$, —NHC(O)NH$R^b$, —C(O)$NR^bR^c$, —$NHSO_2R^a$, and —$SO_2NR^bNR^c$. In another embodiment of formula (II), $R^1$ is $C_{1-8}$-alkyl or $C_{2-8}$-alkenyl, wherein the $C_{1-8}$-alkyl or $C_{2-8}$-alkenyl is unsubstituted. In yet another embodiment of formula (II), $R^1$ is —$CH_3$, —$CH_2CH_3$, —$CH_2CH_2CH_3$, —$CH_2CH_2CH_2CH_3$, —CH($CH_3$)$_2$, —$CH_2CH(CH_3)_2$, —$CH_2CH=CH_2$, $CH_2CH=CHCH_2$, or —$CH_2CH_2CH=CH_2$.

In another embodiment of formula (II), $R^1$ is aryl, wherein the aryl is phenyl, naphthyl, tetrahydronaphthyl, indenyl, or indanyl. In yet another embodiment, the phenyl, naphthyl, tetrahydronaphthyl, indenyl, or indanyl is unsubstituted. In yet another embodiment, the phenyl, naphthyl, tetrahydronaphthyl, indenyl, or indanyl is optionally substituted with one, two, or three substituents selected from the group consisting of $C_{1-6}$-alkyl, $C_{1-6}$-haloalkyl, $C_{2-6}$-alkenyl, heterocycloalkyl, aryl, heteroaryl, halo, oxo, CN, $NO_2$, —$OR^d$, —C(O)$R^d$, —C(O)O$R^d$, —OC(O)$R^d$, —$SR^d$, —S(O)$R^d$, —$SO_2R^d$, —$NR^eR^f$, —NHC(O)$R^e$, —NHC(O)NH$R^e$, —NHC(O)O$R^e$, —$NHSO_2R^d$, —C(O)NH$R^e$, and —$SO_2NHNR^e$.

In another embodiment of formula (II), $R^1$ is phenyl, wherein the phenyl is optionally substituted with one, two, or three substituents selected from the group consisting of CN, $NO_2$, $C_{1-6}$-alkyl, $C_{1-6}$-haloalkyl, halo, —$OR^a$, —C(O)$R^a$, —C(O)O$R^a$, —OC(O)$R^a$, —$NR^bR^c$, —$NR^bC(O)R^a$, —NHC(O)NH$R^b$, —C(O)$NR^bR^c$, —$NHSO_2R^a$, and —$SO_2NR^bNR^c$. In yet another embodiment, the phenyl is unsubstituted. In yet another embodiment, the phenyl is substituted with one, two, or three halo or $C_{1-6}$-haloalkyl.

In another embodiment of formula (II), $R^1$ is aryl-$C_{1-6}$-alkyl-, wherein the $R^1$ aryl is optionally substituted with one or more substituents independently selected from the group consisting of $C_{1-6}$-alkyl, $C_{1-6}$-haloalkyl, $C_{2-6}$-alkenyl, heterocycloalkyl, aryl, heteroaryl, halo, oxo, CN, $NO_2$, —$OR^d$, —C(O)$R^d$, —C(O)O$R^d$, —OC(O)$R^d$, —$SR^d$, —S(O)$R^d$, —$SO_2R^d$, —$NR^eR^f$, —NHC(O)$R^e$, —NHC(O)NH$R^e$, —NHC(O)O$R^e$, —$NHSO_2R^d$, —C(O)NH$R^e$, and —$SO_2NHNR^e$. In another embodiment of formula (II), $R^1$ is aryl-$C_{1-6}$-alkyl-, wherein the $R^1$ aryl is phenyl. In another embodiment, $R^1$ is phenyl-$C_{1-3}$-alkyl-. In yet another embodiment, the phenyl is unsubstituted. In yet another embodiment, the phenyl is substituted with one, two, or three substituents independently selected from the group consisting of CN, $NO_2$, halo, —$OR^a$, —C(O)$R^a$, —C(O)$OR^a$, —OC(O)$R^a$, —$NR^bR^c$, —$NR^bC(O)R^a$, —NHC(O)NH$R^b$, —C(O)$NR^bR^c$, —$NHSO_2R^a$, and —$SO_2NR^bNR^c$. In yet another embodiment, the phenyl is substituted with one, two, or three halo or $C_{1-6}$-haloalkyl.

In another embodiment of formula (II), $R^1$ is $C_{3-8}$ cycloalkyl-$C_{1-6}$-alkyl-, wherein the $R^1C_{3-8}$-cycloalkyl is optionally substituted with one or more substituents independently selected from the group consisting of $C_{1-6}$-alkyl, $C_{1-6}$-haloalkyl, $C_{2-6}$-alkenyl, heterocycloalkyl, aryl, heteroaryl, halo, oxo, CN, $NO_2$, —$OR^d$, —C(O)$R^d$, —C(O)O$R^d$, —OC(O)$R^d$, —$SR^d$, —S(O)$R^d$, —$SO_2R^d$, —$NR^eR^f$, —NHC(O)$R^e$, —NHC(O)NH$R^e$, —NHC(O)O$R^e$, —$NHSO_2R^d$, —C(O)NH$R^e$, and —$SO_2NHNR^e$ In another embodiment of formula (II), $R^1$ is $C_{3-8}$ cycloalkyl-$C_{1-6}$-alkyl-, wherein the $R^1C_{3-8}$-cycloalkyl is unsubstituted.

In one embodiment of formula (II), $R^3$ is hydrogen or halo.

In another embodiment of formula (II), $R^3$ is $C_{1-6}$-alkyl or $C_{2-6}$-alkenyl, wherein the $C_{1-6}$-alkyl or $C_{2-6}$-alkenyl is optionally substituted with one, two, three, four or five substituents independently selected from the group consisting of halo, hydroxy, and $C_{1-6}$-alkoxy. In another embodiment of formula (II), is $C_{1-6}$-alkyl or $C_{2-6}$-alkenyl, wherein the $C_{1-6}$-alkyl or $C_{2-6}$-alkenyl is unsubstituted. In another embodiment, the $C_{1-6}$-alkyl or $C_{2-6}$-alkenyl is substituted with one, two, or three halo.

In one embodiment of formula (II), $R^3$ is aryl or heteroaryl, wherein the aryl or heteroaryl is optionally substituted with one, two, or three substituents independently selected from the group consisting of halo, $C_{1-6}$-alkyl, $C_{1-6}$-haloalkyl, $C_{1-6}$-hydroxyalkyl, hydroxy, oxo, $C_{1-6}$-alkoxy, $C_{1-6}$-haloalkoxy, —$NH_2$, —NH($C_{1-6}$-alkyl), and N($C_{1-6}$-alkyl)$_2$.

In one embodiment of formula (II), $R^3$ is aryl, wherein the aryl is phenyl, naphthyl, tetrahydronaphthyl, indenyl, or indanyl. In yet another embodiment, the phenyl, naphthyl, tetrahydronaphthyl, indenyl, or indanyl is unsubstituted. In yet another embodiment, the phenyl, naphthyl, tetrahydronaphthyl, indenyl, or indanyl is optionally substituted with one, two, or three substituents selected from the group consisting of halo, $C_{1-6}$-alkyl, $C_{1-6}$-haloalkyl, $C_{1-6}$-hydroxyalkyl, hydroxy, $C_{1-6}$-alkoxy, $C_{1-6}$-haloalkoxy, —$NH_2$, —NH($C_{1-6}$-alkyl), and N($C_{1-6}$-alkyl)$_2$. In yet another embodiment of formula (II), $R^3$ is phenyl.

In another embodiment of formula (II), $R^3$ is 4-8 membered monocyclic heteroaryl or a 7-11 membered bicyclic heteroaryl, wherein the heteroaryl is optionally substituted with one, two, or three substituents selected from the group consisting of halo, $C_{1-6}$-alkyl, $C_{1-6}$-haloalkyl, $C_{1-6}$-hydroxyalkyl, hydroxy, oxo, $C_{1-6}$-alkoxy, $C_{1-6}$-haloalkoxy, —$NH_2$, —NH($C_{1-6}$-alkyl), and N($C_{1-6}$-alkyl)$_2$. In another embodiment, the heteroaryl is unsubstituted. In yet another embodiment of formula (II), $R^3$ is pyridyl, pyrazyl, pyridinyl, pyrimidinyl, pyridazinyl, 1,3,5-, 1,2,4- or 1,2,3-triazinyl, imidazyl, furanyl, thiophenyl, pyrazolyl, oxazolyl, isoxazolyl, thiazolyl, 1,2,3-, 1,2,4-, 1,2,5-, or 1,3,4-oxadiazolyl, or isothiazolyl. In yet another embodiment of formula (II), $R^3$ is benzothiazolyl, benzoxazolyl, benzothienyl, benzimidazolyl, benzofuryl, benzisothiazolyl, benzisoxazolyl, benzodiazinyl, benzofurazanyl, benzothiopyranyl, benzotriazolyl, or benzopyrazolyl.

In one embodiment of formula (II), $R^3$ is C(O)$R^7$, C(O)$NR^8R^9$, or C(O)O$R^7$, wherein $R^7$ at each occurrence, is independently is hydrogen, $C_{1-6}$ alkyl, $C_{1-6}$ haloalkyl, aryl, $C_{3-8}$ cycloalkyl, heteroaryl, or heterocycloalkyl; and wherein $R^8$ and $R^9$, at each occurrence, are independently hydrogen, $C_{1-6}$ alkyl, $C_{1-6}$ haloalkyl, aryl, $C_{3-8}$ cycloalkyl, heteroaryl, or heterocycloalkyl. In one embodiment of formula (II), $R^3$ is $C(O)R^7$ or $C(O)OR^7$, wherein $R^7$ is hydrogen or $C_{1-6}$-alkyl. In yet another embodiment, $R^3$ is $C(O)NR^8R^9$, wherein $R^8$ and $R^9$ are independently hydrogen or $C_{1-6}$ alkyl.

In one embodiment of formula (II), $R^3$ is or —$C_{1-4}$-alkyl-$NR^{10}R^{11}$, wherein $R^{10}$ is H and $R^{11}$ is selected from the group consisting of $C_{1-6}$ alkyl, $C_{1-6}$ haloalkyl, aryl, $C_{3-8}$ cycloalkyl, heteroaryl, and heterocycloalkyl.

In one embodiment of formula (II), B is $C_{3-8}$ cyloalkyl, wherein the $C_{3-8}$ cyloalkyl is unsubstituted. In another embodiment of formula (II), B is $C_{3-8}$ cyloalkyl, wherein $C_{3-8}$ cyloalkyl is substituted with one, two, or three $R^5$, wherein $R^5$ is selected from the group consisting of halo, $C_{1-6}$-alkyl, $C_{1-6}$-haloalkyl, $OR^i$, $SR^i$, $C(O)R^i$, $C(O)NR^jR^k$, $C(O)OR^i$, $NR^jR^k$, $NR^jC(O)R^i$, $S(O)_2R^i$, $NR^jS(O)_2R^i$, and $S(O)_2NR^jR^k$.

In another embodiment of formula (II), B is naphthyl, tetrahydronaphthyl, indenyl, or indanyl, wherein the naphthyl, tetrahydronaphthyl, indenyl, or indanyl is unsubstituted. In yet another embodiment of formula (II), B is naphthyl, tetrahydronaphthyl, indenyl, or indanyl, wherein the naphthyl, tetrahydronaphthyl, indenyl, or indanyl are substituted with one, two, or three $R^5$, wherein $R^5$ is selected from the group consisting of CN, $NO_2$, halo, $C_{1-6}$-alkyl, $C_{1-6}$-haloalkyl, $OR^i$, $SR^i$, $C(O)R^i$, $C(O)NR^jR^k$, $C(O)OR^i$, $NR^jR^k$, $NR^jC(O)R^i$, $S(O)_2R^i$, $NR^jS(O)_2R^i$, and $S(O)_2NR^jR^k$.

In one embodiment of formula (II), B is phenyl. In another embodiment of formula (II), B is phenyl, wherein the phenyl is unsubstituted. In another embodiment of formula (II), B is phenyl, wherein the phenyl is substituted with one, two, or three $R^5$, and $R^5$ is halo, $C_{1-6}$-alkyl, $C_{1-6}$ haloalkyl, $OR^i$, cycloalkyl, heterocycloalkyl, heterocycloalkyl-$C_{1-6}$-alkyl-, or heteroaryl, wherein the cycloalkyl, heteroaryl and heterocycloalkyl, alone or as part of another moiety, are optionally substituted with one, two, or three $R^{12}$; wherein $R^{12}$ is halo, $C_{1-6}$-alkyl, $C_{1-6}$-haloalkyl, $OR^p$, $C(O)R^p$, $C(O)NR^qR^r$, $C(O)OR^p$, $NR^qR^r$, $NR^qC(O)R^p$, $S(O)_2R^p$, or $S(O)_2NR^qR^r$. In yet another embodiment of formula (II), $R^{12}$ is $C_{1-6}$-alkyl, $C_{1-6}$ haloalkyl, or $C(O)R^p$; $R^p$ is $C_{1-6}$ alkyl, $C_{1-6}$ haloalkyl, and $C_{3-8}$ cycloalkyl.

In one embodiment of formula (II), B is phenyl, wherein the phenyl is substituted with heterocycloalkyl and optionally one or two $R^5$, wherein $R^5$ is halo, $C_{1-6}$-alkyl, $C_{1-6}$ haloalkyl, or $OR^i$, wherein the heterocycloalkyl is optionally substituted with one, two, or three $R^{12}$; wherein $R^{12}$ is halo, $C_{1-6}$-alkyl, $C_{1-6}$-haloalkyl, $OR^p$, $C(O)R^p$, $C(O)NR^qR^r$, $C(O)OR^p$, $NR^qR^r$, $NR^qC(O)R^p$, $S(O)_2R^p$, or $S(O)_2NR^qR^r$. In yet another embodiment, phenyl is substituted with heterocycloalkyl, and heterocycloalkyl is selected from the group consisting of azetidinyl, pyrrolidinyl, piperidinyl, morpholinyl, piperazinyl, azepanyl, diazepanyl, and hexahydropyrrolo[1,2-a]pyrazin-2(1H)yl.

In another embodiment of formula (II), B is

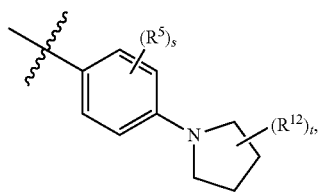

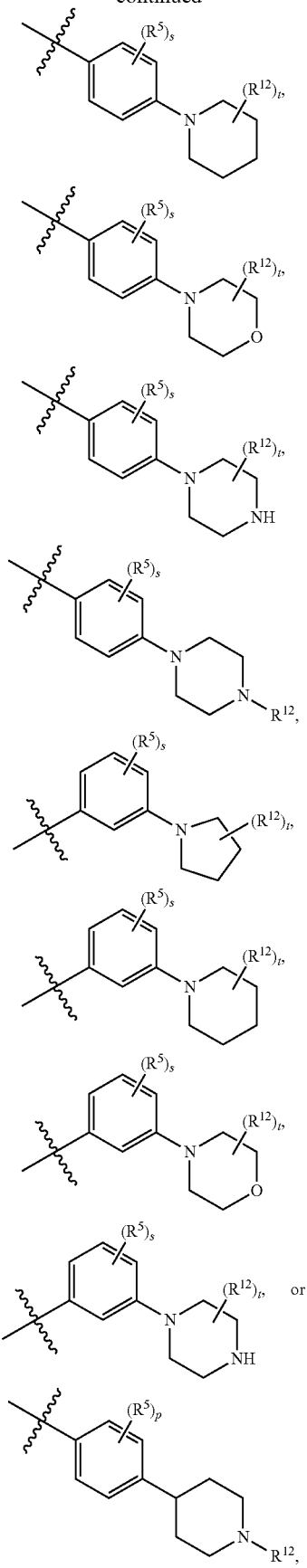

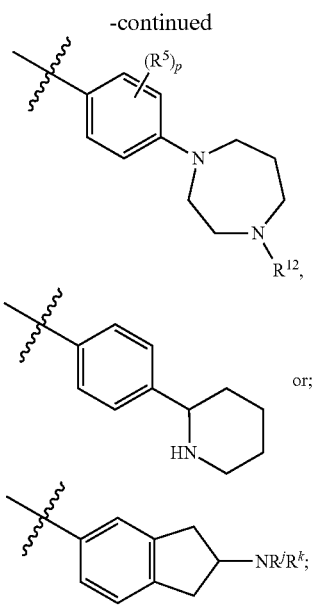

wherein $R^5$ is halo, $C_{1-6}$-alkyl, $C_{1-6}$ haloalkyl, or $OR^i$; s is 0 or 1; $R^{12}$ is $C_{1-6}$-alkyl, $C_{1-6}$-haloalkyl, $OR^p$, $C(O)R^p$, $C(O)NR^qR^r$, $C(O)OR^p$, $NR^qR^r$, $NR^qC(O)R^p$, $S(O)_2R^p$, or $S(O)_2NR^qR^r$; and t is 0 or 1.

In one embodiment of formula (II), B is

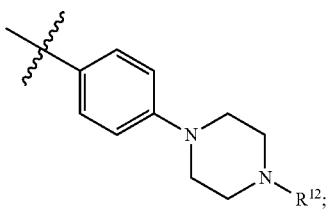

and $R^{12}$ is $C_{1-6}$-alkyl.

In one embodiment of formula (II), B is a 4-8 membered monocyclic heterocyclyl. In another embodiment, B is a 4-8 membered heterocycloalkyl or heterocycloalkenyl. In another embodiment, B is a 5-7 membered heteroaryl. In yet another embodiment of formula (II), B is pyrrolidinyl, tetrahydrofuryl, tetrahydrothienyl, imidazolidinyl, pyrazolidinyl, piperidinyl, tetrahydropyranyl, piperazinyl, dioxanyl, morpholinyl, 2-oxopyrrolidinyl, 2,5-dioxopyrrolidinyl, 2-oxopiperidinyl, 4-oxopiperidinyl, or 2,6-dioxopiperidinyl. In yet another embodiment of formula (II), B is pyridyl, pyrazyl, pyridinyl, pyrimidinyl, pyridazinyl, 1,3,5-, 1,2,4- or 1,2,3-triazinyl, imidazyl, furanyl, thiophenyl, pyrazolyl, oxazolyl, isoxazolyl, thiazolyl, 1,2,3-, 1,2,4-, 1,2,5-, or 1,3, 4-oxadiazolyl, or isothiazolyl. In one embodiment, B is unsubstituted. In another embodiment, B is substituted with one, two, or three $R^6$, and $R^6$ is halo, $C_{1-6}$-alkyl, $C_{1-6}$-haloalkyl, $OR^i$, $C(O)R^i$, $C(O)OR^i$, $NR'''R''$, or $S(O)_2R^i$.

In one embodiment of formula (II), B is a 7-11 membered bicyclic heterocyclyl. In another embodiment, B is a 7-11 membered bicyclic heterocycloalkyl or bicyclic heterocycloalkenyl. In another embodiment, B is a 7-11 membered bicyclic heteroaryl. In yet another embodiment, B is 2,3-dihydro-2-oxo-1H-indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl, dihydroisoindolyl, dihydroquinazolinyl, 3,4-dihydro-4-oxo-quinazolinyl, benzisothiazolyl, benzisoxazolyl, benzodiazinyl, benzofurazanyl, benzothiopyranyl, benzotriazolyl, benzpyrazolyl, 1,3-benzodioxolyl, dihydrobenzofuryl, dihydrobenzothienyl, dihydrobenzothiopyranyl, dihydrobenzothiopyranyl sulfone, dihydrobenzopyranyl, dihydrobenzoxazinyl, 3-oxo-3,4-dihydro-1,4-benzoxazinyl, indolinyl, indazolyl, isochromanyl, isoindolinyl, naphthyridinyl, phthalazinyl, piperonyl, purinyl, pyridopyridyl, pyrrolotriazinyl, quinazolinyl, tetrahydroquinolinyl, thienofuryl, thienopyridyl, 3H-imidazo[4,5-c]pyridinyl, or thienothienyl. In one embodiment of formula (II), B is unsubstituted. In another embodiment of formula (II), B is substituted with one, two, or three $R^6$, and $R^6$ is halo, $C_{1-6}$-alkyl, $C_{1-6}$-haloalkyl, $OR^i$, $C(O)R^i$, $C(O)OR^i$, $NR'''R''$, or $S(O)_2R^i$.

In one embodiment of formula (II), B is 10-15 membered tricyclic heterocyclyl. In another embodiment, B is a 10-15 membered tricyclic heterocycloalkyl or tricyclic heterocycloalkenyl. In another embodiment, B is a 10-15 membered tricyclic heteroaryl. In one embodiment of formula (II), B is unsubstituted. In another embodiment of formula (II), B is substituted with one, two, or three $R^6$, and $R^6$ is halo, $C_{1-6}$-alkyl, $C_{1-6}$-haloalkyl, $OR^i$, $C(O)R^i$, $C(O)OR^i$, $NR'''R''$, or $S(O)_2R^i$.

In one embodiment of formula (II), B is

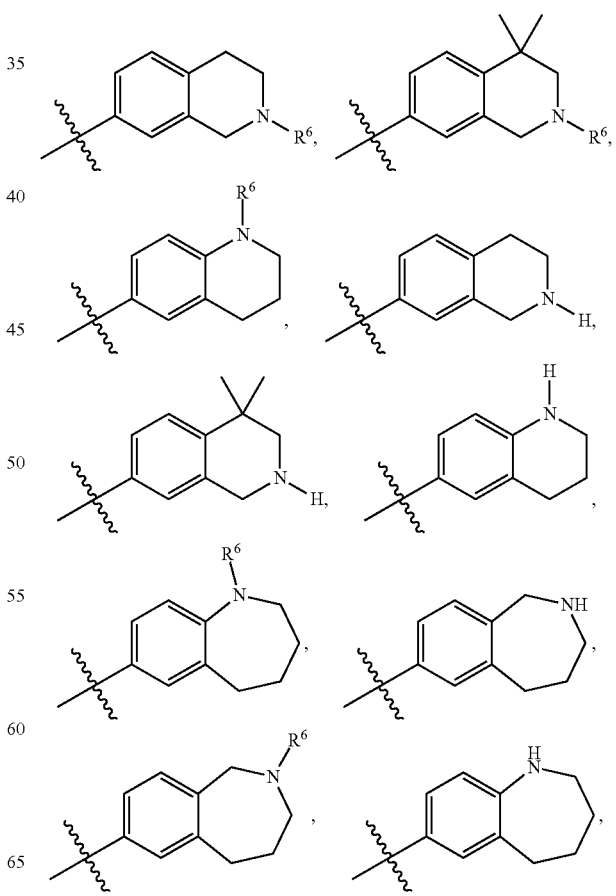

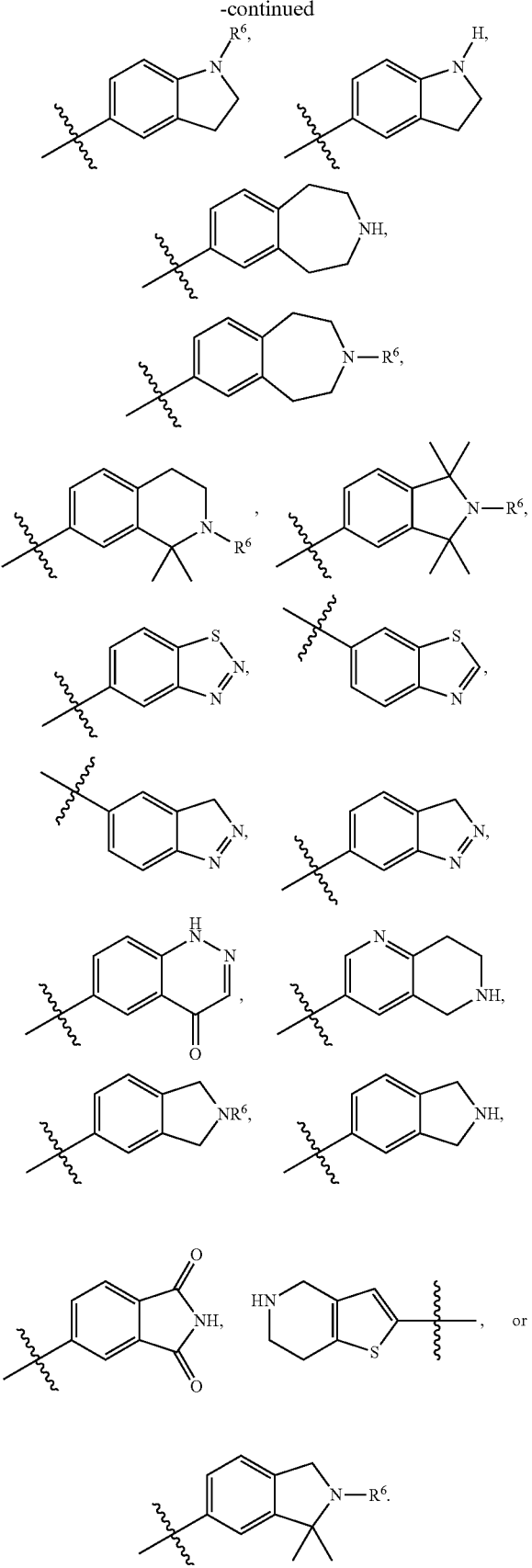

In another embodiment of formula (II), B is

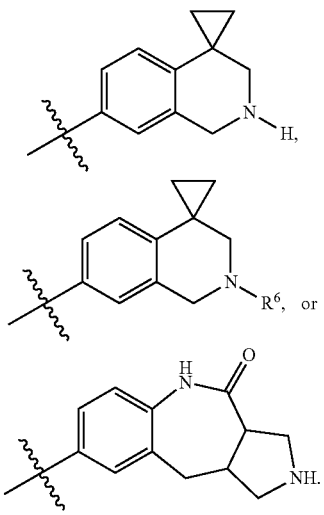

In one embodiment, the present invention is directed, in part, to a class of compounds having a structure of formula (IIa) or (IIb):

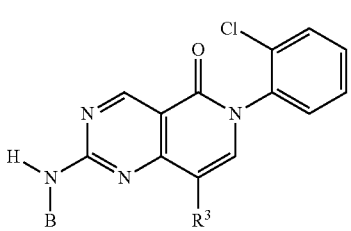

formula (IIa)

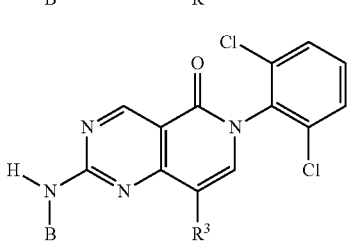

formula (IIb)

wherein $R^3$ and B are as defined above for formula (II).

Embodiments of Formula (III)

In one embodiment, the present invention is directed, in part, to a class of compounds having a structure of formula (III),

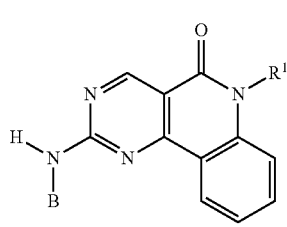

formula (III)

wherein $R^1$ and B are as described in formula (I).

In one embodiment of formula (III), $R^1$ is $C_{1-8}$alkyl or $C_{2-8}$-alkenyl, wherein the $C_{1-8}$-alkyl or $C_{2-8}$-alkenyl is optionally substituted with one or more substituents selected from the group consisting of halo, CN, $NO_2$, —$OR^a$, —$C(O)R^a$, —$C(O)OR^a$, —$OC(O)R^a$, —$NR^bR^c$, $NR^bC(O)R^a$, —$NHC(O)NHR^b$, —$C(O)NR^bR^c$, —$NHSO_2R^a$, and —$SO_2NR^bNR^c$. In another embodiment of formula (III), $R^1$ is $C_{1-8}$alkyl or $C_{2-8}$-alkenyl, wherein the $C_{1-8}$alkyl or $C_{2-8}$-alkenyl is unsubstituted. In yet another embodiment of formula (III), $R^1$ is —$CH_3$, —$CH_2CH_3$, —$CH_2CH_2CH_3$, —$CH_2CH_2CH_2CH_3$, —$CH(CH_3)_2$, —$CH_2CH(CH_3)_2$, —$CH_2CH=CH_2$, $CH_2CH=CHCH_3$, or —$CH_2CH_2CH=CH_2$.

In another embodiment of formula (III), $R^1$ is aryl, wherein the aryl is phenyl, naphthyl, tetrahydronaphthyl, indenyl, or indanyl. In yet another embodiment, the phenyl, naphthyl, tetrahydronaphthyl, indenyl, or indanyl is unsubstituted. In yet another embodiment, the phenyl, naphthyl, tetrahydronaphthyl, indenyl, or indanyl is optionally substituted with one, two, or three substituents selected from the group consisting of $C_{1-6}$-alkyl, $C_{1-6}$haloalkyl, $C_{2-6}$alkenyl, heterocycloalkyl, aryl, heteroaryl, halo, oxo, CN, $NO_2$, $OR^d$, —$C(O)R^d$, —$C(O)OR^d$, —$OC(O)R^d$, —$SR^d$, —$S(O)R^d$, —$SO_2R^d$, —$NR^eR^f$, —$NHC(O)R^e$, —$NHC(O)NHR^e$, —$NHC(O)OR^e$, —$NHSO_2R^d$, —$C(O)NHR^e$, and —$SO_2NHNR^e$.

In another embodiment of formula (III), $R^1$ is phenyl, wherein the phenyl is optionally substituted with one, two, or three substituents selected from the group consisting of CN, $NO_2$, $C_{1-6}$-alkyl, $C_{1-6}$-haloalkyl, halo, —$OR^a$, —$C(O)R^a$, —$C(O)OR^a$, —$OC(O)R^a$, —$NR^bR^c$, —$NR^bC(O)R^a$, —$NHC(O)NHR^b$, —$C(O)NR^bR^c$, —$NHSO_2R^a$, and —$SO_2NR^bNR^c$. In yet another embodiment, the phenyl is unsubstituted. In yet another embodiment, the phenyl is substituted with one, two, or three halo or $C_{1-6}$-haloalkyl.

In another embodiment of formula (III), $R^1$ is aryl-$C_{1-6}$-alkyl-, wherein the $R^1$aryl is optionally substituted with one or more substituents independently selected from the group consisting of $C_{1-6}$-alkyl, $C_{1-6}$-haloalkyl, $C_{2-6}$-alkenyl, heterocycloalkyl, aryl, heteroaryl, halo, oxo, CN, $NO_2$, —$OR^d$, —$C(O)R^d$, —$C(O)OR^d$, —$OC(O)R^d$, —$SR^d$, —$S(O)R^d$, —$SO_2R^d$, —$NR^eR^f$, —$NHC(O)R^e$, —$NHC(O)NHR^e$, —$NHC(O)OR^e$, —$NHSO_2R^d$, —$C(O)NHR^e$, and —$SO_2NHNR^e$. In another embodiment of formula (III), $R^1$ is aryl-$C_{1-6}$-alkyl-, wherein the $R^1$aryl is phenyl. In another embodiment, $R^1$ is phenyl-$C_{1-3}$-alkyl-. In yet another embodiment, the phenyl is unsubstituted. In yet another embodiment, the phenyl is substituted with one, two, or three substituents independently selected from the group consisting of CN, $NO_2$, halo, —$OR^a$, —$C(O)R^a$, —$C(O)OR^a$, —$OC(O)R^a$, —$NR^bR^c$, —$NR^bC(O)R^a$, —$NHC(O)NHR^b$, —$C(O)NR^bR^c$, —$NHSO_2R^a$, and —$SO_2NR^bNR^c$. In yet another embodiment, the phenyl is substituted with one, two, or three halo or $C_{1-6}$-haloalkyl.

In another embodiment of formula (III), $R^1$ is $C_{3-8}$ cycloalkyl-$C_{1-6}$-alkyl-, wherein the $R^1C_{3-8}$-cycloalkyl is optionally substituted with one or more substituents independently selected from the group consisting of $C_{1-6}$-alkyl, $C_{1-6}$-haloalkyl, $C_{2-6}$-alkenyl, heterocycloalkyl, aryl, heteroaryl, halo, oxo, CN, $NO_2$, —$OR^d$, —$C(O)R^d$, —$C(O)OR^d$, —$OC(O)R^d$, —$SR^d$, —$S(O)R^d$, —$SO_2R^d$, —$NR^eR^f$, —$NHC(O)R^e$, —$NHC(O)NHR^e$, —$NHC(O)OR^e$, —$NHSO_2R^d$, —$C(O)NHR^e$, and —$SO_2NHNR^e$ In another embodiment of formula (III), $R^1$ is $C_{3-8}$ cycloalkyl-$C_{1-6}$-alkyl-, wherein the $R^1C_{3-8}$-cycloalkyl is unsubstituted.

In one embodiment of formula (III), B is $C_{3-8}$ cyloalkyl, wherein the $C_{3-8}$ cyloalkyl is unsubstituted. In another embodiment of formula (III), B is $C_{3-8}$ cyloalkyl, wherein $C_{3-8}$ cyloalkyl is substituted with one, two, or three $R^5$, wherein $R^5$ is selected from the group consisting of halo, $C_{1-6}$-alkyl, $C_{1-6}$-haloalkyl, $OR^i$, $SR^i$, $C(O)R^i$, $C(O)NR^jR^k$, $C(O)OR^i$, $NR^jR^k$, $NR^jC(O)R^i$, $S(O)_2R^i$, $NR^jS(O)_2R^i$, and $S(O)_2NR^jR^k$.

In another embodiment of formula (III), B is naphthyl, tetrahydronaphthyl, indenyl, or indanyl, wherein the naphthyl, tetrahydronaphthyl, indenyl, or indanyl is unsubstituted. In yet another embodiment of formula (III), B is naphthyl, tetrahydronaphthyl, indenyl, or indanyl, wherein the naphthyl, tetrahydronaphthyl, indenyl, or indanyl are substituted with one, two, or three $R^5$, wherein $R^5$ is selected from the group consisting of CN, $NO_2$, halo, $C_{1-6}$-alkyl, $C_{1-6}$-haloalkyl, $OR^i$, $SR^i$, $C(O)R^i$, $C(O)NR^jR^k$, $C(O)OR^i$, $NR^jR^k$, $NR^jC(O)R^i$, $S(O)_2R^i$, $NR^jS(O)_2R^i$, and $S(O)_2NR^jR^k$.

In one embodiment of formula (III), B is phenyl. In another embodiment of formula (III), B is phenyl, wherein the phenyl is unsubstituted. In another embodiment of formula (III), B is phenyl, wherein the phenyl is substituted with one, two, or three $R^5$, and $R^5$ is halo, $C_{1-6}$-alkyl, $C_{1-6}$ haloalkyl, $OR^i$, cycloalkyl, heterocycloalkyl, heterocycloalkyl-$C_{1-6}$-alkyl-, or heteroaryl, wherein the cycloalkyl, heteroaryl and heterocycloalkyl, alone or as part of another moiety, are optionally substituted with one, two, or three $R^{12}$; wherein $R^{12}$ is halo, $C_{1-6}$-alkyl, $C_{1-6}$-haloalkyl, $OR^p$, $C(O)R^p$, $C(O)NR^qR^r$, $C(O)OR^p$, $NR^qR^r$, $NR^qC(O)R^p$, $S(O)_2R^p$, or $S(O)_2NR^qR^r$. In yet another embodiment of formula (III), $R^{12}$ is $C_{1-6}$-alkyl, $C_{1-6}$ haloalkyl, or $C(O)R^p$; $R^p$ is $C_{1-6}$ alkyl, $C_{1-6}$ haloalkyl, and $C_{3-8}$ cycloalkyl.

In one embodiment of formula (III), B is phenyl, wherein the phenyl is substituted with heterocycloalkyl and optionally one or two $R^5$, wherein $R^5$ is halo, $C_{1-6}$-alkyl, $C_{1-6}$ haloalkyl, or $OR^i$, wherein the heterocycloalkyl is optionally substituted with one, two, or three $R^{12}$; wherein $R^{12}$ is halo, $C_{1-6}$-alkyl, $C_{1-6}$-haloalkyl, $OR^p$, $C(O)R^p$, $C(O)NR^qR^r$, $C(O)OR^p$, $NR^qR^r$, $NR^qC(O)R^p$, $S(O)_2R^p$, or $S(O)_2NR^qR^r$. In yet another embodiment, phenyl is substituted with heterocycloalkyl, and heterocycloalkyl is selected from the group consisting of azetidinyl, pyrrolidinyl, piperidinyl, morpholinyl, piperazinyl, azepanyl, diazepanyl, and hexahydropyrrolo[1,2-a]pyrazin-2(1H)yl.

In another embodiment of formula (III), B is

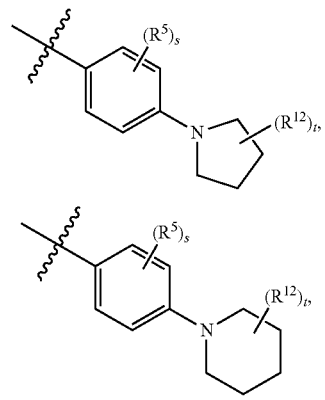

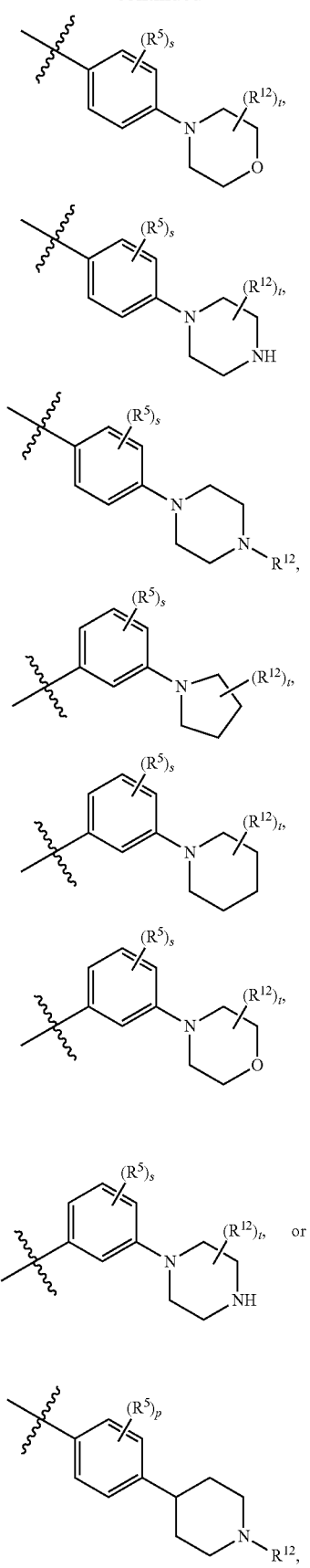

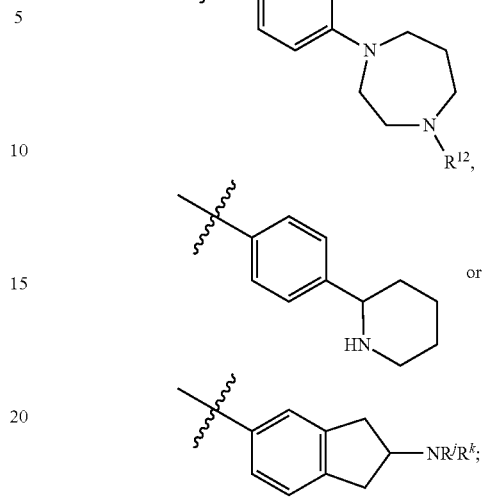

wherein R⁵ is halo, $C_{1-6}$-alkyl, $C_{1-6}$ haloalkyl, or $OR^i$; s is 0 or 1; $R^{12}$ is $C_{1-6}$-alkyl, $C_{1-6}$-haloalkyl, $OR^p$, $C(O)R^p$, $C(O)NR^qR^r$, $C(O)OR^p$, $NR^qR^r$, $NR^qC(O)R^p$, $S(O)_2R^p$, or $S(O)_2NR^qR^r$; and t is 0 or 1.

In one embodiment of formula (III), B is

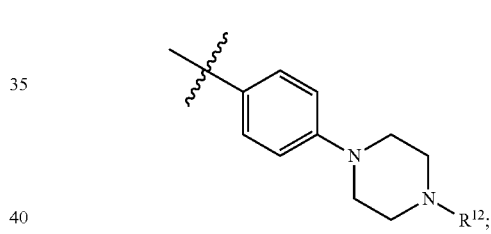

and $R^{12}$ is $C_{1-6}$-alkyl.

In one embodiment of formula (III), B is a 4-8 membered monocyclic heterocyclyl. In another embodiment, B is a 4-8 membered heterocycloalkyl or heterocycloalkenyl. In another embodiment, B is a 5-7 membered heteroaryl. In yet another embodiment of formula (III), B is pyrrolidinyl, tetrahydrofuryl, tetrahydrothienyl, imidazolidinyl, pyrazolidinyl, piperidinyl, tetrahydropyranyl, piperazinyl, dioxanyl, morpholinyl, 2-oxopyrrolidinyl, 2,5-dioxopyrrolidinyl, 2-oxopiperidinyl, 4-oxopiperidinyl, or 2,6-dioxopiperidinyl. In yet another embodiment of formula (III), B is pyridyl, pyrazyl, pyridinyl, pyrimidinyl, pyridazinyl, 1,3,5-, 1,2,4- or 1,2,3-triazinyl, imidazyl, furanyl, thiophenyl, pyrazolyl, oxazolyl, isoxazolyl, thiazolyl, 1,2,3-, 1,2,4-, 1,2,5-, or 1,3,4-oxadiazolyl, or isothiazolyl. In one embodiment, B is unsubstituted. In another embodiment, B is substituted with one, two, or three R⁶, and R⁶ is halo, $C_{1-6}$-alkyl, $C_{1-6}$-haloalkyl, $OR^l$, $C(O)R^l$, $C(O)OR^l$, $NR^mR^n$, or $S(O)_2R^l$.

In one embodiment of formula (III), B is a 7-11 membered bicyclic heterocyclyl. In another embodiment, B is a 7-11 membered bicyclic heterocycloalkyl or bicyclic heterocycloalkenyl. In another embodiment, B is a 7-11 membered bicyclic heteroaryl. In yet another embodiment, B is 2,3-dihydro-2-oxo-1H-indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl, dihydroisoindolyl, dihydroquinazolinyl, 3,4-dihydro-4-oxo-quinazolinyl, benzisothiazolyl, benzisoxazolyl, benzodiazinyl, benzofurazanyl, benzothiopyranyl, benzotriazolyl, benzpyrazolyl, 1,3-benzodioxolyl, dihydrobenzofuryl, dihydrobenzothienyl, dihydrobenzothiopyranyl, dihydrobenzothiopyranyl sulfone, dihydrobenzopyranyl, dihydrobenzoxazinyl, 3-oxo-3,4-dihydro-1,4-benzoxazinyl, indolinyl, indazolyl, isochromanyl, isoindolinyl, naphthyridinyl, phthalazinyl, piperonyl, purinyl, pyridopyridyl, pyrrolotriazinyl, quinazolinyl, tetrahydroquinolinyl, thienofuryl, thienopyridyl, 3H-imidazo[4,5-c]pyridinyl, or thienothienyl. In one embodiment of formula (III), B is unsubstituted. In another embodiment of formula (III), B is substituted with one, two, or three $R^6$, and $R^6$ is halo, $C_{1-6}$-alkyl, $C_{1-6}$-haloalkyl, $OR^l$, $C(O)R^l$, $C(O)OR^l$, $NR'''R''$, or $S(O)_2R^l$.

In one embodiment of formula (III), B is 10-15 membered tricyclic heterocyclyl. In another embodiment, B is a 10-15 membered tricyclic heterocycloalkyl or tricyclic heterocycloalkenyl. In another embodiment, B is a 10-15 membered tricyclic heteroaryl. In one embodiment of formula (III), B is unsubstituted. In another embodiment of formula (III), B is substituted with one, two, or three $R^6$, and $R^6$ is halo, $C_{1-6}$-alkyl, $C_{1-6}$-haloalkyl, $OR^l$, $C(O)R^l$, $C(O)OR^l$, $NR'''R''$, or $S(O)_2R^l$.

In one embodiment of formula (III), B is

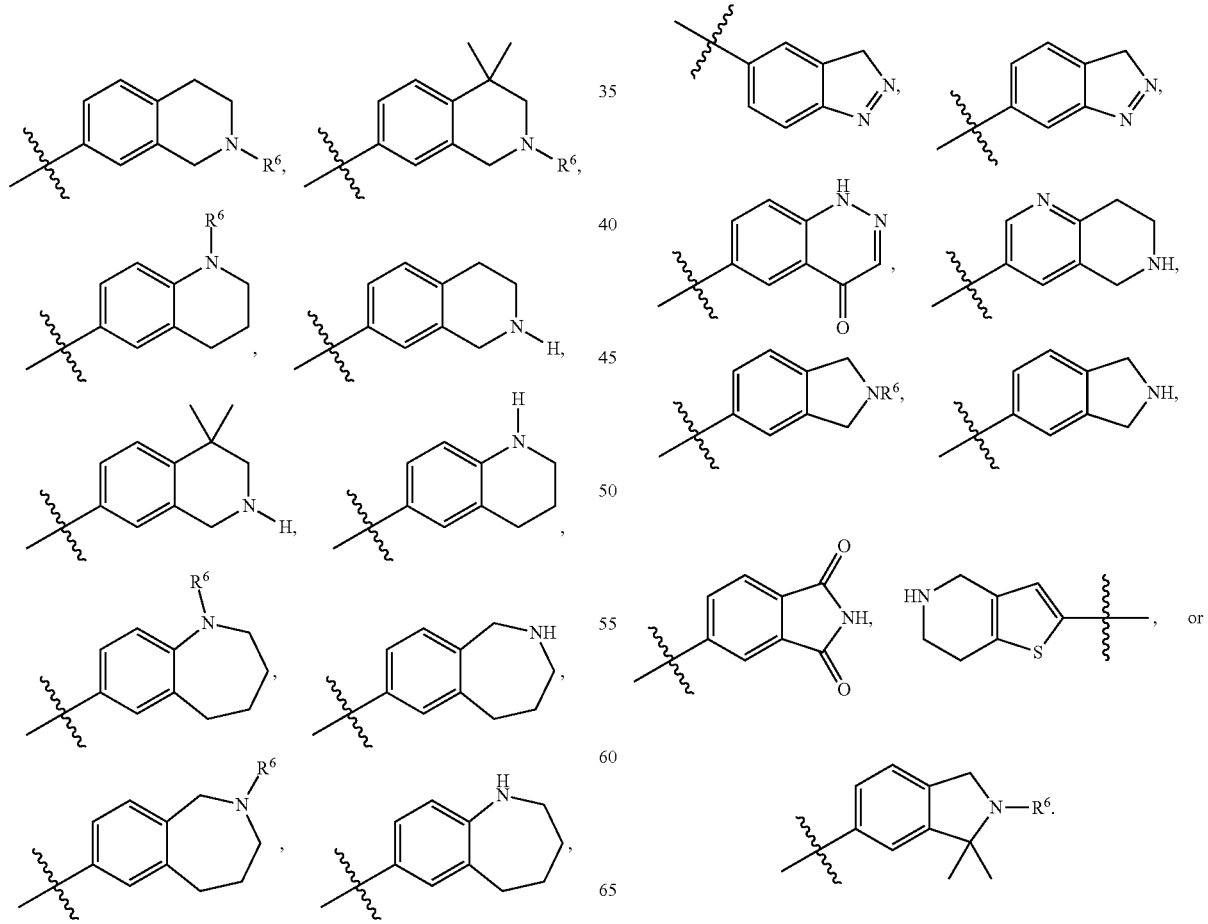

In another embodiment of formula (III), B is

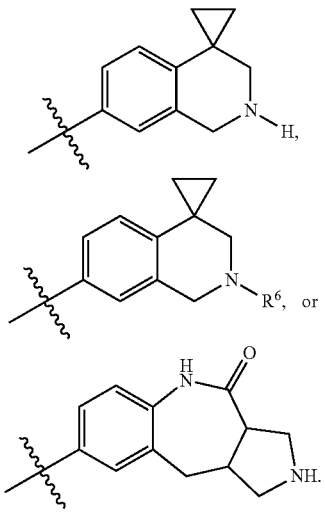

Embodiments of Formula (IV)

In one embodiment, the present invention is directed, in part, to a class of compounds having a structure of formula (IV),

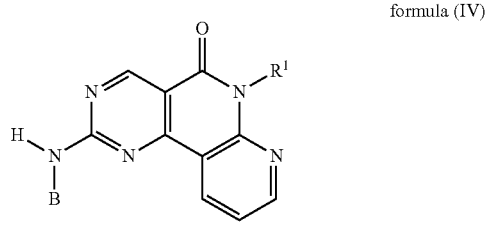

formula (IV)

wherein $R^1$ and B are as described in formula (I).

In one embodiment of formula (IV), $R^1$ is $C_{1-8}$alkyl or $C_{2-8}$-alkenyl, wherein the $C_{1-8}$-alkyl or $C_{2-8}$-alkenyl is optionally substituted with one or more substituents selected from the group consisting of halo, CN, $NO_2$, —$OR^a$, —$C(O)R^a$, —$C(O)OR^a$, —$OC(O)R^a$, —$NR^bR^c$, $NR^bC(O)R^a$, —$NHC(O)NHR^b$, —$C(O)NR^bR^c$, —$NHSO_2R^a$, and —$SO_2NR^bNR^c$. In another embodiment of formula (IV), $R^1$ is $C_{1-8}$alkyl or $C_{2-8}$-alkenyl, wherein the $C_{1-8}$alkyl or $C_{2-8}$-alkenyl is unsubstituted. In yet another embodiment of formula (III), $R^1$ is —$CH_3$, —$CH_2CH_3$, —$CH_2CH_2CH_3$, —$CH_2CH_2CH_2CH_3$, —$CH(CH_3)_2$, —$CH_2CH(CH_3)_2$, —$CH_2CH$=$CH_2$, $CH_2CH$=$CHCH_3$, or —$CH_2CH_2CH$=$CH_2$.

In another embodiment of formula (IV), $R^1$ is aryl, wherein the aryl is phenyl, naphthyl, tetrahydronaphthyl, indenyl, or indanyl. In yet another embodiment, the phenyl, naphthyl, tetrahydronaphthyl, indenyl, or indanyl is unsubstituted. In yet another embodiment, the phenyl, naphthyl, tetrahydronaphthyl, indenyl, or indanyl is optionally substituted with one, two, or three substituents selected from the group consisting of $C_{1-6}$-alkyl, $C_{1-6}$-haloalkyl, $C_{2-6}$-alkenyl, heterocycloalkyl, aryl, heteroaryl, halo, oxo, CN, $NO_2$, —$OR^d$, —$C(O)R^d$, —$C(O)OR^d$, —$OC(O)R^d$, —$SR^d$, —$S(O)R^d$, —$SO_2R^d$, —$NR^eR^f$, —$NHC(O)R^e$, —$NHC(O)NHR^e$, —$NHC(O)OR^e$, —$NHSO_2R^d$, —$C(O)NHR^e$, and —$SO_2NHNR^e$.

In another embodiment of formula (IV), $R^1$ is phenyl, wherein the phenyl is optionally substituted with one, two, or three substituents selected from the group consisting of CN, $NO_2$, $C_{1-6}$-alkyl, $C_{1-6}$-haloalkyl, halo, —$OR^a$, —$C(O)R^a$, —$C(O)OR^a$, —$OC(O)R^a$, —$NR^bR^c$, —$NR^bC(O)R^a$, —$NHC(O)NHR^b$, —$C(O)NR^bR^c$, —$NHSO_2R^a$, and —$SO_2NR^bNR^c$. In yet another embodiment, the phenyl is unsubstituted. In yet another embodiment, the phenyl is substituted with one, two, or three halo or $C_{1-6}$-haloalkyl.

In another embodiment of formula (IV), $R^1$ is aryl-$C_{1-6}$-alkyl-, wherein the $R^1$ aryl is optionally substituted with one or more substituents independently selected from the group consisting of $C_{1-6}$-alkyl, $C_{1-6}$-haloalkyl, $C_{2-6}$-alkenyl, heterocycloalkyl, aryl, heteroaryl, halo, oxo, CN, $NO_2$, —$OR^d$, —$C(O)R^d$, —$C(O)OR^d$, —$OC(O)R^d$, —$SR^d$, —$S(O)R^d$, —$SO_2R^d$, —$NR^eR^f$, —$NHC(O)R^e$, —$NHC(O)NHR^e$, —$NHC(O)OR^e$, —$NHSO_2R^d$, —$C(O)NHR^e$, and —$SO_2NHNR^e$. In another embodiment of formula (IV), $R^1$ is aryl-$C_{1-6}$-alkyl-, wherein the $R^1$ aryl is phenyl. In another embodiment, $R^1$ is phenyl-$C_{1-3}$-alkyl-. In yet another embodiment, the phenyl is unsubstituted. In yet another embodiment, the phenyl is substituted with one, two, or three substituents independently selected from the group consisting of CN, $NO_2$, halo, —$OR^a$, —$C(O)R^a$, —$C(O)OR^a$, —$OC(O)R^a$, —$NR^bR^c$, —$NR^bC(O)R^a$, —$NHC(O)NHR^b$, —$C(O)NR^bR^c$, —$NHSO_2R^a$, and —$SO_2NR^bNR^c$. In yet another embodiment, the phenyl is substituted with one, two, or three halo or $C_{1-6}$-haloalkyl.

In another embodiment of formula (IV), $R^1$ is $C_{3-8}$ cycloalkyl-$C_{1-6}$-alkyl-, wherein the $R^1C_{3-8}$-cycloalkyl is optionally substituted with one or more substituents independently selected from the group consisting of $C_{1-6}$-alkyl, $C_{1-6}$-haloalkyl, $C_{2-6}$-alkenyl, heterocycloalkyl, aryl, heteroaryl, halo, oxo, CN, $NO_2$, —$OR^d$, —$C(O)R^d$, —$C(O)OR^d$, —$OC(O)R^d$, —$SR^d$, —$S(O)R^d$, —$SO_2R^d$, —$NR^eR^f$, —$NHC(O)R^e$, —$NHC(O)NHR^e$, —$NHC(O)OR^e$, —$NHSO_2R^d$, —$C(O)NHR^e$, and —$SO_2NHNR^e$ In another embodiment of formula (IV), $R^1$ is $C_{3-8}$ cycloalkyl-$C_{1-6}$-alkyl-, wherein the $R^1C_{3-8}$-cycloalkyl is unsubstituted.

In another embodiment of formula (IV), B is $C_{3-8}$ cyloalkyl, wherein the $C_{3-8}$ cyloalkyl is unsubstituted. In another embodiment of formula (IV), B is $C_{3-8}$ cyloalkyl, wherein $C_{3-8}$ cyloalkyl is substituted with one, two, or three $R^5$, wherein $R^5$ is selected from the group consisting of halo, $C_{1-6}$-alkyl, $C_{1-6}$-haloalkyl, $OR^i$, $SR^i$, $C(O)R^i$, $C(O)NR^jR^k$, $C(O)OR^i$, $NR^jR^k$, $NR^jC(O)R^i$, $S(O)_2R^i$, $NR^jS(O)_2R^i$, and $S(O)_2NR^jR^k$.

In another embodiment of formula (IV), B is naphthyl, tetrahydronaphthyl, indenyl, or indanyl, wherein the naphthyl, tetrahydronaphthyl, indenyl, or indanyl is unsubstituted. In another embodiment of formula (IV), B is naphthyl, tetrahydronaphthyl, indenyl, or indanyl, wherein the naphthyl, tetrahydronaphthyl, indenyl, or indanyl are substituted with one, two, or three $R^5$, wherein $R^5$ is selected from the group consisting of CN, $NO_2$, halo, $C_{1-6}$-alkyl, $C_{1-6}$-haloalkyl, $OR^i$, $SR^i$, $C(O)R^i$, $C(O)NR^jR^k$, $C(O)OR^i$, $NR^jR^k$, $NR^jC(O)R^i$, $S(O)_2R^i$, $NR^jS(O)_2R^i$, and $S(O)_2NR^jR^k$.

In one embodiment of formula (IV), B is phenyl. In another embodiment of formula (IV), B is phenyl, wherein the phenyl is unsubstituted. In another embodiment of formula (IV), B is phenyl, wherein the phenyl is substituted with one, two, or three $R^5$, and $R^5$ is halo, $C_{1-6}$-alkyl, $C_{1-6}$ haloalkyl, $OR^i$, cycloalkyl, heterocycloalkyl, heterocycloalkyl-$C_{1-6}$-alkyl-, or heteroaryl, wherein the cycloalkyl, heteroaryl and heterocycloalkyl, alone or as part of another moiety, are optionally substituted with one, two, or three R¹²; wherein R¹² is halo, $C_{1-6}$-alkyl, $C_{1-6}$-haloalkyl, OR$^p$, C(O)R$^p$, C(O)NR$^q$R$^r$, C(O)OR$^p$, NR$^q$R$^r$, NR$^q$C(O)R$^p$, S(O)$_2$R$^p$, or S(O)$_2$NR$^q$R$^r$. In yet another embodiment of formula (IV), R¹² is $C_{1-6}$-alkyl, haloalkyl, or C(O)R$^p$; R$^p$ is $C_{1-6}$ alkyl, $C_{1-6}$ haloalkyl, and $C_{3-8}$ cycloalkyl.

In one embodiment of formula (IV), B is phenyl, wherein the phenyl is substituted with heterocycloalkyl and optionally one or two R⁵, wherein R⁵ is halo, $C_{1-6}$-alkyl, $C_{1-6}$ haloalkyl, or OR$^i$, wherein the heterocycloalkyl is optionally substituted with one, two, or three R¹²; wherein R¹² is halo, $C_{1-6}$-alkyl, $C_{1-6}$-haloalkyl, OR$^p$, C(O)R$^p$, C(O)NR$^q$R$^r$, C(O) OR$^p$, NR$^q$R$^r$, NR$^q$C(O)R$^p$, S(O)$_2$R$^p$, or S(O)$_2$NR$^q$R$^r$. In yet another embodiment, phenyl is substituted with heterocycloalkyl, and heterocycloalkyl is selected from the group consisting of azetidinyl, pyrrolidinyl, piperidinyl, morpholinyl, piperazinyl, azepanyl, diazepanyl, and hexahydropyrrolo[1,2-a]pyrazin-2(1H)yl.

In another embodiment of formula (IV), B is

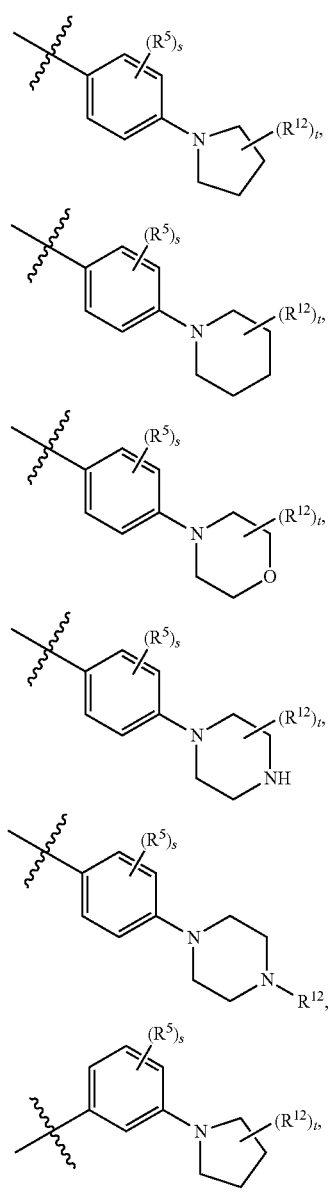

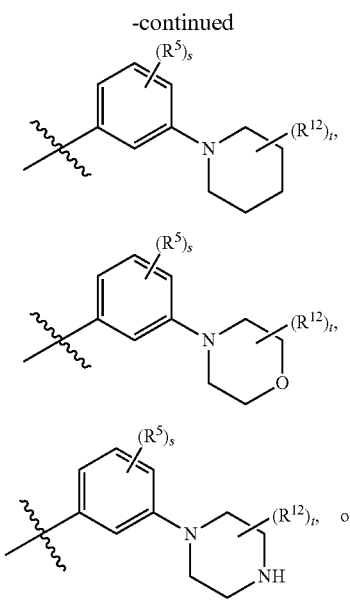

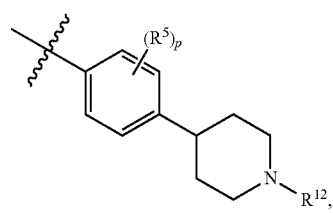

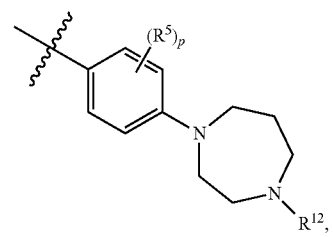

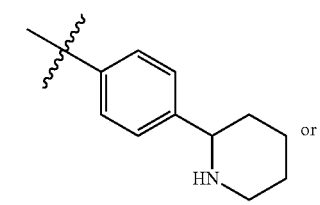

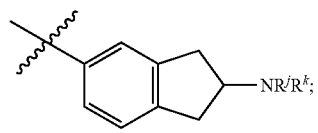

wherein R⁵ is halo, $C_{1-6}$-alkyl, $C_{1-6}$ haloalkyl, or OR$^i$; s is 0 or 1; R¹² is $C_{1-6}$-alkyl, $C_{1-6}$-haloalkyl, OR$^p$, C(O)R$^p$, C(O)NR$^q$R$^r$, C(O)OR$^p$, NR$^q$R$^r$, NR$^q$C(O)R$^p$, S(O)$_2$R$^p$, or S(O)$_2$NR$^q$R$^r$; and t is 0 or 1.

In one embodiment of formula (IV), B is

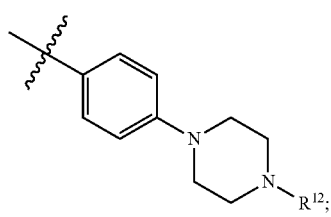

and $R^{12}$ is $C_{1-6}$-alkyl.

In one embodiment of formula (IV), B is a 4-8 membered monocyclic heterocyclyl. In another embodiment, B is a 4-8 membered heterocycloalkyl or heterocycloalkenyl. In another embodiment, B is a 5-7 membered heteroaryl. In yet another embodiment of formula (IV), B is pyrrolidinyl, tetrahydrofuryl, tetrahydrothienyl, imidazolidinyl, pyrazolidinyl, piperidinyl, tetrahydropyranyl, piperazinyl, dioxanyl, morpholinyl, 2-oxopyrrolidinyl, 2,5-dioxopyrrolidinyl, 2-oxopiperidinyl, 4-oxopiperidinyl, or 2,6-dioxopiperidinyl. In yet another embodiment of formula (IV), B is pyridyl, pyrazyl, pyridinyl, pyrimidinyl, pyridazinyl, 1,3,5-, 1,2,4- or 1,2,3-triazinyl, imidazyl, furanyl, thiophenyl, pyrazolyl, oxazolyl, isoxazolyl, thiazolyl, 1,2,3-, 1,2,4-, 1,2,5-, or 1,3,4-oxadiazolyl, or isothiazolyl. In one embodiment, B is unsubstituted. In another embodiment, B is substituted with one, two, or three $R^6$, and $R^6$ is halo, $C_{1-6}$-alkyl, $C_{1-6}$-haloalkyl, $OR^l$, $C(O)R^l$, $C(O)OR^l$, $NR'''R''$, or $S(O)_2R^l$.

In one embodiment of formula (IV), B is a 7-11 membered bicyclic heterocyclyl. In another embodiment, B is a 7-11 membered bicyclic heterocycloalkyl or bicyclic heterocyloalkenyl. In another embodiment, B is a 7-11 membered bicyclic heteroaryl. In yet another embodiment, B is 2,3-dihydro-2-oxo-1H-indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl, dihydroisoindolyl, dihydroquinazolinyl, 3,4-dihydro-4-oxo-quinazolinyl, benzisothiazolyl, benzisoxazolyl, benzodiazinyl, benzofurazanyl, benzothiopyranyl, benzotriazolyl, benzpyrazolyl, 1,3-benzodioxolyl, dihydrobenzofuryl, dihydrobenzothienyl, dihydrobenzothiopyranyl, dihydrobenzothiopyranyl sulfone, dihydrobenzopyranyl, dihydrobenzoxazinyl, 3-oxo-3,4-dihydro-1,4-benzoxazinyl, indolinyl, indazolyl, isochromanyl, isoindolinyl, naphthyridinyl, phthalazinyl, piperonyl, purinyl, pyridopyridyl, pyrrolotriazinyl, quinazolinyl, tetrahydroquinolinyl, thienofuryl, thienopyridyl, 3H-imidazo[4,5-c]pyridinyl, or thienothienyl. In one embodiment of formula (IV), B is unsubstituted. In another embodiment of formula (IV), B is substituted with one, two, or three $R^6$, and $R^6$ is halo, $C_{1-6}$-alkyl, $C_{1-6}$-haloalkyl, $OR^l$, $C(O)R^l$, $C(O)OR^l$, $NR'''R''$, or $S(O)_2R^l$.

In one embodiment of formula (IV), B is 10-15 membered tricyclic heterocyclyl. In another embodiment, B is a 10-15 membered tricyclic heterocycloalkyl or tricyclic heterocyloalkenyl. In another embodiment, B is a 10-15 membered tricyclic heteroaryl. In one embodiment of formula (IV), B is unsubstituted. In another embodiment of formula (IV), B is substituted with one, two, or three $R^6$, and $R^6$ is halo, $C_{1-6}$-alkyl, $C_{1-6}$-haloalkyl, $OR^l$, $C(O)R^l$, $C(O)OR^l$, $NR'''R''$, or $S(O)_2R^l$.

In one embodiment of formula (IV), B is

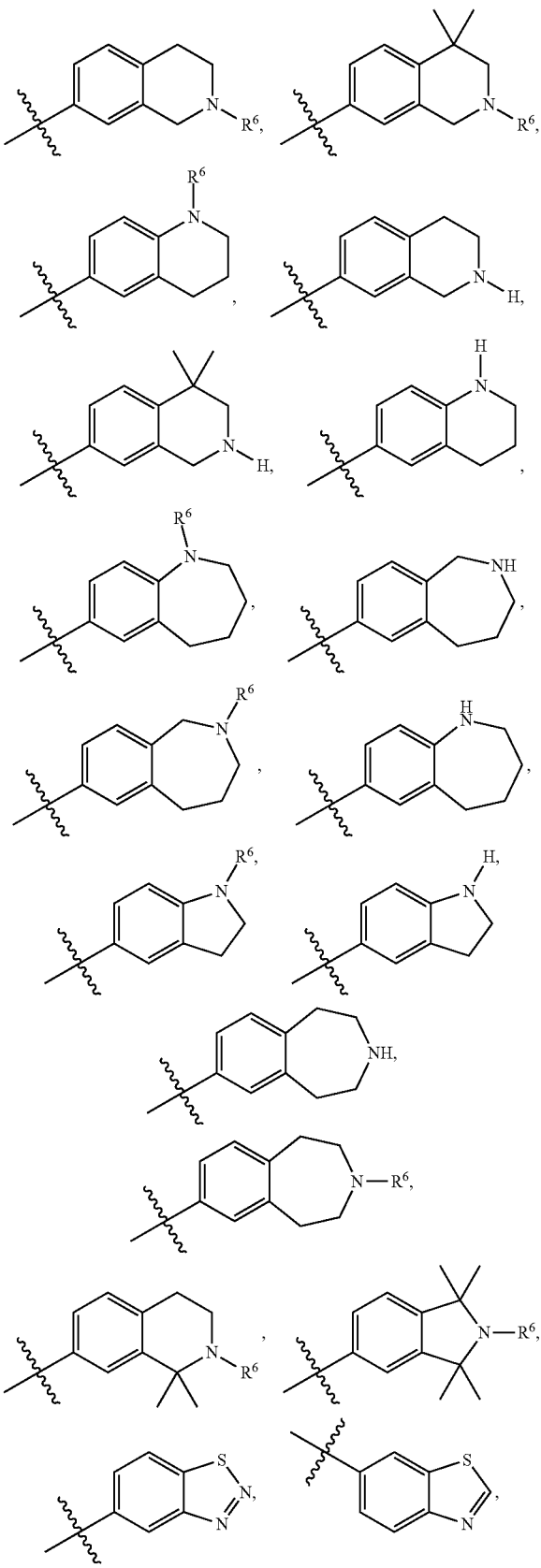

-continued

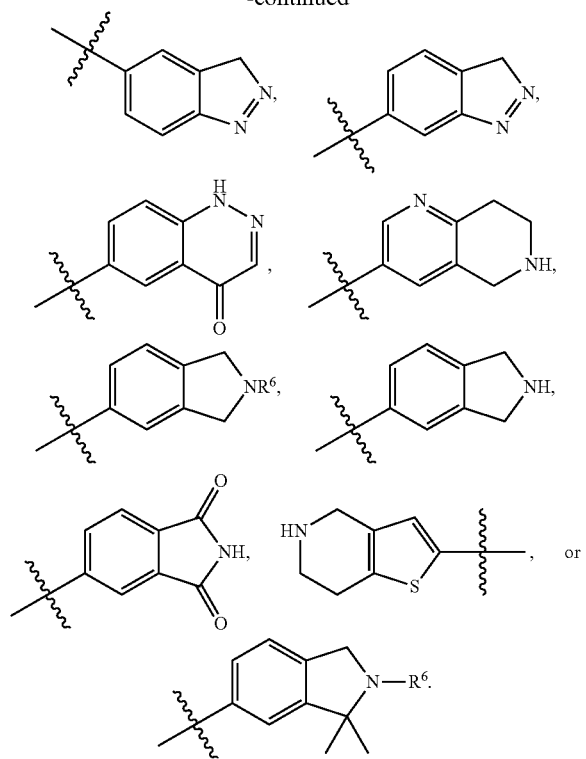

In another embodiment of formula (IV), B is

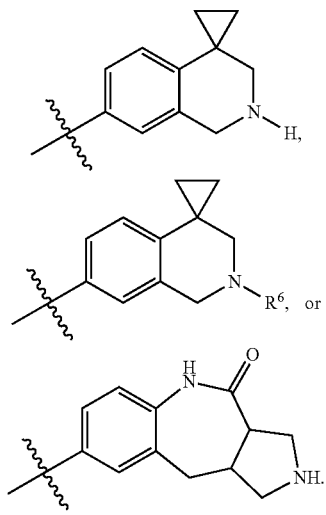

Compounds of this invention may contain asymmetrically substituted carbon atoms in the R or S configuration, wherein the terms "R" and "S" are as defined in Pure Appl. Chem. (1976) 45, 13-10. Compounds having asymmetrically substituted carbon atoms with equal amounts of R and S configurations are racemic at those atoms. Atoms having excess of one configuration over the other are assigned the configuration in excess, preferably an excess of about 85%-90%, more preferably an excess of about 95%-99%, and still more preferably an excess greater than about 99%. Accordingly, this invention is meant to embrace racemic mixtures and relative and absolute diastereoisomers of the compounds thereof.

Compounds of this invention may also contain carbon-carbon double bonds or carbon-nitrogen double bonds in the E or Z configuration, wherein the term "E" represents higher order substituents on opposite sides of the carbon-carbon or carbon-nitrogen double bond and the term "Z" represents higher order substituents on the same side of the carbon-carbon or carbon-nitrogen double bond as determined by the Cahn-Ingold-Prelog Priority Rules. The compounds of this invention may also exist as a mixture of "E" and "Z" isomers.

Additional geometric isomers may exist in the present compounds. For example, the invention contemplates the various geometric isomers and mixtures thereof resulting from the disposition of substituents around a cycloalkyl group or a heterocycle group. Substituents around a cycloalkyl or a heterocycle are designated as being of cis or trans configuration.

Compounds of this invention may also exist as tautomers or equilibrium mixtures thereof wherein a proton of a compound shifts from one atom to another. Examples of tautomers include, but are not limited to, keto-enol, phenol-keto, oxime-nitroso, nitro-aci, imine-enamine and the like. Tautomeric forms are intended to be encompassed by the scope of this invention, even though only one tautomeric form may be depicted.

This invention also is directed, in part, to all salts of the compounds of formula (I). A salt of a compound may be advantageous due to one or more of the salt's properties, such as, for example, enhanced pharmaceutical stability in differing temperatures and humidities, or a desirable solubility in water or other solvents. Where a salt is intended to be administered to a patient (as opposed to, for example, being in use in an in vitro context), the salt preferably is pharmaceutically acceptable and/or physiologically compatible. The term "pharmaceutically acceptable" is used adjectivally in this patent application to mean that the modified noun is appropriate for use as a pharmaceutical product or as a part of a pharmaceutical product. Pharmaceutically acceptable salts include salts commonly used to form alkali metal salts and to form addition salts of free acids or free bases. In general, these salts typically may be prepared by conventional means by reacting, for example, the appropriate acid or base with a compound of the invention.

Pharmaceutically acceptable acid addition salts of the compounds of formula (I) can be prepared from an inorganic or organic acid. Examples of often suitable inorganic acids include hydrochloric, hydrobromic, hydroiodic, nitric, carbonic, sulfuric, and phosphoric acid. Suitable organic acids generally include, for example, aliphatic, cycloaliphatic, aromatic, araliphatic, heterocyclic, carboxylic, and sulfonic classes of organic acids. Specific examples of often suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), ethanesulfonate, benzenesulfonate, pantothenate, 2-hydroxyethanesulfonate, sulfanilate, cyclohexylaminosulfonate, algenic acid, beta-hydroxybutyric acid, galactarate, galacturonate, adipate, alginate, bisulfate, butyrate, camphorate, camphorsulfonate, cyclopentanepropionate, dodecylsulfate, glycoheptanoate, glycerophosphate, heptanoate, hexanoate, nicotinate, oxalate, palmoate, pectinate, 2-naphthalesulfonate, 3-phenylpropionate, picrate, pivalate, thiocyanate, tosylate, and undecanoate.

Pharmaceutically acceptable base addition salts of the compounds of formula (I) include, for example, metallic salts and organic salts. Preferred metallic salts include alkali metal (group Ia) salts, alkaline earth metal (group IIa) salts, and other physiologically acceptable metal salts. Such salts may be made from aluminum, calcium, lithium, magnesium, potassium, sodium, and zinc. Preferred organic salts can be made from amines, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups can be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

Compounds of formula (I) (and salts thereof) with any level of purity (including pure and substantially pure) are within the scope of Applicants' invention. The term "substantially pure" in reference to a compound/salt/isomer, means that the preparation/composition containing the compound/salt/isomer contains more than about 85% by weight of the compound/salt/isomer, preferably more than about 90% by weight of the compound/salt/isomer, preferably more than about 95% by weight of the compound/salt/isomer, preferably more than about 97% by weight of the compound/salt/isomer, and preferably more than about 99% by weight of the compound/salt/isomer.

Preparation of Compounds

Compounds of this invention may be made by synthetic chemical processes, examples of which are shown herein. It is meant to be understood that the order of the steps in the processes may be varied, that reagents, solvents and reaction conditions may be substituted for those specifically mentioned, and that vulnerable moieties may be protected and deprotected, as necessary.

Protecting groups for C(O)OH moieties include, but are not limited to, acetoxymethyl, allyl, benzoylmethyl, benzyl, benzyloxymethyl, tert-butyl, tert-butyldiphenylsilyl, diphenylmethyl, cyclobutyl, cyclohexyl, cyclopentyl, cyclopropyl, diphenylmethylsilyl, ethyl, para-methoxybenzyl, methoxymethyl, methoxyethoxymethyl, methyl, methylthiomethyl, naphthyl, para-nitrobenzyl, phenyl, n-propyl, 2,2,2-trichloroethyl, triethylsilyl, 2-(trimethylsilyl)ethyl, 2-(trimethylsilyl)ethoxymethyl, triphenylmethyl and the like. Protecting groups for C(O) and C(O)H moieties include, but are not limited to, 1,3-dioxylketal, diethylketal, dimethylketal, 1,3-dithianylketal, O-methyloxime, O-phenyloxime and the like. Protecting groups for NH moieties include, but are not limited to, acetyl, alanyl, benzoyl, benzyl (phenylmethyl), benzylidene, benzyloxycarbonyl (Cbz), tert-butoxycarbonyl (Boc), 3,4-dimethoxybenzyloxycarbonyl, diphenylmethyl, diphenylphosphoryl, formyl, methanesulfonyl, para-methoxybenzyloxycarbonyl, phenylacetyl, phthaloyl, succinyl, trichloroethoxycarbonyl, triethylsilyl, trifluoroacetyl, trimethylsilyl, triphenylmethyl, triphenylsilyl, para-toluenesulfonyl and the like.

Protecting groups for OH and SH moieties include, but are not limited to, acetyl, allyl, allyloxycarbonyl, benzyloxycarbonyl (Cbz), benzoyl, benzyl, tert-butyl, tert-butyldimethylsilyl, tert-butyldiphenylsilyl, 3,4-dimethoxybenzyl, 3,4-dimethoxybenzyloxycarbonyl, 1,1-dimethyl-2-propenyl, diphenylmethyl, formyl, methanesulfonyl, methoxyacetyl, 4-methoxybenzyloxycarbonyl, para-methoxybenzyl, methoxycarbonyl, methyl, para-toluenesulfonyl, 2,2,2-trichloroethoxycarbonyl, 2,2,2-trichloroethyl, triethylsilyl, trifluoroacetyl, 2-(trimethylsilyl)ethoxycarbonyl, 2-trimethylsilylethyl, triphenylmethyl, 2-(triphenylphosphonio) ethoxycarbonyl and the like.

Schemes

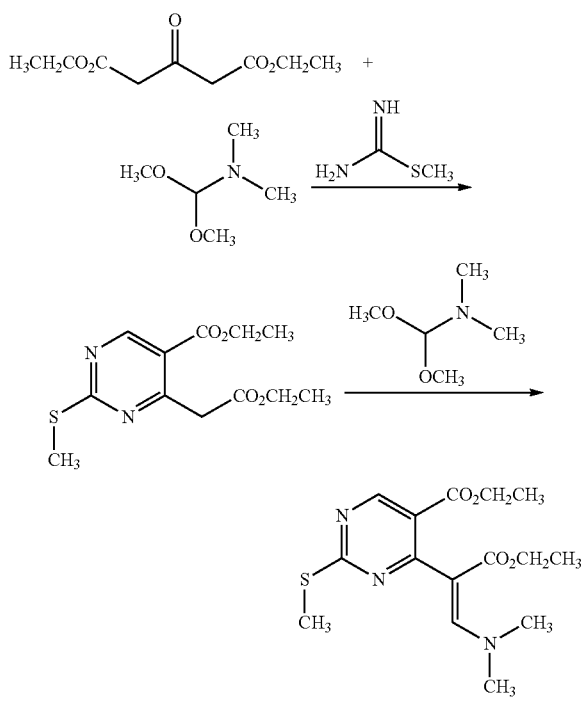

As shown in Scheme 1, diethyl 3-oxopentanedioate can be reacted with 1,1-dimethoxy-N,N-dimethylmethanamine, followed by the addition of methyl carbamimidothioate, to provide ethyl 4-(2-ethoxy-2-oxoethyl)-2-(methylthio)pyrimidine-5-carboxylate. The reaction is typically performed in a solvent such as but not limited to ethanol, and the diethyl 3-oxopentanedioate and 1,1-dimethoxy-N,N-dimethylmethanamine are typically stirred at ambient temperature before the addition of the methyl carbamimidothioate with stirring at an elevated temperature. 1,1-Dimethoxy-N,N-dimethylmethanamine can be reacted with ethyl 4-(2-ethoxy-2-oxoethyl)-2-(methylthio)pyrimidine-5-carboxylate at an elevated temperature to provide (Z)-ethyl 4-(1-(dimethylamino)-3-ethoxy-3-oxoprop-1-en-2-yl)-2-(methylthio)pyrimidine-5-carboxylate.

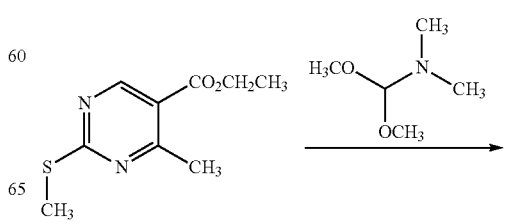

-continued

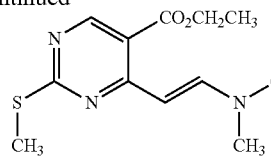

As shown above in Scheme 2, (E)-ethyl 4-(2-(dimethylamino)vinyl)-2-(methylthio)pyrimidine-5-carboxylate can be prepared by reacting ethyl 4-methyl-2-(methylthio)pyrimidine-5-carboxylate with 1,1-dimethoxy-N,N-dimethylmethanamine at an elevated temperature.

Scheme 3

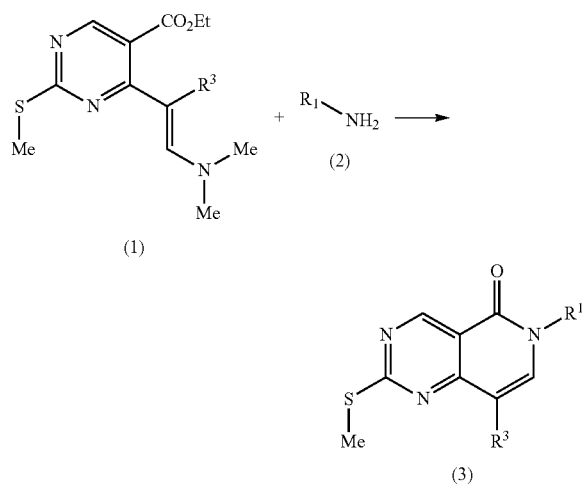

Compounds of formula (1), which can be prepared as described in Scheme 1 and Scheme 2, can be reacted with a suitable amine of formula (2), wherein R¹ is as described herein, in the presence of an acid such as but not limited to hydrochloric acid, to provide compounds of formula (3). The reaction is typically performed at an elevated temperature in a solvent such as but not limited to ethanol.

Alternatively, the reaction can be performed in the presence of ytterbium triflate at an elevated temperature in a solvent such as but not limited to tetrahydrofuran.

Scheme 4

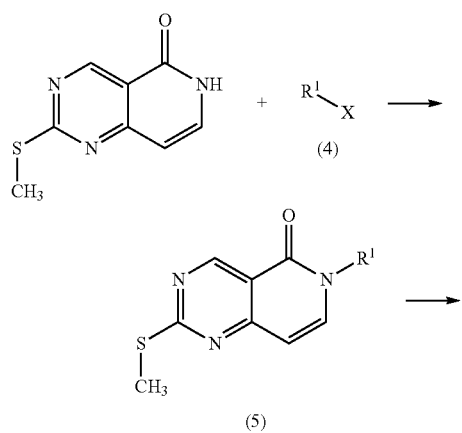

-continued

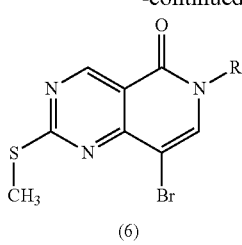 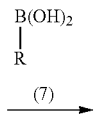

2-(Methylthio)pyrido[4,3-d]pyrimidin-5(6H)-one can be reacted with appropriate compounds of formula (4) wherein R¹ is as described herein and X is a halide, in the presence of a base such as but not limited to cesium carbonate, to provide compounds of formula (5). The reaction is typically performed at ambient temperature in a solvent such as but not limited to N,N-dimethylformamide. Compounds of formula (5) can be reacted with bromine in acetic acid to provide compounds of formula (6). Compounds of formula (3) can be prepared by reacting compounds of formula (6) with boronic acids (or the boronate ester equivalent) of formula (7) under Suzuki coupling conditions known to those skilled in the art and widely available in the literature.

Scheme 5

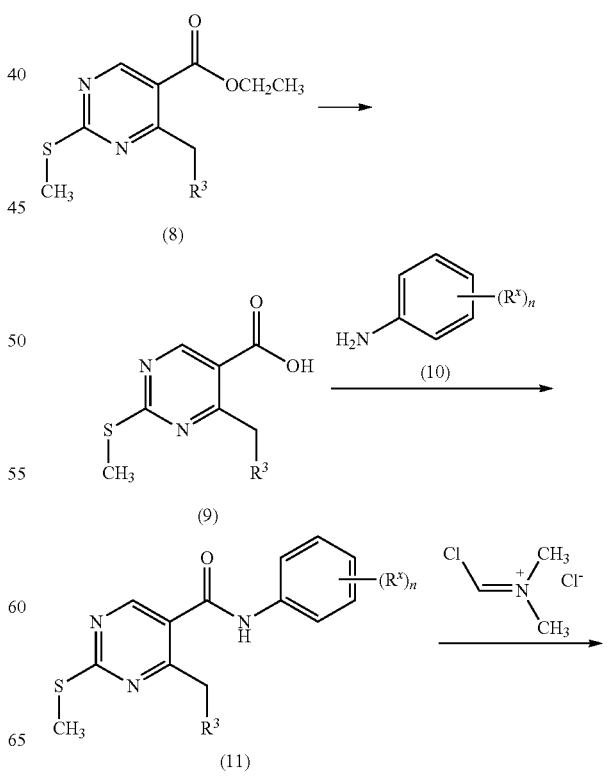

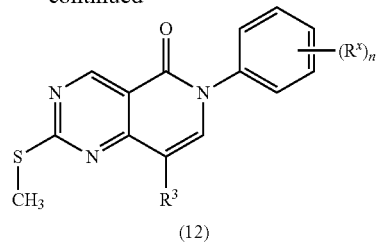

(12)

As shown in Scheme 5, compounds of formula (8), wherein R³ is as described herein, can be reacted with a base such as but not limited to lithium hydroxide to provide compounds of formula (9). The reaction is typically performed at ambient temperature in a solvent such as but not limited to tetrahydrofuran, methanol or mixtures thereof. Compounds of formula (9) can be reacted with thionyl chloride, followed by an amine of formula (10), wherein $R^x$ is as described herein for substituents on the $R^1$ aryl group and n is 0-5, to provide compounds of formula (11). The thionyl chloride addition is typically performed at ambient temperature, and the reaction with the amine is typically performed at elevated temperature. The reaction is typically performed in a solvent such as but not limited to dioxane, N,N-dimethylformamide or mixtures thereof. Compounds of formula (12) can be prepared by reacting compounds of formula (11) with (chloromethylene)dimethyliminium chloride. The reaction is typically performed at ambient temperature in a solvent such as but not limited to N,N-dimethylformamide.

Scheme 6

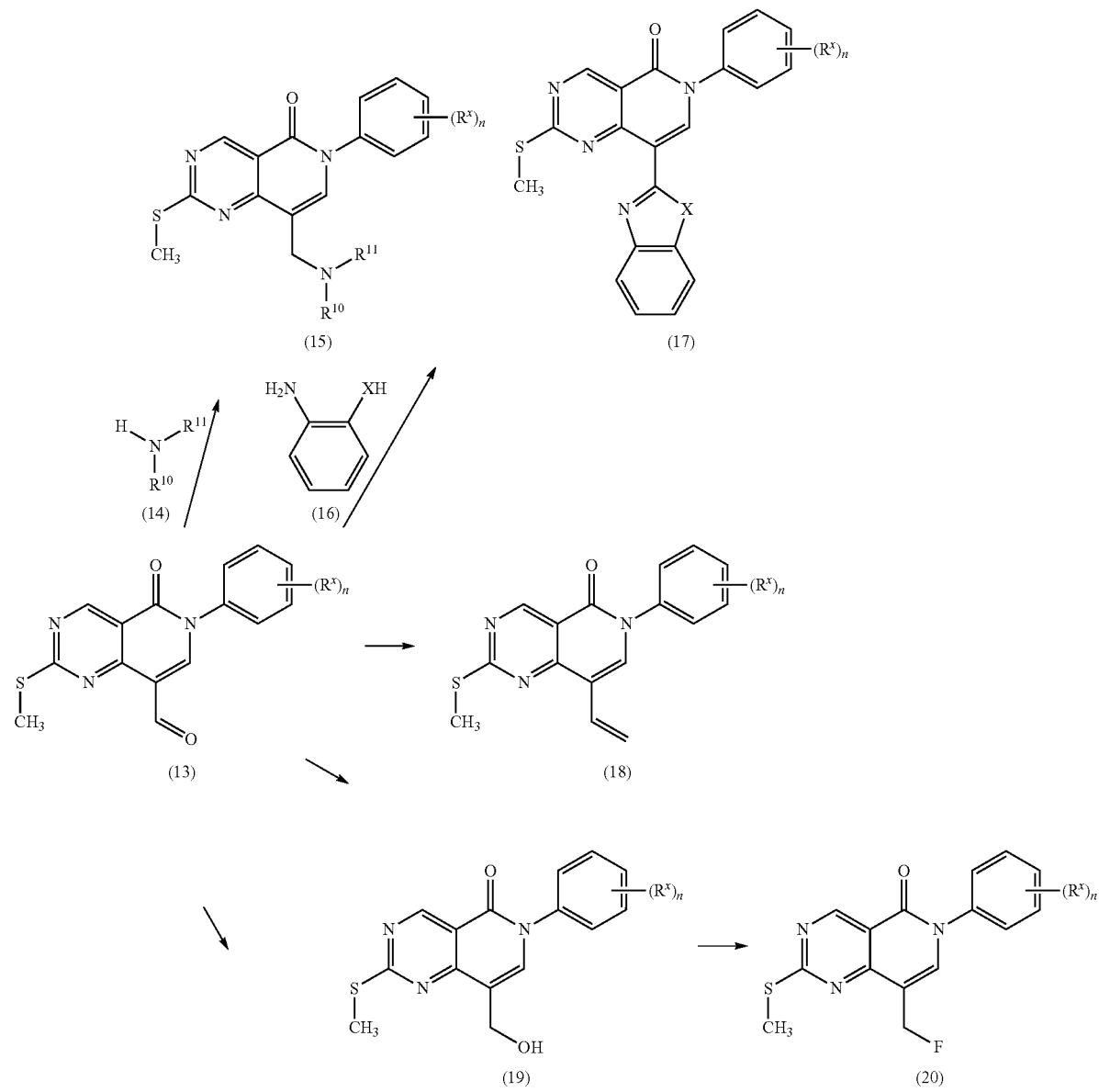

-continued

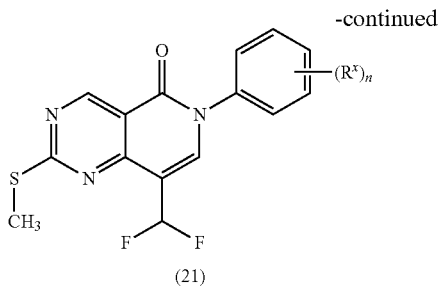

(21)

As shown in Scheme 6, compounds of formula (13), which can be prepared as shown in Scheme 5 wherein $R^3$ is H in formula (8), can be reacted with compounds of formula (14) wherein $R^{10}$ and $R^{11}$ are as described herein, in the presence of a reducing agent such as but not limited to sodium cyanoborohydride, to provide compounds of formula (15). The reaction is typically performed with a drop of acetic acid in a solvent such as but not limited to 2-propanol.

Compounds of formula (13) can also be reacted with compounds of formula (16), wherein X is S or NH, to provide compounds of formula (17). The reaction is typically performed at ambient temperature in a solvent such as but not limited to 1,2-dichloroethane.

Compounds of formula (13) can be reacted with methyltriphenylphosphonium bromide in the presence of potassium t-butoxide to provide compounds of formula (18). The reaction is typically performed at ambient temperature in a solvent such as but not limited to tetrahydrofuran.

Reaction of compounds of formula (13) with $CeCl_3$ heptahydrate and a reducing agent such as but not limited to sodium borohydride, will provide compounds of formula (19). The reaction is typically performed at reduced temperature in a solvent such as but not limited to dichloromethane, methanol or mixtures thereof. Diethylaminosulfur trifluoride can be reacted with compounds of formula (19) to provide compounds of formula (20). The reaction is typically performed at reduced temperature in a solvent such as but not limited to dichloromethane.

Alternatively, compounds of formula (13) can be reacted directly with diethylaminosulfur trifluoride to provide compounds of formula (21). The reaction is typically performed at ambient temperature in a solvent such as but not limited to dichloromethane.

Scheme 7

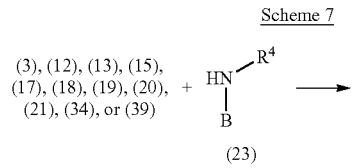

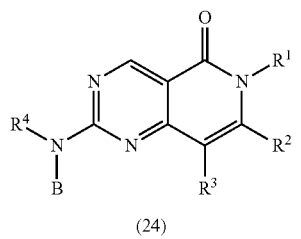

As shown in Scheme 7, compounds of formula (3), (12), (13) (15), (17), (18), (19), (20), (21), (34), or (39) can be reacted with amines of formula (23), wherein $R^4$ is as described herein, to provide compounds of formula (24) which are representative of the compounds of Formula (I). The reaction is typically performed at an elevated temperature. Alternatively, compounds of formula (3), (12), (13) (15), (17), (18), (19), (20), (21), (34), or (39) can be treated with m-CPBA at ambient temperature, followed by reaction with compounds of formula (23) with or without an acid such as but not limited to trifluoroacetic acid. The reaction is also typically performed at an elevated temperature and in a solvent such as but not limited to acetonitrile, dichloromethane or dichloroethane to provide compounds of formula (24) which are representative of compounds of formula (I).

Scheme 8

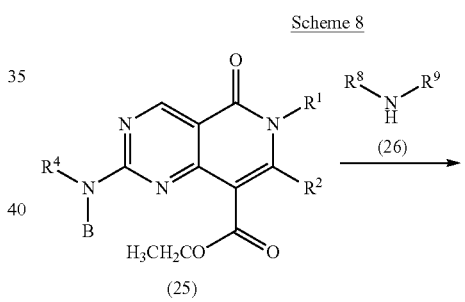

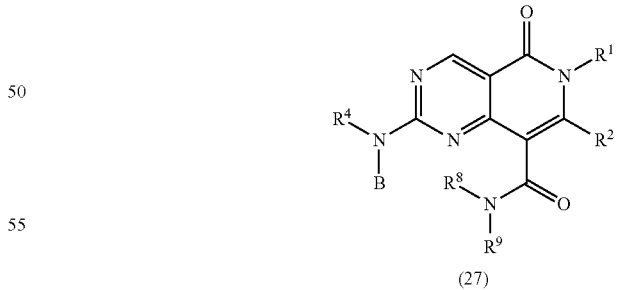

Compounds of formula (25) can be reacted with amines of formula (26), wherein $R^8$ and $R^9$ are as described herein, to provide compounds of formula (27). The reaction may be performed in a solvent such as but not limited to tetrahydrofuran and is typically performed at an elevated temperature.

Scheme 9

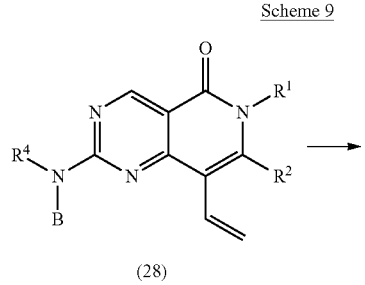

As shown in Scheme 9, compounds of formula (28) can be reacted with Pd/C under a hydrogen atmosphere to provide compounds of formula (29), which are representative of the compounds of Formula (I). The reaction is typically performed at ambient temperature in a solvent such as but not limited to methanol.

Scheme 10

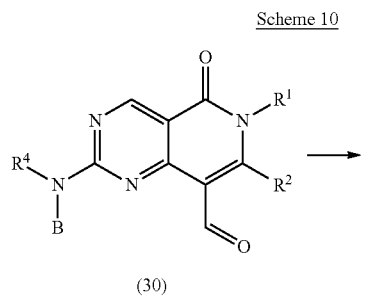

Compounds of formula (31), which are representative of compounds of Formula (I), wherein B, $R^1$, $R^2$, and $R^4$ are as described herein, can be prepared by treating compounds of formula (30) with oxalaldehyde/water solution and ammonia in methanol. The reaction is typically performed at ambient temperature.

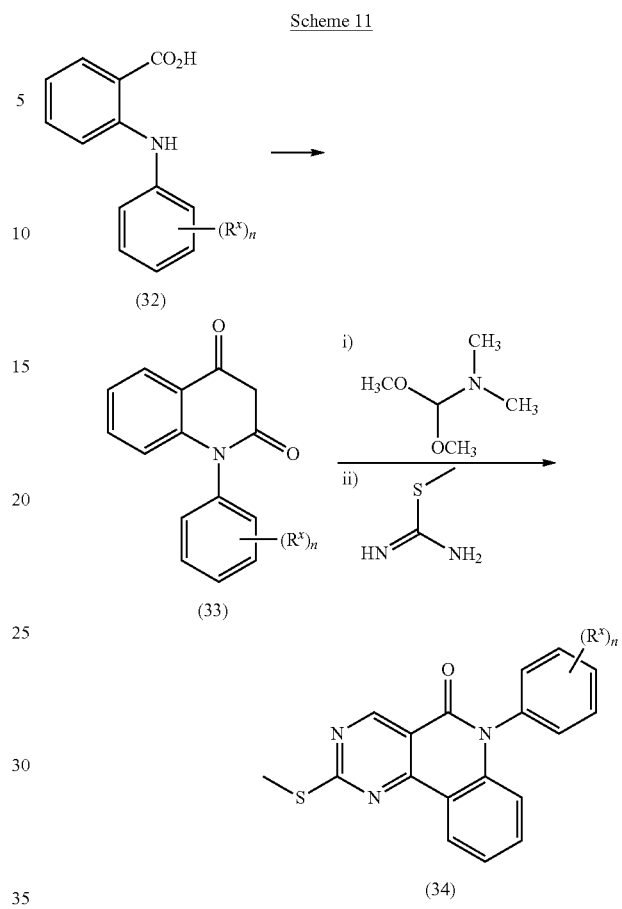

As shown in Scheme 11, compounds of formula (32), wherein each $R^x$ is as described herein for substituents on the $R^1$ aryl group and n is 0-5, can be treated with acetic anhydride in acetic acid, to provide compounds of formula (33). The reaction is typically performed at an elevated temperature. Compounds of formula (33) can be treated with 1,1-dimethoxy-N,N-dimethylmethanamine at an elevated temperature, followed by S-methylisothiourea sulfate in acetic acid to provide compounds of formula (34).

-continued

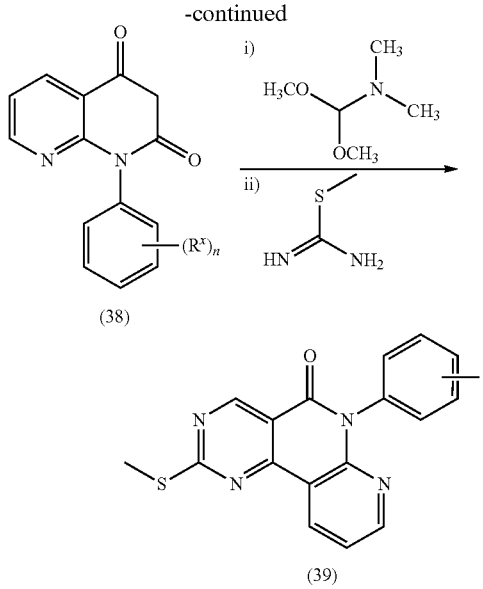

2-Chloronicotinic acid can be treated with a compound of formula (35) wherein each $R^x$ is as described herein for substituents on the $R^1$ aryl group and n is 0-5, in the presence of p-toluenesulfonic acid in water, followed by treatment with chloroacetonitrile and triethylamine in acetone to provide compounds of formula (36). The reaction is typically performed at elevated temperature. Compounds of formula (36) can be treated with acetic acid at an elevated temperature to provide compounds (37). Compounds of formula (38) can be prepared by treating compounds of formula (37) with potassium t-butoxide. The reaction is typically performed at an elevated temperature in a solvent such as but not limited to m-xylene. Compounds of formula (38) can be treated with N,N-dimethylformamide dimethyl acetal at an elevated temperature, followed by reaction with S-methylisothiourea sulfate in acetic acid at an elevated temperature to provide compounds of formula (39).

Compositions

In another aspect, the present invention provides pharmaceutical compositions for modulating kinase activity in a humans and animals that will typically contain a compound of formula (I) and a pharmaceutically acceptable carrier.

Compounds having formula (I) may be administered, for example, bucally, ophthalmically, orally, osmotically, parenterally (intramuscularly, intraperintoneally intrasternally, intravenously, subcutaneously), rectally, topically, transdermally, vaginally and intraarterially as well as by intraarticular injection, infusion, and placement in the body, such as, for example, the vasculature.

Compounds having formula (I) may be administered with or without an excipient. Excipients include, but are not limited to, encapsulators and additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents, mixtures thereof and the like.

Excipients for preparation of compositions comprising a compound having formula (I) to be administered orally include, but are not limited to, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, crosspovidone, diglycerides, ethanol, ethyl cellulose, ethyl laureate, ethyl oleate, fatty acid esters, gelatin, germ oil, glucose, glycerol, groundnut oil, hydroxypropylmethyl celluose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, mixtures thereof and the like. Excipients for preparation of compositions comprising a compound having formula (I) to be administered ophthalmically or orally include, but are not limited to, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water, mixtures thereof and the like. Excipients for preparation of compositions comprising a compound having formula (I) to be administered osmotically include, but are not limited to, chlorofluorohydrocarbons, ethanol, water, mixtures thereof and the like. Excipients for preparation of compositions comprising a compound having formula (I) to be administered parenterally include, but are not limited to, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water, mixtures thereof and the like. Excipients for preparation of compositions comprising a compound having formula (I) to be administered rectally or vaginally include, but are not limited to, cocoa butter, polyethylene glycol, wax, mixtures thereof and the like.

The pharmaceutical composition and the method of the present invention may further comprise other therapeutically active compounds as noted herein which are usually applied in the treatment of the above-mentioned pathological conditions.

Methods of Use

In another aspect, the present invention provides methods of using a compound or composition of the invention to treat or prevent a disease or condition involving mediation, overexpression or disregulation of kinases in a mammal In particular, compounds of this invention are expected to have utility in treatment of diseases or conditions during which protein kinases such as any or all wee-1 family members are expressed.

In one group of embodiments, diseases and conditions of humans or other animals that can be treated with inhibitors of kinases, include, but are not limited to, acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myleogeneous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, heavy chain disease, hemangioblastoma, hepatoma, hepatocellular cancer, hormone insensitive prostate cancer, leiomyosarcoma, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

In one group of embodiments, diseases and conditions of humans or other animals that can be treated with inhibitors of kinases, include, but are not limited to, tumors that are deficient in the p53 protein. The p53 protein is a tumor suppressor protein that is encoded in humans by the TP53 gene. The p53 protein regulates the cell cycle and therefore functions as a tumor suppressor that is involved in preventing cancer Inhibition of Wee1 kinases sensitizes tumor cells to DNA damage and/or cell cycle perturbation, especially tumors that have lost their $G_1$-phase checkpoint due to a deficiency in the p53 protein.

A discussion of the loss of expression of Wee1 and how it relates to deficiency in the p53 protein can be found in *Annual Review of Biochemistry,* 2004, 73:39-85.

Involvement of mutations in the p53 gene and human tumor types can be found in *Nature,* 1989, 342:705-708.

A discussion of Wee1 kinase and p53 deficient tumor cells can be found in *Molecular Cancer Therapy,* 2009, 8:11.

A discussion of p53 and Wee1 kinases and anti-cancer therapies can be found in *BMC Cancer* 2006, 6:292.

A discussion of Wee1 kinase and p53 deficient tumor cells can be found in *Current Clinical Pharmacology,* 2010, 5:186-191.

The methods of the present invention typically involve administering to a subject in need of therapeutic treatment an effective amount of a compound of formula (I). Therapeutically effective amounts of a compound having formula (I) depend on recipient of treatment, disease treated and severity thereof, composition comprising it, time of administration, route of administration, duration of treatment, potency, rate of clearance and whether or not another drug is co-administered. The amount of a compound having formula (I) used to make a composition to be administered daily to a patient in a single dose or in divided doses is from about 0.03 to about 200 mg/kg body weight. Single dose compositions contain these amounts or a combination of submultiples thereof.

Combination Therapy

The present invention further provides methods of using a compound or composition of the invention in combination with one or more additional active agents. Compounds having Formula (I) are expected to be useful when used with alkylating agents, angiogenesis inhibitors, antibodies, antimetabolites, antimitotics, antiproliferatives, antivirals, aurora kinase inhibitors, apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (PI3K) inhibitors, proteosome inhibitors, purine analogs, pyrimidine analogs, receptor tyrosine kinase inhibitors, etinoids/deltoids plant alkaloids, small inhibitory ribonucleic acids (siRNAs), topoisomerase inhibitors, ubiquitin ligase inhibitors, and the like, and in combination with one or more of these agents.

BiTE antibodies are bi-specific antibodies that direct T-cells to attack cancer cells by simultaneously binding the two cells. The T-cell then attacks the target cancer cell. Examples of BiTE antibodies include adecatumumab (Micromet MT201), blinatumomab (Micromet MT 103) and the like. Without being limited by theory, one of the mechanisms by which T-cells elicit apoptosis of the target cancer cell is by exocytosis of cytolytic granule components, which include perforin and granzyme B. In this regard, Bcl-2 has been shown to attenuate the induction of apoptosis by both perforin and granzyme B. These data suggest that inhibition of Bcl-2 could enhance the cytotoxic effects elicited by T-cells when targeted to cancer cells (V. R. Sutton, D. L. Vaux and J. A. Trapani, *J. of Immunology* 1997, 158 (12), 5783).

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-$OCH_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand.

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site. Multispecific DVDs include DVD binding proteins that bind DLL4 and VEGF, or C-met and EFGR or ErbB3 and EGFR.

Alkylating agents include altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, rofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Antivirals include ritonavir, hydroxychloroquine and the like.

Aurora kinase inhibitors include ABT-348, AZD-1152, MLN-8054, VX-680, Aurora A-specific kinase inhibitors, Aurora B-specific kinase inhibitors and pan-Aurora kinase inhibitors and the like.

Bcl-2 protein inhibitors include AT-101 ((−)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl) propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (ABT-263), GX-070 (obatoclax) and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecfic antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FC1, PU-3, radicicol, SNX-2112, STA-9090 VER49009 and the like.

Inhibitors of inhibitors of apoptosis proteins include HGS1029, GDC-0145, GDC-0152, LCL-161, LBW-242 and the like.

Antibody drug conjugates include anti-CD22-MC-MMAF, anti-CD22-MC-MMAE, anti-CD22-MCC-DM1, CR-011-vcMMAE, PSMA-ADC, MEDI-547, SGN-19 Am SGN-35, SGN-75 and the like Activators of death receptor pathway include TRAIL, antibodies or other agents that target TRAIL or death receptors (e.g., DR4 and DR5) such as Apomab, conatumumab, ETR2-ST01, GDC0145, (lexatumumab), HGS-1029, LBY-135, PRO-1762 and trastuzumab.

Kinesin inhibitors include Eg5 inhibitors such as AZD4877, ARRY-520; CENPE inhibitors such as GSK923295A and the like.

JAK-2 inhibitors include CEP-701 (lesaurtinib), XL019 and INCB018424 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus, ATP-competitive TORC1/TORC2 inhibitors, including PI-103, PP242, PP30, Torin 1 and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin, picoplatin and the like.

Polo-like kinase inhibitors include BI-2536 and the like.

Phosphoinositide-3 kinase (PI3K) inhibitors include wortmannin, LY294002, XL-147, CAL-120, ONC-21, AEZS-127, ETP-45658, PX-866, GDC-0941, BGT226, BEZ235, XL765 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474), GA101, ofatumumab, ABT-806 (mAb-806), ErbB3 specific antibodies, BSG2 specific antibodies, DLL4 specific antibodies and C-met specific antibodies, and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirubicin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab, CD20 antibodies types I and II and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

PARP inhibitors include ABT-888 (veliparib), olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b) or interferon gamma-n1, combinations thereof and the like. Other agents include ALFAFERONE°, (IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN° (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth or differentiation of tissue cells to direct them to have anti-tumor activity and include krestin, lentinan, sizofiran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Ubiquitin ligase inhibitors include MDM2 inhibitors, such as nutlins, NEDD8 inhibitors such as MLN4924 and the like.

Compounds of this invention can also be used as radiosensitizers that enhance the efficacy of radiotherapy. Examples of radiotherapy include external beam radiotherapy, teletherapy, brachytherapy and sealed, unsealed source radiotherapy and the like.

Additionally, compounds having Formula (I) may be combined with other chemotherapeutic agents such as ABRAXANE™ (ABI-007), ABT-100 (farnesyl transferase inhibitor), ADVEXIN° (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine)(ONCOVIN®); P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EPO906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTATAAE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paclitaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (Streptomyces staurospores), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zolendronic acid), zorubicin and the like.

EXAMPLE 1 ethyl 2-{[4-(4-methylpiperazin-1-yl)phenyl]amino}-5-oxo-6-(prop-2-en-1-yl)-5,6-dihydropyrido[4,3-d]pyrimidine-8-carboxylate

EXAMPLE 1A ethyl 4-(2-ethoxy-2-oxoethyl)-2-(methylthio)pyrimidine-5-carboxylate To a solution of diethyl 3-oxopentanedioate (4.03 ml, 22.19 mmol) in ethanol (44.4 ml), 1,1-dimethoxy-N,N-dimethylmethanamine (2.95 ml, 22.19 mmol) was added and the mixture was stirred at ambient temperature for 45 minutes. Methyl carbamimidothioate sulfate (3.08 g, 22.19 mmol) was then added and the mixture was stirred under refluxing conditions for 3 hours. After cooling to ambient temperature, the solution was concentrated and the residue was dissolved in 200 mL of ethyl acetate. The solution was poured into a separatory funnel, washed with saturated aqueous sodium bicarbonate (1×150 mL) and brine (1×150 mL), dried over magnesium sulfate, filtered and concentrated. Purification by flash chromatography (Isco®, Redi-Sep® column, 0-100% ethyl acetate/hexane, linear gradient) afforded the title compound. MS (ESI) m/z 285 (M+H)$^+$.

EXAMPLE 1B (Z)-ethyl 4-(1-(dimethylamino)-3-ethoxy-3-oxoprop-1-en-2-yl)-2-(methylthio)pyrimidine-5-carboxylate Example 1A (3.87 g, 13.61 mmol), and 1,1-dimethoxy-N,N-dimethylmethanamine (3.62 ml, 27.2 mmol) were stirred at 100° C. After stirring for 4 hours, the reaction mixture was cooled to ambient temperature and the crude product was purified directly by silica gel flash chromatography (Isco®, Redi-Sep® column, 10-100% ethyl acetate/hexane, linear gradient) to afford the title compound. MS (ESI) m/z 340 (M+H)$^+$.

EXAMPLE 1C ethyl 6-allyl-2-(methylthio)-5-oxo-5,6-dihydropyrido[4,3-d]pyrimidine-8-carboxylate To a solution of Example 1B (339 mg, 1 mmol) with allylamine (375 μl, 5.00 mmol), in 20 mL of ethanol, was added aqueous concentrated HCl (10 μl, 0.329 mmol). The reaction mixture was stirred under refluxing conditions for three hours. After cooling to ambient temperature, dichloromethane was added to completely dissolve the solid obtained. The mixture was then concentrated and purified directly by silica gel flash chromatography (Isco®, Redi-Sep® column, 0-100% ethyl acetate/hexane, linear gradient) to afford the title compound. MS (ESI) m/z 306 (M+H)$^+$.

EXAMPLE 1D ethyl 2-{[4-(4-methylpiperazin-1-yl)phenyl]amino}-5-oxo-6-(prop-2-en-1-yl)-5,6-dihydropyrido[4,3-d]pyrimidine-8-carboxylate Example 1C (80 mg, 0.262 mmol) was dissolved in dichloromethane (2.62 mL) and meta-chloroperoxybenzoic acid (65 mg, 0.314 mmol) was added. The mixture was stirred at ambient temperature for 20 minutes then 4-(4-methylpiperazin-1-yl)aniline (60 mg, 0.314 mmol) followed by TFA (40 L, 0.524 mmol) was added. The mixture was then concentrated by applying a nitrogen flow until most of the solvent was evaporated. Next, the crude oil was dissolved in 1.5 mL of acetonitrile and transferred into a sealed tube. The tube was capped and the mixture was stirred at 100° C. for 6 hours. After cooling to ambient temperature, the mixture was concentrated, dissolved in ethyl acetate (30 mL) and the organic solution was washed with saturated sodium bicarbonate (1×20 mL) and saturated aqueous brine (1×20 mL), dried over magnesium sulfate, filtered and concentrated. Purification by Gilson® reverse-phase preparative HPLC (10-70% acetonitrile/water containing 0.2% TFA, linear gradient) afforded the title compound as a TFA salt. $^1$H NMR (300 MHz, DMSO-d$_6$) δ 10.21 (s, 1H), 9.63 (s, 1H), 9.13 (s, 1H), 8.50 (s, 1H), 8.20-7.88 (m, 2H), 6.99 (d, J=9.1, 2H), 5.99 (ddt, J=15.7, 10.6, 5.4, 1H), 5.31-5.12 (m, 2H), 4.65 (d, J=5.4, 2H), 4.38 (q, J=7.0, 2H), 3.90-3.70 (m, 2H), 3.60-3.43 (m, 2H), 3.28-3.08 (m, 2H), 3.02-2.81 (m, 5H), 1.33 (t, J=7.1, 3H). MS (ESI) m/z 449 (M+H)$^+$.

EXAMPLE 2 ethyl 2-{[4-(4-methylpiperazin-1-yl)phenyl]amino}-5-oxo-6-phenyl-5,6-dihydropyrido[4,3-d]pyrimidine-8-carboxylate

EXAMPLE 2A ethyl 2-(methylthio)-5-oxo-6-phenyl-5,6-dihydro-pyrido[4,3-d]pyrimidine-8-carboxylate The title compound was prepared as described in Example 1C substituting allylamine with aniline. MS (ESI) m/z 342 (M+H)$^+$.

EXAMPLE 2B ethyl 2-{[4-(4-methylpiperazin-1-yl)phenyl]amino}-5-oxo-6-phenyl-5,6-dihydropyrido[4,3-d]pyrimidine-8-carboxylate The title compound was prepared as described in Example 1D substituting Example 1C with Example 2A to give the title compound as a TFA salt. $^1$H NMR (300 MHz, DMSO-d$_6$) δ 10.30 (s, 1H), 9.62 (s, 1H), 9.16 (s, 1H), 8.36 (s, 1H), 8.12-8.01 (m, 2H), 7.63-7.46 (m, 5H), 7.00 (d, J=9.1, 2H), 4.35 (dd, J=14.0, 6.9, 2H), 3.86-3.76 (m, 2H), 3.62-3.47 (m, 2H), 3.30-3.08 (m, 2H), 3.02-2.81 (m, 5H), 1.31 (t, J=7.0, 3H). MS (ESI) m/z 485 (M+H)$^+$.

EXAMPLE 3

2-{[4-(4-methylpiperazin-1-yl)phenyl]amino}-6-phenylpyrido[4,3-d]pyrimidin-5(6H)-one

EXAMPLE 3A (E)-ethyl 4-(2-(dimethylamino)vinyl)-2-(methylthio)pyrimidine-5-carboxylate A mixture of ethyl 4-methyl-2-(methylthio)pyrimidine-5-carboxylate (314 mg, 1.48 mmol) and 1,1-dimethoxy-N,N-dimethylmethanamine (8 ml, 59.8 mmol) was heated in a sealed tube with stirring at 110° C. for 12 hours. The mixture was then cooled to ambient temperature, diluted with ethyl acetate (50 mL), and silica gel was added (for dry loading). After concentration, the crude material was purified by silica gel flash chromatography (Isco®, Redi-Sep® column, 0-50% ethyl acetate/hex, linear gradient) to afford the title compound. MS (ESI) m/z 268 (M+H)$^+$.

EXAMPLE 3B 2-(methylthio)-6-phenylpyrido[4,3-d]pyrimidin-5(6H)-one

The title compound was prepared as described in Example 1C substituting Example 1B with Example 3A and substituting allylamine with aniline. MS (ESI) m/z 270 (M+H)$^+$.

EXAMPLE 3C

2-{[4-(4-methylpiperazin-1-yl)phenyl]amino}-6-phenylpyrido[4,3-d]pyrimidin-5(6H)-one The title compound was prepared as described in Example 1D substituting Example 1C with Example 3B. The title compound was obtained as a TFA salt. $^1$H NMR (300 MHz, DMSO-d$_6$) δ 10.10 (s, 1H), 9.59 (s, 1H), 9.13 (s, 1H), 7.81 (d, J=7.7, 1H), 7.73 (d, J=4.5, 2H), 7.61-7.40 (m, 5H), 7.02 (d, J=9.1, 2H), 6.39 (d, J=8.0, 1H), 3.85-3.72 (m, 2H), 3.56-3.48 (m, 2H), 3.28-3.09 (m, 2H), 2.99-2.81 (m, 5H). MS (ESI) m/z 413 (M+H)$^+$.

EXAMPLE 4

6-benzyl-N-methyl-2-{[4-(4-methylpiperazin-1-yl)phenyl]amino}-5-oxo-5,6-dihydropyrido[4,3-d]pyrimidine-8-carboxamide A 5 mL high pressure tube was charged with Example 5B (10 mg, 0.020 mmol) and 0.5 mL of 2 molar methylamine in tetrahydrofuran. The vessel was capped and heated at 200° C. for 75 minutes. After cooling to ambient temperature, the mixture was concentrated in vacuo and purified by Gilson® reverse-phase preparative HPLC (10-70% acetonitrile/water containing 0.2% TFA, linear gradient) to afford the title compound as a TFA salt. $^1$H NMR (300 MHz, DMSO-d$_6$) δ 10.25 (s, 1H), 9.65 (s, 1H), 9.56 (s, 1H), 9.17 (s, 1H), 8.66 (s, 1H), 7.60-7.22 (m, 7H), 7.18-7.01 (m, 2H), 5.26 (s, 2H), 3.90-3.75 (m, 2H), 3.59-3.47 (m, 2H), 3.24-3.12 (m, 3H), 3.01-2.81 (m, 5H), 2.73-2.65 (m, 2H). MS (ESI) m/z 484 (M+H)$^+$.

EXAMPLE 5 ethyl 6-benzyl-2-{[4-(4-methylpiperazin-1-yl)phenyl]amino}-5-oxo-5,6-dihydropyrido[4,3-d]pyrimidine-8-carboxylate

EXAMPLE 5A ethyl 6-benzyl-2-(methylthio)-5-oxo-5,6-dihydro-pyrido[4,3-d]pyrimidine-8-carboxylate The title compound was prepared as described in Example 1C, substituting allylamine with benzylamine MS (ESI) m/z 356 (M+H)$^+$.

EXAMPLE 5B ethyl 6-benzyl-2-{[4-(4-methylpiperazin-1-yl)phenyl]amino}-5-oxo-5,6-dihydropyrido[4,3-d]pyrimidine-8-carboxylate The title compound was prepared as described in Example 1D, substituting Example 1C with Example 5A to give the title compound as a TFA salt. $^1$H NMR (300 MHz, DMSO-d$_6$) δ 10.30 (s, 1H), 9.62 (s, 1H), 9.16 (s, 1H), 8.36 (s, 1H), 8.12-8.01 (m, 2H), 7.63-7.46 (m, 5H), 7.00 (d, J=9.1, 2H), 4.35 (dd, J=14.0, 6.9, 2H), 3.86-3.76 (m, 2H), 3.62-3.47 (m, 2H), 3.30-3.08 (m, 2H), 3.02-2.81 (m, 8.2, 5H), 1.31 (t, J=7.0, 3H). MS (ESI) m/z 499 (M+H)+.

EXAMPLE 6 ethyl 6-(2-chlorophenyl)-2-{[4-(4-methylpiperazin-1-yl)phenyl]amino}-5-oxo-5,6-dihydropyrido[4,3-d]pyrimidine-8-carboxylate

EXAMPLE 6A ethyl 6-(2-chlorophenyl)-2-(methylthio)-5-oxo-5,6-dihydropyrido[4,3-d]pyrimidine-8-carboxylate A 4 dram vial, equipped with stir bar and septa, was charged with Example 1B (500 mg, 1.473 mmol), ytterbium (III)trifluoromethane sulfonate (914 mg, 1.473 mmol) and molecular sieves (4 Å, 200 mg). The reaction vessel was evacuated and backfilled with nitrogen twice. Tetrahydrofuran (7366 µl) was added followed by 2-chloroaniline (171 µl, 1.620 mmol). The reaction mixture was stirred at 60° C. for 4 days. After cooling to ambient temperature, the mixture was concentrated and purified directly by silica gel flash chromatography (Isco®, Redi-Sep® column, 0-40% ethyl acetate/hexane, linear gradient) to afford the title compound. MS (ESI) m/z 376 (M+H)+.

EXAMPLE 6B ethyl 6-(2-chlorophenyl)-2-{[4-(4-methylpiperazin-1-yl)phenyl]amino}-5-oxo-5,6-dihydropyrido[4,3-d]pyrimidine-8-carboxylate The title compound was prepared as described in Example 1D, substituting Example 1C with Example 6A to give the title compound as a TFA salt. MS (ESI) m/z 519 (M+H)+.

EXAMPLE 7 ethyl 2-{[4-(4-methylpiperazin-1-yl)phenyl]amino}-5-oxo-5,6-dihydropyrido[4,3-d]pyrimidine-8-carboxylate

EXAMPLE 7A ethyl 2-(methylthio)-5-oxo-5,6-dihydropyrido[4,3-d]pyrimidine-8-carboxylate The title compound was prepared as described in Example 1C substituting allylamine with 1.4 equivalent of ammonia (7 molar in methanol). MS (ESI) m/z 266 (M+H)+.

EXAMPLE 7B ethyl 2-{[4-(4-methylpiperazin-1-yl)phenyl]amino}-5-oxo-5,6-dihydropyrido[4,3-d]pyrimidine-8-carboxylate A 2 dram vial was charged with Example 7A (30 mg, 0.113 mmol) and 4-(4-methylpiperazin-1-yl)aniline (76 mg, 0.396 mmol). The vial was capped and the solid mixture heated at 150° C. for 12 hours, then cooled to ambient temperature. The crude product was purified by Gilson® reverse-phase preparative HPLC (10-70% acetonitrile/water containing 0.2% TFA, linear gradient) to afford the title compound as a TFA salt. 1H NMR (300 MHz, DMSO-d6) δ 11.94 (d, J=6.6, 1H), 10.19 (s, 1H), 9.60 (brs, 1H), 9.08 (s, 1H), 8.17 (d, J=6.8, 1H), 8.12-7.97 (m, 2H), 6.98 (d, J=9.1, 2H), 4.34 (q, J=7.1, 2H), 3.84-3.75 (m, 2H), 3.59-3.47 (m, 2H), 3.28-3.06 (m, 2H), 2.98-2.83 (m, 5H), 1.32 (t, J=7.1, 3H). MS (ESI) m/z 409 (M+H)+.

EXAMPLE 8

6-benzyl-2-{[4-(4-methylpiperazin-1-yl)phenyl]amino}-8-phenylpyrido[4,3-d]pyrimidin-5(6H)-one

EXAMPLE 8A 6-benzyl-2-(methylthio)pyrido[4,3-d]pyrimidin-5(6H)-one

To a solution of Example 3A (267 mg, 1 mmol), and benzylamine (109 µl, 1.000 mmol), in 5 mL of ethanol was added concentrated aqueous HCl (10 µl, 0.329 mmol). The reaction mixture was then refluxed for 16 hours. After cooling to ambient temperature, the mixture was concentrated and then purified directly by silica gel flash chromatography (Isco®, Redi-Sep® column, 0-50% ethyl acetate/hexane, linear gradient) to give the title compound. MS (ESI) m/z 284 (M+H)+.

EXAMPLE 8B 6-benzyl-8-bromo-2-(methylthio)pyrido[4,3-d]pyrimidin-5(6H)-one

To a suspension of Example 8A (110 mg, 0.388 mmol) in acetic acid (1.5 ml, 26.2 mmol) at ambient temperature was slowly added a solution of bromine (0.020 ml, 0.388 mmol) in 0.5 mL of acetic acid. The reaction was stirred for 2 hours. Next, the reaction mixture was poured onto crushed ice and the mixture was transferred into a 30 mL separatory funnel and extracted with three portions of dichloromethane (10 mL each). The organic extracts were combined and washed with saturated aqueous sodium bicarbonate (2×25 mL), dried over sodium sulfate, filtered, and concentrated. The crude product was purified by silica gel flash chromatography (Isco®, Redi-Sep® column, 0-50% ethyl acetate/hexane, linear gradient) to give the title compound. MS (ESI) m/z 364 (M+H)+.

EXAMPLE 8C 6-benzyl-2-(methylthio)-8-phenylpyrido[4,3-d]pyrimidin-5(6H)-one

Example 8B (53 mg, 0.146 mmol), with phenylboronic acid (21.41 mg, 0.176 mmol) and tetrakis(triphenylphosphine)palladium(0) (11.83 mg, 10.24 µmol) were added into a 2 dram vial. The vial was capped with septa then evacuated and backfilled with nitrogen three times. N,N-dimethylformamide (1.643 ml), 2-propanol (0.657 ml) and potassium carbonate (0.219 ml, 0.439 mmol) were added and the mixture was evacuated and backfilled with nitrogen three times. The mixture was then stirred at 100° C. under nitrogen overnight. After cooling to ambient temperature, the reaction mixture was poured into a separatory funnel, and 10 mL of water was added and the aqueous layer was extracted with two portions of ethyl acetate (10 mL each). The organic fractions were combined and dried over magnesium sulfate, filtered and concentrated. The crude product was purified by silica gel flash chromatography (Isco®, Redi-Sep® column, 0-50% ethyl acetate/hexane, linear gradient) to give the title compound. MS (ESI) m/z 360 (M+H)+.

EXAMPLE 8D 6-benzyl-2-{[4-(4-methylpiperazin-1-yl)phenyl]amino}-8-phenylpyrido[4,3-d]pyrimidin-5(6H)-one The title compound was prepared as described in Example 7B, substituting Example 7A with Example 8C to afford the title compound as a TFA salt. $^1$H NMR (300 MHz, DMSO-$d_6$) δ 10.06 (brs, 1H), 9.59 (brs, 1H), 9.19 (s, 1H), 8.11 (s, 1H), 7.73-7.59 (m, 4H), 7.55-7.22 (m, 8H), 6.86 (d, J=8.7, 2H), 5.21 (s, 2H), 3.79-3.70 (m, 2H), 3.57-3.46 (m, 2H), 3.28-3.08 (m, 2H), 2.97-2.77 (m, 5H). MS (ESI) m/z 503 (M+H)+.

EXAMPLE 9

6-(2-methylbenzyl)-2-{[4-(4-methylpiperazin-1-yl)phenyl]amino}-8-phenylpyrido[4,3-d]pyrimidin-5(6H)-one

EXAMPLE 9A 2-(methylthio)pyrido[4,3-d]pyrimidin-5(6H)-one

To a solution of Example 3A in methanol (151 ml) was added ammonium chloride (5.66 g, 106 mmol). The pressure tube was then capped and the mixture was heated at 120° C. for 48 hours. After cooling to ambient temperature, a solid formed. The solid was filtered and washed with cold methanol to give the title compound. MS (ESI) m/z 194 (M+H)+.

EXAMPLE 9B 6-(2-methylbenzyl)-2-(methylthio)pyrido[4,3-d]pyrimidin-5(6H)-one A suspension of Example 9A (200 mg, 1.04 mmol), cesium carbonate (506 mg, 1.55 mmol), and 1-(bromomethyl)-2-methylbenzene (287 mg, 1.55 mmol) in anhydrous N,N-dimethylformamide (5 mL) was stirred at ambient temperature for 16 hours. Water (10 mL) was added to the reaction mixture and it was stirred for 20 minutes after which the precipitated solid was filtered and dried under vacuo to provide the title compound. MS (ESI) m/z 298 (M+H)+.

EXAMPLE 9C 8-bromo-6-(2-methylbenzyl)-2-(methylthio)pyrido[4,3-d]pyrimidin-5(6H)-one The title compound was prepared as described in Example 8B substituting Example 8A with Example 9B. The crude material obtained was purified by silica gel flash chromatography (Isco®, Redi-Sep® column, 10-40% ethyl acetate/hexane, linear gradient) to afford the title compound. MS (ESI) m/z 378 (M+H)+.

EXAMPLE 9D 6-(2-methylbenzyl)-2-(methylthio)-8-phenylpyrido[4,3-d]pyrimidin-5(6H)-one The title compound was prepared as described in Example 8C, substituting Example 8B with Example 9C. MS (ESI) m/z 374 (M+H)+.

EXAMPLE 9E 6-(2-methylbenzyl)-2-{[4-(4-methylpiperazin-1-yl)phenyl]amino}-8-phenylpyrido[4,3-d]pyrimidin-5(6H)-one To a high pressure tube was added Example 9D (32 mg, 0.09 mmol) and 4-(4-methylpiperazin-1-yl)aniline (131 mg, 0.69 mmol). The vessel was capped then heated at 190° C. for 4 hours and then cooled to ambient temperature. The crude residue was purified by silica gel flash chromatography (Isco®, Redi-Sep® column, 5% methanol in dichloromethane) to provide the title compound. The title compound was further purified by Gilson® reverse-phase preparative HPLC (10-70% acetonitrile/water containing 0.2% TFA, linear gradient) to yield the title compound as a TFA salt. $^1$H NMR (300 MHz, DMSO-$d_6$) 2.37 (3H, s), 2.83-2.96 (2H, m), 2.88 (3H, s), 3.10-3.25 (2H, m), 3.52 (2H, d, J=11.87 Hz), 3.75 (2H, d, J=13.56 Hz), 5.21 (2H, s), 6.87 (2H, d, J=8.82 Hz), 6.98 (1H, d, J=8.82 Hz), 7.10-7.26 (3H, m), 7.35-7.42 (1H, m), 7.48 (2H, t, J=7.46 Hz), 7.64 (2H, d, J=8.14 Hz), 7.68 (2H, d, J=8.48 Hz), 7.93 (1H, s), 9.21 (1H, s), 9.53 (1H, br s), 10.06 (1H, br s). MS (ESI) m/z 518 (M+H)+.

EXAMPLE 10

8-bromo-6-(2,6-difluorobenzyl)-2-{[4-(4-methylpiperazin-1-yl)phenyl]amino}pyrido[4,3-d]pyrimidin-5(6H)-one

EXAMPLE 10A 6-(2-methylbenzyl)-2-(methylthio)pyrido[4,3-d]pyrimidin-5(6H)-one The title compound was prepared as described in Example 9B, substituting 1-(bromomethyl)-2-methylbenzene with 2-(bromomethyl)-1,3-difluorobenzene. MS (ESI) m/z 320 (M+H)+.

EXAMPLE 10B 8-bromo-6-(2,6-difluorobenzyl)-2-(methylthio)pyrido[4,3-d]pyrimidin-5(6H)-one The title compound was prepared as described in Example 8B, substituting Example 8A with Example 10A. The crude material obtained was purified by silica gel flash chromatography (Isco®, Redi-Sep® column, 10-40% ethyl acetate/hexane, linear gradient) to afford the title compound. MS (ESI) m/z 398 (M+H)+.

EXAMPLE 10C 8-bromo-6-(2,6-difluorobenzyl)-2-{[4-(4-methylpiperazin-1-yl)phenyl]amino}pyrido[4,3-d]pyrimidin-5(6H)-one The title compound was prepared as described in Example 9E substituting Example 9D with Example 10B. The crude product was further purified by Gilson® reverse-phase preparative HPLC (10-70% acetonitrile/water containing 0.2% TFA, linear gradient) to yield the title product as a TFA salt. $^1$H NMR (300 MHz, DMSO-$d_6$) δ 10.29 (s, 1H), 9.58 (s, 1H), 9.01 (s, 1H), 8.43 (s, 1H), 8.08-7.86 (m, 2H), 7.51-7.35 (m, 1H), 7.19-7.05 (m, 2H), 7.01 (d, J=9.1, 2H), 5.20 (s, 2H), 3.84-3.75 (m, 2H), 3.56-3.48 (m, 2H), 3.26-3.09 (m, 2H), 2.99-2.81 (m, 5H). MS (ESI) m/z 543 (M+H)$^+$.

EXAMPLE 11

6-(3-methylbenzyl)-2-{[4-(4-methylpiperazin-1-yl)phenyl]amino}-8-phenylpyrido[4,3-d]pyrimidin-5(6H)-one

EXAMPLE 11A 6-(3-methylbenzyl)-2-(methylthio)pyrido[4,3-d]pyrimidin-5(6H)-one The title compound was prepared as described in Example 9B, substituting 1-(bromomethyl)-2-methylbenzene with 1-(bromomethyl)-3-methylbenzene. MS (ESI) m/z 298 (M+H)$^+$.

EXAMPLE 11B 8-bromo-6-(3-methylbenzyl)-2-(methylthio)pyrido[4,3-d]pyrimidin-5(6H)-one The title compound was prepared as described in Example 8B substituting Example 8A with Example 11A. The crude material obtained was purified by silica gel flash chromatography (Isco®, Redi-Sep® column, 10-40% ethyl acetate/hexane, linear gradient) to afford the title compound. MS (ESI) m/z 376 (M+H)$^+$.

EXAMPLE 11C 6-(3-methylbenzyl)-2-(methylthio)-8-phenylpyrido[4,3-d]pyrimidin-5(6H)-one The title compound was prepared as described in Example 8C, substituting Example 8B with Example 11B. MS (ESI) m/z 374 (M+H)$^+$.

EXAMPLE 11D 6-(3-methylbenzyl)-2-{[4-(4-methylpiperazin-1-yl)phenyl]amino}-8-phenylpyrido[4,3-d]pyrimidin-5(6H)-one The title compound was prepared as described in Example 9E, substituting Example 9D with Example 11C. The crude residue was purified by Gilson® reverse-phase preparative HPLC (10-70% acetonitrile/water containing 0.2% TFA, linear gradient) to yield the title product as a TFA salt. $^1$H NMR (300 MHz, methanol-$d_4$) δ 9.27 (s, 1H), 7.79 (s, 1H), 7.65 (d, J=9.0, 2H), 7.59 (dd, J=8.2, 1.4, 2H), 7.48-7.34 (m, 4H), 7.28-7.09 (m, 5H), 6.88 (d, J=8.9, 2H), 5.21 (s, 2H), 3.80-3.69 (m, 2H), 3.65-3.55 (m, 2H), 3.30-3.20 (m, 2H), 3.04-2.90 (m, 5H). MS (ESI) m/z 518 (M+H)$^+$.

EXAMPLE 12

6-[2-fluoro-6-(trifluoromethyl)benzyl]-2-{[4-(4-methylpiperazin-1-yl)phenyl]amino}-8-phenylpyrido[4,3-d]pyrimidin-5(6H)-one

EXAMPLE 12A 6-(2-fluoro-6-(trifluoromethyl)benzyl)-2-(methylthio)pyrido[4,3-d]pyrimidin-5(6H)-one The title compound was prepared as described in Example 9B, substituting 1-(bromomethyl)-2-methylbenzene with 2-(bromomethyl)-1-fluoro-3-(trifluoromethyl)benzene. MS (ESI) m/z 370 (M+H)$^+$.

EXAMPLE 12B 8-bromo-6-(2-fluoro-6-(trifluoromethyl)benzyl)-2-(methylthio)pyrido[4,3-d]pyrimidin-5(6H)-one The title compound was prepared as described in Example 8B substituting Example 8A with Example 12A. The crude material obtained was purified by silica gel flash chromatography (Isco®, Redi-Sep® column, 10-40% ethyl acetate/hexane, linear gradient) to afford the title compound. MS (ESI) m/z 448 (M+H)$^+$.

EXAMPLE 12C 6-(2-fluoro-6-(trifluoromethyl)benzyl)-2-(methylthio)-8-phenylpyrido[4,3-d]pyrimidin-5(6H)-one The title compound was prepared as described in Example 8C, substituting Example 8B for Example 12B. MS (ESI) m/z 446 (M+H)$^+$.

EXAMPLE 12D

6-[2-fluoro-6-(trifluoromethyl)benzyl]-2-{[4-(4-methylpiperazin-1-yl)phenyl]amino}-8-phenylpyrido[4,3-d]pyrimidin-5(6H)-one The title compound was prepared as described in Example 9E, substituting Example 9D with Example 12C. The crude residue was purified by Gilson® reverse-phase preparative HPLC (10-70% acetonitrile/water containing 0.2% TFA, linear gradient) to yield the title product as a TFA salt. $^1$H NMR (300 MHz, methanol-$d_4$) δ 9.24 (s, 1H), 7.71-7.58 (m, 5H), 7.56-7.32 (m, 8H), 6.88 (d, J=8.9, 2H), 5.48 (s, 2H), 3.79-3.70 (m, 2H), 3.65-3.56 (m, 2H), 3.27-3.20 (m, 2H), 3.03-2.89 (m, 5H). MS (ESI) m/z 589 (M+H)$^+$.

EXAMPLE 13

6-(2-fluorobenzyl)-2-{[4-(4-methylpiperazin-1-yl)phenyl]amino}-8-phenylpyrido[4,3-d]pyrimidin-5(6H)-one

EXAMPLE 13A 6-(2-fluorobenzyl)-2-(methylthio)pyrido[4,3-d]pyrimidin-5(6H)-one The title compound was prepared as described in Example 9B substituting 1-(bromomethyl)-2-methylbenzene with 1-(bromomethyl)-2-fluorobenzene. MS (ESI) m/z 302 (M+H)$^+$.

EXAMPLE 13B 8-bromo-6-(2-fluorobenzyl)-2-(methylthio)pyrido[4,3-d]pyrimidin-5(6H)-one The title compound was prepared as described in Example 8B, substituting Example 8A with Example 13A. The crude material obtained was purified by silica gel flash chromatography (Isco®, Redi-Sep® column, 10-40% ethyl acetate/hexane, linear gradient) to afford the title compound. MS (ESI) m/z 382 (M+H)$^+$.

EXAMPLE 13C 66-(2-fluorobenzyl)-2-(methylthio)-8-phenylpyrido[4,3-d]pyrimidin-5(6H)-one The title compound was prepared as described in Example 8C, substituting Example 8B for Example 13B. MS (ESI) m/z 378 (M+H)$^+$.

EXAMPLE 13D 6-(2-fluorobenzyl)-2-{[4-(4-methylpiperazin-1-yl)phenyl]amino}-8-phenylpyrido[4,3-d]pyrimidin-5(6H)-one The title compound was prepared as described in Example 9E, substituting Example 9D with Example 13C. The crude residue was purified by Gilson® reverse-phase preparative HPLC (10-70% acetonitrile/water containing 0.2% TFA, linear gradient) to yield the title product as a TFA salt. $^1$H NMR (300 MHz, methanol-d$_4$) δ 9.24 (s, 1H), 7.83 (s, 1H), 7.71-7.57 (m, 5H), 7.52-7.29 (m, 6H), 7.22-7.08 (m, 2H), 6.88 (d, J=8.8, 2H), 5.30 (s, 2H), 3.78-3.70 (m, 2H), 3.64-3.55 (m, 2H), 3.29-3.20 (m, 2H), 3.04-2.86 (m, 5H). MS (ESI) m/z 521 (M+H)$^+$.

EXAMPLE 14

2-{[2-{[4-(4-methylpiperazin-1-yl)phenyl]amino}-5-oxo-8-phenylpyrido[4,3-d]pyrimidin-6(5H)-yl]methyl}benzonitrile

EXAMPLE 14A 2-((2-(methylthio)-5-oxopyrido[4,3-d]pyrimidin-6(5H)-yl)methyl)benzonitrile The title compound was prepared as described in Example 9B, substituting 1-(bromomethyl)-2-methylbenzene with 2-(bromomethyl)benzonitrile. MS (ESI) m/z 309 (M+H)$^+$.

EXAMPLE 14B 2-((8-bromo-2-(methylthio)-5-oxopyrido[4,3-d]pyrimidin-6(5H)-yl)methyl)benzonitrile The title compound was prepared as described in Example 8B, substituting Example 8A with Example 14A. The crude material obtained was purified by silica gel flash chromatography (Isco®, Redi-Sep® column, 10-40% ethyl acetate/hexane, linear gradient) to afford the title compound. MS (ESI) m/z 387 (M+H)$^+$.

EXAMPLE 14C 2-((2-(methylthio)-5-oxo-8-phenylpyrido[4,3-d]pyrimidin-6(5H)-yl)methyl)benzonitrile The title compound was prepared as described in Example 8C, substituting Example 8B with Example 14B. MS (ESI) m/z 385 (M+H)$^+$.

EXAMPLE 14D

2-{[2-{[4-(4-methylpiperazin-1-yl)phenyl]amino}-5-oxo-8-phenylpyrido[4,3-d]pyrimidin-6(5H)-yl]methyl}benzonitrile The title compound was prepared as described in Example 9E, substituting Example 9D with Example 14C. The crude residue was purified by Gilson® reverse-phase preparative HPLC (10-70% acetonitrile/water containing 0.2% TFA, linear gradient) to yield the title product as a TFA salt. $^1$H NMR (300 MHz, methanol-d$_4$) δ 9.22 (s, 1H), 7.93 (s, 1H), 7.79 (dd, J=8.2, 1.3, 1H), 7.71-7.60 (m, 6H), 7.53-7.36 (m, 6H), 6.89 (d, J=8.8, 2H), 5.45 (s, 2H), 3.81-3.70 (m, 2H), 3.60 (d, 2H), 3.27-3.20 (m, 2H), 3.04-2.92 (m, 5H). MS (ESI) m/z 528 (M+H)$^+$.

EXAMPLE 15

6-(2-chlorobenzyl)-2-{[4-(4-methylpiperazin-1-yl)phenyl]amino}-8-phenylpyrido[4,3-d]pyrimidin-5(6H)-one

EXAMPLE 15A 6-(2-chlorobenzyl)-2-(methylthio)pyrido[4,3-d]pyrimidin-5(6H)-one The title compound was prepared as described in Example 9B, substituting 1-(bromomethyl)-2-methylbenzene with 1-(bromomethyl)-2-chlorobenzene. MS (ESI) m/z 319 (M+H)$^+$.

EXAMPLE 15B 8-bromo-6-(2-chlorobenzyl)-2-(methylthio)pyrido[4,3-d]pyrimidin-5(6H)-one The title compound was prepared as described in Example 8B, substituting Example 8A with Example 15A. The crude material obtained was purified by silica gel flash chromatography (Isco®, Redi-Sep® column, 10-40% ethyl acetate/hexane, linear gradient) to afford the title compound. MS (ESI) m/z 398 (M+H)$^+$.

EXAMPLE 15C 6-(2-chlorobenzyl)-2-(methylthio)-8-phenylpyrido[4,3-d]pyrimidin-5(6H)-one The title compound was prepared as described in Example 8C, substituting Example 8B for Example 15B. MS (ESI) m/z 394 (M+H)$^+$.

EXAMPLE 15D 6-(2-chlorobenzyl)-2-{[4-(4-methylpiperazin-1-yl)phenyl]amino}-8-phenylpyrido[4,3-d]pyrimidin-5(6H)-one The title compound was prepared as described in Example 9E, substituting Example 9D with Example 15C. The crude residue was purified by Gilson® reverse-phase preparative HPLC (10-70% acetonitrile/water containing 0.2% TFA, linear gradient) to yield the title product as a TFA salt. $^1$H NMR (300 MHz, methanol-$d_4$) δ 9.25 (s, 1H), 7.77 (s, 1H), 7.73-7.56 (m, 4H), 7.50-7.22 (m, 9H), 6.88 (d, J=8.7, 2H), 5.36 (s, 2H), 3.82-3.70 (m, 2H), 3.66-3.53 (m, 2H), 3.27-3.21 (m, 2H), 3.04-2.90 (m, 5H). MS (ESI) m/z 537 (M+H)$^+$.

EXAMPLE 16

6-(2,6-dichlorobenzyl)-2-{[4-(4-methylpiperazin-1-yl)phenyl]amino}-8-phenylpyrido[4,3-d]pyrimidin-5(6H)-one

EXAMPLE 16A 6-(2,6-dichlorobenzyl)-2-(methylthio)pyrido[4,3-d]pyrimidin-5(6H)-one The title compound was prepared as described in Example 9B, substituting 1-(bromomethyl)-2-methylbenzene with 2-(bromomethyl)-1,3-dichlorobenzene. MS (ESI) m/z 352 (M+H)$^+$.

EXAMPLE 16B 8-bromo-6-(2,6-dichlorobenzyl)-2-(methylthio)pyrido[4,3-d]pyrimidin-5(6H)-one The title compound was prepared as described in Example 8B, substituting Example 8A with Example 16A. The crude material obtained was purified by silica gel flash chromatography (Isco®, Redi-Sep® column, 10-40% ethyl acetate/hexane, linear gradient) to afford the title compound. MS (ESI) m/z 430 (M+H)$^+$.

EXAMPLE 16C 6-(2,6-dichlorobenzyl)-2-(methylthio)-8-phenylpyrido[4,3-d]pyrimidin-5(6H)-one The title compound was prepared as described in Example 8C, substituting Example 8B for Example 16B. MS (ESI) m/z 428 (M+H)$^+$.

EXAMPLE 16D 6-(2,6-dichlorobenzyl)-2-{[4-(4-methylpiperazin-1-yl)phenyl]amino}-8-phenylpyrido[4,3-d]pyrimidin-5(6H)-one The title compound was prepared as described in Example 9E, substituting Example 9D with Example 16C. The crude residue was purified by Gilson® reverse-phase preparative HPLC (10-70% acetonitrile/water containing 0.2% TFA, linear gradient) to yield the title product as a TFA salt. $^1$H NMR (300 MHz, CD$_3$OD) δ 2.90-3.06 (2H, m), 2.97 (3H, s), 3.21-3.40 (2H, m), 3.60 (2H, d, J=12.69 Hz), 3.74 (2H, d, J=13.48 Hz), 5.54 (2H, s), 6.87 (2H, d, J=8.73 Hz), 7.31-7.37 (2H, m), 7.38-7.45 (3H, m), 7.45-7.54 (4H, m), 7.64 (2H, d, J=8.73 Hz), 9.25 (1H, s). MS (ESI) m/z 572 (M+H)$^+$.

EXAMPLE 17

6-(2-chloro-4-fluorobenzyl)-2-{[4-(4-methylpiperazin-1-yl)phenyl]amino}-8-phenylpyrido[4,3-d]pyrimidin-5(6H)-one

EXAMPLE 17A 6-(2-chloro-4-fluorobenzyl)-2-(methylthio)pyrido[4,3-d]pyrimidin-5(6H)-one The title compound was prepared as described in Example 9B, substituting 1-(bromomethyl)-2-methylbenzene with 1-(bromomethyl)-2-chloro-4-fluorobenzene. MS (ESI) m/z 336 (M+H)$^+$.

EXAMPLE 17B 8-bromo-6-(2-chloro-4-fluorobenzyl)-2-(methylthio)pyrido[4,3-d]pyrimidin-5(6H)-one The title compound was prepared as described in Example 8B, substituting Example 8A with Example 17A. The crude material obtained was purified by silica gel flash chromatography (Isco®, Redi-Sep® column, 10-40% ethyl acetate/hexane, linear gradient) to afford the title compound. MS (ESI) m/z 416 (M+H)$^+$.

EXAMPLE 17C 6-(2-chloro-4-fluorobenzyl)-2-(methylthio)-8-phenylpyrido[4,3-d]pyrimidin-5(6H)-one The title compound was prepared as described in Example 8C, substituting Example 8B with Example 17B. MS (ESI) m/z 412 (M+H)$^+$.

EXAMPLE 17D 6-(2-chloro-4-fluorobenzyl)-2-{[4-(4-methylpiperazin-1-yl)phenyl]amino}-8-phenylpyrido[4,3-d]pyrimidin-5(6H)-one The title compound was prepared as described in Example 9E, substituting Example 9D with Example 17C. The crude residue was purified by Gilson® reverse-phase preparative HPLC (10-70% acetonitrile/water containing 0.2% TFA, linear gradient) to yield the title product as a TFA salt. $^1$H NMR (300 MHz, CD$_3$OD) δ 2.93-3.07 (2H, m), 2.98 (3H, s), 3.22-3.35 (2H, m), 3.56-3.64 (2H, m), 3.70-3.81 (2H, m), 5.32 (2H, s), 6.88 (2H, d, J=9.16 Hz), 7.05-7.13 (1H, m), 7.28-7.36 (2H, m), 7.37-7.41 (1H, m), 7.43-7.49 (2H, m), 7.57-7.63 (2H, m), 7.66 (2H, d, J=9.16 Hz), 7.79 (1H, s), 9.25 (1H, s). MS (ESI) m/z 556 (M+H)$^+$.

EXAMPLE 18

6-(4-tert-butylbenzyl)-2-{[4-(4-methylpiperazin-1-yl)phenyl]amino}-8-phenylpyrido[4,3-d]pyrimidin-5(6H)-one

EXAMPLE 18A 6-(4-tert-butylbenzyl)-2-(methylthio)pyrido[4,3-d]pyrimidin-5(6H)-one The title compound was prepared as described in Example 9B, substituting 1-(bromomethyl)-2-methylbenzene with 1-(bromomethyl)-4-tert-butylbenzene. MS (ESI) m/z 340 (M+H)$^+$.

EXAMPLE 18B 8-bromo-6-(4-tert-butylbenzyl)-2-(methylthio)pyrido[4,3-d]pyrimidin-5(6H)-one The title compound was prepared as described in Example 8B, substituting Example 8A with Example 18A. The crude material obtained was purified by silica gel flash chromatography (Isco®, Redi-Sep® column, 10-40% ethyl acetate/hexane, linear gradient) to afford the title compound. MS (ESI) m/z 420 (M+H)$^+$.

EXAMPLE 18C 6-(4-tert-butylbenzyl)-2-(methylthio)-8-phenylpyrido[4,3-d]pyrimidin-5(6H)-one The title compound was prepared as described in Example 8C, substituting Example 8B for Example 18B. MS (ESI) m/z 412 (M+H)$^+$.

EXAMPLE 18D 6-(4-tert-butylbenzyl)-2-{[4-(4-methylpiperazin-1-yl)phenyl]amino}-8-phenylpyrido[4,3-d]pyrimidin-5(6H)-one The title compound was prepared as described in Example 9E, substituting Example 9D with Example 18C. The crude residue was purified by Gilson® reverse-phase preparative HPLC (10-70% acetonitrile/water containing 0.2% TFA, linear gradient) to yield the title product as a TFA salt. $^1$H NMR (300 MHz, methanol-$d_4$) δ 9.26 (s, 1H), 7.81 (s, 1H), 7.69-7.56 (m, 4H), 7.50-7.27 (m, 9H), 6.88 (d, J=9.0, 2H), 5.22 (s, 2H), 3.80-3.69 (m, 2H), 3.65-3.56 (m, 2H), 3.28-3.22 (m, 2H), 3.04-2.90 (m, 5H), 1.29 (s, 9H). MS (ESI) m/z 560 (M+H)$^+$.

EXAMPLE 19

6-[2-fluoro-5-(trifluoromethyl)benzyl]-2-{[4-(4-methylpiperazin-1-yl)phenyl]amino}-8-phenylpyrido[4,3-d]pyrimidin-5(6H)-one

EXAMPLE 19A 6-(2-fluoro-5-(trifluoromethyl)benzyl)-2-(methylthio)pyrido[4,3-d]pyrimidin-5(6H)-one The title compound was prepared as described in Example 9B, substituting 1-(bromomethyl)-2-methylbenzene with 2-(bromomethyl)-1-fluoro-4-(trifluoromethyl)benzene. MS (ESI) m/z 370 (M+H)$^+$.

EXAMPLE 19B 8-bromo-6-(2-fluoro-5-(trifluoromethyl)benzyl)-2-(methylthio)pyrido[4,3-d]pyrimidin-5(6H)-one The title compound was prepared as described in Example 8B, substituting Example 8A with Example 19A. The crude material obtained was purified by silica gel flash chromatography (Isco®, Redi-Sep® column, 10-40% ethyl acetate/hexane, linear gradient) to afford the title compound. MS (ESI) m/z 448 (M+H)$^+$.

EXAMPLE 19C 6-(2-fluoro-5-(trifluoromethyl)benzyl)-2-(methylthio)-8-phenylpyrido[4,3-d]pyrimidin-5(6H)-one The title compound was prepared as described in Example 8C, substituting Example 8B with Example 19B. MS (ESI) m/z 446 (M+H)$^+$.

EXAMPLE 19D

6-[2-fluoro-5-(trifluoromethyl)benzyl]-2-{[4-(4-methylpiperazin-1-yl)phenyl]amino}-8-phenylpyrido[4,3-d]pyrimidin-5(6H)-one The title compound was prepared as described in Example 9E, substituting Example 9D with Example 19C. The crude residue was purified by Gilson® reverse-phase preparative HPLC (10-70% acetonitrile/water containing 0.2% TFA, linear gradient) to yield the title product as a TFA salt. $^1$H NMR (300 MHz, CD$_3$OD) δ 2.90-3.07 (2H, m), 2.98 (3H, s), 3.23-3.36 (2H, m), 3.60 (2H, d, J=11.50 Hz), 3.75 (2H, d, J=12.29 Hz), 5.33 (2H, s), 6.88 (2H, d, J=8.33 Hz), 7.31-7.43 (2H, m), 7.47 (2H, t, J=7.14 Hz), 7.61-7.71 (5H, m), 7.81 (1H, dd, J=6.74, 1.98 Hz), 7.91 (1H, s), 9.23 (1H, s). MS (ESI) m/z 589 (M+H)$^+$.

EXAMPLE 20 ethyl [2-{[4-(4-methylpiperazin-1-yl)phenyl]amino}-5-oxo-8-phenylpyrido[4,3-d]pyrimidin-6(5H)-yl]acetate

EXAMPLE 20A ethyl 2-(2-(methylthio)-5-oxopyrido[4,3-d]pyrimidin-6(5H)-yl)acetate The title compound was prepared as described in Example 9B substituting 1-(bromomethyl)-2-methylbenzene with ethyl 2-bromoacetate. MS (ESI) m/z 280 (M+H)$^+$.

EXAMPLE 20B ethyl 2-(8-bromo-2-(methylthio)-5-oxopyrido[4,3-d]pyrimidin-6(5H)-yl)acetate The title compound was prepared as described in Example 8B, substituting Example 8A with Example 20A. The crude material obtained was purified by silica gel flash chromatography (Isco®, Redi-Sep® column, 10-40% ethyl acetate/hexane, linear gradient) to afford the title compound. MS (ESI) m/z 358 (M+H)$^+$.

EXAMPLE 20C ethyl 2-(2-(methylthio)-5-oxo-8-phenylpyrido[4,3-d]pyrimidin-6(5H)-yl)acetate The title compound was prepared as described in Example 8C substituting Example 8B with Example 20B. MS (ESI) m/z 356 (M+H)$^+$.

EXAMPLE 20D ethyl [2-{[4-(4-methylpiperazin-1-yl)phenyl]amino}-5-oxo-8-phenylpyrido[4,3-d]pyrimidin-6(5H)-yl]acetate The title compound was prepared as described in Example 9E, substituting Example 9D with Example 20C. The crude residue was purified by Gilson® reverse-phase preparative HPLC (10-70% acetonitrile/water containing 0.2% TFA, linear gradient) to yield the title product as a TFA salt. $^1$H NMR (300 MHz, CD$_3$OD) δ 1.30 (3H, t, J=7.12 Hz), 2.93-3.08 (2H, m), 2.98 (3H, s), 3.24-3.38 (2H, m), 3.61 (2H, d, J=11.53 Hz), 3.70-3.82 (2H, m), 4.26 (2H, q, J=7.12 Hz), 4.81 (2H, s), 6.89 (2H, d, J=8.82 Hz), 7.35-7.42 (1H, m), 7.43-7.51 (2H, m), 7.61-7.69 (4H, m), 7.77 (1H, s), 9.23 (1H, s). MS (ESI) m/z 499 (M+H)$^+$.

EXAMPLE 21

6-(2,6-dichlorophenyl)-2-{[4-(4-methylpiperazin-1-yl)phenyl]amino}-8-[(phenylamino)methyl]pyrido[4,3-d]pyrimidin-5(6H)-one

EXAMPLE 21A 4-methyl-2-(methylthio)pyrimidine-5-carboxylic acid

Ethyl 4-methyl-2-(methylthio)pyrimidine-5-carboxylate (26 g, 122 mmol) was dissolved in tetrahydrofuran (245 ml) and LiOH (245 ml, 245 mmol) was added. Methanol (90 mL) was then added and the mixture was stirred at ambient temperature for 12 hours. Next, the mixture was quenched with 1 molar aqueous HCl (250 mL) and extracted with ethyl acetate (3×300 mL). The extracts were combined and washed with saturated aqueous brine, dried over magnesium sulfate, filtered and concentrated. Recrystallization (ethyl acetate/hexane) afforded the title compound. MS (ESI) m/z 185 (M+H)$^+$.

EXAMPLE 21B

N-(2,6-dichlorophenyl)-4-methyl-2-(methylthio)pyrimidine-5-carboxamide

Example 21A (23.0 g, 125 mmol) was dissolved in dioxane (400 mL) and thionyl chloride (10.93 ml, 150 mmol) followed by N,N-dimethylformamide (3 drops) were added. The mixture was stirred for 60 minutes at ambient temperature then 2,6-dichloroaniline (24.27 g, 150 mmol) was added. The mixture was stirred at 100° C. overnight. After concentrating in vacuo, the mixture was quenched with saturated aqueous sodium bicarbonate (300 mL) and ethyl acetate (300 mL) was added. The mixture was stirred vigorously for 10 minutes. The precipitate that formed was filtered and washed with diluted aqueous sodium bicarbonate and ethyl acetate to yield the title compound. The filtrate was then poured into a separatory funnel, the organic layer was removed and the aqueous layer was extracted with two portions of ethyl acetate (200 mL each). The organic layers were combined, washed with brine, dried over magnesium sulfate, filtered and concentrated. The material obtained was recrystallized (ethyl acetate/hexane) to provide an additional amount of the title compound. MS (ESI) m/z 328 (M+H)$^+$.

EXAMPLE 21C 6-(2,6-dichlorophenyl)-2-(methylthio)-5-oxo-5,6-dihydropyrido[4,3-d]pyrimidine-8-carbaldehyde To a solution of (chloromethylene)dimethyliminium chloride (17.93 g, 140 mmol) in N,N-dimethylformamide (70 mL) was added Example 21B (13.93 g, 42.4 mmol). After stirring at room temperature for 24 hours, the reaction mixture was poured into a separatory funnel, diluted with ethyl acetate (500 mL) and washed with aqueous sodium bicarbonate (300 mL), water (300 mL), and brine (300 mL), dried over sodium sulfate, filtered and concentrated. Purification by silica gel flash chromatography (Isco®, Redi-Sep® column, 3-65% ethyl acetate/hexane, linear gradient) afforded the title compound. MS (ESI) m/z 366 (M+H)$^+$.

EXAMPLE 21D 6-(2,6-dichlorophenyl)-2-(methylthio)-8-((phenylamino)methyl)pyrido[4,3-d]pyrimidin-5(6H)-one To a solution of Example 21C (75 mg, 0.21 mmol) and aniline (0.02 mL, 0.21 mmol) in 2-propanol (4 mL) was added sodium cyanoborohydride (15.4 mg, 0.25 mmol) and acetic acid (0.01 mL, 0.21 mmol). After stirring for 16 hours, the reaction mixture was concentrated in vacuo. The crude residue was purified by silica gel flash chromatography (Isco®, Redi-Sep® column, 25% ethyl acetate/hexane) to provide the title compound. MS (ESI) m/z 444 (M+H)$^+$.

EXAMPLE 21E 6-(2,6-dichlorophenyl)-2-{[4-(4-methylpiperazin-1-yl)phenyl]amino}-8-[(phenylamino)methyl]pyrido[4,3-d]pyrimidin-5(6H)-one The title compound was prepared as described in Example 9E, substituting Example 9D with Example 21D. The crude residue was purified by Gilson® reverse-phase preparative HPLC (10-70% acetonitrile/water containing 0.2% TFA, linear gradient) to yield the title compound as a TFA salt. $^1$H NMR (300 MHz, CD$_3$OD) δ 2.91-3.07 (2H, m), 2.98 (3H, s), 3.22-3.37 (2H, m), 3.56-3.66 (2H, m), 3.70-3.83 (2H, m), 4.48 (2H, s), 6.74-6.91 (5H, m), 7.19 (2H, t, J=7.97 Hz), 7.46-7.53 (2H, m), 7.57-7.64 (2H, m), 7.73 (2H, d, J=8.82 Hz), 9.22 (1H, s). MS (ESI) m/z 586 (M+H)$^+$.

EXAMPLE 22

6-(2,6-dichlorophenyl)-2-{[4-(4-methylpiperazin-1-yl)phenyl]amino}-8-{[(2,2,2-trifluoroethyl)amino]methyl}pyrido[4,3-d]pyrimidin-5(6H)-one

EXAMPLE 22A 6-(2,6-dichlorophenyl)-2-(methylthio)-8-((2,2,2-trifluoroethylamino)methyl)pyrido[4,3-d]pyrimidin-5(6H)-one To a solution of Example 21C (90 mg, 0.246 mmol) and 2,2,2-trifluoroethanamine (29.2 mg, 0.295 mmol) in isopropanol (4 mL) and N,N-dimethylformamide (0.2 mL) was added sodium cyanoborohydride (18.53 mg, 0.295 mmol) and acetic acid (0.014 ml, 0.246 mmol). The mixture was stirred at room temperature for 16 hours and then concentrated in vacuo. The residue was purified by flash chromatography (silica gel, 5-60% ethyl acetate/hexanes, linear gradient) to provide the title compound.

EXAMPLE 22B 6-(2,6-dichlorophenyl)-2-{[4-(4-methylpiperazin-1-yl)phenyl]amino}-8-{[(2,2,2-trifluoroethyl)amino]methyl}pyrido[4,3-d]pyrimidin-5(6H)-one Example 22A (39 mg, 0.087 mmol) and 4-(4-methylpiperazin-1-yl)aniline (166 mg, 0.868 mmol) were stirred at 180° C. for 16 hours. The reaction mixture was purified by reverse-phase HPLC performed on a Phenomenex Luna C8 AXIA column (30×75 mm, 100 Å) using a gradient of 10% to 95% acetonitrile: 10 mM ammonium acetate in water over 12 minutes at a flow rate of 50 mL/minutes to give the title compound. $^1$H NMR (400 MHz, DMSO-$d_6$) δ ppm 2.32 (s, 3 H) 2.55-2.63 (m, 4 H) 3.13-3.19 (m, 4 H) 3.24 (q, J=10.07 Hz, 2 H) 3.89 (s, 2 H) 6.92 (d, J=9.16 Hz, 2 H) 7.53 (s, 1 H) 7.56 (d, J=7.63 Hz, 1 H) 7.60-7.72 (m, 4 H) 9.11 (s, 1 H) 9.78 (s, 1 H). MS (ESI) m/e 592 (M+H)$^+$

EXAMPLE 23

8-(1,3-benzothiazol-2-yl)-6-(2,6-dichlorophenyl)-2-{[4-(4-methylpiperazin-1-yl)phenyl]amino}pyrido[4,3-d]pyrimidin-5(6H)-one

EXAMPLE 23A 8-(benzo[d]thiazol-2-yl)-6-(2,6-dichlorophenyl)-2-(methylthio)pyrido[4,3-d]pyrimidin-5(6H)-one A mixture of Example 21C (90 mg, 0.246 mmol) and 2-aminobenzenethiol (30.8 mg, 0.246 mmol) in 1,2-dichloroethane (3 ml) was stirred at room temperature for 3 days. The formed solid was filtered and washed with hexanes to provide the title compound.

EXAMPLE 23B 8-(1,3-benzothiazol-2-yl)-6-(2,6-dichlorophenyl)-2-{[4-(4-methylpiperazin-1-yl)phenyl]amino}pyrido[4,3-d]pyrimidin-5(6H)-one Example 23A (38 mg, 0.081 mmol) and 4-(4-methylpiperazin-1-yl)aniline (154 mg, 0.806 mmol) were well mixed and heated at 180° C. for 3 hours. The reaction mixture was purified by reverse-phase HPLC performed on a Phenomenex Luna C8 AXIA column (30×75 mm, 100 Å) using a gradient of 10% to 95% acetonitrile: 10 mM ammonium acetate in water over 12 minutes at a flow rate of 50 mL/minute to give the title compound. $^1$H NMR (400 MHz, DMSO-$d_6$) δ ppm 2.38 (s, 3 H) 2.63-2.72 (m, 4 H) 3.20-3.29 (m, 4 H) 7.00 (d, J=8.85 Hz, 2 H) 7.40 (t, J=7.63 Hz, 1 H) 7.45-7.52 (m, 1 H) 7.55 (d, J=9.16 Hz, 2 H) 7.58-7.65 (m, 1 H) 7.69-7.76 (m, 2 H) 7.93 (d, J=8.24 Hz, 2 H) 8.67 (s, 1 H) 9.22 (s, 1 H) 9.96 (s, 1 H). MS (ESI) m/e 614 (M+H)$^+$

EXAMPLE 24

8-(1H-benzimidazol-2-yl)-6-(2,6-dichlorophenyl)-2-{[4-(4-methylpiperazin-1-yl)phenyl]amino}pyrido[4,3-d]pyrimidin-5(6H)-one

EXAMPLE 24A 8-(1H-benzo[d]imidazol-2-yl)-6-(2,6-dichlorophenyl)-2-(methylthio)pyrido[4,3-d]pyrimidin-5(6H)-one A mixture of Example 21C (90 mg, 0.246 mmol) and 1,2-diaminobenzene (31.9 mg, 0.295 mmol) in 1,2-dichloroethane (3 ml) was stirred at room temperature for one day. The formed solid was filtered and washed with hexanes to give the title compound.

EXAMPLE 24B 8-(1H-benzimidazol-2-yl)-6-(2,6-dichlorophenyl)-2-{[4-(4-methylpiperazin-1-yl)phenyl]amino}pyrido[4,3-d]pyrimidin-5 (6H)-one Example 24A (43 mg, 0.095 mmol) and 4-(4-methylpiperazin-1-yl)aniline (181 mg, 0.946 mmol) was well mixed and heated at 180° C. for 3 hours. The reaction mixture was purified by reverse-phase HPLC performed on a Phenomenex Luna C8 AXIA column (30×75 mm, 100 Å) using a gradient of 10% to 95% acetonitrile: 10 mM ammonium acetate in water over 12 minutes at a flow rate of 50 mL/minutes to give the title compound. $^1$H NMR (400 MHz, DMSO-$d_6$) δ ppm 2.29 (s, 3 H) 2.51-2.58 (m, 4 H) 3.20-3.29 (m, 4 H) 7.05 (d, J=8.85 Hz, 2 H) 7.15-7.25 (m, 2 H) 7.36-7.45 (m, 1 H) 7.51 (d, J=8.85 Hz, 2 H) 7.54-7.65 (m, 2 H) 7.70-7.76 (m, 2 H) 8.59 (s, 1 H) 9.26 (s, 1 H) 10.10 (s, 1 H). MS (ESI) m/e 597 (M+H)$^+$

EXAMPLE 25

6-(2,6-dichlorophenyl)-8-ethenyl-2-{[4-(4-methylpiperazin-1-yl)phenyl]amino}pyrido[4,3-d]pyrimidin-5(6H)-one

EXAMPLE 25A 6-(2,6-dichlorophenyl)-2-(methylthio)-8-vinylpyrido[4,3-d]pyrimidin-5(6H)-one To a mixture of Example 21C (600 mg, 1.638 mmol) and methyltriphenylphosphonium bromide (702 mg, 1.966 mmol) in tetrahydrofuran (30 ml) at room temperature under nitrogen was added potassium t-butoxide solution (1.0 M in tetrahydrofuran, 2.130 ml, 2.130 mmol). The mixture was stirred at room temperature for 2 days. The resulting mixture was partitioned between dichloromethane and water. The organic phase was dried over sodium sulfate, filtered, and concentrated in vacuo. The residue was purified by flash chromatography (silica gel, 2~40% ethyl acetate/hexanes, linear gradient) to give the title compound.

EXAMPLE 25B 6-(2,6-dichlorophenyl)-8-ethenyl-2-{[4-(4-methylpiperazin-1-yl)phenyl]amino}pyrido[4,3-d]pyrimidin-5(6H)-one To a solution of Example 25A (50 mg, 0.137 mmol) in dichloromethane (1.4 mL) was added 3-chlorobenzoperoxoic acid (40.6 mg, 0.165 mmol). The mixture was stirred at room temperature for 20 minutes. Then 4-(4-methylpiperazin-1-yl)aniline (31.5 mg, 0.165 mmol) followed by TFA (21.15 µl, 0.275 mmol) was added. The mixture was stirred at room temperature for 2 days. The reaction mixture was concentrated in vacuo and purified by reverse-phase HPLC performed on a Phenomenex Luna C8 AXIA column (30×75 mm, 100 Å) using a gradient of 10% to 95% acetonitrile: 10 mM ammonium acetate in water over 12 minutes at a flow rate of 50 mL/minutes to give the title compound. $^1$H NMR (400 MHz, DMSO-$d_6$) δ ppm 2.24 (s, 3 H) 2.45-2.50 (m, 4 H) 3.10-3.16 (m, 4 H) 5.26 (dd, J=11.60, 1.53 Hz, 1 H) 6.00 (dd, J=17.70, 1.53 Hz, 1 H) 6.88-7.01 (m, 3 H) 7.53-7.59 (m, 1 H) 7.59-7.64 (m, 2 H) 7.65-7.70 (m, 2 H) 7.85 (s, 1 H) 9.12 (s, 1 H) 9.78 (s, 1 H). MS (ESI) m/e 507 (M+H)$^+$.

EXAMPLE 26

6-(2,6-dichlorophenyl)-8-ethyl-2-{[4-(4-methylpiperazin-1-yl)phenyl]amino}pyrido[4,3-d]pyrimidin-5(6H)-one A mixture of Example 25B (10 mg, 0.020 mmol) and 10% Pd—C (6 mg) in methanol (3 mL) was stirred under hydrogen for 3 hours. After removing the solid by filtration, the filtrate was concentrated in vacuo to give the title compound. $^1$H NMR (400 MHz, DMSO-$d_6$) δ ppm 1.22 (t, J=7.32 Hz, 3 H) 2.25 (s, 3 H) 2.44-2.54 (m, 4 H) 2.70 (q, J=7.43 Hz, 2 H) 3.09-3.17 (m, 4 H) 6.85-6.96 (m, 2 H) 7.38 (s, 1 H) 7.48-7.59 (m, 1 H) 7.62-7.76 (m, 4 H) 9.10 (s, 1 H) 9.73 (s, 1 H). MS (ESI) m/e 509 (M+H)$^+$.

EXAMPLE 27

6-(2,6-dichlorophenyl)-2-{[4-(4-methylpiperazin-1-yl)phenyl]amino}-5-oxo-5,6-dihydropyrido[4,3-d]pyrimidine-8-carbaldehyde To a solution of Example 21C (100 mg, 0.273 mmol) in dichloromethane (2 mL) was added 3-chlorobenzoperoxoic acid (74.0 mg, 0.300 mmol). After stirring at room temperature for 30 minutes, 4-(4-methylpiperazin-1-yl)aniline (62.7 mg, 0.328 mmol) was added. The mixture was stirred at room temperature for 16 hours and then at 35° C. for 4 hours. The resulting mixture was concentrated and purified by flash chromatography (silica gel, 10-40% ethyl acetate in methanol/CH$_2$Cl$_2$ (2/1), linear gradient) to give the title compound. $^1$H NMR (400 MHz, DMSO-$d_6$) δ ppm 2.24 (s, 3 H) 2.44-2.52 (m, 4 H) 3.10-3.18 (m, 4 H) 6.93 (d, J=8.85 Hz, 2 H) 7.56-7.62 (m, 1 H) 7.65-7.74 (m, 4 H) 8.35 (s, 1 H) 9.14 (s, 1 H) 10.03 (s, 1 H) 10.42 (s, 1 H). MS (ESI) m/e 509 (M+H)$^+$.

EXAMPLE 28

6-(2,6-dichlorophenyl)-8-methyl-2-{[4-(4-methylpiperazin-1-yl)phenyl]amino}pyrido[4,3-d]pyrimidin-5(6H)-one

EXAMPLE 28A ethyl 4-ethyl-2-(methylthio)pyrimidine-5-carboxylate

Ethyl 3-oxopentanoate (5.18 g, 35.9 mmol) was added to 1,1-dimethoxy-N,N-dimethylmethanamine (5.77 ml, 43.1 mmol) and the mixture was heated at 80° C. for 10 minutes. Next, methyl carbamimidothioate sulfate (4.99 g, 35.9 mmol) was added and the mixture was refluxed (~110° C.) for 16 hours. After cooling to ambient temperature the reaction mixture was diluted with ethyl acetate (~80 mL) and poured into a 250 mL separatory funnel. The organic layer was then washed with aqueous sodium bicarbonate (1×80 mL)), water (1×80 mL), brine (1×80 mL), dried over sodium sulfate, filtered and concentrated. The crude residue was purified by silica gel flash chromatography (Isco®, Redi-Sep® column, 0-30% ethyl acetate/hexane) to give the title compound. $^1$H NMR (300 MHz, CDCL$_3$) δ 8.92 (s, 1H), 4.38 (q, J=7.1, 2H), 3.14 (q, J=7.5, 2H), 2.60 (s, 3H), 1.40 (t, J=7.1, 3H), 1.29 (t, J=7.5, 3H).

EXAMPLE 28B 4-ethyl-2-(methylthio)pyrimidine-5-carboxylic acid

Example 28A (3.26 g, 14.41 mmol) was dissolved in 30 mL tetrahydrofuran (30 ml) and 1 molar aqueous LiOH (28.8 ml, 28.8 mmol) was added. Methanol (~10 mL) was then added and the mixture was stirred at ambient temperature for 3 hours. Next, the mixture was quenched with aqueous HCl (1M, 50 mL) and extracted with ethyl acetate (3×60 mL). The organic extracts were combined, washed with brine (60 mL), dried over magnesium sulfate, filtered and concentrated. Recrystallization (ethyl acetate/hexane) afforded the title compound. MS (ESI) m/z 199 (M+H)$^+$.

EXAMPLE 28C

N-(2,6-dichlorophenyl)-4-ethyl-2-(methylthio)pyrimidine-5-carboxamide

Example 28B (2.1 g, 10.59 mmol) was dissolved in dioxane (42.4 ml) and thionyl chloride (0.928 ml, 12.71 mmol) was slowly added followed by two drops of anhydrous N,N-dimethylformamide. The mixture was stirred for 30 minutes at ambient temperature then 2,6-dichloroaniline (2.060 g, 12.71 mmol) was added. The mixture was then stirred at 100° C. for 16 hours. After cooling to ambient temperature, the mixture was carefully quenched with saturated aqueous sodium bicarbonate (50 mL) and extracted with ethyl acetate (3×50 mL). The organic extracts were combined then washed with diluted aqueous sodium bicarbonate (80 mL), saturated aqueous brine (80 mL), dried over magnesium sulfate, filtered and concentrated. Purification by silica gel flash chromatography (Isco®, Redi-Sep® column, 0-85%, ethyl acetate/hexane gradient, linear gradient) followed by recrystallization (ethyl acetate/hexane) yielded the title compound. MS (ESI) m/z 342 (M+H)$^+$.

EXAMPLE 28D 6-(2,6-dichlorophenyl)-8-methyl-2-(methylthio)pyrido[4,3-d]pyrimidin-5(6H)-one An oven dried 50 mL round bottom flask, equipped with septa and stir bar, was charged with Example 28C (0.800 g, 2.338 mmol) and (chloromethylene)dimethyliminium chloride (0.898 g, 7.01 mmol). The flask was capped then evacuated and backfilled with nitrogen three times. Next, N,N-dimethylformamide (9.35 ml) was added and the mixture was stirred at 60° C. for 3 hours. The flask was then put into an ice bath and the mixture was quenched by careful addition of saturated aqueous sodium bicarbonate (60 mL). After diluting with 60 mL of ethyl acetate, the mixture was poured into a separatory funnel, the aqueous was removed and the organic layer was washed with saturated aqueous sodium bicarbonate (1×50 mL), diluted aqueous sodium bicarbonate (1×50 mL), brine (1×50 mL), dried over magnesium sulfate, filtered and concentrated. Purification by silica gel flash chromatography (Isco®, Redi-Sep® column, 0-100% ethyl acetate/hexane, linear gradient) afforded the title compound. MS (ESI) m/z 352 (M+H)$^+$.

EXAMPLE 28E 6-(2,6-dichlorophenyl)-8-methyl-2-{[4-(4-methylpiperazin-1-yl)phenyl]amino}pyrido[4,3-d]pyrimidin-5(6H)-one The title compound was prepared as described in Example 1D substituting Example 1C with Example 28D. The crude residue was purified by silica gel flash chromatography (Isco®, Redi-Sep® column, 0-50% 2:1 methanol/water in ethyl acetate, linear gradient) to yield the title product. $^1$H NMR (300 MHz, DMSO-d$_6$) δ 10.15 (s, 1H), 9.11 (s, 1H), 7.90-7.67 (m, 4H), 7.65-7.52 (m, 2H), 6.94 (d, J=9.1, 2H), 3.13-3.07 (m, 4H), 2.47-2.42 (m, J=4.9, 4H), 2.27-2.16 (m, 6H). MS (ESI) m/z 495 (M+H)$^+$.

EXAMPLE 29

6-(2,6-dichlorophenyl)-8-methyl-2-[(2'-methyl-2',3'-dihydro-1'H-spiro[cyclopropane-1,4'-isoquinolin]-7'-yl)amino]pyrido[4,3-d]pyrimidin-5(6H)-one The title compound was prepared as described in Example 1D substituting Example 1C with Example 28D and substituting 4-(4-methylpiperazin-1-yl)aniline with 2'-methyl-2',3'-dihydro-1'H-spiro[cyclopropane-1,4'-isoquinolin]-7'-amine The crude residue was purified by silica gel flash chromatography (Isco®, Redi-Sep® column, 0-40% 2:1 methanol/water in ethyl acetate, linear gradient) to yield the title product. $^1$H NMR (300 MHz, DMSO-d$_6$) δ 10.25 (s, 1H), 9.15 (s, 1H), 7.77-7.53 (m, 6H), 6.70 (d, J=8.6, 1H), 3.59 (s, 2H), 2.45 (s, 2H), 2.33 (s, 3H), 2.22 (s, 3H), 0.96-0.80 (m, 4H). MS (ESI) m/z 492 (M+H)$^+$.

EXAMPLE 30

6-(2,6-dichlorophenyl)-2-(2',3'-dihydro-1'H-spiro[cyclopropane-1,4'-isoquinolin]-7'-ylamino)-8-methylpyrido[4,3-d]pyrimidin-5(6H)-one The title compound was prepared as described in Example 1D, substituting Example 1C with Example 28D and substituting 4-(4-methylpiperazin-1-yl)aniline with tert-butyl 7'-amino-1'H-spiro[cyclopropane-1,4'-isoquinoline]-2'(3'H)-carboxylate. The crude residue was purified by silica gel flash chromatography (Isco®, Redi-Sep® column, 0-70% 2:1 methanol/water in ethyl acetate, linear gradient) to yield the title product. $^1$H NMR (300 MHz, DMSO-d$_6$) δ 10.26 (s, 1H), 9.15 (s, 1H), 7.81-7.52 (m, 6H), 6.74 (d, J=8.6, 1H), 4.04 (s, 2H), 2.86 (s, 2H), 2.23 (s, 3H), 1.00-0.75 (m, 4H). MS (ESI) m/z 478 (M+H)$^+$.

EXAMPLE 31

6-(2,6-dichlorophenyl)-2-{[2-(dimethylamino)-2,3-dihydro-1H-inden-5-yl]amino}-8-methylpyrido[4,3-d]pyrimidin-5(6H)-one The title compound was prepared as described in Example 1D, substituting Example 1C with Example 28D and substituting 4-(4-methylpiperazin-1-yl)aniline with N$^2$,N$^2$-dimethyl-2,3-dihydro-1H-indene-2,5-diamine. The crude residue was purified by silica gel flash chromatography (Isco®, Redi-Sep® column, 0-70% 2:1 methanol/water in ethyl acetate, linear gradient) to yield the title product. $^1$H NMR (300 MHz, DMSO-d$_6$) δ 10.26 (s, 1H), 9.15 (s, 1H), 7.79 (s, 1H), 7.77-7.70 (m, 2H), 7.68-7.53 (m, 3H), 7.16 (d, J=8.2, 1H), 3.08-2.90 (m, 2H), 2.85-2.66 (m, 2H), 2.24-2.20 (m, 9H). MS (ESI) m/z 480 (M+H)$^+$.

EXAMPLE 32

6-(2,6-dichlorophenyl)-8-ethenyl-2-[(2'-methyl-2',3'-dihydro-1'H-spiro[cyclopropane-1,4'-isoquinolin]-7'-yl)amino]pyrido[4,3-d]pyrimidin-5(6H)-one Example 25A (71 mg, 0.195 mmol) was dissolved in dichloromethane (2 mL) and 3-chlorobenzoperoxoic acid (48.1 mg, 0.195 mmol) was added. After stirring at room temperature for 30 minutes, 2'-methyl-2',3'-dihydro-1'H-spiro[cyclopropane-1,4'-isoquinolin]-7'-amine (44.0 mg, 0.234 mmol) followed by TFA (30.0 µl, 0.390 mmol) was added. The resulting mixture was stirred at 50° C. for 24 hours and then concentrated in vacuo. The residue was purified by reverse-phase preparative HPLC on a Phenomenex Luna C8(2) 5 um 100 Å AXIA column (30 mm×75 mm) using a gradient of acetonitrile (A) and 0.1% trifluoroacetic acid in water (B) at a flow rate of 50 mL/min (0-0.5 min 10% A, 0.5-7.0 min linear gradient 10-95% A, 7.0-10.0 min 95% A, 10.0-12.0 min linear gradient 95-10% A) to give of the title compound as a TFA salt. $^1$H NMR (400 MHz, DMSO-d$_6$) δ ppm 1.09-1.19 (m, 4 H) 2.96 (s, 3 H) 3.39 (s, 2 H) 4.50 (s, 2 H) 5.30-5.36 (m, 1 H) 6.03 (dd, J=17.85, 1.37 Hz, 1 H) 6.85-6.91 (m, 1 H) 6.98 (dd, J=17.70, 11.29 Hz, 1 H) 7.54-7.61 (m, 1 H) 7.69 (d, J=8.24 Hz, 4 H) 7.92 (s, 1 H) 9.20 (s, 1 H) 10.11 (s, 1 H). MS (ESI) m/e 504 (M+H)$^+$.

EXAMPLE 33

6,8-dimethyl-2-{[4-(4-methylpiperazin-1-yl)phenyl]amino}pyrido[4,3-d]pyrimidin-5(6H)-one Example 33A 6,8-dimethyl-2-(methylthio)pyrido[4,3-d]pyrimidin-5(6H)-one An oven dried 50 mL round bottom flask, equipped with septa and stir bar, was charged with Example 28C (0.800 g, 2.338 mmol) and (chloromethylene)dimethyliminium chloride (0.898 g, 7.01 mmol). The flask was capped then evacuated and backfilled with nitrogen three times. Next, N,N-dimethylformamide (9.35 ml) was added and the mixture was stirred at 60° C. for 3 hours. The flask was then put into an ice bath and the mixture was quenched by careful addition of saturated aqueous sodium bicarbonate (60 mL). After diluting with 60 mL of ethyl acetate, the mixture was poured into a separatory funnel, the aqueous layer was removed and the organic layer was washed with saturated aqueous sodium bicarbonate (1×50 mL), diluted aqueous sodium bicarbonate (1×50 mL), brine (1×50 mL), dried over magnesium sulfate, filtered and concentrated. Purification by silica gel flash chromatography (Isco®, Redi-Sep® column, 0-100% ethyl acetate/hexane, linear gradient) afforded the title compound. MS (ESI) m/z 222 (M+H)$^+$.

EXAMPLE 33B 6,8-dimethyl-2-{[4-(4-methylpiperazin-1-yl)phenyl]amino}pyrido[4,3-d]pyrimidin-5(6H)-one The title compound was prepared as described in Example 1D, substituting Example 1C with Example 33A. The crude residue was purified by Gilson® reverse-phase preparative HPLC (10-70% acetonitrile/water containing 0.2% TFA, linear gradient) to afford the title compound as a TFA salt. $^1$H NMR (300 MHz, DMSO-$d_6$) δ 10.01 (s, 1H), 9.60 (brs, 1H), 9.10 (s, 1H), 7.81 (d, J=7.2, 2H), 7.71 (s, 1H), 7.01 (d, J=9.1, 2H), 3.78 (s, 3H), 3.57-3.48 (m, 3H), 3.24-3.09 (m, 3H), 2.96-2.82 (m, 5H), 2.17 (s, 3H). MS (ESI) m/z 365 (M+H)$^+$.

EXAMPLE 34

6-(2,6-dichlorophenyl)-8-(1H-imidazol-2-yl)-2-{[4-(4-methylpiperazin-1-yl)phenyl]amino}pyrido[4,3-d]pyrimidin-5(6H)-one A mixture of Example 27 (30 mg, 0.059 mmol), oxalaldehyde solution (40% in H$_2$O) (85 mg, 0.589 mmol) and ammonia (7M in methanol, 421 µl, 2.94 mmol) was stirred at room temperature for 24 hours. The resulting mixture was concentrated in vacuo and purified by reverse-phase preparative HPLC on a Phenomenex Luna C8(2) 5 um 100 Å AXIA column (30 mm×75 mm) using a gradient of acetonitrile (A) and 0.1% trifluoroacetic acid in water (B) at a flow rate of 50 mL/min (0-0.5 min 10% A, 0.5-7.0 min linear gradient 10-95% A, 7.0-10.0 min 95% A, 10.0-12.0 min linear gradient 95-10% A) to give the title compound as a TFA salt. $^1$H NMR (400 MHz, DMSO-$d_6$) δ ppm 2.45-2.55 (m, 4 H) 2.88 (s, 3 H) 3.32-3.47 (m, 4 H) 7.04 (d, J=8.85 Hz, 2 H) 7.43 (s, 2 H) 7.54-7.66 (m, 3 H) 7.70-7.76 (m, 2 H) 8.45 (s, 1 H) 9.24 (s, 1 H) 10.17 (s, 1 H). MS (ESI) m/e 547 (M+H)$^+$.

EXAMPLE 35

6-(2,6-dichlorophenyl)-2-({4-[4-(dimethylamino)piperidin-1-yl]phenyl}amino)-8-methylpyrido[4,3-d]pyrimidin-5(6H)-one The title compound was prepared as described in Example 1D, substituting Example 1C with Example 28D and substituting 4-(4-methylpiperazin-1-yl)aniline with 1-(4-aminophenyl)-N,N-dimethylpiperidin-4-amine. The crude residue was purified by Gilson® reverse-phase preparative HPLC (10-70% acetonitrile/water containing 0.2% TFA, linear gradient) afforded the title compound as a TFA salt. $^1$H NMR (300 MHz, DMSO-$d_6$) δ 10.19 (s, 1H), 9.48 (s, 1H), 9.12 (s, 1H), 7.92-7.69 (m, 4H), 7.68-7.52 (m, 2H), 7.01 (d, J=9.1, 2H), 3.86-3.75 (m, 2H), 3.34-3.23 (m, 1H), 2.79 (d, J=5.0, 6H), 2.75-2.63 (m, 2H), 2.21 (s, 3H), 2.12-2.02 (m, 2H), 1.80-1.62 (m, 2H). MS (ESI) m/z 523 (M+H)$^+$.

EXAMPLE 36

6-(2,6-dichlorophenyl)-8-(difluoromethyl)-2-{[4-(4-methylpiperazin-1-yl)phenyl]amino}pyrido[4,3-d]pyrimidin-5(6H)-one

EXAMPLE 36A 6-(2,6-dichlorophenyl)-8-(difluoromethyl)-2-(methylthio)pyrido[4,3-d]pyrimidin-5(6H)-one To a solution of Example 21C (200 mg, 0.546 mmol) in dichloromethane (2 mL) was added diethylaminosulfur trifluoride (352 mg, 2.184 mmol). The mixture was stirred at room temperature for 3 hours. The resulting mixture was quenched with aqueous sodium bicarbonate solution (1M) and then extracted with dichloromethane. The organic phase was combined, dried over sodium sulfate, filtered, and concentrated. The residue was purified by flash chromatography (silica gel, 5-50% ethyl acetate/hexanes, linear gradient) to afford the title compound.

EXAMPLE 36B 6-(2,6-dichlorophenyl)-8-(difluoromethyl)-2-{[4-(4-methylpiperazin-1-yl)phenyl]amino}pyrido[4,3-d]pyrimidin-5(6H)-one Example 36A (50 mg, 0.129 mmol) was dissolved in dichloromethane (1.2 mL) and 3-chlorobenzoperoxoic acid (38.1 mg, 0.155 mmol) was added. The mixture was stirred at room temperature for 1 hour. Then 4-(4-methylpiperazin-1-yl)aniline (24.63 mg, 0.129 mmol) followed by TFA (19.85 µl, 0.258 mmol) was added. After stirring at room temperature for 24 hours, the reaction mixture was concentrated in vacuo and purified by reverse-phase HPLC performed on a Phenomenex Luna C8 AXIA column (30×75 mm, 100 Å) using a gradient of 10% to 95% acetonitrile: 10 mM ammonium acetate in water over 12 minutes at a flow rate of 50 mL/minutes to give the title compound. $^1$H NMR (400 MHz, DMSO-$d_6$) δ ppm 2.23 (s, 3 H) 2.43-2.54 (m, 4 H) 3.09-3.20 (m, 4 H) 6.91 (d, J=9.16 Hz, 2 H) 7.14 (t, J=54.78 Hz, 1 H) 7.53-7.61 (m, 1 H) 7.63-7.72 (m, 4 H) 8.04 (s, 1 H) 9.13 (s, 1 H) 9.95 (s, 1 H). MS (ESI) m/e 531 (M+H)$^+$.

EXAMPLE 37

6-(2,6-dichlorophenyl)-8-(fluoromethyl)-2-{[4-(4-methylpiperazin-1-yl)phenyl]amino}pyrido[4,3-d]pyrimidin-5(6H)-one

EXAMPLE 37A 6-(2,6-dichlorophenyl)-8-(hydroxymethyl)-2-(methylthio)pyrido[4,3-d]pyrimidin-5(6H)-one To a mixture of Example 21C (1000 mg, 2.73 mmol) and CeCl$_3$ heptahydrate (1017 mg, 2.73 mmol) in CH$_2$Cl$_2$/methanol (3/1, 20 mL) at 0° C. was added sodium borohydride (103 mg, 2.73 mmol). After stirring at 0° C. for 10 minutes, the reaction mixture was quenched with aqueous HCl (0.1M), and extracted with ethyl acetate. The organic layer was concentrated in vacuo and purified by flash chromatography (silica gel, 5-80% ethyl acetate/hexanes: linear gradient) to give the title compound.

EXAMPLE 37B 6-(2,6-dichlorophenyl)-8-(fluoromethyl)-2-(methylthio)pyrido[4,3-d]pyrimidin-5(6H)-one To a solution of Example 37A (56 mg, 0.152 mmol) in dichloromethane (2 mL) at 0° C. was added diethylaminosulfur trifluoride (73.5 mg, 0.456 mmol). The mixture was stirred at 0° C. for 1 hour and then neutralized with triethylamine (0.1 mL). The reaction mixture was concentrated and purified by flash chromatography (silica gel, 3-50% ethyl acetate/hexanes: linear gradient) to give the title compound.

EXAMPLE 37C 6-(2,6-dichlorophenyl)-8-(fluoromethyl)-2-{[4-(4-methylpiperazin-1-yl)phenyl]amino}pyrido[4,3-d]pyrimidin-5(6H)-one To a solution of Example 37B (25 mg, 0.068 mmol) in dichloromethane (1 mL) was added 3-chlorobenzoperoxoic acid (19.98 mg, 0.081 mmol). The mixture was stirred at room temperature for 20 minutes. Then 4-(4-methylpiperazin-1-yl)aniline (15.50 mg, 0.081 mmol) followed by TFA (10.40 µl, 0.135 mmol) was added. The mixture was concentrated in vacuo and acetonitrile (1.5 mL) was added. After stirring at 70° C. for 80 minutes, the reaction mixture was concentrated in vacuo and purified by reverse-phase HPLC performed on a Phenomenex Luna C8 AXIA column (30×75 mm, 100 Å) using a gradient of 10% to 95% acetonitrile: 10 mM ammonium acetate in water over 12 minutes at a flow rate of 50 mL/minutes to give the title compound. $^1$H NMR (400 MHz, DMSO-$d_6$) δ ppm 2.23 (s, 3 H) 2.42-2.52 (m, 4 H) 3.09-3.17 (m, 4 H) 5.48 (d, J=48.52 Hz, 2 H) 6.91 (d, J=9.16 Hz, 2 H) 7.52-7.60 (m, 1 H) 7.68 (d, J=7.63 Hz, 4 H) 7.92 (d, J=3.97 Hz, 1 H) 9.12 (s, 1 H) 9.87 (s, 1 H). MS (ESI) m/e 513 (M+H)$^+$.

EXAMPLE 38

6-(2,6-dichlorophenyl)-8-(hydroxymethyl)-2-{[4-(4-methylpiperazin-1-yl)phenyl]amino}pyrido[4,3-d]pyrimidin-5 (6H)-one To a solution of Example 37A (80 mg, 0.217 mmol) in dichloromethane (2 mL) was added 3-chlorobenzoperoxoic acid (53.6 mg, 0.217 mmol). The mixture was stirred at room temperature for 25 minutes. Then 4-(4-methylpiperazin-1-yl)aniline (45.7 mg, 0.239 mmol) was added. After stirring at 45° C. for 1 day, the reaction mixture was concentrated in vacuo and purified by reverse-phase HPLC performed on a Phenomenex Luna C8 AXIA column (30×75 mm, 100 Å) using a gradient of 10% to 95% acetonitrile: 10 mM ammonium acetate in water over 12 minutes at a flow rate of 50 mL/minutes to give the title compound. $^1$H NMR (400 MHz, DMSO-$d_6$) δ ppm 2.53 (s, 3 H) 2.80-2.93 (m, 4 H) 3.19-3.31 (m, 4 H) 4.67 (s, 2 H) 4.71-4.83 (m, 1 H) 6.90-7.01 (m, 2 H) 7.41 (s, 1 H) 7.50-7.60 (m, 1 H) 7.64-7.75 (m, 4 H) 9.12 (s, 1 H) 9.79 (s, 1 H). MS (ESI) m/e 511 (M+H)$^+$.

EXAMPLE 39

8-bromo-6-(cyclopropylmethyl)-2-{[4-(4-methylpiperazin-1-yl)phenyl]amino}pyrido[4,3-d]pyrimidin-5 (6H)-one

EXAMPLE 39A 6-(cyclopropylmethyl)-2-(methylthio)pyrido[4,3-d]pyrimidin-5(6H)-one To a mixture of Example 9A (200 mg, 1.03 mmol) and cesium carbonate (1012 mg, 3.11 mmol), in 10 mL N,N-dimethylformamide, was added (bromomethyl)cyclopropane (154 mg, 1.139 mmol). The reaction mixture was stirred at room temperature overnight and then diluted with water and extracted with ethyl acetate. The ethyl acetate phase was washed with water, brine, dried with MgSO$_4$ and filtered. The filtrate was concentrated to dryness and purified by silica-gel column chromatography with 0-20% ethyl acetate/hexane to afford the title compound. $^1$H NMR (300 MHz, DMSO-$d_6$) δ ppm 0.30-0.62 (m, J=28.48 Hz, 4 H) 1.07-1.53 (m, 1 H) 2.59 (s, 3 H) 3.82 (d, J=7.12 Hz, 2 H) 6.53 (d, J=7.46 Hz, 1 H) 8.04 (d, J=7.46 Hz, 1 H) 9.24 (s, 1 H). MS (ESI) m/z 248 (M+H)$^+$.

EXAMPLE 39B 8-bromo-6-(cyclopropylmethyl)-2-(methylthio)pyrido[4,3-d]pyrimidin-5(6H)-one To a solution of Example 39A (500 mg, 2.022 mmol), in 5 mL acetic acid, was slowly added Br$_2$ (0.104 ml, 2.022 mmol) in 1 mL acetic acid. The reaction mixture was stirred at room temperature for 3 hours then poured into 50 mL of ice-water. The reaction mixture was extracted with ethyl acetate (3×50 mL) and the organic extracts was combined then washed with saturated aqueous sodium bicarbonate solution (50 mL), water (50 mL), saturated aqueous brine (50 mL), dried over MgSO$_4$, filtered, and concentrated. The crude residue was purified by silica gel flash chromatography with 0-25% ethyl acetate/hexane to afford the title compound. $^1$H NMR (300 MHz, DMSO-$d_6$) δ ppm 0.25-0.69 (m, 4 H) 1.02-1.42 (m, 1 H) 2.65 (s, 3 H) 3.83 (d, J=7.46 Hz, 2 H) 8.51 (s, 1 H) 9.23 (s, 1 H). MS (ESI) m/z 326 (M+H)$^+$.

EXAMPLE 39C 8-bromo-6-(cyclopropylmethyl)-2-{[4-(4-methylpiperazin-1-yl)phenyl]amino}pyrido[4,3-d]pyrimidin-5 (6H)-one To a suspension of Example 39B (100 mg, 0.307 mmol), in 3 mL of toluene, was added m-CPBA (98 mg, 0.399 mmol). The reaction mixture was stirred at room temperature for 1 hour then 4-(4-methylpiperazin-1-yl)aniline (70.4 mg, 0.368 mmol) and N-ethyl-N-isopropylpropan-2-amine (119 mg, 0.91 mmol) were added. The reaction mixture was heated at 80° C. for 10 hours then cooled to room temperature, diluted with water and extracted with ethyl acetate. The ethyl acetate layer was washed with water, saturated aqueous brine, dried over MgSO$_4$ and filtered. The filtrate was concentrated to dryness and the residue was purified by silica gel flash chromatography with 0-5% methanol/CH$_2$Cl$_2$ (linear gradient) to obtain the title compound. $^1$H NMR (300 MHz, DMSO-$d_6$) δ ppm 0.28-0.60 (m, 4 H) 0.75-0.90 (m, 1 H) 2.22 (s, 3 H) 2.36-2.48 (m, 4 H) 2.98-3.17 (m, 4 H) 3.78 (d, J=7.14 Hz, 2 H) 6.93 (d, J=9.12 Hz, 2 H) 7.92 (d, J=5.55 Hz, 2 H) 8.35 (s, 1 H) 9.08 (s, 1 H) 10.22 (s, 1 H). MS (ESI) m/z 469 (M+H)$^+$.

EXAMPLE 40

8-(cyclohex-1-en-1-yl)-6-(cyclopropylmethyl)-2-{[4-(4-methylpiperazin-1-yl)phenyl]amino}pyrido[4,3-d]pyrimidin-5(6H)-one A mixture of 8-bromo-6-(cyclopropylmethyl)-2-(methylthio)pyrido[4,3-d]pyrimidin-5(6H)-one (25 mg, 0.053 mmol), cyclohexenylboronic acid (8.05 mg, 0.064 mmol), and cesium carbonate (35 mg, 0.106 mmol) in 1.5 mL dioxane and 0.5 mL water were degassed with nitrogen and then Pd(PPh$_3$)$_2$Cl$_2$ (3.7 mg, 0.005 mmol) was added. The reaction was heated in a Biotage Initiator® microwave reactor at 140° C. for 20 minutes. The reaction mixture was diluted with water and extracted with ethyl acetate. The ethyl acetate phase was washed with water, brine, dried with MgSO$_4$ and filtered. The filtrate was concentrated to dryness and the residue was purified by silica gel flash chromatography with 0-10% methanol/CH$_2$Cl$_2$ (linear gradient) to afford the title compound. $^1$H NMR (400 MHz, DMSO-d$_6$) δ ppm 0.30-0.56 (m, 4 H) 1.17-1.29 (m, 1 H) 1.53-1.83 (m, 4 H) 2.18 (d, J=3.05 Hz, 2 H) 2.25 (s, 3 H) 2.36-2.48 (m, 4 H) 2.91-3.19 (m, 6 H) 3.77 (d, J=7.02 Hz, 2 H) 5.87 (s, 1 H) 6.67-6.98 (m, 2 H) 7.55-7.81 (m, 3 H) 9.10 (s, 1 H) 9.93 (s, 1 H). MS (ESI) m/z 471 (M+H)$^+$.

EXAMPLE 41

8-(cyclopent-1-en-1-yl)-6-(cyclopropylmethyl)-2-{[4-(4-methylpiperazin-1-yl)phenyl]amino}pyrido[4,3-d]pyrimidin-5(6H)-one The title compound was prepared as described in Example 40 substituting cyclohexenylboronic acid with cyclopentenylboronic acid. The crude residue was purified by silica gel flash chromatography with 0-10% methanol/CH$_2$Cl$_2$ (linear gradient) to afford the title compound. $^1$H NMR (300 MHz, DMSO-d$_6$) δ ppm 0.26-0.66 (m, 4 H) 1.05-1.45 (m, 1 H) 1.75-2.07 (m, J=7.46 Hz, 2 H) 2.11-2.34 (m, 4 H) 2.40-2.55 (m, 5 H) 2.61-2.83 (m, 2 H) 3.03-3.19 (m, 4 H) 3.81 (d, J=7.12 Hz, 2 H) 6.92 (d, J=9.16 Hz, 3 H) 7.57 (d, J=8.82 Hz, 2 H) 7.72 (s, 1 H) 9.13 (s, 1 H) 9.86 (s, 1 H). MS (ESI) m/z 457 (M+H)$^+$.

EXAMPLE 42

8-bromo-6-ethyl-2-{[4-(4-methylpiperazin-1-yl)phenyl]amino}pyrido[4,3-d]pyrimidin-5(6H)-one

EXAMPLE 42A 6-ethyl-2-(methylthio)pyrido[4,3-d]pyrimidin-5(6H)-one

Iodoethane (0.747 ml, 9.34 mmol) was slowly added to a suspension of Example 9A (1.64 g, 8.49 mmol) and cesium carbonate (8.30 g, 25.5 mmol) in N,N-dimethylformamide (15 mL). After stirring at room temperature for 3 hours, the reaction mixture was diluted with water (80 mL) and extracted with three portions of ethyl acetate (75 mL each). The organic extracts were combined and washed with water (100 mL), saturated aqueous brine (100 mL), dried over MgSO$_4$ and filtered. The filtrate was concentrated to dryness and purified by silica gel flash chromatography with 0-20% ethyl acetate/hexane (linear gradient) to obtain to title compound. $^1$H NMR (300 MHz, DMSO-d$_6$) δ ppm 1.25 (t, J=7.14 Hz, 3 H) 2.59 (s, 3 H) 3.98 (q, J=7.14 Hz, 2 H) 6.53 (d, J=7.54 Hz, 1 H) 8.01 (d, J=7.54 Hz, 1 H) 9.23 (s, 1 H). MS (ESI) m/z 222 (M+H)$^+$.

EXAMPLE 42B 8-bromo-6-ethyl-2-(methylthio)pyrido[4,3-d]pyrimidin-5(6H)-one

To a solution of Example 42A (800 mg, 3.62 mmol) in 5 mL of acetic acid was slowly added a solution of bromine (578 mg, 3.62 mmol) in 1 mL acetic acid. The reaction mixture was stirred at room temperature for 3 hours and then quenched with a saturated aqueous Na$_2$S$_2$O$_3$ solution (30 mL). The reaction mixture was extracted with ethyl acetate (3×30 mL) and the organic extracts were combined, washed with water (50 mL), saturated aqueous brine (50 mL), dried over MgSO$_4$ and filtered. The filtrate was concentrated to dryness and purified by silica gel flash chromatography with 0-20% ethyl acetate/hexane (linear gradient) to afford the title compound. $^1$H NMR (300 MHz, DMSO-d$_6$) δ ppm 1.26 (t, J=7.14 Hz, 3 H) 2.65 (s, 3 H) 3.99 (q, J=7.01 Hz, 2 H) 8.50 (s, 1 H) 9.22 (s, 1 H). MS (ESI) m/z 302 (M+H)$^+$.

EXAMPLE 42C 8-bromo-6-ethyl-2-{[4-(4-methylpiperazin-1-yl)phenyl]amino}pyrido[4,3-d]pyrimidin-5(6H)-one To a suspension of Example 42B (530 mg, 1.77 mmol) in 15 mL of toluene was added meta-chloroperbenzoic acid (566 mg, 2.30 mmol). After stirring the reaction mixture at room temperature for 1 hour, 4-(4-methylpiperazin-1-yl) aniline (405 mg, 2.11 mmol) and N-ethyl-N-isopropylpropan-2-amine (685 mg, 5.30 mmol) were added. The reaction mixture was heated at 80° C. for 10 hours, then cooled to room temperature and diluted with water (80 mL). The aqueous mixture extracted with ethyl acetate (3×50 mL). The organic extracts were combined and washed with water (80 mL), saturated aqueous brine (80 mL), dried over MgSO$_4$ and filtered. The filtrate was concentrated to dryness and purified by silica gel flash chromatography with 0-5% methanol/CH$_2$Cl$_2$ (linear gradient) to afford the title compound. $^1$H NMR (300 MHz, DMSO-d$_6$) δ ppm 1.24 (t, J=6.94 Hz, 3 H) 2.22 (s, 3 H) 2.36-2.51 (m, 4 H) 2.91-3.19 (m, 4 H) 3.94 (q, J=7.01 Hz, 2 H) 6.93 (d, J=9.12 Hz, 2 H) 7.80-8.12 (m, 2 H) 8.33 (s, 1 H) 9.07 (s, 1 H) 10.21 (s, 1 H). MS (ESI) m/z 443 (M+H)$^+$.

EXAMPLE 43

8-(cyclohex-1-en-1-yl)-6-ethyl-2-{[4-(4-methylpiperazin-1-yl)phenyl]amino}pyrido[4,3-d]pyrimidin-5(6H)-one A mixture of Example 42C (130 mg, 0.293 mmol), cyclohexenylboronic acid (44 mg, 0.35 mmol), and cesium carbonate (191 mg, 0.586 mmol) in dioxane (1.5 mL) and water (0.5 mL) was purged with nitrogen and then Pd(PPh$_3$)$_2$Cl$_2$ (21 mg, 0.029) was added. The mixture was heated in a Biotage Initiator® microwave reactor at 140° C. for 20 minutes. The reaction was diluted with water (25 mL) and extracted with ethyl acetate (3×25 mL). The organic extracts were combined and washed with water (40 mL) and saturated aqueous brine (40 mL), dried over MgSO$_4$ and filtered. The filtrate was concentrated to dryness and purified by silica gel flash chromatography with 0-4% methanol/CH$_2$Cl$_2$ (linear gradient) to afford the title compound. $^1$H NMR (300 MHz, DMSO-d$_6$) δ ppm 1.23 (t, J=6.94 Hz, 3 H) 1.56-1.89 (m, 4 H) 2.05-2.30 (m, 5 H) 2.35-2.52 (m, 6 H) 2.92-3.19 (m, 4 H) 3.93 (q, J=7.14 Hz, 2 H) 5.87 (s, 1 H) 6.88 (d, J=8.72 Hz, 2 H) 7.37-7.89 (m, 3 H) 9.09 (s, 1 H) 9.90 (s, 1 H). MS (ESI) m/z 445 (M+H)$^+$.

EXAMPLE 44

2-{[4-(4-methylpiperazin-1-yl)phenyl]amino}-6-phenylpyrimido[5,4-c]quinolin-5 (6H)-one

EXAMPLE 44A 1-phenylquinoline-2,4(1H,3H)-dione

To a solution of 2-(phenylamino)benzoic acid (3 g, 14.07 mmol) in acetic acid (10 ml) under nitrogen was added acetic anhydride (10 ml, 14.07 mmol) dropwise. The mixture was heated at 120° C. for 6 hours. The reaction mixture was poured onto ice, concentrated in vacuo, neutralized with aqueous NaOH (1M) and extracted with dichloromethane. The organic phase was washed with brine, dried over sodium sulfate, filtered, and concentrated. The residue was purified by flash chromatography (silica gel, 0-6% methanol/CH$_2$Cl$_2$, linear gradient) to afford the title compound.

EXAMPLE 44B 2-(methylthio)-6-phenylpyrimido[5,4-c]quinolin-5(6H)-one

A mixture of Example 44A (0.800 g, 3.37 mmol) and 1,1-dimethoxy-N,N-dimethylmethanamine (2.247 ml, 16.86 mmol) was heated at 60° C. for 1 day and then concentrated in vacuo. To the mixture were added S-methylisothiourea sulfate (0.334 g, 3.71 mmol) and acetic acid (11.5 ml). After stirring at 110° C. for 50 minutes, the reaction mixture was concentrated in vacuo and purified by flash chromatography (silica gel, 7-70% ethyl acetate/hexanes, linear gradient) to give the title compound.

EXAMPLE 44C

2-{[4-(4-methylpiperazin-1-yl)phenyl]amino}-6-phenylpyrimido[5,4-c]quinolin-5 (6H)-one 3-Chlorobenzoperoxoic acid (67.6 mg, 0.274 mmol) was added to a solution of Example 44B (73 mg, 0.229 mmol) in toluene (5 mL) and the mixture was stirred at room temperature for 1 day. To the mixture were added 4-(4-methylpiperazin-1-yl)aniline (52.5 mg, 0.274 mmol) and Hunig's base (108 µl, 0.617 mmol) and the mixture was stirred at 40° C. for 3 days. The reaction mixture was concentrated in vacuo and purified by reverse-phase HPLC performed on a Phenomenex Luna C8 AXIA column (30×75 mm, 100 Å) using a gradient of 10% to 95% acetonitrile: 10 mM ammonium acetate in water over 12 minutes at a flow rate of 50 mL/minutes to give the title compound. $^1$H NMR (300 MHz, DMSO-d$_6$) δ ppm 2.24 (s, 3 H) 2.43-2.54 (m, 4 H) 3.07-3.21 (m, 4 H) 6.55 (d, J=7.80 Hz, 1 H) 7.02 (d, J=9.16 Hz, 2 H) 7.28-7.47 (m, 3 H) 7.50-7.86 (m, 6 H) 8.61 (dd, J=7.80, 1.36 Hz, 1 H) 9.18 (s, 1 H) 10.20 (s, 1 H). MS (ESI) m/e 463 (M+H)$^+$.

EXAMPLE 45

6-(2-chlorophenyl)-2-{[4-(4-methylpiperazin-1-yl)phenyl]amino}pyrimido[5,4-c]quinolin-5(6H)-one

EXAMPLE 45A 1-(2-chlorophenyl)quinoline-2,4(1H,3H)-dione

The title compound was prepared as described in Example 44A substituting 2-(phenylamino)benzoic acid with 2-(2-chlorophenylamino)benzoic acid.

EXAMPLE 45B 6-(2-chlorophenyl)-2-(methylthio)pyrimido[5,4-c]quinolin-5(6H)-one A mixture of Example 45A (1.285 g, 4.73 mmol) and 1,1-dimethoxy-N,N-dimethylmethanamine (3.15 ml, 23.65 mmol) was heated at 65° C. for 2 hours and then concentrated in vacuo. To the mixture were added S-methylisothiourea sulfate (1.445 g, 5.20 mmol) and acetic acid (16 ml). After stirring at 110° C. for 16 hours, the reaction mixture was concentrated in vacuo. The residue was purified by flash chromatography (silica gel, 10-70% ethyl acetate/hexanes, linear gradient) to give the title compound.

EXAMPLE 45C 6-(2-chlorophenyl)-2-{[4-(4-methylpiperazin-1-yl)phenyl]amino}pyrimido[5,4-c]quinolin-5(6H)-one 3-Chlorobenzoperoxoic acid (223 mg, 0.904 mmol) was added to a solution of Example 45B (200 mg, 0.565 mmol) in toluene (10 mL) and the mixture was stirred at room temperature for 1 day. To the reaction mixture were added 4-(4-methylpiperazin-1-yl)aniline (130 mg, 0.678 mmol) and Hunig's base (267 µl, 1.526 mmol) and the mixture was stirred at 40° C. for 3 days. The resulting mixture was concentrated in vacuo and purified by reverse-phase HPLC performed on a Phenomenex Luna C8 AXIA column (30×75 mm, 100 Å) using a gradient of 10% to 95% acetonitrile: 10 mM ammonium acetate in water over 12 minutes at a flow rate of 50 mL/minutes to give the title compound. $^1$H NMR (300 MHz, DMSO-d$_6$) δ ppm 2.24 (s, 3 H) 2.40-2.55 (m, 4 H) 3.06-3.19 (m, 4 H) 6.47 (d, J=7.80 Hz, 1 H) 7.02 (d, J=8.82 Hz, 2 H) 7.41 (t, J=7.46 Hz, 1 H) 7.53-7.88 (m, 7 H) 8.62 (d, J=7.80 Hz, 1 H) 9.20 (s, 1 H) 10.26 (s, 1 H). MS (ESI) m/e 497 (M+H)$^+$.

EXAMPLE 46

2-{[4-(4-methylpiperazin-1-yl)phenyl]amino}-6-phenylpyrimido[5,4-c][1,8]naphthyridin-5(6H)-one

EXAMPLE 46A 2-(phenylamino)nicotinic acid

2-Chloronicotinic acid (1.03 g), aniline (1.2 mL), and p-toluenesulfonic acid (112 mg) were refluxed in 10 mL water for 18 hours. After cooling to room temperature, the resultant solid was collected by filtration, washed with water, and dried under high vacuum at 70° C. to provide the title compound. MS (ESI) m/e 215.1 (M+H)$^+$.

EXAMPLE 46B methyl 2-(phenylamino)nicotinate

To a solution of Example 46A (946 mg) and triethylamine (0.65 mL) in acetone (10 mL) was added chloroacetonitrile (0.3 mL). The reaction mixture was refluxed for 18 hours. After cooling to room temperature, the reaction mixture was concentrated in vacuo and the residue was dissolved in anhydrous methanol, to which sodium methoxide was added (95%, 9 mg). The reaction was refluxed again for 12 hours then concentrated. The crude product was purified on silica gel (40 g) eluting with 1:10 ethyl acetate:hexanes to give the title compound. MS (ESI) m/e 229.1 (M+H)$^+$.

EXAMPLE 46C methyl 2-(N-phenylacetamido)nicotinate

Example 46B (770 mg) was refluxed in acetic acid for 24 hours. After cooling to room temperature and concentrating in vacuo, the residue was partitioned between ethyl acetate and water. The organic phase was dried over magnesium sulfate, filtered, and concentrated to give the title compound which was used without any further purification. MS (ESI) m/e 270.9 (M+H)$^+$.

EXAMPLE 46D 4-hydroxy-1-phenyl-1,8-naphthyridin-2(1H)-one

To Example 46C (930 mg) in m-xylene (10 mL) was added potassium t-butoxide (95%, 810 mg). The reaction was refluxed for 18 hours. After cooling to room temperature, 40 mL water was added. The layers were separated, and the aqueous phase was acidified to pH 6 with glacial acetic acid. The resultant solid was collected, washed with water, and dried at room temperature for 24 hours. The title compound was used without any further purification. $^1$H NMR (400 MHz, DMSO-d$_6$) δ 11.60 (br s, 1H), 8.40 (m, 1H), 8.27 (m, 1H), 7.48 (m, 3H), 7.24 (m, 3H), 5.94 (s, 1H). MS (ESI) m/e 239.2 (M+H)$^+$.

EXAMPLE 46E 3-((dimethylamino)methylene)-1-phenyl-1,8-naphthyridine-2,4(1H,3H)-dione Example 46D (617 mg) and N,N-dimethylformamide dimethyl acetal (6 mL) were heated to 65° C. for 5 hours. The reaction was concentrated to give the title compound which was used without any further purification.

EXAMPLE 46F 2-(methylthio)-6-phenylpyrimido[5,4-c][1,8]naphthyridin-5(6H)-one Example 46E (703 mg) and S-methylisothiourea sulfate (841 mg) were dissolved in acetic acid (15 mL) and the mixture was heated at 100° C. for 24 hours. The reaction mixture was concentrated to give a solid which was washed with methanol and used in the next step without any further purification. MS (ESI) m/e 321.3 (M+H)$^+$.

EXAMPLE 46G 2-(methylsulfinyl)-6-phenylpyrimido[5,4-c][1,8]naphthyridin-5(6H)-one and 2-(methylsulfonyl)-6-phenylpyrimido[5,4-c][1,8]naphthyridin-5(6H)-one Example 46F (1.16 g) in methanol (75 mL) was added to a solution of potassium peroxymonosulfate (22 g) in 200 mL 5:1 methanol:water. The reaction was stirred for 24 hours at room temperature then concentrated in vacuo. The residue was partitioned between ethyl acetate and water. The organic phase was dried over magnesium sulfate, filtered, and concentrated. The title product was obtained as a mixture of the sulfoxide and the sulfone which was used in the next step without any further purification.

EXAMPLE 46H

2-{[4-(4-methylpiperazin-1-yl)phenyl]amino}-6-phenylpyrimido[5,4-c][1,8]naphthyridin-5(6H)-one Example 46G (78 mg), 4-(4-methylpiperazino)aniline (55 mg) and trifluoroacetic acid (1 μL) were stirred in acetonitrile (2 mL) at 70° C. for 24 hours. The crude product was purified by RP-HPLC (5 μm Sunfire 50×250 mm) using a gradient elution of 10/90 to 50/50 acetonitrile/0.1% TFA in water over 30 minutes at 254 nm to give the title compound. $^1$H NMR (400 MHz, DMSO-d$_6$, 90° C.) δ 10.00 (s, 1H), 9.20 (s, 1H), 8.85 (d, 1H), 8.49 (m, 1H), 7.78 (d, 2H), 7.42 (m, 4H), 7.29 (m, 2H), 7.06 (d, 2H), 3.42 (m, 4H), 3.11 (m, 4H), 2.86 (s, 3H). MS (ESI) m/e 464.3 (M+H)$^+$.

EXAMPLE 47

6-(2-chlorophenyl)-2-{[4-(4-methylpiperazin-1-yl)phenyl]amino}pyrimido[5,4-c][1,8]naphthyridin-5(6H)-one

EXAMPLE 47A 2-(2-chlorophenylamino)nicotinic acid

The title compound was prepared as described in Example 46A, substituting 2-chloroaniline for aniline. MS (ESI) m/e 249.1 (M+H)$^+$.

EXAMPLE 47B methyl 2-(2-chlorophenylamino)nicotinate

The title compound was prepared as described in Example 46B, substituting Example 47A for Example 46A. MS (ESI) m/e 263.1 (M+H)$^+$.

EXAMPLE 47C methyl 2-(N-(2-chlorophenyl)acetamido)nicotinate

The title compound was prepared as described in Example 46C, substituting Example 47B for Example 46B. MS (ESI) m/e 304.9 (M+H)$^+$.

EXAMPLE 47D 1-(2-chlorophenyl)-4-hydroxy-1,8-naphthyridin-2(1H)-one

The title compound was prepared as described in Example 46D, substituting Example 47C for Example 46C. $^1$H NMR (500 MHz, DMSO-d$_6$) δ 12.01 (br s, 1H), 8.42 (m, 1H), 8.29 (m, 1H), 7.63 (m, 1H), 7.48 (m, 2H), 7.40 (m, 1H), 7.30 (m, 1H), 5.97 (s, 1H). MS (ESI) m/e 273.2 (M+H)$^+$.

EXAMPLE 47E 1-(2-chlorophenyl)-3-((dimethylamino)methylene)-1,8-naphthyridine-2,4(1H,3H)-dione The title compound was prepared as described in Example 46E, substituting Example 47D for Example 46D.

EXAMPLE 47F 6-(2-chlorophenyl)-2-(methylthio)pyrimido[5,4-c][1,8]naphthyridin-5(6H)-one The title compound was prepared as described in Example 46F, substituting Example 47E for Example 46E. MS (ESI) m/e 355.2 (M+H)$^+$.

EXAMPLE 47G 6-(2-chlorophenyl)-2-(methylsulfinyl)pyrimido[5,4-c][1,8]naphthyridin-5(6H)-one and 6-(2-chlorophenyl)-2-(methylsulfonyl)pyrimido[5,4-c][1,8]naphthyridin-5(6H)-one The title compound was prepared as described in Example 46G, substituting Example 47F for Example 46F.

EXAMPLE 47H 6-(2-chlorophenyl)-2-{[4-(4-methylpiperazin-1-yl)phenyl]amino}pyrimido[5,4-c][1,8]naphthyridin-5(6H)-one The compound was prepared as described in Example 46H, substituting Example 47G for Example 46G. $^1$H NMR (400 MHz, DMSO-$d_6$, 90° C.) δ 10.05 (s, 1H), 9.21 (s, 1H), 8.86 (d, 1H), 8.51 (m, 1H), 7.76 (d, 2H), 7.65 (m, 1H), 7.47 (m, 4H), 7.06 (d, 2H), 3.40 (m, 4H), 3.27 (m, 4H), 2.81 (s, 3H). MS (ESI) m/e 498.2 (M+H)$^+$.

EXAMPLE 48

2-amino-6-(2,6-dichlorophenyl)-8-(1H-imidazol-2-yl)pyrido[4,3-d]pyrimidin-5(6H)-one A mixture of Example 21C (160 mg, 0.437 mmol), oxalaldehyde (1268 mg, 8.74 mmol) and ammonia (7M in methanol, 6.24 mL, 43.7 mmol) was stirred at room temperature overnight. The reaction mixture was concentrated in vacuo and purified by flash chromatography (silica gel, 10-100% ethyl acetate/hexanes, linear gradient) to give the title compound. $^1$H NMR (400 MHz, DMSO-$d_6$) ppm 6.98 (s, 1 H) 7.20 (s, 1 H) 7.51-7.66 (m, 3 H) 7.66-7.74 (m, 2 H) 8.21 (s, 1 H) 9.11 (s, 1 H) 12.45 (s, 1 H). MS (ESI) m/e 404 (M+H)$^+$.

EXAMPLE 49

6-(2,6-dichlorophenyl)-2-{[2-(dimethylamino)-2,3-dihydro-1H-inden-5-yl]amino}-8-ethenylpyrido[4,3-d]pyrimidin-5(6H)-one Example 25A (80 mg, 0.220 mmol) was dissolved in dichloromethane (2 mL), and 3-chlorobenzoperoxoic acid (54.1 mg, 0.220 mmol) was added. After stirring at room temperature for 30 minutes, N$^2$,N$^2$-dimethyl-2,3-dihydro-1H-indene-2,5-diamine (42.6 mg, 0.242 mmol) followed by TFA (33.8 µl, 0.440 mmol) was added. The resulting mixture was stirred at 50° C. for 24 hours and was concentrated in vacuo. The residue was purified by reverse-phase preparative HPLC on a Phenomenex Luna C8(2) 5 um 100 Å AXIA column (30 mm×75 mm) using a gradient of acetonitrile (A) and 0.1% trifluoroacetic acid in water (B) at a flow rate of 50 mL/min (0-0.5 min 10% A, 0.5-7.0 min linear gradient 10-95% A, 7.0-10.0 min 95% A, 10.0-12.0 min linear gradient 95-10% A) to afford the title compound as a TFA salt. $^1$H NMR (400 MHz, dimethylsulfoxide-$d_6$) δ 10.03 (s, 1H), 9.19 (s, 1H), 7.91 (s, 1H), 7.76 (s, 1H), 7.71-7.68 (m, 2H), 7.64 (dd, J=8.2, 1.8, 1H), 7.58 (dd, J=8.9, 7.4, 1H), 7.25 (d, J=8.3, 1H), 6.98 (dd, J=17.8, 11.5, 1H), 6.10-5.99 (m, 1H), 5.35-5.25 (m, 1H), 4.16 (p, J=7.7, 1H), 3.40-3.27 (m, 3H), 3.25-3.17 (m, 2H), 2.85 (s, 6H). MS (ESI) m/z 492 (M+H)$^+$.

EXAMPLE 50

6-(2,6-dichlorophenyl)-2-({4-[4-(dimethylamino)piperidin-1-yl]phenyl}amino)-8-ethenylpyrido[4,3-d]pyrimidin-5(6H)-one The title compound was prepared as described in Example 49, substituting N$^2$,N$^2$-dimethyl-2,3-dihydro-1H-indene-2,5-diamine with 1-(4-aminophenyl)-N,N-dimethylpiperidin-4-amine The crude residue was purified by Gilson® reverse-phase preparative HPLC (10-70% acetonitrile/water containing 0.2% TFA, linear gradient) and afforded the title compound as a TFA salt. $^1$H NMR (400 MHz, dimethylsulfoxide-$d_6$) δ 9.82 (s, 1H), 9.14 (s, 1H), 7.87 (s, 1H), 7.72-7.62 (m, 4H), 7.57 (dd, J=8.8, 7.4, 1H), 7.03-6.92 (m, 3H), 6.02 (dd, J=17.8, 1.4, 1H), 5.27 (dd, J=11.4, 1.4, 1H), 3.87-3.77 (m, 2H), 3.37-3.27 (m, 1H), 2.81 (s, 6H), 2.79-2.72 (m, 2H), 2.13-2.04 (m, 2H), 1.80-1.68 (m, 2H). MS (ESI) m/z 535 (M+H)$^+$.

EXAMPLE 51

6-(2,6-dichlorophenyl)-2-(2',3'-dihydro-1'H-spiro[cyclopropane-1,4'-isoquinolin]-7'-ylamino)-8-ethenylpyrido[4,3-d]pyrimidin-5(6H)-one Example 25A (50 mg, 0.137 mmol) was dissolved in dichloromethane (2 mL) and 3-chlorobenzoperoxoic acid (33.8 mg, 0.137 mmol) was added. The reaction mixture was stirred at ambient temperature for 45 minutes and tert-butyl 7'-amino-1'H-spiro[cyclopropane-1,4'-isoquinoline]-2'(3'H)-carboxylate (41.4 mg, 0.151 mmol) was added. The reaction mixture was stirred at room temperature overnight. Next, the reaction mixture was concentrated and the residue was purified by silica gel flash chromatography (20-80% ethyl acetate/hexane, linear gradient) to afford the boc protected intermediate. The intermediate (51 mg, 0.086 mmol)) was treated with a trifluoroacetic acid-dichloromethane mixture (0.4 mL, 1:1) at room temperature for 1 hour and was concentrated to afford the title compound as a TFA salt. $^1$H NMR (400 MHz, dimethylsulfoxide-$d_6$) δ 10.08 (s, 1H), 9.20 (s, 2H), 7.91 (s, 1H), 7.75-7.63 (m, 4H), 7.58 (dd, J=8.8, 7.4, 1H), 6.99 (dd, J=17.8, 11.4, 1H), 6.87 (d, J=8.6, 1H), 6.03 (dd, J=17.8, 1.4, 1H), 5.31 (dd, J=11.4, 1.4, 1H), 4.40 (s, 2H), 3.28 (s, 2H), 1.21-1.02 (m, 4H). MS (ESI) m/z 490 (M+H)$^+$.

EXAMPLE 52

6-(2,6-dichlorophenyl)-8-ethenyl-2-{[4-(hexahydropyrrolo[3,4-c]pyrrol-2(1H)-yl)phenyl]amino}pyrido[4,3-d]pyrimidin-5(6H)-one The title compound was prepared as described in Example 51, substituting tert-butyl 7'-amino-1'H-spiro[cyclopropane-1,4'-isoquinoline]-2'(3'H)-carboxylate with tert-butyl 5-(4-aminophenyl)hexahydropyrrolo[3,4-c]pyrrole-2(1H)-carboxylate. The title compound was obtained as a TFA salt. $^1$H NMR (400 MHz, dimethylsulfoxide-$d_6$) δ 9.74 (s, 1H), 9.12 (s, 1H), 8.82 (brs, 2H), 7.85 (s, 1H), 7.71-7.65 (m, 2H), 7.64-7.53 (m, 3H), 6.96 (dd, J=17.8, 11.4, 1H), 6.70 (d, J=8.9, 2H), 6.02 (dd, J=17.8, 1.3, 1H), 5.26 (dd, J=11.4, 1.4, 1H), 3.54-3.46 (m, 2H), 3.37-3.27 (m, 6H). MS (ESI) m/z 519 (M+H)$^+$.

EXAMPLE 53

6-(2,6-dichlorophenyl)-8-(hydroxymethyl)-2-[(2'-methyl-2',3'-dihydro-1'H-spiro[cyclopropane-1,4'-isoquinolin]-7'-yl)amino]pyrido[4,3-d]pyrimidin-5(6H)-one Example 37A (80 mg, 0.217 mmol) was dissolved in 2 mL of dichloromethane and 3-chlorobenzoperoxoic acid (53.6 mg, 0.217 mmol) was added. The reaction mixture was stirred at ambient temperature for 30 minutes then 2'-methyl-2',3'-dihydro-1'H-spiro[cyclopropane-1,4'-isoquinolin]-7'-amine (45.0 mg, 0.239 mmol) and TFA (33.5 µl, 0.435 mmol) were added. The mixture stirred at 50° C. for 3 hours. After cooling to ambient temperature, the reaction mixture was concentrated and the residue was purified with reverse-phase preparative HPLC on a Phenomenex Luna C8(2) 5 um 100 Å AXIA column (30 mm×75 mm) using a gradient of acetonitrile (A) and 0.1% ammonium acetate buffer in water (B) at a flow rate of 50 mL/min (0-0.5 min 10% A, 0.5-7.0 min linear gradient 10-95% A, 7.0-10.0 min 95% A, 10.0-12.0 min linear gradient 95-10% A) to afford the title compound. $^1$H NMR (400 MHz, dimethylsulfoxide-$d_6$) δ 9.98 (s, 1H), 9.17 (s, 1H), 7.70-7.67 (m, 3H), 7.64 (dd, J=8.6, 2.1, 1H), 7.59-7.54 (m, 1H), 7.46 (s, 1H), 6.78 (d, J=8.6, 1H), 4.69 (s, 2H), 4.10 (s, 2H), 2.89 (s, 2H), 2.68 (s, 3H), 1.09-0.95 (m, 4H). MS (ESI) m/z 508 (M+H)$^+$.

EXAMPLE 54

6-(2,6-dichlorophenyl)-2-{[2-(dimethylamino)-2,3-dihydro-1H-inden-5-yl]amino}-8-(hydroxymethyl)pyrido[4,3-d]pyrimidin-5(6H)-one The title compound was prepared as described in Example 53, substituting 2'-methyl-2',3'-dihydro-1'H-spiro[cyclopropane-1,4'-isoquinolin]-7'-amine with $N^2,N^2$-dimethyl-2,3-dihydro-1H-indene-2,5-diamine to afford the title compound. $^1$H NMR (400 MHz, dimethylsulfoxide-$d_6$) δ 9.72 (s, 1H), 8.93 (s, 1H), 7.54 (s, 1H), 7.47-7.38 (m, 3H), 7.32 (dd, J=8.8, 7.4, 1H), 7.20 (s, 1H), 6.98 (d, J=8.2, 1H), 4.57 (brs, 1H), 4.45 (s, 2H), 3.78-3.65 (m, 1H), 3.09-2.87 (m, 4H), 2.49 (s, 6H). MS (ESI) m/z 496 (M+H)$^+$.

EXAMPLE 55

6-(2,6-dichlorophenyl)-2-({4-[4-(dimethylamino)piperidin-1-yl]phenyl}amino)-8-(hydroxymethyl)pyrido[4,3-d]pyrimidin-5(6H)-one The title compound was prepared as described in Example 53, substituting 2'-methyl-2',3'-dihydro-1'H-spiro[cyclopropane-1,4'-isoquinolin]-7'-amine with 1-(4-aminophenyl)-N,N-dimethylpiperidin-4-amine to afford the title compound. $^1$H NMR (400 MHz, dimethylsulfoxide-$d_6$) δ 9.92 (s, 1H), 9.28 (s, 1H), 7.87-7.81 (m, 4H), 7.73 (dd, J=8.8, 7.4, 1H), 7.57 (s, 1H), 7.10 (d, J=9.1, 2H), 4.85 (s, 2H), 3.90-3.81 (m, 2H), 2.92-2.82 (m, 2H), 2.62-2.53 (m, 1H), 2.49 (s, 6H), 2.09-2.01 (m, 2H), 1.80-1.67 (m, 2H). MS (ESI) m/z 539 (M+H)$^+$.

EXAMPLE 56

6-(2,6-dichlorophenyl)-2-[(4,4-dimethyl-1,2,3,4-tetrahydroisoquinolin-7-yl)amino]-8-ethenylpyrido[4,3-d]pyrimidin-5(6H)-one The title compound was prepared as described in Example 51, substituting tert-butyl 7'-amino-1'H-spiro[cyclopropane-1,4'-isoquinoline]-2'(3'H)-carboxylate with tert-butyl 7-amino-4,4-dimethyl-3,4-dihydroisoquinoline-2(1H)-carboxylate. The title compound was obtained as a TFA salt. $^1$H NMR (400 MHz, dimethylsulfoxide-$d_6$) δ 10.09 (s, 1H), 9.21 (s, 1H), 7.92 (s, 1H), 7.73-7.69 (m, 3H), 7.68 (s, 1H), 7.58 (dd, J=8.8, 7.4, 1H), 7.48-7.44 (m, 1H), 7.00 (dd, J=17.8, 11.4, 1H), 6.03 (dd, J=17.8, 1.5, 1H), 5.32 (dd, J=11.4, 1.4, 1H), 4.30 (s, 2H), 3.25 (s, 2H), 1.39 (s, 6H). MS (ESI) m/z 492 (M+H)$^+$.

EXAMPLE 57

6-(2,6-dichlorophenyl)-2-(2',3'-dihydro-1'H-spiro[cyclopropane-1,4'-isoquinolin]-7'-ylamino)-8-(hydroxymethyl)pyrido[4,3-d]pyrimidin-5(6H)-one Example 37A (80 mg, 0.217 mmol) was dissolved in 2 mL of dichloromethane and 3-chlorobenzoperoxoic acid (53.6 mg, 0.217 mmol) was added. The reaction mixture was stirred at ambient temperature for 30 minutes then tert-butyl 7'-amino-1'H-spiro[cyclopropane-1,4'-isoquinoline]-2'(3'H)-carboxylate (65.6 mg, 0.239 mmol) was added. The reaction mixture was stirred at ambient temperature for 16 hours. The boc protected intermediate that precipitated was filtered and treated with a trifluoroacetic acid-dichloromethane mixture (0.4 mL, 1:1) at room temperature for 1 hour. After concentration, the resulting crude residue was purified by reverse-phase preparative HPLC on a Phenomenex Luna C8(2) 5 um 100 Å AXIA column (30 mm×75 mm) using a gradient of acetonitrile (A) and 0.1% trifluoroacetic acid in water (B) at a flow rate of 50 mL/min (0-0.5 min 10% A, 0.5-7.0 min linear gradient 10-95% A, 7.0-10.0 min 95% A, 10.0-12.0 min linear gradient 95-10% A) to afford the title compound as a TFA salt. $^1$H NMR (400 MHz, dimethylsulfoxide-$d_6$) δ 10.05 (s, 1H), 9.17 (s, 1H), 9.14 (brs, 2H), 7.82 (d, J=1.9, 1H), 7.72-7.63 (m, 3H), 7.56 (dd, J=8.8, 7.4, 1H), 7.47 (s, 1H), 6.86 (d, J=8.6, 1H), 4.69 (s, 2H), 4.39 (s, 2H), 3.27 (s, 2H), 1.16-1.04 (m, 4H). MS (ESI) m/z 494 (M+H)$^+$.

EXAMPLE 58

6-(2,6-dichlorophenyl)-2-[(4,4-dimethyl-1,2,3,4-tetrahydroisoquinolin-7-yl)amino]-8-(hydroxymethyl)pyrido[4,3-d]pyrimidin-5(6H)-one The title compound was prepared as described in Example 57, substituting tert-butyl 7'-amino-1'H-spiro[cyclopropane-1,4'-isoquinoline]-2'(3'H)-carboxylate with tert-butyl 7-amino-4,4-dimethyl-3,4-dihydroisoquinoline-2(1H)-carboxylate to afford the title compound. $^1$H NMR (400 MHz, dimethylsulfoxide-$d_6$) δ 10.07 (s, 1H), 9.18 (s, 1H), 9.02 (brs, 2H), 7.80 (d, J=2.0, 1H), 7.73 (dd, J=8.6, 2.2, 1H), 7.70-7.66 (m, 2H), 7.56 (dd, J=8.8, 7.4, 1H), 7.48 (s, 1H), 7.44 (d, J=8.6, 1H), 4.70 (s, 2H), 4.29 (s, 2H), 3.24 (s, 2H), 1.38 (s, 6H). MS (ESI) m/z 496 (M+H)$^+$.

EXAMPLE 59

6-(2,6-dichlorophenyl)-8-ethenyl-2-(1,2,3,4-tetrahydroisoquinolin-6-ylamino)pyrido[4,3-d]pyrimidin-5(6H)-one The title compound was prepared as described in Example 51, substituting tert-butyl 7'-amino-1'H-spiro[cyclopropane-1,4'-isoquinoline]-2'(3'H)-carboxylate with tert-butyl 6-amino-3,4-dihydroisoquinoline-2(1H)-carboxylate to afford the title compound as a TFA salt. $^1$H NMR (400 MHz, dimethylsulfoxide-$d_6$) δ 9.87 (s, 1H), 9.16 (s, 1H), 7.87 (s, 1H), 7.70-7.65 (m, 2H), 7.60-7.53 (m, 2H), 7.48 (dd, J=8.2, 2.0, 1H), 7.01-6.92 (m, 2H), 6.04 (dd, J=17.8, 1.4, 1H), 5.29 (dd, J=11.4, 1.4, 1H), 3.86 (s, 2H), 3.02-2.97 (m, 2H), 2.74-2.69 (m, 2H). MS (ESI) m/z 464 (M+H)$^+$.

EXAMPLE 60

6-(2-chloro-6-fluorophenyl)-2-({4-[4-(dimethyl-amino)piperidin-1-yl]phenyl}amino)-8-ethe-nylpyrido[4,3-d]pyrimidin-5(6H)-one

EXAMPLE 60A

N-(2-chloro-6-fluorophenyl)-4-methyl-2-(methyl-thio)pyrimidine-5-carboxamide

Example 21A (16.5 g, 90 mmol) was dissolved in a mixture of 358 mL of dioxane and thionyl chloride (7.84 ml, 107 mmol). Four drops of N,N-dimethylformamide were added. The reaction mixture was stirred for 30 minutes at ambient temperature then 2-chloro-6-fluoroaniline (17.41 g, 120 mmol) was added and the reaction mixture was stirred at 100° C. overnight. After cooling to room temperature, the reaction mixture was slowly poured into a 1000 mL separatory funnel containing 400 mL of saturated aqueous sodium bicarbonate and the mixture extracted with ethyl acetate (3×200 mL). The combined organic extracts were washed with aqueous sodium bicarbonate (10% wt, 200 mL) and saturated aqueous brine (200 mL), dried over magnesium sulfate, filtered and concentrated. Purification by silica gel flash chromatography (Isco®, Redi-Sep® column, 2-85% ethyl acetate/hexane, linear gradient) yielded the title compound.

EXAMPLE 60B 6-(2-chloro-6-fluorophenyl)-2-(methylthio)-5-oxo-5,6-dihydropyrido[4,3-d]pyrimidine-8-carbaldehyde A 500 mL round bottom flask, equipped with stir bar and septa, was charged with Example 60A (13.19 g, 42.3 mmol) and N-(chloromethylene)-N-methylmethanaminium (16.25 g, 127 mmol). The flask was capped then evacuated and backfilled with nitrogen twice. N,N-dimethylformamide (169 ml) was added and the reaction mixture was stirred at ambient temperature overnight. The reaction mixture was cooled to 0° C. and quenched by careful addition of 200 mL of aqueous sodium bicarbonate. To the reaction mixture was added 250 mL of ethyl acetate and the reaction mixture was poured into a separatory funnel The aqueous layer was removed and the organic layer was washed with saturated aqueous sodium bicarbonate (200 mL) and saturated aqueous brine (200 mL), dried over magnesium sulfate, filtered and concentrated. Purification by silica gel flash chromatography (Isco®, Redi-Sep® column, 2-60% ethyl acetate/hexane, linear gradient) afforded the title compound.

EXAMPLE 60C 6-(2-chloro-6-fluorophenyl)-2-(methylthio)-8-vi-nylpyrido[4,3-d]pyrimidin-5(6H)-one To a mixture of Example 60B (1000 mg, 2.86 mmol) and methyltriphenylphosphonium bromide (1226 mg, 3.43 mmol) in tetrahydrofuran (50 ml) at room temperature under nitrogen was added potassium tert-butoxide (1.0 molar in tetrahydrofuran, 3.72 ml, 3.72 mmol). The resulting mixture was stirred at room temperature for 24 hours and was concentrated. The residue was redissolved in dichloromethane (125 mL), poured into a 250 mL separatory funnel and washed with 100 mL of water and 100 mL of saturated aqueous brine, dried over sodium sulfate, filtered, and was concentrated. The residue was purified by silica gel flash chromatography (Isco®, Redi-Sep® column, 2-40% ethyl acetate/hexane, linear gradient) to afford the title compound.

EXAMPLE 60D 6-(2-chloro-6-fluorophenyl)-2-({4-[4-(dimethyl-amino)piperidin-1-yl]phenyl}amino)-8-ethe-nylpyrido[4,3-d]pyrimidin-5(6H)-one Example 60C (60 mg, 0.173 mmol) was dissolved in dichloromethane (2 mL) and 3-chlorobenzoperoxoic acid (42.5 mg, 0.173 mmol) was added. After stirring at room temperature for 30 minutes, 1-(4-aminophenyl)-N,N-dim-ethylpiperidin-4-amine (41.6 mg, 0.190 mmol) was added and the resulting mixture was stirred at 60° C. for 24 hours and was concentrated in vacuo. The residue was purified by reverse-phase preparative HPLC on a Phenomenex Luna C8(2) 5 um 100 Å AXIA column (30 mm×75 mm) using a gradient of acetonitrile (A) and 0.1% trifluoroacetic acid in water (B) at a flow rate of 50 mL/min (0-0.5 min 10% A, 0.5-7.0 min linear gradient 10-95% A, 7.0-10.0 min 95% A, 10.0-12.0 min linear gradient 95-10% A) to afford the title compound as a TFA salt. $^1$H NMR (400 MHz, dimethylsulfoxide-$d_6$) δ 9.81 (s, 1H), 9.13 (s, 1H), 7.92 (s, 1H), 7.68-7.51 (m, 4H), 7.48-7.40 (m, 1H), 7.03-6.91 (m, 3H), 6.00 (dd, J=17.8, 1.4, 1H), 5.27 (dd, J=11.4, 1.4, 1H), 3.85-3.77 (m, 2H), 3.36-3.26 (m, 1H), 2.80 (s, 6H), 2.77-2.69 (m, 2H), 2.14-2.04 (m, 2H), 1.80-1.66 (m, 2H). MS (ESI) m/z 519 (M+H)$^+$.

EXAMPLE 61

6-(2-chloro-6-fluorophenyl)-8-ethenyl-2-{[4-(1-methylpiperidin-4-yl)phenyl]amino}pyrido[4,3-d]pyrimidin-5(6H)-one The title compound was prepared as described in Example 60D, substituting 1-(4-aminophenyl)-N,N-dimethylpiperi-din-4-amine with 4-(1-methylpiperidin-4-yl)aniline to afford the title compound as a TFA salt. $^1$H NMR (400 MHz, dimethylsulfoxide-$d_6$) δ 10.01 (s, 1H), 9.18 (s, 1H), 7.96 (s, 1H), 7.78 (d, J=8.5, 2H), 7.64-7.53 (m, 2H), 7.48-7.42 (m, 1H), 7.28-7.21 (m, 2H), 7.04-6.94 (m, 1H), 6.00 (dd, J=17.8, 1.4, 1H), 5.29 (dd, J=11.4, 1.4, 1H), 3.59-3.49 (m, 2H), 3.23-3.16 (m, 1H), 2.87-2.77 (m, 5H), 2.13-2.00 (m, 2H), 1.94-1.78 (m, 2H). MS (ESI) m/z 490 (M+H)$^+$

EXAMPLE 62

6-(2-chloro-6-fluorophenyl)-8-ethenyl-2-{[4-(4-methylpiperazin-1-yl)phenyl]amino}pyrido[4,3-d]pyrimidin-5(6H)-one The title compound was prepared as described in Example 60D, substituting 1-(4-aminophenyl)-N,N-dimethylpiperi-din-4-amine with 4-(4-methylpiperazin-1-yl)aniline to afford the title compound as a TFA salt. $^1$H NMR (400 MHz, dimethylsulfoxide-$d_6$) δ 9.87 (s, 1H), 9.14 (s, 1H), 7.93 (s, 1H), 7.70 (d, J=9.0, 2H), 7.64-7.52 (m, 2H), 7.49-7.40 (m, 1H), 7.05-6.91 (m, 3H), 6.00 (dd, J=17.8, 1.3, 1H), 5.27 (dd, J=11.4, 1.3, 1H), 3.61-3.38 (m, 8H), 2.88 (s, 3H). MS (ESI) m/z 491 (M+H)+.

EXAMPLE 63

6-(2-chloro-6-fluorophenyl)-8-ethenyl-2-[(2'-methyl-2',3'-dihydro-1'H-spiro[cyclopropane-1,4'-isoquinolin]-7'-yl)amino]pyrido[4,3-d]pyrimidin-5(6H)-one The title compound was prepared as described in Example 60D, substituting 1-(4-aminophenyl)-N,N-dimethylpiperidin-4-amine with 2'-methyl-2',3'-dihydro-1'H-spiro[cyclopropane-1,4'-isoquinolin]-7'-amine. Purification of the residue by reverse-phase preparative HPLC on a Phenomenex Luna C8(2) 5 um 100 Å AXIA column (30 mm×75 mm) using a gradient of acetonitrile (A) and 0.1% ammonium acetate in water (B) at a flow rate of 50 mL/min (0-0.5 min 10% A, 0.5-7.0 min linear gradient 10-95% A, 7.0-10.0 min 95% A, 10.0-12.0 min linear gradient 95-10% A) afforded the title compound. $^1$H NMR (400 MHz, dimethylsulfoxide-$d_6$) δ 9.89 (brs, 1H), 9.15 (s, 1H), 7.92 (s, 1H), 7.64-7.41 (m, 6H), 6.95 (dd, J=17.8, 11.4, 1H), 6.69 (d, J=8.5, 1H), 6.02 (dd, J=17.8, 1.5, 1H), 5.29 (dd, J=11.4, 1.5, 1H), 3.61 (s, 2H), 3.19 (s, 2H), 2.35 (s, 3H), 0.95-0.80 (m, 4H). MS (ESI) m/z 488 (M+H)+.

EXAMPLE 64

6-(2-chloro-6-fluorophenyl)-2-{[2-(dimethylamino)-2,3-dihydro-1H-inden-5-yl]amino}-8-ethenylpyrido[4,3-d]pyrimidin-5(6H)-one The title compound was prepared as described in Example 60D, substituting 1-(4-aminophenyl)-N,N-dimethylpiperidin-4-amine with $N^2,N^2$-dimethyl-2,3-dihydro-1H-indene-2,5-diamine to afford the title compound as a TFA salt. $^1$H NMR (400 MHz, dimethylsulfoxide-$d_6$) δ 10.02 (s, 1H), 9.18 (s, 1H), 7.95 (s, 1H), 7.76 (s, 1H), 7.65-7.53 (m, 3H), 7.48-7.42 (m, 1H), 7.24 (d, J=8.2, 1H), 6.97 (dd, J=17.8, 11.5, 1H), 6.03 (dd, J=17.8, 1.5, 1H), 5.30 (dd, J=11.4, 1.5, 1H), 4.15 (p, J=7.7, 1H), 3.39-3.27 (m, 2H), 3.26-3.18 (m, 2H), 2.84 (s, 6H). MS (ESI) m/z 476 (M+H)+.

EXAMPLE 65

6-(2,6-dichlorophenyl)-8-methyl-2-(methylamino)pyrido[4,3-d]pyrimidin-5(6H)-one

A 2 dram vial was charged with Example 28D (35 mg, 0.099 mmol) and dichloromethane (994 µl) followed by 3-chlorobenzoperoxoic acid (26.7 mg, 0.119 mmol). The reaction mixture was stirred at ambient temperature for 20 minutes and methanamine (2 molar in THF, 149 µl, 0.298 mmol) was added. The flask was capped and the reaction mixture was stirred at 40° C. until completion of the reaction. After concentration, the residue was purified by reverse-phase preparative HPLC on a Phenomenex Luna C8(2) 5 um 100 Å AXIA column (30 mm×75 mm) using a gradient of acetonitrile (A) and 0.1% trifluoroacetic acid in water (B) at a flow rate of 50 mL/min (0-0.5 min 10% A, 0.5-7.0 min linear gradient 10-95% A, 7.0-10.0 min 95% A, 10.0-12.0 min linear gradient 95-10% A) to afford the title compound. $^1$H NMR (300 MHz, dimethylsulfoxide-$d_6$) δ 8.96 (s, 1H), 8.07-7.97 (m, 1H), 7.74-7.68 (m, 2H), 7.60-7.48 (m, 2H), 2.97-2.90 (m, 3H), 2.15 (s, 3H). MS (ESI) m/z 335 (M+H)+.

EXAMPLE 66

6-(2-chloro-6-fluorophenyl)-8-methyl-2-{[4-(4-methylpiperazin-1-yl)phenyl]amino}pyrido[4,3-d]pyrimidin-5(6H)-one

EXAMPLE 66A

N-(2-chloro-6-fluorophenyl)-4-ethyl-2-(methylthio)pyrimidine-5-carboxamide

Example 28B (15 g, 76 mmol) was dissolved in dioxane (300 mL) and sulfurous dichloride (6.62 ml, 91 mmol). N,N-dimethylformamide (3 drops) were added. The reaction mixture was stirred for 60 minutes at ambient temperature then 2-chloro-6-fluoroaniline (13.22 g, 91 mmol) was added. The reaction mixture was then stirred at 100° C. for 16 hours. The flask was then put into an ice bath and the reaction mixture was quenched by careful addition of saturated aqueous sodium bicarbonate (200 mL). After diluting with 200 mL of ethyl acetate, the reaction mixture was poured into a separatory funnel, the aqueous layer was removed and the organic layer was washed with saturated aqueous sodium bicarbonate (1×150 mL), diluted aqueous sodium bicarbonate (10% wt, 1×150 mL), and saturated aqueous brine (1×150 mL), dried over magnesium sulfate, filtered and concentrated. Purification by silica gel flash chromatography (Isco®, Redi-Sep® column, 5-85% ethyl acetate/hexane, linear gradient) afforded the title compound.

EXAMPLE 66B 6-(2-chloro-6-fluorophenyl)-8-methyl-2-(methylthio)pyrido[4,3-d]pyrimidin-5(6H)-one To a solution of and N-(chloromethylene)-N-methylmethanaminium (10.64 g, 83 mmol) in DMF (40 mL) was added Example 66A (9.03 g, 27.7 mmol) (1355) and the reaction mixture was stirred at room temperature for 16 hours. The reaction mixture was cooled to 0° C. and quenched by careful addition of 150 mL of aqueous sodium bicarbonate. To the reaction mixture was added 150 mL of ethyl acetate and the reaction mixture was poured into a separatory funnel. The aqueous layer was removed and the organic layer was washed with saturated aqueous sodium bicarbonate (150 mL) and saturated aqueous brine (100 mL), dried over magnesium sulfate, filtered and concentrated. Purification by silica gel flash chromatography (Isco®, Redi-Sep® column, 2-65% ethyl acetate/hexane, linear gradient) afforded the title compound.

EXAMPLE 66C 6-(2-chloro-6-fluorophenyl)-8-methyl-2-{[4-(4-methylpiperazin-1-yl)phenyl]amino}pyrido[4,3-d]pyrimidin-5(6H)-one The title compound was prepared as described in Example 60D, substituting 1-(4-aminophenyl)-N,N-dimethylpiperidin-4-amine with 4-(4-methylpiperazin-1-yl)aniline and substituting Example 60C with Example 66B. Purification of the residue by reverse-phase preparative HPLC on a Phenomenex Luna C8(2) 5 um 100 Å AXIA column (30 mm×75 mm) using a gradient of acetonitrile (A) and 0.1% ammonium acetate in water (B) at a flow rate of 50 mL/min (0-0.5 min 10% A, 0.5-7.0 min linear gradient 10-95% A, 7.0-10.0 min 95% A, 10.0-12.0 min linear gradient 95-10%

A) afforded the title compound. $^1$H NMR (400 MHz, dimethylsulfoxide-d$_6$) δ 9.76 (s, 1H), 9.10 (s, 1H), 7.73 (d, J=9.0, 2H), 7.61-7.50 (m, 3H), 7.46-7.40 (m, 1H), 6.94 (d, J=9.0, 2H), 3.22-3.17 (m, 4H), 2.75-2.70 (m, 4H), 2.42 (s, 3H), 2.20 (s, 3H). MS (ESI) m/z 479 (M+H)$^+$.

EXAMPLE 67

6-(2-chloro-6-fluorophenyl)-8-methyl-2-[(2'-methyl-2',3'-dihydro-1'H-spiro[cyclopropane-1,4'-isoquinolin]-7'-yl)amino]pyrido[4,3-d]pyrimidin-5(6H)-one The title compound was prepared as described in Example 60D, substituting 1-(4-aminophenyl)-N,N-dimethylpiperidin-4-amine with 2'-methyl-2',3'-dihydro-1'H-spiro[cyclopropane-1,4'-isoquinolin]-7'-amine and substituting Example 60C with Example 66B. Purification of the residue by reverse-phase preparative HPLC on a Phenomenex Luna C8(2) 5 um 100 Å AXIA column (30 mm×75 mm) using a gradient of acetonitrile (A) and 0.1% ammonium acetate in water (B) at a flow rate of 50 mL/min (0-0.5 min 10% A, 0.5-7.0 min linear gradient 10-95% A, 7.0-10.0 min 95% A, 10.0-12.0 min linear gradient 95-10% A) afforded the title compound. $^1$H NMR (400 MHz, dimethylsulfoxide-d$_6$) δ 9.85 (brs, 1H), 9.12 (s, 1H), 7.66-7.50 (m, 5H), 7.46-7.38 (m, 1H), 6.68 (d, J=8.5, 1H), 3.61 (s, 2H), 2.34 (s, 2H), 2.22 (s, 2H), 1.89 (s, 2H), 0.95-0.80 (m, 4H). MS (ESI) m/z 476 (M+H)$^+$.

EXAMPLE 68

6-(2-chloro-6-fluorophenyl)-2-{[2-(dimethylamino)-2,3-dihydro-1H-inden-5-yl]amino}-8-methylpyrido[4,3-d]pyrimidin-5(6H)-one The title compound was prepared as described in Example 60D, substituting 1-(4-aminophenyl)-N,N-dimethylpiperidin-4-amine with N$^2$,N$^2$-dimethyl-2,3-dihydro-1H-indene-2,5-diamine and substituting Example 60C with Example 66B. Purification of the residue by reverse-phase preparative HPLC on a Phenomenex Luna C8(2) 5 um 100 Å AXIA column (30 mm×75 mm) using a gradient of acetonitrile (A) and 0.1% ammonium acetate in water (B) at a flow rate of 50 mL/min (0-0.5 min 10% A, 0.5-7.0 min linear gradient 10-95% A, 7.0-10.0 min 95% A, 10.0-12.0 min linear gradient 95-10% A) afforded the title compound. $^1$H NMR (400 MHz, dimethylsulfoxide-d$_6$) δ 9.98 (s, 1H), 9.15 (s, 1H), 7.85 (s, 1H), 7.70 (dd, J=8.2, 1.1, 1H), 7.62-7.51 (m, 3H), 7.47-7.39 (m, 1H), 7.22 (d, J=8.2, 1H), 4.07 (p, J=7.7, 1H), 3.36-3.24 (m, 2H), 3.21-3.07 (m, 2H), 2.80 (s, 6H), 2.23 (s, 3H). MS (ESI) m/z 464 (M+H)$^+$.

EXAMPLE 69

6-(2-chloro-6-fluorophenyl)-2-({4-[4-(dimethylamino)piperidin-1-yl]phenyl}amino)-8-methylpyrido[4,3-d]pyrimidin-5(6H)-one The title compound was prepared as described in Example 60D, substituting 1-(4-aminophenyl)-N,N-dimethylpiperidin-4-amine with 1-(4-aminophenyl)-N,N-dimethylpiperidin-4-amine and substituting Example 60C with Example 66B. Purification of the residue by reverse-phase preparative HPLC on a Phenomenex Luna C8(2) 5 um 100 Å AXIA column (30 mm×75 mm) using a gradient of acetonitrile (A) and 0.1% ammonium acetate in water (B) at a flow rate of 50 mL/min (0-0.5 min 10% A, 0.5-7.0 min linear gradient 10-95% A, 7.0-10.0 min 95% A, 10.0-12.0 min linear gradient 95-10% A) afforded the title compound. $^1$H NMR (400 MHz, dimethylsulfoxide-d$_6$) δ 9.73 (s, 1H), 9.09 (s, 1H), 7.69 (d, J=9.0, 2H), 7.61-7.49 (m, 3H), 7.46-7.39 (m, 1H), 6.94-6.89 (m, 2H), 3.69-3.61 (m, 2H), 2.74-2.65 (m, 2H), 2.26 (s, 6H), 2.20 (s, 3H), 1.88-1.81 (m, 2H), 1.61-1.47 (m, 2H). MS (ESI) m/z 507 (M+H)$^+$.

EXAMPLE 70

6-(2-chloro-6-fluorophenyl)-8-methyl-2-[(2,4,4-trimethyl-1,2,3,4-tetrahydroisoquinolin-7-yl)amino]pyrido[4,3-d]pyrimidin-5(6H)-one The title compound was prepared as described in Example 60D, substituting 1-(4-aminophenyl)-N,N-dimethylpiperidin-4-amine with 2,4,4-trimethyl-1,2,3,4-tetrahydroisoquinolin-7-amine and substituting Example 60C with Example 66B. Purification of the residue by reverse-phase preparative HPLC on a Phenomenex Luna C8(2) 5 um 100 Å AXIA column (30 mm×75 mm) using a gradient of acetonitrile (A) and 0.1% ammonium acetate in water (B) at a flow rate of 50 mL/min (0-0.5 min 10% A, 0.5-7.0 min linear gradient 10-95% A, 7.0-10.0 min 95% A, 10.0-12.0 min linear gradient 95-10% A) afforded the title compound. $^1$H NMR (400 MHz, dimethylsulfoxide-d$_6$) δ 9.99-9.93 (m, 1H), 9.15 (s, 1H), 7.85 (d, J=8.6, 1H), 7.72-7.65 (m, 1H), 7.62-7.50 (m, 3H), 7.47-7.39 (m, 1H), 7.36 (d, J=8.5, 1H), 7.23 (d, J=8.6, 1H), 3.51-3.42 (m, 2H), 2.81 (s, 3H), 2.63 (s, 2H), 2.24 (s, 3H), 1.32 (s, 6H). MS (ESI) m/z 478 (M+H)$^+$.

EXAMPLE 71

6-(2-chloro-6-fluorophenyl)-8-methyl-2-{[4-(1-methylpiperidin-4-yl)phenyl]amino}pyrido[4,3-d]pyrimidin-5(6H)-one The title compound was prepared as described in Example 60D, substituting 1-(4-aminophenyl)-N,N-dimethylpiperidin-4-amine with 4-(1-methylpiperidin-4-yl)aniline and substituting Example 60C with Example 66B. Purification of the residue by reverse-phase preparative HPLC on a Phenomenex Luna C8(2) 5 um 100 Å AXIA column (30 mm×75 mm) using a gradient of acetonitrile (A) and 0.1% ammonium acetate in water (B) at a flow rate of 50 mL/min (0-0.5 min 10% A, 0.5-7.0 min linear gradient 10-95% A, 7.0-10.0 min 95% A, 10.0-12.0 min linear gradient 95-10% A) afforded the title compound. $^1$H NMR (400 MHz, dimethylsulfoxide-d$_6$) δ 9.93 (s, 1H), 9.14 (s, 1H), 7.82 (d, J=8.6, 2H), 7.62-7.51 (m, 3H), 7.46-7.39 (m, 1H), 7.22 (d, J=8.6, 2H), 3.15-3.10 (m, 2H), 2.65-2.55 (m, 1H), 2.51-2.47 (m, 2H), 2.47 (s, 3H), 2.23 (s, 3H), 1.88-1.70 (m, 4H). MS (ESI) m/z 478 (M+H)$^+$.

EXAMPLE 72

6-(2-chloro-6-fluorophenyl)-8-methyl-2-(1,2,3,4-tetrahydroisoquinolin-6-ylamino)pyrido[4,3-d]pyrimidin-5(6H)-one Example 66B (60 mg, 0.179 mmol) was dissolved in dichloromethane (2 mL) and 3-chlorobenzoperoxoic acid (44.1 mg, 0.179 mmol) was added. The reaction mixture was stirred at ambient temperature for 30 minutes then tert-butyl 6-amino-3,4-dihydroisoquinoline-2(1H)-carboxylate (48.8 mg, 0.197 mmol) was added. The reaction mixture was stirred at room temperature for 36 hours and was concentrated. The crude boc protected intermediate was treated with a TFA/dichloromethane mixture (1:1, 0.6 mL) and stirred at room temperature for 1 hour then concentrated. Purification of the residue by reverse-phase preparative HPLC on a Phenomenex Luna C8(2) 5 um 100 Å AXIA column (30 mm×75 mm) using a gradient of acetonitrile (A) and 0.1% ammonium acetate in water (B) at a flow rate of 50 mL/min (0-0.5 min 10% A, 0.5-7.0 min linear gradient 10-95% A, 7.0-10.0 min 95% A, 10.0-12.0 min linear gradient 95-10% A) afforded the title compound. $^1$H NMR (400 MHz, dimethylsulfoxide-$d_6$) δ 10.19 (brs, 1H), 9.36 (s, 1H), 8.02 (s, 1H), 7.90-7.86 (m, 2H), 7.82-7.71 (m, 3H), 7.68-7.60 (m, 1H), 7.34 (d, J=8.4, 1H), 4.36 (s, 2H), 3.52 (t, J=6.3, 2H), 3.17 (t, J=6.2, 2H), 2.43 (s, 3H). MS (ESI) m/z 436 (M+H)$^+$.

EXAMPLE 73

6-(2-chloro-6-fluorophenyl)-2-[(4,4-dimethyl-1,2,3,4-tetrahydroisoquinolin-7-yl)amino]-8-methylpyrido[4,3-d]pyrimidin-5(6H)-one The title compound was prepared as described in Example 72, substituting tert-butyl 6-amino-3,4-dihydroisoquinoline-2(1H)-carboxylate with tert-butyl 7-amino-4,4-dimethyl-3,4-dihydroisoquinoline-2(1H)-carboxylate to afford the title compound. $^1$H NMR (400 MHz, dimethylsulfoxide-$d_6$) δ 10.05 (s, 1H), 9.17 (s, 1H), 7.81-7.73 (m, 2H), 7.63-7.50 (m, 3H), 7.48-7.36 (m, 2H), 4.28 (s, 2H), 3.22 (s, 2H), 2.24 (s, 2H), 1.37 (s, 6H). MS (ESI) m/z 464 (M+H)$^+$.

EXAMPLE 74

6-(2-chloro-6-fluorophenyl)-2-(2',3'-dihydro-1'H-spiro[cyclopropane-1,4'-isoquinolin]-7'-ylamino)-8-methylpyrido[4,3-d]pyrimidin-5(6H)-one The title compound was prepared as described in Example 72, substituting tert-butyl 6-amino-3,4-dihydroisoquinoline-2(1H)-carboxylate with tert-butyl 7'-amino-1'H-spiro[cyclopropane-1,4'-isoquinoline]-2'(3'H)-carboxylate to afford the title compound. $^1$H NMR (400 MHz, dimethylsulfoxide-$d_6$) δ 9.96 (s, 1H), 9.15 (s, 1H), 7.75 (d, J=1.4, 1H), 7.65 (dd, J=8.6, 2.0, 1H), 7.61-7.51 (m, 3H), 7.46-7.40 (m, 1H), 6.80 (d, J=8.6, 1H), 4.24 (s, 2H), 3.09 (s, 2H), 2.23 (s, 3H), 1.08-0.93 (m, 4H). MS (ESI) m/z 462 (M+H)$^+$.

EXAMPLE 75

6-(2-chloro-6-fluorophenyl)-8-methyl-2-(1,2,3,4-tetrahydroisoquinolin-7-ylamino)pyrido[4,3-d]pyrimidin-5(6H)-one The title compound was prepared as described in Example 72, substituting tert-butyl 6-amino-3,4-dihydroisoquinoline-2(1H)-carboxylate with tert-butyl 7-amino-3,4-dihydroisoquinoline-2(1H)-carboxylate to afford the title compound. $^1$H NMR (400 MHz, dimethylsulfoxide-$d_6$) δ 9.87 (s, 1H), 9.14 (s, 1H), 7.66 (s, 1H), 7.62-7.50 (m, 4H), 7.46-7.39 (m, 1H), 7.06 (d, J=8.3, 2H), 3.95 (s, 2H), 3.06 (t, J=6.0, 2H), 2.73 (t, J=5.9, 2H), 2.22 (s, 3H). MS (ESI) m/z 436 (M+H)$^+$.

EXAMPLE 76

6-(2,6-dichlorophenyl)-8-methyl-2-(1,2,3,4-tetrahydroisoquinolin-6-ylamino)pyrido[4,3-d]pyrimidin-5(6H)-one The title compound was prepared as described in Example 72, substituting tert-butyl 6-amino-3,4-dihydroisoquinoline-2(1H)-carboxylate with tert-butyl 6-amino-3,4-dihydroisoquinoline-2(1H)-carboxylate and substituting Example 66B with Example 28D to afford the title compound as an acetic acid salt. $^1$H NMR (400 MHz, dimethylsulfoxide-$d_6$) δ 9.85 (s, 1H), 9.14 (s, 1H), 7.72-7.64 (m, 3H), 7.60-7.51 (m, 2H), 7.48 (d, J=1.2, 1H), 6.99 (d, J=8.3, 1H), 3.89 (s, 2H), 3.03 (t, J=6.0, 2H), 2.75 (t, J=5.9, 2H), 2.23 (s, 3H). MS (ESI) m/z 436 (M+H)$^+$.

EXAMPLE 77

6-(2,6-dichlorophenyl)-2-[(4,4-dimethyl-1,2,3,4-tetrahydroisoquinolin-7-yl)amino]-8-methylpyrido[4,3-d]pyrimidin-5(6H)-one The title compound was prepared as described in Example 72, substituting tert-butyl 6-amino-3,4-dihydroisoquinoline-2(1H)-carboxylate with tert-butyl 7-amino-4,4-dimethyl-3,4-dihydroisoquinoline-2(1H)-carboxylate and substituting Example 66B with Example 28D to afford the title compound as an acetic acid salt. $^1$H NMR (400 MHz, dimethylsulfoxide-$d_6$) δ 9.85 (s, 1H), 9.14 (s, 1H), 7.68-7.60 (m, 4H), 7.54 (dd, J=8.8, 7.5, 1H), 7.48 (d, J=1.1, 1H), 7.32-7.28 (m, 1H), 3.93 (s, 2H), 2.79 (s, 2H), 2.24 (s, 3H), 1.90 (s, 3H), 1.25 (s, 6H). MS (ESI) m/z 480 (M+H)$^+$.

EXAMPLE 78

6-(2,6-dichlorophenyl)-8-methyl-2-{[4-(1-methylpiperidin-4-yl)phenyl]amino}pyrido[4,3-d]pyrimidin-5(6H)-one Example 28D (60 mg, 0.170 mmol) was dissolved in dichloromethane (2 mL) and 3-chlorobenzoperoxoic acid (42.0 mg, 0.170 mmol) was added. The reaction mixture was stirred at ambient temperature for 30 minutes then 4-(1-methylpiperidin-4-yl)aniline (36.1 mg, 0.190 mmol) and TFA (0.05 mL) were added. The reaction mixture was stirred at room temperature for 48 hours and was concentrated. Purification of the residue by reverse-phase preparative HPLC on a Phenomenex Luna C8(2) 5 um 100 Å AXIA column (30 mm×75 mm) using a gradient of acetonitrile (A) and 0.1% ammonium acetate in water (B) at a flow rate of 50 mL/min (0-0.5 min 10% A, 0.5-7.0 min linear gradient 10-95% A, 7.0-10.0 min 95% A, 10.0-12.0 min linear gradient 95-10% A) afforded the title compound. $^1$H NMR (400 MHz, dimethylsulfoxide-$d_6$) δ 9.91 (s, 1H), 9.15 (s, 1H), 7.82 (d, J=8.6, 2H), 7.69-7.64 (m, 2H), 7.54 (dd, J=8.8, 7.5, 1H), 7.48 (d, J=1.1, 1H), 7.21 (d, J=8.6, 2H), 3.05 (d, 2H), 2.60-2.51 (m, 1H), 2.39 (s, 3H), 2.37-2.29 (m, 2H), 2.23 (s, 3H), 1.88-1.67 (m, 4H). MS (ESI) m/z 494 (M+H)$^+$.

EXAMPLE 79

6-(2,6-dichlorophenyl)-8-methyl-2-[(2,4,4-trimethyl-1,2,3,4-tetrahydroisoquinolin-7-yl)amino]pyrido[4,3-d]pyrimidin-5(6H)-one The title compound was prepared as described in Example 78, substituting 4-(1-methylpiperidin-4-yl)aniline with 2,4,4-trimethyl-1,2,3,4-tetrahydroisoquinolin-7-amine to afford the title compound. $^1$H NMR (400 MHz, dimethylsulfoxide-$d_6$) δ 9.89 (s, 1H), 9.14 (s, 1H), 7.68-7.62 (m, 4H), 7.54 (dd, J=8.8, 7.4, 1H), 7.49 (d, J=1.1, 1H), 7.31 (d, J=8.3, 1H), 3.70-3.56 (m, 2H), 2.59-2.49 (m, 2H), 2.24 (s, 3H), 1.28 (s, 6H). MS (ESI) m/z 494 (M+H)$^+$.

EXAMPLE 80

6-(2,6-dichlorophenyl)-8-methyl-2-(1,2,3,4-tetrahydroisoquinolin-7-ylamino)pyrido[4,3-d]pyrimidin-5(6H)-one The title compound was prepared as described in Example 72, substituting tert-butyl 6-amino-3,4-dihydroisoquinoline-2(1H)-carboxylate with tert-butyl 7-amino-3,4-dihydroisoquinoline-2(1H)-carboxylate and substituting Example 66B with Example 28D to afford the title compound as an acetic acid salt. $^1$H NMR (400 MHz, dimethylsulfoxide-$d_6$) δ 10.04 (s, 1H), 9.17 (s, 1H), 7.83 (d, J=1.6, 1H), 7.72 (dd, J=8.4, 2.0, 1H), 7.69-7.65 (m, 2H), 7.55 (dd, J=8.8, 7.5, 1H), 7.51 (d, J=1.1, 1H), 7.21 (d, J=8.4, 1H), 4.28 (s, 2H), 3.40 (t, J=6.3, 2H), 3.00 (t, J=6.3, 2H), 2.24 (s, 3H). MS (ESI) m/z 452 (M+H)$^+$.

EXAMPLE 81

6-(2,6-dichlorophenyl)-8-(1H-imidazol-2-yl)-2-(1,2,3,4-tetrahydroisoquinolin-6-ylamino)pyrido[4,3-d]pyrimidin-5(6H)-one

EXAMPLE 81A tert-butyl 6-(6-(2,6-dichlorophenyl)-8-formyl-5-oxo-5,6-dihydropyrido[4,3-d]pyrimidin-2-ylamino)-3,4-dihydroisoquinoline-2(1H)-carboxylate Example 21C (240 mg, 0.655 mmol) was dissolved in dichloromethane (8 mL) and 3-chlorobenzoperoxoic acid (178 mg, 0.721 mmol) was added. The reaction mixture was stirred at ambient temperature for 30 minutes and tert-butyl 6-amino-3,4-dihydroisoquinoline-2(1H)-carboxylate (179 mg, 0.721 mmol) was added. The resulting mixture was stirred at ambient temperature for 24 hours and was concentrated. The crude residue was purified by silica gel flash chromatography (Isco®, Redi-Sep® column, 5-70% ethyl acetate/hexane, linear gradient) to afford the title compound.

EXAMPLE 81B tert-butyl 6-(6-(2,6-dichlorophenyl)-8-(1H-imidazol-2-yl)-5-oxo-5,6-dihydropyrido[4,3-d]pyrimidin-2-ylamino)-3,4-dihydroisoquinoline-2(1H)-carboxylate A mixture of oxalaldehyde (512 mg, 3.53 mmol), Example 81A (100 mg, 0.177 mmol) and ammonia (2522 µl, 17.65 mmol) was stirred at room temperature for 72 hours and was concentrated. The residue was purified by silica gel flash chromatography (Isco®, Redi-Sep® column, 1-8% CH$_3$OH/dichloromethane, linear gradient) (1-8%% CH$_3$OH/CH$_2$Cl$_2$, gradient) to afford the title compound.

EXAMPLE 81C 6-(2,6-dichlorophenyl)-8-(1H-imidazol-2-yl)-2-(1,2,3,4-tetrahydroisoquinolin-6-ylamino)pyrido[4,3-d]pyrimidin-5(6H)-one A mixture of Example 81B (48 mg, 0.079 mmol) and TFA/dichloromethane (1:1 mixture, 1 mL) was stirred at room temperature and was concentrated. The residue was purified by reverse-phase preparative HPLC on a Phenomenex Luna C8(2) 5 um 100 Å AXIA column (30 mm×75 mm) using a gradient of acetonitrile (A) and 0.1% trifluoroacetic acid in water (B) at a flow rate of 50 mL/min (0-0.5 min 10% A, 0.5-7.0 min linear gradient 10-95% A, 7.0-10.0 min 95% A, 10.0-12.0 min linear gradient 95-10% A) to afford the title compound as a TFA salt. $^1$H NMR (400 MHz, dimethylsulfoxide-$d_6$) δ 10.33 (s, 1H), 9.29 (s, 1H), 8.42 (s, 1H), 7.74-7.71 (m, 2H), 7.64-7.59 (m, 2H), 7.56 (dd, J=8.3, 2.1, 1H), 7.41 (s, 2H), 7.24 (d, J=8.4, 1H), 4.27 (s, 2H), 3.42 (t, J=6.4, 2H), 3.02 (t, J=6.3, 2H). MS (ESI) m/z 504 (M+H)$^+$.

EXAMPLE 82

6-(2,6-dichlorophenyl)-8-(difluoromethyl)-2-{[4-(1-methylpiperidin-4-yl)phenyl]amino}pyrido[4,3-d]pyrimidin-5(6H)-one The title compound was prepared as described in Example 36B, substituting 4-(4-methylpiperazin-1-yl)aniline with 4-(1-methylpiperidin-4-yl)aniline. Purification of the residue by reverse-phase preparative HPLC on a Phenomenex Luna C8(2) 5 um 100 Å AXIA column (30 mm×75 mm) using a gradient of acetonitrile (A) and 0.1% ammonium acetate in water (B) at a flow rate of 50 mL/min (0-0.5 min 10% A, 0.5-7.0 min linear gradient 10-95% A, 7.0-10.0 min 95% A, 10.0-12.0 min linear gradient 95-10% A) afforded the title compound. $^1$H NMR (400 MHz, dimethylsulfoxide-$d_6$) δ 10.10 (s, 1H), 9.18 (s, 1H), 8.08 (s, 1H), 7.76 (d, J=8.5, 2H), 7.71-7.66 (m, 2H), 7.58 (dd, J=8.9, 7.4, 1H), 7.21 (d, J=8.6, 2H), 7.16 (t, J=54.7, 1H), 2.91-2.85 (m, 2H), 2.47-2.39 (m, 1H), 2.23 (s, 3H), 2.09-1.98 (m, 2H), 1.81-1.59 (m, 4H).). MS (ESI) m/z 530 (M+H)$^+$.

EXAMPLE 83

6-(2,6-dichlorophenyl)-8-(difluoromethyl)-2-{[2-(dimethylamino)-2,3-dihydro-1H-inden-5-yl]amino}pyrido[4,3-d]pyrimidin-5(6H)-one The title compound was prepared as described in Example 36B, substituting 4-(4-methylpiperazin-1-yl)aniline with N$^2$,N$^2$-dimethyl-2,3-dihydro-1H-indene-2,5-diamine Purification of the residue by reverse-phase preparative HPLC on a Phenomenex Luna C8(2) 5 um 100 Å AXIA column (30 mm×75 mm) using a gradient of acetonitrile (A) and 0.1% ammonium acetate in water (B) at a flow rate of 50 mL/min (0-0.5 min 10% A, 0.5-7.0 min linear gradient 10-95% A, 7.0-10.0 min 95% A, 10.0-12.0 min linear gradient 95-10% A) afforded the title compound. $^1$H NMR (400 MHz, dimethylsulfoxide-$d_6$) δ 10.05 (s, 1H), 9.17 (s, 1H), 8.07 (s, 1H), 7.73-7.66 (m, 4H), 7.61-7.52 (m, 3H), 7.14 (d, J=5.5, 1H), 7.13 (t, J=54.7, 1H), 3.21-2.72 (m, 5H), 2.23 (s, 6H). MS (ESI) m/z 516 (M+H)$^+$.

EXAMPLE 84

6-(2,6-dichlorophenyl)-8-(difluoromethyl)-2-({4-[4-(dimethylamino)piperidin-1-yl]phenyl}amino)pyrido[4,3-d]pyrimidin-5(6H)-one The title compound was prepared as described in Example 36B, substituting 4-(4-methylpiperazin-1-yl)aniline with 1-(4-aminophenyl)-N,N-dimethylpiperidin-4-amine Purification of the residue by reverse-phase preparative HPLC on a Phenomenex Luna C8(2) 5 um 100 Å AXIA column (30 mm×75 mm) using a gradient of acetonitrile (A) and 0.1% ammonium acetate in water (B) at a flow rate of 50 mL/min (0-0.5 min 10% A, 0.5-7.0 min linear gradient 10-95% A, 7.0-10.0 min 95% A, 10.0-12.0 min linear gradient 95-10% A) afforded the title compound. $^1$H NMR (400 MHz, dimethylsulfoxide-d$_6$) δ 9.94 (s, 1H), 9.12 (s, 1H), 8.04 (s, 1H), 7.71-7.62 (m, 4H), 7.57 (dd, J=8.9, 7.4, 1H), 7.14 (t, J=54.7, 1H), 6.91 (d, J=9.1, 2H), 3.69-3.63 (m, 2H), 2.75-2.65 (m, 2H), 2.32-2.26 (m, 1H), 2.24 (s, 6H), 1.87-1.80 (m, 2H), 1.59-1.44 (m, 2H). MS (ESI) m/z 559 (M+H)$^+$.

EXAMPLE 85

6-(2,6-dichlorophenyl)-8-(difluoromethyl)-2-[(4,4-dimethyl-1,2,3,4-tetrahydroisoquinolin-7-yl)amino]pyrido[4,3-d]pyrimidin-5(6H)-one Example 36A (70 mg, 0.180 mmol) was dissolved in dichloromethane (2 mL) and 3-chlorobenzoperoxoic acid (44.5 mg, 0.180 mmol) was added. The reaction mixture was stirred at ambient temperature for 60 minutes then tert-butyl 7-amino-4,4-dimethyl-3,4-dihydroisoquinoline-2(1H)-carboxylate (54.8 mg, 0.198 mmol) was added. After stirring at room temperature for 24 hours, the reaction mixture was concentrated and treated with a TFA/dichloromethane mixture (1:1, 0.6 mL). The reaction mixture was stirred at room temperature for 30 minutes and was concentrated. Purification of the residue by reverse-phase preparative HPLC on a Phenomenex Luna C8(2) 5 um 100 Å AXIA column (30 mm×75 mm) using a gradient of acetonitrile (A) and 0.1% ammonium acetate in water (B) at a flow rate of 50 mL/min (0-0.5 min 10% A, 0.5-7.0 min linear gradient 10-95% A, 7.0-10.0 min 95% A, 10.0-12.0 min linear gradient 95-10% A) afforded the title compound as an acetic acid salt. $^1$H NMR (400 MHz, dimethylsulfoxide-d$_6$) δ 10.14 (brs, 1H), 9.25 (s, 1H), 8.16 (s, 1H), 7.79-7.73 (m, 2H), 7.71-7.60 (m, 3H), 7.38 (d, J=8.5, 1H), 7.23 (t, J=54.7, 1H), 4.02 (s, 2H), 2.88 (s, 2H), 1.33 (s, 6H). MS (ESI) m/z 516 (M+H)$^+$.

EXAMPLE 86

6-(2,6-dichlorophenyl)-8-(difluoromethyl)-2-(2',3'-dihydro-1'H-spiro[cyclopropane-1,4'-isoquinolin]-7'-ylamino)pyrido[4,3-d]pyrimidin-5(6H)-one The title compound was prepared as described in Example 85, substituting tert-butyl 7-amino-4,4-dimethyl-3,4-dihydroisoquinoline-2(1H)-carboxylate with tert-butyl 7'-amino-1'H-spiro[cyclopropane-1,4'-isoquinoline]-2'(3'H)-carboxylate to afford the title compound as an acetic acid salt. $^1$H NMR (400 MHz, dimethylsulfoxide-d$_6$) δ 10.24 (s, 1H), 9.20 (s, 1H), 8.12 (s, 1H), 7.84 (s, 1H), 7.72-7.66 (m, 2H), 7.65-7.54 (m, 2H), 7.16 (t, J=54.5, 1H), 6.86 (d, J=8.6, 1H), 4.38 (s, 2H), 3.27 (s, 2H), 1.17-1.03 (m, 4H). MS (ESI) m/z 514 (M+H)$^+$.

EXAMPLE 87

6-(2,6-dichlorophenyl)-8-(difluoromethyl)-2-(1,2,3,4-tetrahydroisoquinolin-7-ylamino)pyrido[4,3-d]pyrimidin-5(6H)-one The title compound was prepared as described in Example 85, substituting tert-butyl 7-amino-4,4-dimethyl-3,4-dihydroisoquinoline-2(1H)-carboxylate with tert-butyl 7-amino-3,4-dihydroisoquinoline-2(1H)-carboxylate to afford the title compound. $^1$H NMR (400 MHz, dimethylsulfoxide-d$_6$) δ 10.25 (s, 1H), 9.21 (s, 1H), 8.11 (s, 1H), 7.85 (s, 1H), 7.72-7.62 (m, 3H), 7.59 (dd, J=8.9, 7.4, 1H), 7.21 (d, J=8.4, 1H), 7.16 (t, J=54.6, 1H), 4.28 (s, 2H), 3.41 (t, J=6.3, 2H), 3.02-2.94 (m, J=6.3, 2H). MS (ESI) m/z 488 (M+H)$^+$.

EXAMPLE 88

6-(2,6-dimethylphenyl)-8-methyl-2-[(2'-methyl-2',3'-dihydro-1'H-spiro[cyclopropane-1,4'-isoquinolin]-7'-yl)amino]pyrido[4,3-d]pyrimidin-5(6H)-one

EXAMPLE 88A

N-(2,6-dimethylphenyl)-4-ethyl-2-(methylthio)pyrimidine-5-carboxamide

To a solution of Example 28B (539 mg, 2.72 mmol) in dichloromethane (5440 μl) was added a catalytic amount of N,N-dimethylformamide (5.27 μl, 0.068 mmol). The free-flowing slurry was cooled to ~5° C. Oxalyl chloride (250 μl, 2.86 mmol) was added dropwise via syringe. The reaction mixture was allowed to proceed at 5-10° C. for 1 hour, then the cooling bath was removed and the mixture stirred at ambient temperature for an additional hour (it should be noted that, at ambient temperature, the solids completely dissolved). To the slurry was added 2,6-dimethylaniline (352 μl, 2.86 mmol). The reaction mixture was stirred at ambient temperature for 16 hours. The reaction mixture was poured into a 125 mL separatory funnel, and diluted with 50 mL of dichloromethane. The organic layer was washed with water (1×40 mL), 1 molar aqueous phosphoric acid (1×40 mL), and saturated aqueous brine (1×40 mL), dried over magnesium sulfate, filtered and concentrated. The crude product was recrystallized in ethyl acetate/hexane mixture to afford the title compound.

EXAMPLE 88B 6-(2,6-dimethylphenyl)-8-methyl-2-(methylthio)pyrido[4,3-d]pyrimidin-5(6H)-one A scintillation vial, equipped with stir bar and septa, was charged with Example 88A (555 mg, 1.841 mmol) and N,N-dimethylformamide (7365 μl) followed by N-(chloromethylene)-N-methylmethanaminium (707 mg, 5.52 mmol) and the reaction mixture was stirred at ambient temperature for 16 hours. The reaction mixture was cooled to 0° C. and quenched by careful addition of saturated aqueous sodium bicarbonate. To the reaction mixture was added 80 mL of ethyl acetate and the reaction mixture was poured into a 250 mL separatory funnel. The aqueous layer was removed and the organic layer was washed with diluted aqueous sodium bicarbonate (10% wt, 50 mL) and saturated aqueous brine (50 mL), dried over magnesium sulfate, filtered, and was concentrated. Purification by silica gel flash chromatography (Isco®, Redi-Sep® column, 2-100% ethyl acetate/hexane, linear gradient) afforded the title compound.

EXAMPLE 88C 6-(2,6-dimethylphenyl)-8-methyl-2-[(2'-methyl-2',3'-dihydro-1'H-spiro[cyclopropane-1,4'-isoquinolin]-7'-yl)amino]pyrido[4,3-d]pyrimidin-5(6H)-one Example 88B (70 mg, 0.225 mmol) was dissolved in dichloromethane (2248 μl) and 3-chlorobenzoperoxoic acid (60.5 mg, 0.270 mmol) was added. The reaction mixture was stirred at ambient temperature for 30 minutes then 2'-methyl-2',3'-dihydro-1'H-spiro[cyclopropane-1,4'-isoquinolin]-7'-amine (50.8 mg, 0.270 mmol) followed by TFA (34.6 μl, 0.450 mmol) were added. The reaction mixture was concentrated, 1 mL of acetonitrile was added and the reaction mixture was stirred at 90° C. overnight. The reaction mixture was then diluted with ethyl acetate (30 mL) and washed with saturated aqueous sodium bicarbonate (20 mL) and saturated aqueous brine (20 mL), dried over magnesium sulfate, filtered and concentrated. Purification by silica gel flash chromatography (Isco®, Redi-Sep® column, 2-50%, 2:1 methanol:$H_2O$ in ethyl acetate, linear gradient) afforded the title compound. $^1$H NMR (300 MHz, dimethylsulfoxide-$d_6$) δ 10.17 (s, 1H), 9.16 (s, 1H), 7.75-7.60 (m, 2H), 7.52 (s, 1H), 7.35-7.18 (m, 3H), 6.70 (d, J=8.6, 1H), 3.58 (s, 2H), 2.44 (s, 2H), 2.32 (s, 3H), 2.23 (s, 3H), 2.04 (s, 6H), 0.97-0.69 (m, 4H). MS (ESI) m/z 452 (M+H)$^+$.

EXAMPLE 89

2-({4-[4-(dimethylamino)piperidin-1-yl] phenyl}amino)-6-(2,6-dimethylphenyl)-8-methyl-pyrido[4,3-d]pyrimidin-5(6H)-one Example 88B (70 mg, 0.225 mmol) was dissolved in dichloromethane (2248 μl) and 3-chlorobenzoperoxoic acid (60.5 mg, 0.270 mmol) was added. The reaction mixture was stirred at ambient temperature for 30 minutes then 1-(4-aminophenyl)-N,N-dimethylpiperidin-4-amine (50.8 mg, 0.270 mmol) followed by TFA (34.6 μl, 0.450 mmol) were added. The reaction mixture was concentrated, 1 mL of acetonitrile was added and the reaction mixture was stirred at 90° C. overnight. The reaction mixture was then diluted with ethyl acetate (30 mL) and washed with saturated aqueous sodium bicarbonate (20 mL) and saturated aqueous brine (20 mL), dried over magnesium sulfate, filtered and concentrated. Purification by silica gel flash chromatography (Isco®, Redi-Sep® column, 2-50%, 2:1 methanol:$H_2O$ in ethyl acetate with 5% triethylamine, linear gradient) followed by recrystallization in ethyl acetate/hexane mixture afforded the title compound. $^1$H NMR (300 MHz, dimethylsulfoxide-$d_6$) δ 10.06 (s, 1H), 9.12 (s, 1H), 7.76 (brs, 2H), 7.49 (s, 1H), 7.34-7.18 (m, 3H), 6.94 (d, J=9.1, 2H), 3.71-3.58 (m, 2H), 2.69-2.56 (m, 2H), 2.31-2.10 (m, 10H), 2.04 (s, 6H), 1.87-1.75 (m, 2H), 1.57-1.36 (m, 2H). MS (ESI) m/z 483 (M+H)$^+$.

EXAMPLE 90

6-(2-chloro-6-methylphenyl)-8-methyl-2-[(2'-methyl-2',3'-dihydro-1'H-spiro[cyclopropane-1,4'-isoquinolin]-7'-yl)amino]pyrido[4,3-d]pyrimidin-5 (6H)-one

EXAMPLE 90A

N-(2-chloro-6-methylphenyl)-4-ethyl-2-(methylthio) pyrimidine-5-carboxamide

To a solution of Example 28B (539 mg, 2.72 mmol) in dichloromethane (5440 μl) was added a catalytic amount of N,N-dimethylformamide (5.27 μl, 0.068 mmol). The free-flowing slurry was cooled to ~5° C. Oxalyl chloride (250 μl, 2.86 mmol) was added dropwise via syringe. The reaction mixture was allowed to stir at 5-10° C. for 1 hour, then the cooling bath was removed and the reaction mixture was stirred at ambient temperature for an additional hour. To the slurry was added the 2-chloro-6-methylaniline (351 μl, 2.86 mmol) and pyridine (495 μl, 6.12 mmol). The reaction mixture was then stirred at ambient overnight. The reaction mixture was poured into a 125 mL separatory funnel, diluted with 50 mL of dichloromethane and the organic layer was washed with water (1×40 mL), 1 molar aqueous phosphoric acid (1×40 mL), and saturated aqueous brine (1×40 mL), dried over magnesium sulfate, filtered and concentrated. The crude product was recrystallized in ethyl acetate/hexane mixture to afford the title compound.

EXAMPLE 90B 6-(2-chloro-6-methylphenyl)-8-methyl-2-(methylthio)pyrido[4,3-d]pyrimidin-5(6H)-one A scintillation vial, equipped with stir bar and septa, was charged with Example 90A (607 mg, 1.886 mmol) and N,N-dimethylformamide (7365 μl) followed by N-(chloromethylene)-N-methylmethanaminium (707 mg, 5.52 mmol) and the reaction mixture was stirred at ambient temperature for 16 hours. The reaction mixture was cooled to 0° C. and quenched by careful addition of saturated aqueous sodium bicarbonate. To the reaction mixture was added 80 mL of ethyl acetate and the reaction mixture was poured into a 250 mL separatory funnel. The aqueous layer was removed and the organic layer was washed with diluted aqueous sodium bicarbonate (10% wt, 50 mL) and saturated aqueous brine (50 mL), dried over magnesium sulfate, filtered, and was concentrated. Purification by silica gel flash chromatography (Isco®, Redi-Sep® column, 2-100% ethyl acetate/hexane, linear gradient) afforded the title compound.

EXAMPLE 90C 6-(2-chloro-6-methylphenyl)-8-methyl-2-[(2'-methyl-2',3'-dihydro-1'H-spiro[cyclopropane-1,4'-isoquinolin]-7'-yl)amino]pyrido[4,3-d]pyrimidin-5 (6H)-one The title compound was prepared as described in Example 88C, substituting Example 88B with Example 90B. Purification by silica gel flash chromatography (Isco®, Redi-Sep® column, 2-50% 2:1 methanol:$H_2O$ in ethyl acetate, linear gradient) followed by recrystallization in ethyl acetate/hexane mixture afforded the title compound. $^1$H NMR (300 MHz, dimethylsulfoxide-$d_6$) δ 10.20 (s, 1H), 9.15 (s, 1H), 7.74-7.59 (m, 2H), 7.58-7.49 (m, 2H), 7.47-7.39 (m, 2H), 6.70 (d, J=8.6, 1H), 3.59 (s, 2H), 2.45 (s, 2H), 2.33 (s, 3H), 2.23 (s, 3H), 2.12 (s, 3H), 0.96-0.76 (m, 4H). MS (ESI) m/z 472 (M+H)$^+$.

EXAMPLE 91

6-(2-chloro-6-methylphenyl)-2-({4-[4-(dimethylamino)piperidin-1-yl]phenyl}amino)-8-methylpyrido [4,3-d]pyrimidin-5(6H)-one The title compound was prepared as described in Example 89, substituting Example 88B with Example 90B. Purification by silica gel flash chromatography (Isco®, Redi-Sep® column, 2-50% 2:1 methanol:$H_2O$ in ethyl acetate with 5% triethylamine, linear gradient) followed by recrystallization in ethyl acetate/hexane mixture afforded the title compound. $^1$H NMR (300 MHz, dimethylsulfoxide-$d_6$) δ 10.10 (brs, 1H), 9.11 (s, 1H), 7.77 (brs, 2H), 7.58-7.49 (m, 2H), 7.46-7.38 (m, 2H), 6.94 (d, J=9.1, 2H), 3.72-3.60 (m, 2H), 2.69-2.55 (m, 2H), 2.27-2.15 (m, 10H), 2.12 (s, 3H), 1.88-1.75 (m, 2H), 1.58-1.38 (m, 2H). MS (ESI) m/z 503 (M+H)$^+$.

EXAMPLE 92

6-(2,6-dichlorophenyl)-2-[(4-{[2-(dimethylamino)ethyl]sulfanyl}phenyl)amino]-8-methylpyrido[4,3-d]pyrimidin-5(6H)-one The title compound was prepared as described in Example 78, substituting 4-(1-methylpiperidin-4-yl)aniline with 4-(2-(dimethylamino)ethylthio)aniline. Purification by silica gel flash chromatography (Isco®, Redi-Sep® column, 2-50%, 2:1 methanol:H$_2$O in ethyl acetate, linear gradient) afforded the title compound. $^1$H NMR (400 MHz, dimethylsulfoxide-d$_6$) δ 10.07 (s, 1H), 9.20 (s, 1H), 7.90 (d, J=8.7, 2H), 7.72-7.67 (m, 2H), 7.58 (dd, J=8.8, 7.5, 1H), 7.53 (d, J=1.2, 1H), 7.39 (d, J=8.7, 2H), 3.10-3.03 (m, 2H), 2.65-2.57 (m, 2H), 2.30-2.24 (m, 9H). MS (ESI) m/z 500 (M+H)$^+$.

EXAMPLE 93

6-(2,6-dichlorophenyl)-8-(difluoromethyl)-2-(1,2,3,4-tetrahydroisoquinolin-6-ylamino)pyrido[4,3-d]pyrimidin-5(6H)-one The title compound was prepared as described in Example 85, substituting tert-butyl 7-amino-4,4-dimethyl-3,4-dihydroisoquinoline-2(1H)-carboxylate with tert-butyl 6-amino-3,4-dihydroisoquinoline-2(1H)-carboxylate to afford the title compound. $^1$H NMR (400 MHz, dimethylsulfoxide-d$_6$) δ 10.24 (s, 1H), 9.21 (s, 1H), 8.95 (brs, 1H), 8.12 (s, 1H), 7.86 (s, 1H), 7.72-7.64 (m, 3H), 7.59 (dd, J=8.9, 7.4, 1H), 7.20 (d, J=8.4, 1H), 7.14 (t, J=54.6, 1H), 4.25 (s, 2H), 3.41 (t, J=6.4, 2H), 3.04 (t, J=6.3, 2H). MS (ESI) m/z 488 (M+H)$^+$.

EXAMPLE 94

6-(2,6-dichlorophenyl)-8-(difluoromethyl)-2-[(2'-methyl-2',3'-dihydro-1'H-spiro[cyclopropane-1,4'-isoquinolin]-7'-yl)amino]pyrido[4,3-d]pyrimidin-5(6H)-one The title compound was prepared as described in Example 36B, substituting 4-(4-methylpiperazin-1-yl)aniline with 2'-methyl-2',3'-dihydro-1'H-spiro[cyclopropane-1,4'-isoquinolin]-7'-amine. Purification of the residue by reverse-phase preparative HPLC on a Phenomenex Luna C8(2) 5 um 100 Å AXIA column (30 mm×75 mm) using a gradient of acetonitrile (A) and 0.1% ammonium acetate in water (B) at a flow rate of 50 mL/min (0-0.5 min 10% A, 0.5-7.0 min linear gradient 10-95% A, 7.0-10.0 min 95% A, 10.0-12.0 min linear gradient 95-10% A) afforded the title compound. $^1$H NMR (400 MHz, dimethylsulfoxide-d$_6$) δ 10.05 (s, 1H), 9.16 (s, 1H), 8.08 (s, 1H), 7.71-7.66 (m, 2H), 7.62 (s, 1H), 7.58 (dd, J=8.9, 7.4, 1H), 7.51 (dd, J=8.5, 2.2, 1H), 7.14 (t, J=54.7, 1H), 6.68 (d, J=8.5, 1H), 3.62 (s, 2H), 2.49 (s, 2H), 2.35 (s, 3H), 0.98-0.76 (m, 4H). MS (ESI) m/z 528 (M+H)$^+$.

EXAMPLE 95

6-(2,6-dichlorophenyl)-8-(difluoromethyl)-2-{[2-(pyrrolidin-1-yl)-2,3-dihydro-1H-inden-5-yl]amino}pyrido[4,3-d]pyrimidin-5(6H)-one

EXAMPLE 95A 1-(2,3-dihydro-1H-inden-2-yl)pyrrolidine

To a solution of 1H-inden-2(3H)-one (6 g, 45.4 mmol) in 100 mL of methanol were added pyrrolidine (7.51 ml, 91 mmol), sodium cyanoborohydride (5.71 g, 91 mmol), and acetic acid (5.20 ml, 91 mmol). The reaction mixture was stirred overnight and was concentrated. The crude residue was dissolved in 400 mL of ethyl acetate and washed with aqueous sodium bicarbonate (2×400 mL) and saturated aqueous brine (1×200 mL), dried over magnesium sulfate, filtered and concentrated. Recrystallization in ethyl acetate/hexane afforded the title compound. MS (ESI) m/z 188 (M+H)$^+$.

EXAMPLE 95B 1-(5-nitro-2,3-dihydro-1H-inden-2-yl)pyrrolidine

To a solution of Example 95A (8.38 g, 44.7 mmol) in TFA (320 ml, 4154 mmol) was added concentrated nitric acid (2.86 ml, 44.7 mmol) dropwise at 0° C. The reaction mixture was stirred at 0-15° C. for 5 hours. The reaction mixture was concentrated and dissolved in 200 mL of ethyl acetate. The organic solution was poured into a separatory funnel and washed with saturated aqueous sodium bicarbonate (2×150 mL) and saturated aqueous brine (1×100 mL), dried over magnesium sulfate, filtered and concentrated. The crude material was recrystallized in ethyl acetate/hexane mixture to afford the title compound. MS (ESI) m/z 233.1 (M+H)$^+$.

EXAMPLE 95C 2-(pyrrolidin-1-yl)-2,3-dihydro-1H-inden-5-amine

To a solution of Example 95B (7.25 g, 31.2 mmol) in 156 mL of methanol was added palladium on carbon (10% wt) (7.25 g, 6.81 mmol). The reaction mixture was evacuated and backfilled with nitrogen three times and evacuated and backfilled with hydrogen. The reaction mixture was then allowed to stirred under H$_2$ (1 atm, balloon) at ambient temperature overnight. The reaction mixture was filtered through diatomaceous earth and was concentrated. The crude product was recrystallized in an ethyl acetate/hexane mixture to obtain the title compound. MS (ESI) m/z 203.1 (M+H)$^+$.

EXAMPLE 95D 6-(2,6-dichlorophenyl)-8-(difluoromethyl)-2-{[2-(pyrrolidin-1-yl)-2,3-dihydro-1H-inden-5-yl]amino}pyrido[4,3-d]pyrimidin-5(6H)-one The title compound was prepared as described in Example 36B, substituting 4-(4-methylpiperazin-1-yl)aniline with Example 95C. Purification of the residue by reverse-phase preparative HPLC on a Phenomenex Luna C8(2) 5 um 100 Å AXIA column (30 mm×75 mm) using a gradient of acetonitrile (A) and 0.1% ammonium acetate in water (B) at a flow rate of 50 mL/min (0-0.5 min 10% A, 0.5-7.0 min linear gradient 10-95% A, 7.0-10.0 min 95% A, 10.0-12.0 min linear gradient 95-10% A) afforded the title compound. $^1$H NMR (400 MHz, dimethylsulfoxide-$d_6$) δ 10.05 (s, 1H), 9.16 (s, 1H), 8.07 (s, 1H), 7.73-7.65 (m, 3H), 7.62-7.51 (m, 2H), 7.28-6.99 (m, 2H), 3.16-2.93 (m, 3H), 2.88-2.74 (m, 2H), 2.58-2.51 (m, 4H), 1.75-1.65 (m, 4H). MS (ESI) m/z 542 (M+H)$^+$.

EXAMPLE 96

6-(2,6-dichlorophenyl)-2-[(4-{[2-(dimethylamino) ethyl]sulfonyl}phenyl)amino]-8-methylpyrido[4,3-d] pyrimidin-5(6H)-one A mixture Example 92 (20 mg, 0.040 mmol) and potassium peroxymonosulfate (200 mg, 0.325 mmol) in methanol (1 mL), tetrahydrofuran (1 mL) and water (0.5 mL) was stirred at room temperature for 1 hour. The precipitate that formed was filtered and the solid was washed with water (5 mL) and ethyl acetate (5 mL), and dried under high vacuum to afford the title compound. $^1$H NMR (400 MHz, dimethylsulfoxide-$d_6$) δ 10.56 (s, 1H), 9.27 (s, 1H), 8.21 (d, J=8.9, 2H), 7.89 (d, J=8.9, 2H), 7.71-7.65 (m, 2H), 7.61-7.53 (m, 2H), 3.64-3.56 (m, 2H), 3.12-3.04 (m, 2H), 2.53 (s, 6H), 2.29 (s, 3H). MS (ESI) m/z 532 (M+H)$^+$.

EXAMPLE 97

8-methyl-2-[(2'-methyl-2',3'-dihydro-1'H-spiro[cyclopropane-1,4'-isoquinolin]-7'-yl)amino]-6-(quinolin-8-yl)pyrido[4,3-d]pyrimidin-5(6H)-one

EXAMPLE 97A 4-ethyl-2-(methylthio)-N-(quinolin-8-yl)pyrimidine-5-carboxamide To a solution of Example 28B (539 mg, 2.72 mmol) in dichloromethane (5440 μl) was added a catalytic amount of N,N-dimethylformamide (5.27 μl, 0.068 mmol). The free-flowing slurry was cooled to ~5° C. Oxalyl chloride (250 μl, 2.86 mmol) was added dropwise via syringe. The reaction mixture was allowed to proceed at 5-10° C. for 1 hour, then the cooling bath was removed and the reaction mixture was stirred at ambient temperature for an additional hour. To the slurry was added the quinolin-8-amine (412 mg, 2.86 mmol) and pyridine (495 μl, 6.12 mmol). The reaction mixture was then stirred at ambient overnight. The reaction mixture was poured into a 125 mL separatory funnel, diluted with 50 mL of dichloromethane and the organic layer was washed with water (1×40 mL), 1 molar aqueous phosphoric acid (1×40 mL), and saturated aqueous brine (1×40 mL), dried over magnesium sulfate, filtered and concentrated. The crude product was recrystallized in an ethyl acetate/hexane mixture to afford the title compound.

EXAMPLE 97B 8-methyl-2-(methylthio)-6-(quinolin-8-yl)pyrido[4,3-d]pyrimidin-5(6H)-one A scintillation vial, equipped with stir bar and septa, was charged with Example 97A (475 mg, 1.464 mmol) and N,N-dimethylformamide (7365 μl) followed by N-(chloromethylene)-N-methylmethanaminium (707 mg, 5.52 mmol) and the reaction mixture was stirred at ambient temperature for 16 hours. The reaction mixture was cooled to 0° C. and quenched by careful addition of saturated aqueous sodium bicarbonate. To the reaction mixture was added 80 mL of ethyl acetate and the reaction mixture was poured into a 250 mL separatory funnel. The aqueous layer was removed and the organic layer was washed with diluted aqueous sodium bicarbonate (10% wt, 50 mL) and saturated aqueous brine (50 mL), dried over magnesium sulfate, filtered and concentrated. Purification by silica gel flash chromatography (Isco®, Redi-Sep® column, 2-100% ethyl acetate/hexane, linear gradient) afforded the title compound.

EXAMPLE 97C 8-methyl-2-[(2'-methyl-2',3'-dihydro-1'H-spiro[cyclopropane-1,4'-isoquinolin]-7'-yl)amino]-6-(quinolin-8-yl)pyrido[4,3-d]pyrimidin-5(6H)-one The title compound was prepared as described in Example 88C, substituting Example 88B with Example 97B. Purification by silica gel flash chromatography (Isco®, Redi-Sep® column, 2-50% 2:1 methanol:H$_2$O in ethyl acetate, linear gradient) followed by recrystallization in ethyl acetate/hexane and purification with reverse-phase preparative HPLC on a Phenomenex Luna C8(2) 5 um 100 Å AXIA column (30 mm×75 mm) using a gradient of acetonitrile (A) and 0.1% trifluoroacetic acid in water (B) at a flow rate of 50 mL/min (0-0.5 min 10% A, 0.5-7.0 min linear gradient 10-95% A, 7.0-10.0 min 95% A, 10.0-12.0 min linear gradient 95-10% A) afforded the title compound as a TFA salt. $^1$H NMR (300 MHz, dimethylsulfoxide-$d_6$) δ 10.34 (s, 1H), 10.22 (s, 1H), 9.17 (s, 1H), 8.89 (dd, J=4.2, 1.7, 1H), 8.54 (dd, J=8.4, 1.6, 1H), 8.18 (dd, J=8.2, 1.3, 1H), 7.92-7.86 (m, 2H), 7.83-7.73 (m, 3H), 7.65 (dd, J=8.3, 4.2, 1H), 6.90 (d, J=8.7, 1H), 4.66-4.43 (m, 2H), 3.61-3.48 (m, 1H), 3.28-3.20 (m, 1H), 2.96 (d, J=4.5, 3H), 2.25 (s, 3H), 1.43-0.87 (m, 4H). MS (ESI) m/z 475 (M+H)$^+$.

EXAMPLE 98

6-(2-chlorophenyl)-8-methyl-2-(1,2,3,4-tetrahydroisoquinolin-7-ylamino)pyrido[4,3-d]pyrimidin-5 (6H)-one

EXAMPLE 98A

N-(2-chlorophenyl)-4-ethyl-2-(methylthio)pyrimidine-5-carboxamide

To a solution of Example 28B (539 mg, 2.72 mmol) in dichloromethane (5440 μl) was added a catalytic amount of N,N-dimethylformamide (5.27 μl, 0.068 mmol). The free-flowing slurry was cooled to 5° C. Oxalyl chloride (250 μl, 2.86 mmol) was added dropwise via syringe. The reaction mixture was allowed to stir at 5-10° C. for 1 hour, then the cooling bath was removed and the reaction mixture was stirred at ambient temperature for an additional hour. To the slurry was added the aniline 2-chloroaniline (301 mg, 2.86 mmol). The reaction mixture was then stirred at ambient temperature for 16 hours. The reaction mixture was poured into a 125 mL separatory funnel, diluted with 50 mL of dichloromethane and the organic layer was washed with water (1×40 mL), 1 molar aqueous phosphoric acid (1×40 mL), and saturated aqueous brine (1×40 mL), dried over magnesium sulfate, filtered and concentrated. The crude product was recrystallized in ethyl acetate/hexane mixture to afford the title compound.

EXAMPLE 98B 6-(2-chlorophenyl)-8-methyl-2-(methylthio)pyrido[4,3-d]pyrimidin-5(6H)-one A scintillation vial, equipped with stir bar and septa, was charged with Example 98A (605 mg, 1.966 mmol) and N,N-dimethylformamide (7365 µl) followed by N-(chloromethylene)-N-methylmethanaminium (755 mg, 5.90 mmol) and the reaction mixture was stirred at ambient temperature for 16 hours. The reaction mixture was cooled to 0° C. and quenched by careful addition of saturated aqueous sodium bicarbonate. To the reaction mixture was added 80 mL of ethyl acetate and the reaction mixture was poured into a 250 mL separatory funnel. The aqueous layer was removed and the organic layer was washed with diluted aqueous sodium bicarbonate (10% wt, 50 mL) and saturated aqueous brine (50 mL), dried over magnesium sulfate, filtered and concentrated. Purification by silica gel flash chromatography (Isco®, Redi-Sep® column, 2-100% ethyl acetate/hexane, linear gradient) afforded the title compound.

EXAMPLE 98C 6-(2-chlorophenyl)-8-methyl-2-(1,2,3,4-tetrahydroisoquinolin-7-ylamino)pyrido[4,3-d]pyrimidin-5(6H)-one Example 98B (70 mg, 0.220 mmol) was dissolved in dichloromethane (2203 µl) and 3-chlorobenzoperoxoic acid (59.2 mg, 0.264 mmol) was added. The reaction mixture was stirred at ambient temperature for 30 minutes and tert-butyl 7-amino-3,4-dihydroisoquinoline-2(1H)-carboxylate (65.6 mg, 0.264 mmol) was added. The reaction mixture was stirred at 45° C. for 16 hours. The reaction mixture was diluted with ethyl acetate (30 mL) and washed with saturated aqueous sodium bicarbonate (20 mL) and saturated aqueous brine (20 mL), dried over magnesium sulfate, filtered and concentrated. Purification by silica gel flash chromatography (Isco®, Redi-Sep® column, 20-80% ethyl acetate/hexane, linear gradient) afforded the Boc protected intermediate. The product was dissolved in a mixture of 0.5 mL of dichloromethane, and 1 mL of ethyl acetate. Hydrochloric acid (2 M in diethyl ether, ~5 mL) was added and the reaction mixture was stirred at 50° C. for 3 hours. The solid was filtered and washed with diethyl ether to afford the title compound as an HCl salt. $^1$H NMR (300 MHz, dimethylsulfoxide-$d_6$) δ 10.36 (s, 1H), 9.26 (brs, 2H), 9.18 (s, 1H), 7.89 (brs, 1H), 7.75-7.65 (m, 3H), 7.62-7.51 (m, 3H), 7.22 (d, J=8.5, 1H), 4.33-4.24 (m, 2H), 3.44-3.33 (m, 2H), 2.98 (t, J=6.0, 2H), 2.23 (s, 3H). MS (ESI) m/z 418 (M+H)$^+$.

EXAMPLE 99

6-(2-chlorophenyl)-2-({4-[4-(dimethylamino)piperidin-1-yl]phenyl}amino)-8-methylpyrido[4,3-d]pyrimidin-5(6H)-one The title compound was prepared as described in Example 89, substituting Example 88B with Example 98B. Purification by silica gel flash chromatography (Isco®, Redi-Sep® column, 2-50% 2:1 methanol:H$_2$O in ethyl acetate with 5% triethylamine, linear gradient) followed by recrystallization in ethyl acetate/hexane mixture afforded the title compound. $^1$H NMR (300 MHz, dimethylsulfoxide-$d_6$) δ 10.09 (brs, 1H), 9.10 (s, 1H), 7.82-7.66 (m, 3H), 7.63-7.48 (m, 4H), 6.96 (d, J=9.1, 2H), 3.78-3.65 (m, 2H), 2.69-2.57 (m, 2H), 2.41 (s, 6H), 2.20 (s, 3H), 1.96-1.86 (m, 2H), 1.65-1.48 (m, 2H). MS (ESI) m/z 489 (M+H)$^+$.

EXAMPLE 100

8-methyl-6-(naphthalen-1-yl)-2-(1,2,3,4-tetrahydroisoquinolin-7-ylamino)pyrido[4,3-d]pyrimidin-5(6H)-one

EXAMPLE 100A 4-ethyl-2-(methylthio)-N-(naphthalen-1-yl)pyrimidine-5-carboxamide To a solution of Example 28B (539 mg, 2.72 mmol) in dichloromethane (5440 µl) was added a catalytic amount of N,N-dimethylformamide (5.27 µl, 0.068 mmol). The free-flowing slurry was cooled to ~5° C. Oxalyl chloride (250 µl, 2.86 mmol) was added dropwise via syringe. The reaction mixture was allowed to stir at 5-10° C. for 1 hour, then the cooling bath was removed and the reaction mixture was stirred at ambient temperature for an additional hour. To the slurry obtained from above was added naphthalen-1-amine (409 mg, 2.86 mmol). The reaction mixture was then stirred at ambient temperature for 16 hours. The reaction mixture was poured into a 125 mL separatory funnel, and diluted with 50 mL of dichloromethane. The organic layer was washed with water (1×40 mL), 1 molar aqueous phosphoric acid (1×40 mL), and saturated aqueous brine (1×40 mL), dried over magnesium sulfate, filtered and concentrated. The crude product was recrystallized in ethyl acetate/hexane mixture to afford the title compound.

EXAMPLE 100B 8-methyl-2-(methylthio)-6-(naphthalen-1-yl)pyrido[4,3-d]pyrimidin-5(6H)-one A scintillation vial, equipped with stir bar and septa, was charged with Example 100A (695 mg, 2.149 mmol) and N,N-dimethylformamide (7365 µl) followed by N-(chloromethylene)-N-methylmethanaminium (755 mg, 5.90 mmol) and the reaction mixture was stirred at ambient temperature for 16 hours. The reaction mixture was cooled to 0° C. and quenched by careful addition of saturated aqueous sodium bicarbonate. To the reaction mixture was added 80 mL of ethyl acetate and the reaction mixture was poured into a 250 mL separatory funnel. The aqueous layer was removed and the organic layer was washed with diluted aqueous sodium bicarbonate (10% wt, 50 mL), and saturated aqueous brine (50 mL), dried over magnesium sulfate, filtered, and was concentrated. Purification by silica gel flash chromatography (Isco®, Redi-Sep® column, 2-100% ethyl acetate/hexane, linear gradient) afforded the title compound.

EXAMPLE 100C 8-methyl-6-(naphthalen-1-yl)-2-(1,2,3,4-tetrahydroisoquinolin-7-ylamino)pyrido[4,3-d]pyrimidin-5(6H)-one The title compound was prepared as described in Example 98C, substituting Example 98B with Example 100B. Purification by silica gel flash chromatography (Isco®, Redi-Sep® column, 10-80% ethyl acetate/hexane, linear gradient) afforded the Boc protected intermediate. The product was dissolved in a mixture of 0.5 mL of dichloromethane, and 1 mL of ethyl acetate. then. Hydrochloric acid (2 M in diethyl ether, ~5 mL) was added and the reaction mixture was stirred at 50° C. for 3 hours. The solid was filtered and washed with diethyl ether to yield the title compound as an HCl salt. $^1$H NMR (300 MHz, dimethylsulfoxide-$d_6$) δ 10.37 (s, 1H), 9.26 (brs, 2H), 9.20 (s, 1H), 8.14-8.07 (m, 2H), 7.93 (brs, 1H), 7.82-7.47 (m, 7H), 7.23 (d, J=8.5, 1H), 4.33-4.27 (m, 2H), 3.43-3.33 (m, 2H), 2.99 (t, J=6.1, 2H), 2.26 (s, 3H). MS (ESI) m/z 434 (M+H)$^+$.

EXAMPLE 101

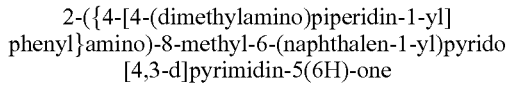
2-({4-[4-(dimethylamino)piperidin-1-yl]
phenyl}amino)-8-methyl-6-(naphthalen-1-yl)pyrido
[4,3-d]pyrimidin-5(6H)-one The title compound was prepared as described in Example 89, substituting Example 88B with Example 100B. Purification by silica gel flash chromatography (Isco®, Redi-Sep® column, 2-50% 2:1 methanol:H$_2$O in ethyl acetate with 5% triethylamine, linear gradient) followed by recrystallization in ethyl acetate/hexane mixture afforded the title compound. $^1$H NMR (300 MHz, dimethylsulfoxide-$d_6$) δ 10.09 (brs, 1H), 9.13 (s, 1H), 8.16-8.05 (m, 2H), 7.80 (brs, 2H), 7.73-7.46 (m, 6H), 6.97 (d, J=9.1, 2H), 3.80-3.66 (m, 2H), 2.71-2.59 (m, 2H), 2.42 (s, 6H), 2.23 (s, 3H), 1.97-1.87 (m, 2H), 1.68-1.46 (m, 2H). MS (ESI) m/z 505 (M+H)$^+$.

EXAMPLE 102

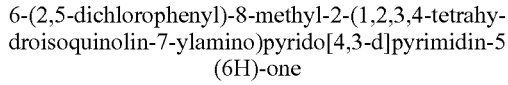
6-(2,5-dichlorophenyl)-8-methyl-2-(1,2,3,4-tetrahydroisoquinolin-7-ylamino)pyrido[4,3-d]pyrimidin-5
(6H)-one

EXAMPLE 102A

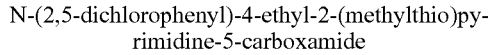
N-(2,5-dichlorophenyl)-4-ethyl-2-(methylthio)pyrimidine-5-carboxamide To a solution of Example 28B (539 mg, 2.72 mmol) in dichloromethane (5440 µl) was added a catalytic amount of N,N-dimethylformamide (5.27 µl, 0.068 mmol). The free-flowing slurry was cooled to 5° C. Oxalyl chloride (250 µl, 2.86 mmol) was added dropwise via syringe. The reaction mixture was allowed to proceed at 5-10° C. for 1 hour, then the cooling bath was removed and the reaction mixture was stirred at ambient temperature for an additional hour. To the slurry was added 2,5-dichloroaniline (463 mg, 2.86 mmol). The reaction mixture was then stirred at ambient temperature for 16 hours. The reaction mixture was poured into a 125 mL separatory funnel, diluted with 50 mL of dichloromethane and the organic layer was washed with water (1×40 mL), 1 molar aqueous phosphoric acid (1×40 mL), and saturated aqueous brine (1×40 mL), dried over magnesium sulfate, filtered and concentrated. The crude product was recrystallized in ethyl acetate/hexane mixture to afford the title compound.

EXAMPLE 102B

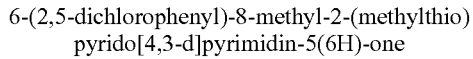
6-(2,5-dichlorophenyl)-8-methyl-2-(methylthio)
pyrido[4,3-d]pyrimidin-5(6H)-one A scintillation vial, equipped with stir bar and septa, was charged with Example 102A (575 mg, 1.68 mmol) and N,N-dimethylformamide (7365 µl) followed by N-(chloromethylene)-N-methylmethanaminium (755 mg, 5.90 mmol) and the reaction mixture was stirred at ambient temperature for 16 hours. The reaction mixture was cooled to 0° C. and quenched by careful addition of saturated aqueous sodium bicarbonate. To the reaction mixture was added 80 mL of ethyl acetate and the reaction mixture was poured into a 250 mL separatory funnel. The aqueous layer was removed and the organic layer was washed with diluted aqueous sodium bicarbonate (10% wt, 50 mL), and saturated aqueous brine (50 mL), dried over magnesium sulfate, filtered, and was concentrated. Purification by silica gel flash chromatography (Isco®, Redi-Sep® column, 2-100% ethyl acetate/hexane, linear gradient) afforded the title compound.

EXAMPLE 102C

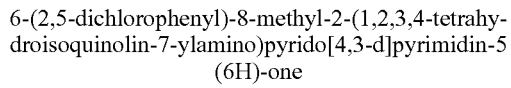
6-(2,5-dichlorophenyl)-8-methyl-2-(1,2,3,4-tetrahydroisoquinolin-7-ylamino)pyrido[4,3-d]pyrimidin-5
(6H)-one The title compound was prepared as described in Example 98C, substituting Example 98B with Example 102B. Purification by silica gel flash chromatography (Isco®, Redi-Sep® column, 10-80% ethyl acetate/hexane, linear gradient) afforded the Boc protected intermediate. The product was dissolved in a mixture of 0.5 mL of dichloromethane, and 1 mL of ethyl acetate. Hydrochloric acid (2 M in diethyl ether, ~5 mL) was added and the reaction mixture was stirred at 50° C. for 3 hours. The solid was filtered and washed with diethyl ether and purified further by reverse-phase preparative HPLC on a Phenomenex Luna C8(2) 5 um 100 Å AXIA column (30 mm×75 mm) using a gradient of acetonitrile (A) and 0.1% trifluoroacetic acid in water (B) at a flow rate of 50 mL/min (0-0.5 min 10% A, 0.5-7.0 min linear gradient 10-95% A, 7.0-10.0 min 95% A, 10.0-12.0 min linear gradient 95-10% A) to afford the title compound as a TFA salt. $^1$H NMR (300 MHz, dimethylsulfoxide-$d_6$) δ 10.39 (brs, 1H), 9.18 (s, 1H), 8.98 (brs, 2H), 7.88 (brs, 1H), 7.83 (d, J=2.5, 1H), 7.77-7.59 (m, 5H), 7.23 (d, J=8.5, 1H), 4.36-4.25 (m, 2H), 3.46-3.35 (m, 2H), 3.02-2.93 (m, 2H), 2.23 (s, 3H). MS (ESI) m/z 452 (M+H)$^+$.

EXAMPLE 103

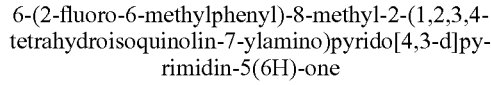
6-(2-fluoro-6-methylphenyl)-8-methyl-2-(1,2,3,4-tetrahydroisoquinolin-7-ylamino)pyrido[4,3-d]pyrimidin-5(6H)-one

EXAMPLE 103A

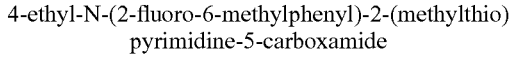
4-ethyl-N-(2-fluoro-6-methylphenyl)-2-(methylthio)
pyrimidine-5-carboxamide To a solution of Example 28B (539 mg, 2.72 mmol) in dichloromethane (5440 µl) was added a catalytic amount of N,N-dimethylformamide (5.27 µl, 0.068 mmol). The free-flowing slurry was cooled to ~5° C. Oxalyl chloride (250 µl, 2.86 mmol) was added dropwise via syringe. The reaction mixture was allowed to proceed at 5-10° C. for 1 hour, then the cooling bath was removed and the mixture stirred at ambient temperature for an additional hour. To the slurry was added 2-fluoro-6-methylaniline (357 mg, 2.86 mmol). The reaction mixture was then stirred at ambient temperature for 16 hours. The reaction mixture was poured into a 125 mL separatory funnel, diluted with 50 mL of dichloromethane and the organic layer was washed with water (1×40 mL), 1 molar aqueous phosphoric acid (1×40 mL), and saturated aqueous brine (1×40 mL), dried over magnesium sulfate, filtered and concentrated. The crude product was recrystallized in ethyl acetate/hexane mixture to afford the title compound.

EXAMPLE 103B 6-(2-fluoro-6-methylphenyl)-8-methyl-2-(methylthio)pyrido[4,3-d]pyrimidin-5(6H)-one A scintillation vial, equipped with stir bar and septa, was charged with Example 103A (585 mg, 1.916 mmol) and N,N-dimethylformamide (7365 µl) followed by N-(chloromethylene)-N-methylmethanaminium (736 mg, 5.75 mmol) and the reaction mixture was stirred at ambient temperature for 16 hours. The reaction mixture was cooled to 0° C. and was quenched by careful addition of saturated aqueous sodium bicarbonate. To the reaction mixture was added 80 mL of ethyl acetate and the reaction mixture was poured into a 250 mL separatory funnel. The aqueous layer was removed and the organic layer was washed with diluted aqueous sodium bicarbonate (10% wt, 50 mL), and saturated aqueous brine (50 mL), dried over magnesium sulfate, filtered and concentrated. Purification by silica gel flash chromatography (Isco®, Redi-Sep® column, 2-100% ethyl acetate/hexane, linear gradient) afforded the title compound.

EXAMPLE 103C 6-(2-fluoro-6-methylphenyl)-8-methyl-2-(1,2,3,4-tetrahydroisoquinolin-7-ylamino)pyrido[4,3-d]pyrimidin-5(6H)-one The title compound was prepared as described in Example 98C, substituting Example 98B with Example 103B. Purification by silica gel flash chromatography (Isco®, Redi-Sep® column, 10-80% ethyl acetate/hexane, linear gradient) afforded the Boc protected intermediate. The product was dissolved in a mixture of 0.5 mL of dichloromethane, and 1 mL of ethyl acetate. Hydrochloric acid (2M in diethyl ether, ~5 mL) was added and the reaction mixture was stirred at 50° C. for 3 hours. The solid was filtered and washed with diethyl ether to afford the title compound as an HCl salt. $^1$H NMR (300 MHz, dimethylsulfoxide-$d_6$) δ 10.37 (s, 1H), 9.30 (brs, 2H), 9.19 (s, 1H), 7.89 (brs, 1H), 7.78-7.63 (m, 2H), 7.52-7.38 (m, 1H), 7.36-7.17 (m, 3H), 4.31-4.23 (m, 2H), 3.44-3.32 (m, 2H), 3.03-2.92 (m, 2H), 2.23 (s, 3H), 2.14 (s, 3H). MS (ESI) m/z 416 (M+H)$^+$.

EXAMPLE 104

2-({4-[4-(dimethylamino)piperidin-1-yl]phenyl}amino)-6-(2-fluoro-6-methylphenyl)-8-methylpyrido[4,3-d]pyrimidin-5(6H)-one The title compound was prepared as described in Example 89, substituting Example 88B with Example 103B. Purification by silica gel flash chromatography (Isco®, Redi-Sep® column, 2-50% 2:1 methanol:$H_2O$ in ethyl acetate with 5% triethylamine, linear gradient) followed by recrystallization in ethyl acetate/hexane mixture afforded the title compound. $^1$H NMR (300 MHz, dimethylsulfoxide-$d_6$) δ 10.10 (brs, 1H), 9.11 (s, 1H), 7.76 (brs, 2H), 7.61 (s, 1H), 7.50-7.38 (m, 1H), 7.32-7.21 (m, 2H), 6.94 (d, J=9.1, 2H), 3.71-3.61 (m, 2H), 2.68-2.57 (m, 2H), 2.22 (s, 6H), 2.20 (d, J=0.6, 3H), 2.13 (s, 3H), 1.90-1.80 (m, 2H), 1.57-1.38 (m, 2H). MS (ESI) m/z 487 (M+H)$^+$.

EXAMPLE 105

8-methyl-6-[2-(1,3-oxazol-5-yl)phenyl]-2-(1,2,3,4-tetrahydroisoquinolin-7-ylamino)pyrido[4,3-d]pyrimidin-5(6H)-one

EXAMPLE 105A 4-ethyl-2-(methylthio)-N-(2-(oxazol-5-yl)phenyl)pyrimidine-5-carboxamide To a solution of Example 28B (539 mg, 2.72 mmol) in dichloromethane (5440 µl) was added a catalytic amount of N,N-dimethylformamide (5.27 µl, 0.068 mmol). The free-flowing slurry was cooled to ~5° C. Oxalyl chloride (250 µl, 2.86 mmol) was added dropwise via syringe. The reaction mixture was allowed to proceed at 5-10° C. for 1 hour, then the cooling bath was removed and the mixture stirred at ambient temperature for an additional hour. To the slurry was added 2-(oxazol-5-yl)aniline (457 mg, 2.86 mmol). The reaction mixture was then stirred at ambient temperature for 16 hours. The reaction mixture was poured into a 125 mL separatory funnel, diluted with 50 mL of dichloromethane and the organic layer was washed with water (1×40 mL), 1 molar aqueous phosphoric acid (1×40 mL), and saturated aqueous brine (1×40 mL), dried over magnesium sulfate, filtered and concentrated. The crude product was recrystallized in ethyl acetate/hexane mixture to afford the title compound.

EXAMPLE 105B 8-methyl-2-(methylthio)-6-(2-(oxazol-5-yl)phenyl)pyrido[4,3-d]pyrimidin-5(6H)-one A scintillation vial, equipped with stir bar and septa, was charged with Example 105A (645 mg, 1.895 mmol) and N,N-dimethylformamide (7365 µl) followed by N-(chloromethylene)-N-methylmethanaminium (736 mg, 5.75 mmol) and the reaction mixture was stirred at ambient temperature for 16 hours. The reaction mixture was cooled to 0° C. and quenched by careful addition of saturated aqueous sodium bicarbonate. To the reaction mixture was added 80 mL of ethyl acetate and the reaction mixture was poured into a 250 mL separatory funnel. The aqueous layer was removed and the organic layer was washed with diluted aqueous sodium bicarbonate (10% wt, 50 mL), and saturated aqueous brine (50 mL), dried over magnesium sulfate, filtered and concentrated. Purification by silica gel flash chromatography (Isco®, Redi-Sep® column, 2-100% ethyl acetate/hexane, linear gradient) afforded the title compound.

EXAMPLE 105C 8-methyl-6-[2-(1,3-oxazol-5-yl)phenyl]-2-(1,2,3,4-tetrahydroisoquinolin-7-ylamino)pyrido[4,3-d]pyrimidin-5(6H)-one The title compound was prepared as described in Example 98C, substituting Example 98B with Example 105B. Purification by silica gel flash chromatography (Isco®, Redi-Sep® column, 10-80% ethyl acetate/hexane, linear gradient) afforded the boc protected intermediate. The product was dissolved in a mixture of 0.5 mL of dichloromethane, and 1 mL of ethyl acetate. Hydrochloric acid (2M in diethylether, ~5 mL) was added and the reaction mixture was stirred at 50° C. for 3 hours. The solid was filtered and washed with diethyl ether to afford the title compound as an HCl salt. $^1$H NMR (300 MHz, dimethylsulfoxide-d$_6$) δ 10.38 (s, 1H), 9.33 (brs, 2H), 9.15 (s, 1H), 8.40 (s, 1H), 7.99-7.87 (m, 2H), 7.77-7.48 (m, 5H), 7.22 (d, J=8.5, 1H), 6.85 (s, 1H), 4.32-4.24 (m, 2H), 3.42-3.31 (m, 2H), 3.04-2.93 (m, 2H), 2.24 (s, 3H). MS (ESI) m/z 451 (M+H)$^+$.

EXAMPLE 106

2-({4-[4-(dimethylamino)piperidin-1-yl]phenyl}amino)-8-methyl-6-[2-(1,3-oxazol-5-yl)phenyl]pyrido[4,3-d]pyrimidin-5(6H)-one The title compound was prepared as described in Example 89, substituting Example 88B with Example 105B. Purification by silica gel flash chromatography (Isco®, Redi-Sep® column, 2-50% 2:1 methanol:H$_2$O in ethyl acetate with 5% triethylamine, linear gradient) followed by recrystallization in ethyl acetate/hexane mixture afforded the title compound. $^1$H NMR (300 MHz, dimethylsulfoxide-d$_6$) δ 10.11 (brs, 1H), 9.07 (s, 1H), 8.40 (s, 1H), 7.97-7.89 (m, 1H), 7.78 (brs, 2H), 7.69-7.46 (m, 4H), 6.95 (d, J=9.1, 2H), 6.85 (s, 1H), 3.71-3.62 (m, 2H), 2.69-2.57 (m, 2H), 2.24 (s, 6H), 2.20 (s, 3H), 1.90-1.80 (m, 2H), 1.60-1.38 (m, 2H). MS (ESI) m/z 522 (M+H)$^+$.

EXAMPLE 107 methyl 4-chloro-3-[8-methyl-5-oxo-2-(1,2,3,4-tetrahydroisoquinolin-7-ylamino)pyrido[4,3-d]pyrimidin-6(5H)-yl]benzoate

EXAMPLE 107A methyl 4-chloro-3-(4-ethyl-2-(methylthio)pyrimidine-5-carboxamido)benzoate

To a solution of Example 28B (539 mg, 2.72 mmol) in dichloromethane (5440 μl) was added a catalytic amount of N,N-dimethylformamide (5.27 μl, 0.068 mmol). The free-flowing slurry was cooled to ~5° C. Oxalyl chloride (250 μl, 2.86 mmol) was added dropwise via syringe. The reaction mixture was allowed to stir at 5-10° C. for 1 hour, then the cooling bath was removed and the reaction mixture was stirred at ambient temperature for an additional hour. To the slurry was added methyl 3-amino-4-chlorobenzoate (530 mg, 2.86 mmol). The reaction mixture was stirred at ambient temperature for 16 hours. The reaction mixture was poured into a 125 mL separatory funnel, diluted with 50 mL of dichloromethane and the organic layer was washed with water (1×40 mL), 1 molar aqueous phosphoric acid (1×40 mL), and saturated aqueous brine (1×40 mL), dried over magnesium sulfate, filtered and concentrated. The crude product was recrystallized in ethyl acetate/hexane mixture to afford the title compound.

EXAMPLE 107B methyl 4-chloro-3-(8-methyl-2-(methylthio)-5-oxopyrido[4,3-d]pyrimidin-6(5H)-yl)benzoate A scintillation vial, equipped with stir bar and septa, was charged with Example 107A (827 mg, 2.255 mmol) and N,N-dimethylformamide (7365 μl) followed by N-(chloromethylene)-N-methylmethanaminium (736 mg, 5.75 mmol). The reaction mixture was stirred at ambient temperature for 16 hours. The reaction mixture was cooled to 0° C. and quenched by careful addition of saturated aqueous sodium bicarbonate. To the reaction mixture was added 80 mL of ethyl acetate and the reaction mixture was poured into a 250 mL separatory funnel. The aqueous layer was removed and the organic layer was washed with diluted aqueous sodium bicarbonate (10% wt, 50 mL), and saturated aqueous brine (50 mL), dried over magnesium sulfate, filtered and concentrated. Purification by silica gel flash chromatography (Isco®, Redi-Sep® column, 2-100% ethyl acetate/hexane, linear gradient) afforded the title compound.

EXAMPLE 107C methyl 4-chloro-3-[8-methyl-5-oxo-2-(1,2,3,4-tetrahydroisoquinolin-7-ylamino)pyrido[4,3-d]pyrimidin-6(5H)-yl]benzoate The title compound was prepared as described in Example 98C, substituting Example 98B with Example 107B. Purification by silica gel flash chromatography (Isco®, Redi-Sep® column, 10-80% ethyl acetate/hexane, linear gradient) afforded the Boc protected intermediate. The product was dissolved in a mixture of 0.5 mL of dichloromethane, and 1 mL of ethyl acetate. Hydrochloric acid (2M diethyl ether, ~5 mL) was added and the reaction mixture was stirred at 50° C. for 3 hours. The solid was filtered and washed with diethyl ether to afford the title compound as an HCl salt. $^1$H NMR (300 MHz, dimethylsulfoxide-d$_6$) δ 10.38 (s, 1H), 9.28 (brs, 2H), 9.18 (s, 1H), 8.14-8.05 (m, 2H), 7.94-7.83 (m, 2H), 7.76-7.67 (m, 2H), 7.22 (d, J=8.5, 1H), 4.33-4.26 (m, 2H), 3.89 (s, 3H), 3.43-3.33 (m, 2H), 3.03-2.94 (m, 2H), 2.23 (d, J=0.9, 3H). MS (ESI) m/z 476 (M+H)$^+$.

EXAMPLE 108 methyl 4-chloro-3-[2-({4-[4-(dimethylamino)piperidin-1-yl]phenyl}amino)-8-methyl-5-oxopyrido[4,3-d]pyrimidin-6(5H)-yl]benzoate The title compound was prepared as described in Example 89, substituting Example 88B with Example 107B. Purification by silica gel flash chromatography (Isco®, Redi-Sep® column, 2-50% 2:1 methanol:H$_2$O in ethyl acetate with 5% triethylamine, linear gradient) followed by recrystallization in ethyl acetate/hexane mixture afforded the title compound. $^1$H NMR (300 MHz, dimethylsulfoxide-d$_6$) δ 10.12 (brs, 1H), 9.10 (s, 1H), 8.12-8.04 (m, 2H), 7.87 (d, J=8.3, 1H), 7.76 (brs, 2H), 7.66 (d, J=0.8, 1H), 6.95 (d, J=9.1, 2H), 3.89 (s, 3H), 3.74-3.62 (m, 2H), 2.69-2.57 (m, 2H), 2.30-2.12 (m, 9H), 1.89-1.79 (m, 2H), 1.57-1.38 (m, 2H). MS (ESI) m/z 548 (M+H)$^+$.

EXAMPLE 109

6-(2,6-dichlorophenyl)-8-(fluoromethyl)-2-(1,2,3,4-tetrahydroisoquinolin-7-ylamino)pyrido[4,3-d]pyrimidin-5(6H)-one The title compound was prepared as described in Example 98C, substituting Example 98B with Example 37B. Purification by silica gel flash chromatography (Isco®, Redi-Sep® column, 10-80% ethyl acetate/hexane, linear gradient) afforded the Boc protected intermediate. The product was dissolved in a mixture of 0.5 mL of dichloromethane, and 1 mL of ethyl acetate. Hydrochloric acid (2M diethylether, ~5 mL) was added and the reaction mixture was stirred at 50° C. for 3 hours. The solid was filtered and washed with diethyl ether to afford the title compound as an HCl salt. $^1$H NMR (400 MHz, dimethylsulfoxide-d$_6$) δ 10.17 (s, 1H), 9.38 (brs, 2H), 9.20 (s, 1H), 8.00 (d, J=4.0, 1H), 7.85 (s, 1H), 7.72-7.65 (m, 3H), 7.59 (dd, J=8.8, 7.4, 1H), 7.21 (d, J=8.4, 1H), 5.53 (d, J=48.4, 2H), 4.25 (s, 2H), 3.44-3.34 (m, 2H), 3.07-2.94 (m, 2H). MS (ESI) m/z 470 (M+H)$^+$.

EXAMPLE 110

6-(2,6-dichlorophenyl)-8-(fluoromethyl)-2-(1,2,3,4-tetrahydro isoquino lin-6-ylamino)pyrido[4,3-d]pyrimidin-5(6H)-one The title compound was prepared as described in Example 98C, substituting Example 98B with Example 37B and substituting tert-butyl 7-amino-3,4-dihydroisoquinoline-2(1H)-carboxylate with tert-butyl 6-amino-3,4-dihydroisoquinoline-2(1H)-carboxylate. Purification by silica gel flash chromatography (Isco®, Redi-Sep® column, 10-80% ethyl acetate/hexane, linear gradient) afforded the Boc protected intermediate. The product was dissolved in a mixture of 0.5 mL of dichloromethane, and 1 mL of ethyl acetate. Hydrochloric acid (2M in diethylether, ~5 mL) was added and the reaction mixture was stirred at 50° C. for 3 hours. The solid was filtered and washed with diethyl ether to afford the title compound as an HCl salt. $^1$H NMR (400 MHz, dimethylsulfoxide-d$_6$) δ 10.17 (s, 1H), 9.39 (brs, 2H), 9.21 (s, 1H), 8.00 (d, J=4.0, 1H), 7.86 (s, 1H), 7.72-7.67 (m, 3H), 7.59 (dd, J=8.9, 7.4, 1H), 7.20 (d, J=8.4, 1H), 5.52 (d, J=48.4, 2H), 4.22 (s, 2H), 3.41-3.33 (m, 2H), 3.05 (t, J=6.3, 2H). MS (ESI) m/z 470 (M+H)$^+$.

EXAMPLE 111

6-(2,6-dichlorophenyl)-2-({4-[4-(dimethylamino)piperidin-1-yl]phenyl}amino)-8-(fluoromethyl)pyrido[4,3-d]pyrimidin-5(6H)-one The title compound was prepared as described in Example 89, substituting Example 88B with Example 37B. Purification of the residue by reverse-phase preparative HPLC on a Phenomenex Luna C8(2) 5 um 100 Å AXIA column (30 mm×75 mm) using a gradient of acetonitrile (A) and 0.1% ammonium acetate in water (B) at a flow rate of 50 mL/min (0-0.5 min 10% A, 0.5-7.0 min linear gradient 10-95% A, 7.0-10.0 min 95% A, 10.0-12.0 min linear gradient 95-10% A) afforded the title compound. $^1$H NMR (400 MHz, dimethylsulfoxide-d$_6$) δ 9.85 (s, 1H), 9.11 (s, 1H), 7.92 (d, J=4.0, 1H), 7.71-7.63 (m, 4H), 7.57 (dd, J=8.8, 7.4, 1H), 6.91 (d, J=9.1, 2H), 5.48 (d, J=48.4, 2H), 3.69-3.59 (m, 2H), 2.75-2.62 (m, 2H), 2.21 (s, 6H), 1.87-1.78 (m, 2H), 1.59-1.43 (m, 2H). MS (ESI) m/z 541 (M+H)$^+$.

EXAMPLE 112

6-(2,6-dichlorophenyl)-2-{[2-(dimethylamino)-2,3-dihydro-1H-inden-5-yl]amino}-8-(fluoromethyl)pyrido[4,3-d]pyrimidin-5(6H)-one The title compound was prepared as described in Example 89, substituting Example 88B with Example 37B and substituting 1-(4-aminophenyl)-N,N-dimethylpiperidin-4-amine with N$^2$,N$^2$-dimethyl-2,3-dihydro-1H-indene-2,5-diamine. Purification of the residue by reverse-phase preparative HPLC on a Phenomenex Luna C8(2) 5 um 100 Å AXIA column (30 mm×75 mm) using a gradient of acetonitrile (A) and 0.1% ammonium acetate in water (B) at a flow rate of 50 mL/min (0-0.5 min 10% A, 0.5-7.0 min linear gradient 10-95% A, 7.0-10.0 min 95% A, 10.0-12.0 min linear gradient 95-10% A) afforded the title compound. $^1$H NMR (400 MHz, dimethylsulfoxide-d$_6$) δ 9.97 (s, 1H), 9.16 (s, 1H), 7.95 (d, J=4.1, 1H), 7.74-7.65 (m, 3H), 7.63-7.49 (m, 2H), 7.13 (d, J=8.1, 1H), 5.49 (d, J=48.4, 2H), 3.12-2.92 (m, 3H), 2.84-2.70 (m, 2H), 2.21 (s, 6H). MS (ESI) m/z 498 (M+H)$^+$.

EXAMPLE 113

6-(2,6-dichlorophenyl)-8-(fluoromethyl)-2-[(2'-methyl-2',3'-dihydro-1'H-spiro[cyclopropane-1,4'-isoquino lin]-7'-yl)amino]pyrido[4,3-d]pyrimidin-5(6H)-one The title compound was prepared as described in Example 89, substituting Example 88B with Example 37B and substituting 1-(4-aminophenyl)-N,N-dimethylpiperidin-4-amine with 2'-methyl-2',3'-dihydro-1'H-spiro[cyclopropane-1,4'-isoquinolin]-7'-amine. Purification of the residue by reverse-phase preparative HPLC on a Phenomenex Luna C8(2) 5 um 100 Å AXIA column (30 mm×75 mm) using a gradient of acetonitrile (A) and 0.1% ammonium acetate in water (B) at a flow rate of 50 mL/min (0-0.5 min 10% A, 0.5-7.0 min linear gradient 10-95% A, 7.0-10.0 min 95% A, 10.0-12.0 min linear gradient 95-10% A) afforded the title compound. $^1$H NMR (400 MHz, dimethylsulfoxide-d$_6$) δ 9.97 (brs, 1H), 9.15 (s, 1H), 7.96 (d, J=4.0, 1H), 7.72-7.66 (m, 2H), 7.64-7.50 (m, 3H), 6.68 (d, J=8.6, 1H), 5.50 (d, J=48.4, 2H), 3.61 (s, 2H), 2.99 (s, 2H), 2.34 (s, 3H), 1.01-0.74 (m, 4H). MS (ESI) m/z 510 (M+H)$^+$.

EXAMPLE 114

2-[(4-{[6-(2,6-dichlorophenyl)-8-methyl-5-oxo-5,6-dihydropyrido[4,3-d]pyrimidin-2-yl]amino}phenyl)sulfanyl]-N-methylacetamide The title compound was prepared as described in Example 78, substituting 4-(1-methylpiperidin-4-yl)aniline with 2-(4-aminophenylthio)-N-methylacetamide. Purification of the residue by reverse-phase preparative HPLC on a Phenomenex Luna C8(2) 5 um 100 Å AXIA column (30 mm×75 mm) using a gradient of acetonitrile (A) and 0.1% ammonium acetate in water (B) at a flow rate of 50 mL/min (0-0.5 min 10% A, 0.5-7.0 min linear gradient 10-95% A, 7.0-10.0 min 95% A, 10.0-12.0 min linear gradient 95-10% A) afforded the title compound. $^1$H NMR (400 MHz, dimethylsulfoxide-d$_6$) δ 10.04 (s, 1H), 9.16 (s, 1H), 7.86 (d, J=8.7, 2H), 7.71-7.62 (m, 2H), 7.58-7.45 (m, 2H), 7.37 (d, J=8.7, 2H), 3.54 (s, 2H), 2.61 (d, J=4.7, 3H), 2.24 (s, 3H). MS (ESI) m/z 500 (M+H)$^+$.

EXAMPLE 115

6-(2,6-dichlorophenyl)-8-methyl-2-[(1,1,2-trimethyl-2,3-dihydro-1H-isoindol-5-yl)amino]pyrido[4,3-d]pyrimidin-5(6H)-one The title compound was prepared as described in Example 78, substituting 4-(1-methylpiperidin-4-yl)aniline with 1,1,2-trimethylisoindolin-5-amine. Purification of the residue by reverse-phase preparative HPLC on a Phenomenex Luna C8(2) 5 um 100 Å AXIA column (30 mm×75 mm) using a gradient of acetonitrile (A) and 0.1% ammonium acetate in water (B) at a flow rate of 50 mL/min (0-0.5 min 10% A, 0.5-7.0 min linear gradient 10-95% A, 7.0-10.0 min 95% A, 10.0-12.0 min linear gradient 95-10% A) afforded the title compound. $^1$H NMR (400 MHz, dimethylsulfoxide-$d_6$) δ 9.90 (brs, 1H), 9.14 (s, 1H), 7.77 (s, 1H), 7.72-7.64 (m, 3H), 7.54 (dd, J=8.8, 7.5, 1H), 7.48 (d, J=1.1, 1H), 7.13 (d, J=8.2, 1H), 3.85 (s, 2H), 2.38 (s, 3H), 2.23 (s, 3H), 1.20 (s, 6H). MS (ESI) m/z 480 (M+H)$^+$.

EXAMPLE 116

6-(2,6-dichlorophenyl)-8-methyl-2-({4-[(1-methylpi-peridin-4-yl)amino]phenyl}amino)pyrido[4,3-d]py-rimidin-5 (6H)-one The title compound was prepared as described in Example 78, substituting 4-(1-methylpiperidin-4-yl)aniline with $N^1$-(1-methylpiperidin-4-yl)benzene-1,4-diamine. Purification of the residue by reverse-phase preparative HPLC on a Phenomenex Luna C8(2) 5 um 100 Å AXIA column (30 mm×75 mm) using a gradient of acetonitrile (A) and 0.1% ammonium acetate in water (B) at a flow rate of 50 mL/min (0-0.5 min 10% A, 0.5-7.0 min linear gradient 10-95% A, 7.0-10.0 min 95% A, 10.0-12.0 min linear gradient 95-10% A) afforded the title compound. $^1$H NMR (400 MHz, dimethylsulfoxide-$d_6$) δ 9.55 (brs, 1H), 9.05 (s, 1H), 7.68-7.62 (m, 2H), 7.57-7.50 (m, 4H), 7.41 (d, J=1.2, 1H), 6.60 (d, J=8.9, 2H), 3.22-3.11 (m, 1H), 2.76-2.66 (m, 2H), 2.18 (s, 3H), 2.12-2.01 (m, 2H), 1.93-1.83 (m, 5H), 1.52-1.36 (m, 2H). MS (ESI) m/z 509 (M+H)$^+$.

EXAMPLE 117

6-(2-hydroxyphenyl)-8-methyl-2-(1,2,3,4-tetrahy-droisoquinolin-7-ylamino)pyrido[4,3-d]pyrimidin-5 (6H)-one

EXAMPLE 117A 4-ethyl-N-(2-hydroxyphenyl)-2-(methylthio)pyrimi-dine-5-carboxamide To a solution of Example 28B (539 mg, 2.72 mmol) in dichloromethane (5440 μl) was added a catalytic amount of N,N-dimethylformamide (5.27 μl, 0.068 mmol). The free-flowing slurry was cooled to ~5° C. Oxalyl chloride (250 μl, 2.86 mmol) was added dropwise via syringe. The reaction mixture was allowed to proceed at 5-10° C. for 1 hour, then the cooling bath was removed and the reaction mixture was stirred at ambient temperature for an additional hour. To the slurry obtained from above was added 2-aminophenol (312 mg, 2.86 mmol). The reaction mixture was then stirred at ambient temperature for 16 hours. The reaction mixture was poured into a 125 mL separatory funnel, diluted with 50 mL of dichloromethane and the organic layer was washed with water (1×40 mL), 1 molar aqueous phosphoric acid (1×40 mL), and saturated aqueous brine (1×40 mL), dried over magnesium sulfate, filtered and concentrated. The crude product was recrystallized in ethyl acetate/hexane mixture to afford the title compound.

EXAMPLE 117B 6-(2-hydroxyphenyl)-8-methyl-2-(methylthio)pyrido [4,3-d]pyrimidin-5(6H)-one A scintillation vial, equipped with stir bar and septa, was charged with Example 117A (595 mg, 2.039 mmol) and N,N-dimethylformamide (7365 μl) followed by N-(chloromethylene)-N-methylmethanaminium (789 mg, 6.12 mmol) and the reaction mixture was stirred at ambient temperature for 16 hours. The reaction mixture was cooled to 0° C. and quenched by careful addition of saturated aqueous sodium bicarbonate. To the reaction mixture was added 80 mL of ethyl acetate and the reaction mixture was poured into a 250 mL separatory funnel. The aqueous layer was removed and the organic layer was washed with diluted aqueous sodium bicarbonate (10% wt, 50 mL), and saturated aqueous brine (50 mL), dried over magnesium sulfate, filtered and concentrated. Purification by silica gel flash chromatography (Isco®, Redi-Sep® column, 2-100% ethyl acetate/hexane, linear gradient) afforded the title compound.

EXAMPLE 117C 6-(2-hydroxyphenyl)-8-methyl-2-(1,2,3,4-tetrahy-droisoquinolin-7-ylamino)pyrido[4,3-d]pyrimidin-5 (6H)-one The title compound was prepared as described in Example 98C, substituting Example 98B with Example 117B. Purification by silica gel flash chromatography (Isco®, Redi-Sep® column, 20-70% ethyl acetate/hexane, linear gradient) afforded the Boc protected intermediate. The product was dissolved in a mixture of 0.5 mL of dichloromethane, and 1 mL of ethyl acetate then. Hydrochloric acid (2M in diethylether, ~5 mL) was added and the reaction mixture was stirred at 50° C. for 3 hours. The solid was filtered and washed with diethyl ether and the product was further purified by reverse-phase preparative HPLC on a Phenomenex Luna C8(2) 5 um 100 Å AXIA column (30 mm×75 mm) using a gradient of acetonitrile (A) and 0.1% trifluoroacetic acid in water (B) at a flow rate of 50 mL/min (0-0.5 min 10% A, 0.5-7.0 min linear gradient 10-95% A, 7.0-10.0 min 95% A, 10.0-12.0 min linear gradient 95-10% A) to afford the title compound as a TFA salt. $^1$H NMR (300 MHz, dimethylsulfoxide-$d_6$) δ 10.29 (s, 1H), 9.91 (brs, 1H), 9.15 (s, 1H), 8.99 (brs, 2H), 7.90 (s, 1H), 7.72 (dd, J=8.4, 1.8, 1H), 7.57 (d, J=1.1, 1H), 7.34-7.18 (m, 3H), 7.03 (dd, J=8.2, 1.2, 1H), 6.92 (td, J=7.6, 1.2, 1H), 4.30 (s, 2H), 3.45-3.33 (m, 2H), 2.97 (t, J=6.1, 2H), 2.22 (s, 3H). MS (ESI) m/z 400 (M+H)$^+$.

EXAMPLE 118

6-(2-hydroxy-6-methylphenyl)-8-methyl-2-(1,2,3,4-tetrahydroisoquinolin-7-ylamino)pyrido[4,3-d]py-rimidin-5(6H)-one

EXAMPLE 118A 4-ethyl-N-(2-hydroxy-6-methylphenyl)-2-(methyl-thio)pyrimidine-5-carboxamide To a solution of Example 28B (539 mg, 2.72 mmol) in dichloromethane (5440 μl) was added a catalytic amount of N,N-dimethylformamide (5.27 μl, 0.068 mmol). The free-flowing slurry was cooled to ~5° C. Oxalyl chloride (250 μl, 2.86 mmol) was added dropwise via syringe. The reaction mixture was allowed to proceed at 5-10° C. for 1 hour, then the cooling bath was removed and the reaction mixture was stirred at ambient temperature for an additional hour. To the slurry was added methyl 2-amino-3-methylphenol (352 mg, 2.86 mmol). The reaction mixture was then stirred at ambient temperature for 16 hours. The reaction mixture was poured into a 125 mL separatory funnel, diluted with 50 mL of dichloromethane and the organic was washed with water (1×40 mL), 1 molar aqueous phosphoric acid (1×40 mL), and saturated aqueous brine (1×40 mL), dried over magnesium sulfate, filtered and concentrated. The crude product was recrystallized in ethyl acetate/hexane mixture to afford the title compound.

EXAMPLE 118B 6-(2-hydroxy-6-methylphenyl)-8-methyl-2-(methylthio)pyrido[4,3-d]pyrimidin-5(6H)-one A scintillation vial, equipped with stir bar and septa, was charged with Example 118A (385 mg, 1.269 mmol) and N,N-dimethylformamide (7365 µl) followed by N-(chloromethylene)-N-methylmethanaminium (789 mg, 6.12 mmol) and the reaction mixture was stirred at ambient temperature for 16 hours. The reaction mixture was cooled to 0° C. and quenched by careful addition of saturated aqueous sodium bicarbonate. To the reaction mixture was added 80 mL of ethyl acetate and the reaction mixture was poured into a 250 mL separatory funnel. The aqueous layer was removed and the organic layer was washed with diluted aqueous sodium bicarbonate (10% wt, 50 mL), and saturated aqueous brine (50 mL), dried over magnesium sulfate, filtered and concentrated. Purification by silica gel flash chromatography (Isco®, Redi-Sep® column, 2-100% ethyl acetate/hexane, linear gradient) afforded the title compound.

EXAMPLE 118C 6-(2-hydroxy-6-methylphenyl)-8-methyl-2-(1,2,3,4-tetrahydroisoquinolin-7-ylamino)pyrido[4,3-d]pyrimidin-5(6H)-one The title compound was prepared as described in Example 98C, substituting Example 98B with Example 118B. Purification by silica gel flash chromatography (Isco®, Redi-Sep® column, 20-70% ethyl acetate/hexane, linear gradient) afforded the Boc protected intermediate. The product was dissolved in a mixture of 0.5 mL of dichloromethane, and 1 mL of ethyl acetate. Hydrochloric acid (2M in diethylether, ~5 mL) was added and the reaction mixture was stirred at 50° C. for 3 hours. The solid was filtered and washed with diethyl ether and the product was further purified by reverse-phase preparative HPLC on a Phenomenex Luna C8(2) 5 um 100 Å AXIA column (30 mm×75 mm) using a gradient of acetonitrile (A) and 0.1% trifluoroacetic acid in water (B) at a flow rate of 50 mL/min (0-0.5 min 10% A, 0.5-7.0 min linear gradient 10-95% A, 7.0-10.0 min 95% A, 10.0-12.0 min linear gradient 95-10% A) to afford the title compound as a TFA salt. $^1$H NMR (300 MHz, dimethylsulfoxide-$d_6$) δ 10.29 (s, 1H), 9.78 (s, 1H), 9.17 (s, 1H), 8.99 (brs, 2H), 7.90 (brs, 1H), 7.79-7.66 (m, 1H), 7.48 (s, 1H), 7.27-7.07 (m, 2H), 6.91-6.74 (m, 2H), 4.30 (s, 2H), 3.47-3.33 (m, 2H), 2.97 (t, J=6.1, 2H), 2.22 (s, 3H), 2.02 (s, 3H). MS (ESI) m/z 414 (M+H)$^+$.

EXAMPLE 119

8-methyl-2-(1,2,3,4-tetrahydroisoquinolin-7-ylamino)-6-(1,3,5-trimethyl-1H-pyrazol-4-yl)pyrido[4,3-d]pyrimidin-5(6H)-one

EXAMPLE 119A 4-ethyl-2-(methylthio)-N-(1,3,5-trimethyl-1H-pyrazol-4-yl)pyrimidine-5-carboxamide To a solution of Example 28B (539 mg, 2.72 mmol) in dichloromethane (5440 µl) was added a catalytic amount of N,N-dimethylformamide (5.27 µl, 0.068 mmol). The free-flowing slurry was cooled to ~5° C. Oxalyl chloride (250 µl, 2.86 mmol) was added dropwise via syringe. The reaction mixture was allowed to proceed at 5-10° C. for 1 hour, then the cooling bath was removed and the reaction mixture was stirred at ambient temperature for an additional hour. To the slurry was added 1,3,5-trimethyl-1H-pyrazol-4-amine (358 mg, 2.86 mmol). The reaction mixture was then stirred at ambient temperature for 16 hours. The reaction mixture was poured into a 125 mL separatory funnel, diluted with 50 mL of dichloromethane and the organic layer was washed with water (1×40 mL), 1 molar aqueous phosphoric acid (1×40 mL), and saturated aqueous brine (1×40 mL), dried over magnesium sulfate, filtered and concentrated. The crude product was recrystallized in ethyl acetate/hexane mixture to afford the title compound.

EXAMPLE 119B 8-methyl-2-(methylthio)-6-(1,3,5-trimethyl-1H-pyrazol-4-yl)pyrido[4,3-d]pyrimidin-5(6H)-one A scintillation vial, equipped with stir bar and septa, was charged with Example 119A (535 mg, 1.929 mmol) and N,N-dimethylformamide (7365 µl) followed by N-(chloromethylene)-N-methylmethanaminium (741 mg, 5.79 mmol) and the reaction mixture was stirred at ambient temperature for 16 hours. The reaction mixture was cooled to 0° C. and quenched by careful addition of saturated aqueous sodium bicarbonate. To the reaction mixture was added 80 mL of ethyl acetate and the reaction mixture was poured into a 250 mL separatory funnel. The aqueous layer was removed and the organic layer was washed with diluted aqueous sodium bicarbonate (10% wt, 50 mL), saturated aqueous brine (50 mL), dried over magnesium sulfate, filtered and concentrated. Purification by silica gel flash chromatography (Isco®, Redi-Sep® column, 2-100% ethyl acetate/hexane, linear gradient) afforded the title compound.

EXAMPLE 119C 8-methyl-2-(1,2,3,4-tetrahydroisoquinolin-7-ylamino)-6-(1,3,5-trimethyl-1H-pyrazol-4-yl)pyrido[4,3-d]pyrimidin-5(6H)-one The title compound was prepared as described in Example 98C, substituting Example 98B with Example 119B. Purification by silica gel flash chromatography (Isco®, Redi-Sep® column, 20-70% ethyl acetate/hexane, linear gradient) afforded the Boc protected intermediate. The product was dissolved in a mixture of 0.5 mL of dichloromethane, and 1 mL of ethyl acetate. Hydrochloric acid (2M in diethyl ether, ~5 mL) was added and the reaction mixture was stirred at 50° C. for 3 hours. The solid was filtered and washed with diethyl ether to afford the title compound as an HCl salt. $^1$H NMR (300 MHz, dimethylsulfoxide-$d_6$) δ 10.31 (s, 1H), 9.33 (brs, 2H), 9.17 (s, 1H), 7.88 (s, 1H), 7.78-7.66 (m, 1H), 7.58 (d, J=1.1, 1H), 7.21 (d, J=8.5, 1H), 4.27 (s, 2H), 3.72 (s, 3H), 3.45-3.33 (m, 2H), 2.97 (t, J=6.1, 2H), 2.21 (s, 3H), 2.07 (s, 3H), 1.97 (s, 3H). MS (ESI) m/z 416 (M+H)$^+$.

EXAMPLE 120

2-[(4-{[6-(2,6-dichlorophenyl)-8-methyl-5-oxo-5,6-dihydropyrido[4,3-d]pyrimidin-2-yl]amino}phenyl)sulfonyl]-N-methylacetamide A mixture Example 114 (50 mg, 0.100 mmol) and potassium peroxymonosulfate (307 mg, 0.500 mmol) in methanol (1 mL), tetrahydrofuran (1 mL) and water (0.5 mL) was stirred at room temperature for 1 hour. After concentration the residue was purified by reverse-phase preparative HPLC on a Phenomenex Luna C8(2) 5 um 100 Å AXIA column (30 mm×75 mm) using a gradient of acetonitrile (A) and 0.1% ammonium acetate in water (B) at a flow rate of 50 mL/min (0-0.5 min 10% A, 0.5-7.0 min linear gradient 10-95% A, 7.0-10.0 min 95% A, 10.0-12.0 min linear gradient 95-10% A) to afford the title compound. $^1$H NMR (400 MHz, dimethylsulfoxide-d$_6$) δ 10.51 (s, 1H), 9.26 (s, 1H), 8.16 (d, J=8.9, 2H), 7.83 (d, J=8.9, 2H), 7.77 (brs, 1H), 7.72-7.65 (m, 2H), 7.61-7.51 (m, 2H), 4.14 (s, 2H), 2.59 (d, J=4.7, 3H), 2.29 (s, 3H). MS (ESI) m/z 532 (M+H)$^+$.

EXAMPLE 121

6-(2,6-dichlorophenyl)-2-[(1,1-dimethyl-2,3-di-hydro-1H-isoindol-5-yl)amino]-8-methylpyrido[4,3-d]pyrimidin-5(6H)-one The title compound was prepared as described in Example 98C, substituting Example 98B with Example 28D and substituting tert-butyl 7-amino-3,4-dihydroisoquinoline-2 (1H)-carboxylate with tert-butyl 5-amino-1,1-dimethyl-isoindoline-2-carboxylate. Purification by silica gel flash chromatography (Isco®, Redi-Sep® column, 3-50% ethyl acetate/hexane, linear gradient) afforded the Boc protected intermediate. The product was dissolved in a mixture of 0.5 mL of dichloromethane, and 1 mL of ethyl acetate. Hydrochloric acid (2M diethylether, ~5 mL) was added and the reaction mixture was stirred at 50° C. for 3 hours.

The solid was filtered and washed with diethyl ether to afford the title compound as an HCl salt. $^1$H NMR (400 MHz, dimethylsulfoxide-d$_6$) δ 10.17 (s, 1H), 9.73 (brs, 2H), 9.19 (s, 1H), 7.96 (s, 1H), 7.92-7.82 (m, 1H), 7.73-7.63 (m, 2H), 7.58-7.48 (m, 2H), 7.32 (d, J=8.4, 1H), 4.53 (s, 2H), 2.25 (s, 3H), 1.66 (s, 6H). MS (ESI) m/z 466 (M+H)$^+$.

EXAMPLE 122

6-(2,6-dichlorophenyl)-8-methyl-2-({4-[(1-methylpi-peridin-4-yl)oxy]phenyl}amino)pyrido[4,3-d]pyrimi-din-5(6H)-one The title compound was prepared as described in Example 78, substituting 4-(1-methylpiperidin-4-yl)aniline with 4-(1-methylpiperidin-4-yloxy)aniline. Purification of the residue by reverse-phase preparative HPLC on a Phenomenex Luna C8(2) 5 um 100 Å AXIA column (30 mm×75 mm) using a gradient of acetonitrile (A) and 0.1% ammonium acetate in water (B) at a flow rate of 50 mL/min (0-0.5 min 10% A, 0.5-7.0 min linear gradient 10-95% A, 7.0-10.0 min 95% A, 10.0-12.0 min linear gradient 95-10% A) afforded the title compound. $^1$H NMR (400 MHz, dimethylsulfoxide-d$_6$) δ 9.81 (s, 1H), 9.12 (s, 1H), 7.76 (d, J=9.0, 2H), 7.69-7.63 (m, 2H), 7.54 (dd, J=8.8, 7.4, 1H), 7.46 (d, J=1.1, 1H), 6.93 (d, J=9.0, 2H), 4.32-4.22 (m, 1H), 2.68-2.56 (m, 2H), 2.23-2.17 (m, 8H), 1.96-1.86 (m, 2H), 1.72-1.59 (m, 2H). MS (ESI) m/z 510 (M+H)$^+$.

EXAMPLE 123

6-(3,5-dimethyl-1H-pyrazol-4-yl)-8-methyl-2-(1,2,3,4-tetrahydroisoquinolin-7-ylamino)pyrido[4,3-d]pyrimidin-5(6H)-one

EXAMPLE 123A

N-(3,5-dimethyl-1H-pyrazol-4-yl)-4-ethyl-2-(meth-ylthio)pyrimidine-5-carboxamide To a solution of Example 28B (539 mg, 2.72 mmol) in dichloromethane (5440 µl) was added a catalytic amount of N,N-dimethylformamide (5.27 µl, 0.068 mmol). The free-flowing slurry was cooled to ~5° C. Oxalyl chloride (250 µl, 2.86 mmol) was added dropwise via syringe. The reaction mixture was allowed to proceed at 5-10° C. for 1 hour, then the cooling bath was removed and the reaction mixture was stirred at ambient temperature for an additional hour. To the slurry was added 3,5-dimethyl-1H-pyrazol-4-amine (317 mg, 2.86 mmol). The reaction mixture was then stirred at ambient temperature for 16 hours. The reaction mixture was poured into a 125 mL separatory funnel, diluted with 50 mL of dichloromethane and the organic layer was washed with water (1×40 mL), 1 molar aqueous phosphoric acid (1×40 mL), and saturated aqueous brine (1×40 mL), dried over magnesium sulfate, filtered and concentrated. The crude product was recrystallized in ethyl acetate/hexane mixture to afford the title compound.

EXAMPLE 123B 6-(3,5-dimethyl-1H-pyrazol-4-yl)-8-methyl-2-(meth-ylthio)pyrido[4,3-d]pyrimidin-5(6H)-one A scintillation vial, equipped with stir bar and septa, was charged with Example 123A (392 mg, 1.345 mmol) and N,N-dimethylformamide (7365 µl) followed by N-(chloromethylene)-N-methylmethanaminium (662 mg, 5.17 mmol) and the reaction mixture was stirred at ambient temperature for 16 hours. The reaction mixture was cooled to 0° C. and quenched by careful addition of saturated aqueous sodium bicarbonate. To the reaction mixture was added 80 mL of ethyl acetate and the reaction mixture was poured into a 250 mL separatory funnel. The aqueous layer was removed and the organic layer was washed with diluted aqueous sodium bicarbonate (10% wt, 50 mL), and saturated aqueous brine (50 mL), dried over magnesium sulfate, filtered and concentrated. Purification by silica gel flash chromatography (Isco®, Redi-Sep® column, 2-100% ethyl acetate/hexane, linear gradient) afforded the title compound.

EXAMPLE 123C 6-(3,5-dimethyl-1H-pyrazol-4-yl)-8-methyl-2-(1,2,3,4-tetrahydroisoquinolin-7-ylamino)pyrido[4,3-d]pyrimidin-5(6H)-one The title compound was prepared as described in Example 98C, substituting Example 98B with Example 119B. Purification by silica gel flash chromatography (Isco®, Redi-Sep® column, 0-20% 2:1 CH$_3$OH:H$_2$O in ethyl acetate, linear gradient) afforded the Boc protected intermediate. The product was dissolved in a mixture of 0.5 mL of dichloromethane, and 1 mL of ethyl acetate. Hydrochloric acid (2M diethylether, ~5 mL) was added and the reaction mixture was stirred at 50° C. for 3 hours. The solid was filtered and washed with diethyl ether to afford the title compound as an HCl salt. $^1$H NMR (300 MHz, dimethylsulfoxide-$d_6$) δ 10.31 (s, 1H), 9.37 (brs, 2H), 9.17 (s, 1H), 7.89 (brs, 1H), 7.71 (d, J=8.4, 1H), 7.61 (s, 1H), 7.21 (d, J=8.5, 1H), 4.27 (s, 2H), 3.43-3.30 (m, 2H), 2.97 (t, J=6.0, 2H), 2.22 (d, J=0.5, 3H), 2.05 (s, 6H). MS (ESI) m/z 402 (M+H)$^+$.

EXAMPLE 124

6-(3,5-dimethyl-1,2-oxazol-4-yl)-8-methyl-2-(1,2,3,4-tetrahydroisoquinolin-7-ylamino)pyrido[4,3-d]pyrimidin-5(6H)-one

EXAMPLE 124A

N-(3,5-dimethylisoxazol-4-yl)-4-ethyl-2-(methylthio)pyrimidine-5-carboxamide

To a solution of Example 28B (539 mg, 2.72 mmol) in dichloromethane (5440 μl) was added a catalytic amount of N,N-dimethylformamide (5.27 μl, 0.068 mmol). The free-flowing slurry was cooled to ~5° C. Oxalyl chloride (250 μl, 2.86 mmol) was added dropwise via syringe. The reaction mixture was allowed to stir at 5-10° C. for 1 hour, then the cooling bath was removed and the reaction mixture was stirred at ambient temperature for an additional hour. To the slurry obtained from above was added 3,5-dimethylisoxazol-4-amine (320 mg, 2.86 mmol). The reaction mixture was then stirred at ambient temperature for 16 hours. The reaction mixture was poured into a 125 mL separatory funnel, diluted with 50 mL of dichloromethane and the organic layer was washed with water (1×40 mL), 1 molar aqueous phosphoric acid (1×40 mL), and saturated aqueous brine (1×40 mL), dried over magnesium sulfate, filtered and concentrated. The crude product was recrystallized in ethyl acetate/hexane mixture to afford the title compound.

EXAMPLE 124B 6-(3,5-dimethylisoxazol-4-yl)-8-methyl-2-(methylthio)pyrido[4,3-d]pyrimidin-5(6H)-one A scintillation vial, equipped with stir bar and septa, was charged with Example 124A (504 mg, 1.724 mmol) and N,N-dimethylformamide (7365 μl) followed by N-(chloromethylene)-N-methylmethanaminium (662 mg, 5.17 mmol) and the reaction mixture was stirred at ambient temperature for 16 hours. The reaction mixture was cooled to 0° C. and quenched by careful addition of saturated aqueous sodium bicarbonate. To the reaction mixture was added 80 mL of ethyl acetate and the reaction mixture was poured into a 250 mL separatory funnel. The aqueous layer was removed and the organic layer was washed with diluted aqueous sodium bicarbonate (10% wt, 50 mL), and saturated aqueous brine (50 mL), dried over magnesium sulfate, filtered and concentrated. Purification by silica gel flash chromatography (Isco®, Redi-Sep® column, 2-100% ethyl acetate/hexane, linear gradient) afforded the title compound.

EXAMPLE 124C 6-(3,5-dimethyl-1,2-oxazol-4-yl)-8-methyl-2-(1,2,3,4-tetrahydroisoquinolin-7-ylamino)pyrido[4,3-d]pyrimidin-5(6H)-one The title compound was prepared as described in Example 98C, substituting Example 98B with Example 124B. Purification by silica gel flash chromatography (Isco®, Redi-Sep® column, 20-100% ethyl acetate/hexane, linear gradient) afforded the Boc protected intermediate. The product was dissolved in a mixture of 0.5 mL of dichloromethane, and 1 mL of ethyl acetate. Hydrochloric acid (2M diethyl ether, ~5 mL) was added and the reaction mixture was stirred at 50° C. for 3 hours. The solid was filtered and washed with diethyl ether to afford the title compound as an HCl salt. $^1$H NMR (300 MHz, dimethylsulfoxide-$d_6$) δ 10.38 (s, 1H), 9.31 (brs, 2H), 9.18 (s, 1H), 7.87 (s, 1H), 7.76-7.63 (m, 2H), 7.21 (d, J=8.5, 1H), 4.27 (s, 2H), 3.47-3.31 (m, 2H), 3.05-2.92 (m, 2H), 2.33 (s, 3H), 2.22 (s, 3H), 2.12 (s, 3H). MS (ESI) m/z 403 (M+H)$^+$.

EXAMPLE 125

6-(2,6-dichlorophenyl)-8-methyl-2-({4[(1-methylpyrrolidin-3-yl)amino]phenyl}amino)pyrido[4,3-d]pyrimidin-5(6H)-one Example 28D (70 mg, 0.199 mmol) was dissolved in dichloroethane (1987 μl) and 3-chlorobenzoperoxoic acid (53.4 mg, 0.238 mmol) was added. The reaction mixture was stirred at ambient temperature for 30 minutes then trifluoroacetic acid (30.6 μl, 0.397 mmol) and N$^1$-(1-methylpyrrolidin-3-yl)benzene-1,4-diamine (45.6 mg, 0.238 mmol) were added and the reaction mixture was concentrated. After addition of 1.5 mL of acetonitrile, the reaction mixture was stirred at 90° C. for 16 hours. The reaction mixture was then diluted with ethyl acetate (30 mL) and washed with saturated aqueous sodium bicarbonate (20 mL), and saturated aqueous brine (20 mL), dried over magnesium sulfate, filtered and concentrated. Purification by silica gel flash chromatography (Isco®, Redi-Sep® column, 2-50% 2:1 methanol:H$_2$O in ethyl acetate with 5% triethylamine, linear gradient) followed by recrystallization in ethyl acetate/hexane mixture afforded the title compound. $^1$H NMR (300 MHz, dimethylsulfoxide-$d_6$) δ 10.00 (brs, 1H), 9.06 (s, 1H), 7.78-7.47 (m, 6H), 6.55 (d, J=8.9, 2H), 5.54 (d, J=7.1, 1H), 3.95-3.76 (m, 1H), 2.81-2.68 (m, 1H), 2.64-2.53 (m, 1H), 2.45-2.29 (m, 2H), 2.25 (s, 3H), 2.22-2.10 (m, 4H), 1.65-1.43 (m, 1H). MS (ESI) m/z 495 (M+H)$^+$.

EXAMPLE 126

6-(2,6-dimethylphenyl)-8-methyl-2-(1,2,3,4-tetrahydroisoquinolin-7-ylamino)pyrido[4,3-d]pyrimidin-5(6H)-one The title compound was prepared as described in Example 98C, substituting Example 98B with Example 88B. Purification by silica gel flash chromatography (Isco®, Redi-Sep® column, 3-50% ethyl acetate/hexane, linear gradient) afforded the Boc protected intermediate. The product was dissolved in a mixture of 0.5 mL of dichloromethane, and 1 mL of ethyl acetate. Hydrochloric acid (2M diethylether, ~5 mL) was added and the reaction mixture was stirred at 50° C. for 3 hours. The solid was filtered and washed with diethyl ether to afford the title compound as a bis HCl salt. $^1$H NMR (400 MHz, dimethylsulfoxide-$d_6$) δ 9.95 (s, 1H), 9.50 (brs, 2H), 9.18 (s, 1H), 7.84 (s, 1H), 7.73 (dd, J=8.4, 2.1, 1H), 7.41 (d, J=1.1, 1H), 7.31-7.14 (m, 4H), 4.24 (s, 2H), 3.38-3.32 (m, 2H), 3.01 (t, J=6.3, 2H), 2.24 (s, 3H), 2.05 (s, 6H). MS (ESI) m/z 412 (M+H)$^+$.

EXAMPLE 127

6-(2-chloro-6-methylphenyl)-8-methyl-2-(1,2,3,4-tetrahydroisoquinolin-7-ylamino)pyrido[4,3-d]pyrimidin-5(6H)-one The title compound was prepared as described in Example 98C, substituting Example 98B with Example 90B. Purification by silica gel flash chromatography (Isco®, Redi-Sep® column, 3-50% ethyl acetate/hexane, linear gradient) afforded the Boc protected intermediate. The product was dissolved in a mixture of 0.5 mL of dichloromethane, and 1 mL of ethyl acetate. Hydrochloric acid (2M diethylether, ~5 mL) was added and the reaction mixture was stirred at 50° C. for 3 hours. The solid was filtered and washed with diethyl ether to afford the title compound as a bis HCl salt. $^1$H NMR (400 MHz, dimethylsulfoxide-d$_6$) δ 9.99 (s, 1H), 9.47 (brs, 2H), 9.17 (s, 1H), 7.84 (s, 1H), 7.72 (dd, J=8.3, 2.0, 1H), 7.51-7.35 (m, 4H), 7.19 (d, J=8.4, 1H), 4.24 (s, 2H), 3.40-3.33 (m, 2H), 3.01 (t, J=6.3, 2H), 2.24 (s, 3H), 2.13 (s, 3H). MS (ESI) m/z 432 (M+H)$^+$.

EXAMPLE 128

6-(2,6-dichlorophenyl)-8-(1-hydroxyethyl)-2-{[4-(4-methylpiperazin-1-yl)phenyl]amino}pyrido[4,3-d]pyrimidin-5(6H)-one Example 27 (48 mg, 0.094 mmol) was dissolved in tetrahydrofuran (1.5 mL) and the reaction mixture was cooled to 0° C. Next, methymagnesium bromide (94 μl, 0.188 mmol) was added and the reaction mixture was stirred at 0° C. for 10 minutes then concentrated. The crude residue was directly purified by silica gel flash chromatography (Isco®, Redi-Sep® column, 3-15% ethyl methanol/dichloromethane, linear gradient) to afford the title compound. $^1$H NMR (400 MHz, dimethylsulfoxide-d$_6$) δ 9.77 (s, 1H), 9.11 (s, 1H), 7.72-7.62 (m, J=8.6, 4H), 7.59-7.50 (m, 1H), 7.38 (s, 1H), 6.94 (d, J=9.1, 2H), 5.21-5.10 (m, 1H), 4.88 (brs, 1H), 3.26-3.19 (m, 4H), 2.79-2.71 (m, 4H), 2.44 (s, 3H), 1.47 (d, J=6.3, 3H). MS (ESI) m/z 525 (M+H)$^+$.

EXAMPLE 129 methyl 5-{[6-(2,6-dichlorophenyl)-8-methyl-5-oxo-5,6-dihydropyrido[4,3-d]pyrimidin-2-yl]amino}-2-(4-methylpiperazin-1-yl)benzoate The title compound was prepared as described in Example 125, substituting N$^1$-(1-methylpyrrolidin-3-yl)benzene-1,4-diamine with methyl 5-amino-2-(4-methylpiperazin-1-yl)benzoate. Purification by silica gel flash chromatography (Isco®, Redi-Sep® column, 2-15% ethyl methanol/dichloromethane, linear gradient) afforded the title compound. $^1$H NMR (400 MHz, dimethylsulfoxide-d$_6$) δ 10.03 (s, 1H), 9.15 (s, 1H), 8.37 (d, J=2.4, 1H), 7.86 (dd, J=8.8, 2.7, 1H), 7.71-7.63 (m, 2H), 7.59-7.47 (m, 2H), 7.15 (d, J=8.8, 1H), 3.83 (s, 3H), 3.12-3.02 (m, 4H), 2.74-2.63 (m, 4H), 2.41 (s, 3H), 2.24 (s, 3H). MS (ESI) m/z 553 (M+H)$^+$.

EXAMPLE 130

6-(2,6-dichlorophenyl)-2-[(4-{[2-(dimethylamino)ethyl]amino}phenyl)amino]-8-methylpyrido[4,3-d]pyrimidin-5(6H)-one The title compound was prepared as described in Example 125, substituting N$^1$-(1-methylpyrrolidin-3-yl)benzene-1,4-diamine with N$^1$-(2-(dimethylamino)ethyl)benzene-1,4-diamine. Purification by reverse-phase preparative HPLC on a Phenomenex Luna C8(2) 5 um 100 Å AXIA column (30 mm×75 mm) using a gradient of acetonitrile (A) and 0.1% trifluoroacetic acid in water (B) at a flow rate of 50 mL/min (0-0.5 min 10% A, 0.5-7.0 min linear gradient 10-95% A, 7.0-10.0 min 95% A, 10.0-12.0 min linear gradient 95-10% A) to afford the title compound as a bis TFA salt. $^1$H NMR (400 MHz, dimethylsulfoxide-d$_6$) δ 9.65 (s, 1H), 9.08 (s, 1H), 7.70-7.60 (m, 4H), 7.54 (dd, J=8.7, 7.5, 1H), 7.44 (d, J=1.1, 1H), 6.68 (d, J=8.7, 2H), 3.46-3.40 (m, 2H), 3.28 (t, J=6.3, 2H), 2.86 (s, 6H), 2.19 (s, 3H). MS (ESI) m/z 483 (M+H)$^+$.

EXAMPLE 131

6-(2,6-dichlorophenyl)-2-[(4-{4-[3-(dimethylamino)propyl]piperazin-1-yl}phenyl)amino]-8-methyl-pyrido[4,3-d]pyrimidin-5(6H)-one The title compound was prepared as described in Example 125, substituting N$^1$-(1-methylpyrrolidin-3-yl)benzene-1,4-diamine with 4-(4-(3-(dimethylamino)propyl)piperazin-1-yl)aniline. Purification of the residue by reverse-phase preparative HPLC on a Phenomenex Luna C8(2) 5 um 100 Å AXIA column (30 mm×75 mm) using a gradient of acetonitrile (A) and 0.1% ammonium acetate in water (B) at a flow rate of 50 mL/min (0-0.5 min 10% A, 0.5-7.0 min linear gradient 10-95% A, 7.0-10.0 min 95% A, 10.0-12.0 min linear gradient 95-10% A) afforded the title compound. $^1$H NMR (400 MHz, dimethylsulfoxide-d$_6$) δ 9.74 (s, 1H), 9.10 (s, 1H), 7.71 (d, J=9.0, 2H), 7.68-7.63 (m, 2H), 7.54 (dd, J=8.7, 7.5, 1H), 7.45 (d, J=1.1, 1H), 6.92 (d, J=9.1, 2H), 3.17-3.11 (m, 2H), 2.72-2.66 (m, 2H), 2.59-2.55 (m, 4H), 2.50-2.40 (m, 10H), 2.21 (s, 3H), 1.79-1.67 (m, 2H). MS (ESI) m/z 566 (M+H)$^+$.

EXAMPLE 132

6-(2,6-dichlorophenyl)-2-[(4-{[trans-4-(dimethylamino)cyclohexyl]amino}phenyl)amino]-8-methyl-pyrido[4,3-d]pyrimidin-5(6H)-one The title compound was prepared as described in Example 125, substituting N$^1$-(1-methylpyrrolidin-3-yl)benzene-1,4-diamine with N$^1$-(4-(dimethylamino)cyclohexyl)benzene-1, 4-diamine (1:1 mixture cis:trans). Purification by reverse-phase preparative HPLC on a Phenomenex Luna C8(2) 5 um 100 Å AXIA column (30 mm×75 mm) using a gradient of acetonitrile (A) and 0.1% trifluoroacetic acid in water (B) at a flow rate of 50 mL/min (0-0.5 min 10% A, 0.5-7.0 min linear gradient 10-95% A, 7.0-10.0 min 95% A, 10.0-12.0 min linear gradient 95-10% A) to afford the title compound (fast eluting isomer) as a bis TFA salt. $^1$H NMR (400 MHz, dimethylsulfoxide-d$_6$) δ 9.68 (s, 1H), 9.09 (s, 1H), 7.72-7.49 (m, 5H), 7.44 (s, 1H), 6.73 (d, J=8.8, 2H), 3.34-3.11 (m, 2H), 2.77 (s, 6H), 2.20 (s, 3H), 2.17-2.01 (m, 4H), 1.68-1.51 (m, 2H), 1.37-1.22 (m, 2H). MS (ESI) m/z 537 (M+H)+.

EXAMPLE 133

6-(2,6-dichlorophenyl)-2-[(4-{[cis-4-(dimethylamino)cyclohexyl]amino}phenyl)amino]-8-methylpyrido[4,3-d]pyrimidin-5(6H)-one The title compound was prepared as described in Example 125, substituting $N^1$-(1-methylpyrrolidin-3-yl)benzene-1,4-diamine with $N^1$-(4-(dimethylamino)cyclohexyl)benzene-1,4-diamine (1:1 mixture cis:trans). Purification by reverse-phase preparative HPLC on a Phenomenex Luna C8(2) 5 um 100 Å AXIA column (30 mm×75 mm) using a gradient of acetonitrile (A) and 0.1% trifluoroacetic acid in water (B) at a flow rate of 50 mL/min (0-0.5 min 10% A, 0.5-7.0 min linear gradient 10-95% A, 7.0-10.0 min 95% A, 10.0-12.0 min linear gradient 95-10% A) to afford the title compound (slow eluting isomer) as a bis TFA salt. $^1$H NMR (400 MHz, dimethylsulfoxide-$d_6$) δ 9.62 (brs, 1H), 9.07 (s, 1H), 7.69-7.50 (m, 5H), 7.43 (s, 1H), 6.70 (d, J=8.8, 2H), 3.64-3.54 (m, 1H), 3.26-3.13 (m, 1H), 2.77 (s, 6H), 2.19 (s, 3H), 2.01-1.90 (m, 2H), 1.85-1.75 (m, 4H), 1.69-1.55 (m, 2H). MS (ESI) m/z 537 (M+H)+.

EXAMPLE 134

7-(2,6-dichlorophenyl)-5-methyl-3-(1,2,3,4-tetrahydroisoquinolin-7-ylamino)pyrido[4,3-e][1,2,4]triazin-8(7H)-one

EXAMPLE 134A ethyl 2-acetoxy-2-chloro-3-oxopentanoate

To a stirred solution of ethyl 3-oxopentanoate (10.1 g, 70.1 mmol) in dichloromethane (40 ml) was slowly added sulfuryl chloride (6.55 ml, 81 mmol). After stirring for 4 hours at room temperature the solution was washed with a saturated solution of sodium carbonate (2×100 mL), and the organic layer was dried over anhydrous magnesium sulfate. After filtration, the filtrate was concentrated to give ethyl 2-chloro-3-oxopentanoate which was used in the subsequent reaction without purification. To a stirred ice-cold solution of glacial acetic acid (50 mL) in N,N-dimethylformamide (250 mL) was slowly added triethylamine (50 mL). After warming to room temperature, the ethyl 2-chloro-3-oxopentanoate (12.5 g, 70.0 mmol) was added and the solution was left stirring at room temperature for 20 hours. The solution was poured into water (200 mL) and extracted twice with dichloromethane. The combined extracts were dried with anhydrous magnesium sulfate, filtered and was concentrated, to afford ethyl 2-acetoxy-3-oxopentanoate. To an ice-cold stirred solution of ethyl 2-acetoxy-3-oxopentanoate (7.7 g, 38.1 mmol) in dichloromethane (95 ml) was slowly added sulfuryl chloride (3.56 ml, 43.8 mmol). The cooling bath was then removed and the mixture stirred at ambient temperature for 16 hours. Next, the reaction mixture was poured into a separatory funnel, washed with saturated aqueous sodium bicarbonate (2×150 mL), dried over anhydrous magnesium sulfate, filtered, and was concentrated to afford the title compound. The product was carried through the next step without purification.

EXAMPLE 134B ethyl 5-ethyl-3-(methylthio)-1,2,4-triazine-6-carboxylate

To a stirred solution of Example 134A (2.93 g, 12.38 mmol) and sodium bicarbonate (2.080 g, 24.76 mmol) in ethanol (141 ml) was added (E)-methyl carbamohydrazonothioate, HI salt (3.9 g, 16.73 mmol). The reaction mixture was then stirred under reflux for 4 hours. The reaction mixture was poured into a separatory funnel, and water (250 mL and ethyl acetate (200 mL) were added. The aqueous was removed and the organic layer was washed with diluted aqueous sodium bicarbonate solution (150 mL), and saturated aqueous brine (150 mL), dried over anhydrous magnesium sulfate, filtered and was concentrated. Purification by silica gel flash chromatography (Isco®, Redi-Sep® column, 3-50% ethyl acetate/hexane, linear gradient) afforded the title compound.

EXAMPLE 134C 5-ethyl-3-(methylthio)-1,2,4-triazine-6-carboxylic acid

To a stirred solution of Example 134B (1.74 g, 7.66 mmol) in tetrahydrofuran (15.31 ml) was added lithium hydroxide (15.31 ml, 15.31 mmol) with 5 mL of methanol. The reaction mixture was stirred at ambient temperature for 1 hour. The reaction mixture was acidified with a one molar aqueous solution of hydrochloric acid (20 mL). The reaction mixture was poured into a separatory funnel and ethyl acetate (80 mL) was added. The aqueous layer was removed and the organic layer was washed with saturated aqueous brine (50 mL), dried over anhydrous magnesium sulfate, filtered and was concentrated. Recrystallization in ethyl acetate/hexane mixture afforded the title compound.

EXAMPLE 134D

N-(2,6-dichlorophenyl)-5-ethyl-3-(methylthio)-1,2,4-triazine-6-carboxamide

To a solution of Example 134C (0.830 g, 4.17 mmol) in dichloromethane (8.33 ml) was added catalytic N,N-dimethylformamide (8.06 μl, 0.104 mmol) and the free-flowing slurry was cooled to ~5° C. Oxalyl chloride (0.383 ml, 4.37 mmol) was added dropwise via syringe. The reaction mixture was allowed to proceed at 5-10° C. for 1 hour, then the cooling bath was removed and the reaction mixture was stirred at ambient temperature for an additional hour. To the slurry obtained was added the aniline 2,6-dichloroaniline (0.709 g, 4.37 mmol) and pyridine (0.758 ml, 9.37 mmol. The reaction mixture was stirred at ambient temperature for 16 hours. The reaction mixture was poured into a 125 mL separatory funnel, and diluted with 50 mL of dichloromethane. The organic layer was washed with water (1×40 mL), 1 molar aqueous phosphoric acid (1×40 mL), and saturated aqueous brine (1×40 mL), dried over magnesium sulfate, filtered, and was concentrated. The crude product was purified by silica gel flash chromatography (Isco®, Redi-Sep® column, 10-100% ethyl acetate/hexane, linear gradient) to afford the title compound.

EXAMPLE 134E 7-(2,6-dichlorophenyl)-5-methyl-3-(methylthio)pyrido[4,3-e][1,2,4]triazin-8(7H)-one A scintillation vial, equipped with stir bar and septa, was charged with Example 134D (430 mg, 1.253 mmol) and N,N-dimethylformamide (5011 µl) followed by N-(chloromethylene)-N-methylmethanaminium (481 mg, 3.76 mmol). The reaction mixture was stirred at ambient temperature for 16 hours. The reaction mixture was cooled to 0° C. and quenched by careful addition of saturated aqueous sodium bicarbonate. To the reaction mixture was added 80 mL of ethyl acetate and the reaction mixture was poured into a 250 mL separatory funnel. The aqueous layer was removed and the organic layer was washed with diluted aqueous sodium bicarbonate (10% wt, 50 mL), and saturated aqueous brine (50 mL), dried over magnesium sulfate, filtered, and was concentrated. Purification by silica gel flash chromatography (Isco®, Redi-Sep® column, 10-60% ethyl acetate/hexane, linear gradient) afforded the title compound.

EXAMPLE 134F 7-(2,6-dichlorophenyl)-5-methyl-3-(1,2,3,4-tetrahydroisoquinolin-7-ylamino)pyrido[4,3-e][1,2,4]triazin-8(7H)-one Example 134E (55 mg, 0.156 mmol) was dissolved in dichloroethane (1557 µl) and 3-chlorobenzoperoxoic acid (41.9 mg, 0.187 mmol) was added. The reaction mixture was stirred at ambient temperature for 30 minutes then tert-butyl 7-amino-3,4-dihydroisoquinoline-2(1H)-carboxylate (46.4 mg, 0.264 mmol) was added and the reaction mixture was stirred at 45° C. for 16 hours. The reaction mixture was diluted with ethyl acetate (30 mL) and washed with saturated aqueous sodium bicarbonate (20 mL), and saturated aqueous brine (20 mL), dried over magnesium sulfate, filtered and concentrated. Purification by silica gel flash chromatography (Isco®, Redi-Sep® column, 20-100% ethyl acetate/hexane, linear gradient) afforded the Boc protected intermediate. The product was dissolved in a mixture of 0.5 mL of dichloromethane, and 1 mL of ethyl acetate. Hydrochloric acid (2M diethylether, ~5 mL) was added and the mixture stirred at 50° C. for 3 hours. The solid was filtered and washed with diethyl ether to afford the title compound as an HCl salt. $^1$H NMR (300 MHz, dimethylsulfoxide-$d_6$) δ 11.23 (brs, 1H), 9.15 (brs, 2H), 7.85-7.70 (m, 5H), 7.62 (dd, J=8.9, 7.4, 1H), 7.27 (d, J=8.5, 1H), 4.31 (s, 2H), 3.48-3.36 (m, 2H), 3.08-2.95 (m, 2H), 2.22 (s, 3H). MS (ESI) m/z 453 (M+H)$^+$.

EXAMPLE 135

7-(2,6-dichlorophenyl)-5-methyl-3-[(2'-methyl-2',3'-dihydro-1'H-spiro[cyclopropane-1,4'-isoquinolin]-7'-yl)amino]pyrido[4,3-e][1,2,4]triazin-8(7H)-one Example 134E (55 mg, 0.156 mmol) was dissolved in dichloromethane (1557 µl) and 3-chlorobenzoperoxoic acid (41.9 mg, 0.187 mmol) was added. The reaction mixture was stirred at ambient temperature for 30 minutes then 2'-methyl-2',3'-dihydro-1'H-spiro[cyclopropane-1,4'-isoquinolin]-7'-amine (35.2 mg, 0.187 mmol) and TFA (24 µl, 0.311 mmol) were added. The reaction mixture was concentrated, 1 mL of acetonitrile was added and the reaction mixture was stirred at 90° C. overnight. The reaction mixture was then diluted with ethyl acetate (30 mL) and washed with saturated aqueous sodium bicarbonate (20 mL), and saturated aqueous brine (20 mL), dried over magnesium sulfate, filtered and concentrated. Purification by silica gel flash chromatography (Isco®, Redi-Sep® column, 2-50% 2:1 methanol:H$_2$O in ethyl acetate with 2% of triethylamine, linear gradient) afforded the title compound. $^1$H NMR (300 MHz, dimethylsulfoxide-$d_6$) δ 11.10 (s, 1H), 7.84-7.72 (m, 3H), 7.70-7.54 (m, 3H), 6.75 (d, J=8.3, 1H), 3.60 (s, 2H), 2.45 (s, 2H), 2.33 (s, 3H), 2.21 (s, 3H), 0.97-0.81 (m, 4H). MS (ESI) m/z 493 (M+H)$^+$.

EXAMPLE 136

6-(2-chloro-6-hydroxyphenyl)-2-[(1,1-dimethyl-2,3-dihydro-1H-isoindol-5-yl)amino]-8-methylpyrido[4,3-d]pyrimidin-5(6H)-one

EXAMPLE 136A

N-(2-chloro-6-hydroxyphenyl)-4-ethyl-2-(methylthio)pyrimidine-5-carboxamide

To a solution of Example 28B (830 mg, 4.19 mmol) in dichloromethane (8370 µl) was added a catalytic amount of N,N-dimethylformamide (8.1 µl, 0.105 mmol). The free-flowing slurry was cooled to ~5° C. Oxalyl chloride (385 µl, 4.40 mmol) was added dropwise via syringe. The reaction mixture was allowed to proceed at 5-10° C. for 1 hour, then the cooling bath was removed and the reaction mixture was stirred at ambient temperature for an additional hour. To the slurry was added methyl 2-amino-3-methylphenol (631 mg, 4.40 mmol). The reaction mixture was then stirred at ambient temperature for 16 hours. The reaction mixture was poured into a 125 mL separatory funnel, diluted with 50 mL of dichloromethane and the organic layer was washed with water (1×40 mL), 1 molar aqueous phosphoric acid (1×40 mL), and saturated aqueous brine (1×40 mL), dried over magnesium sulfate, filtered and concentrated. The crude product was purified by silica gel flash chromatography (Isco®, Redi-Sep® column, 10-100% ethyl acetate/hexane, linear gradient) then recrystallized in ethyl acetate/hexane mixture to afford the title compound.

EXAMPLE 136B 6-(2-chloro-6-hydroxyphenyl)-8-methyl-2-(methylthio)pyrido[4,3-d]pyrimidin-5(6H)-one A scintillation vial, equipped with stir bar and septa, was charged with Example 136A (590 mg, 1.822 mmol) and N,N-dimethylformamide (7288 µl) followed by N-(chloromethylene)-N-methylmethanaminium (700 mg, 5.47 mmol) and the reaction mixture was stirred at ambient temperature for 16 hours. The reaction mixture was cooled to 0° C. and quenched by careful addition of saturated aqueous sodium bicarbonate. To the reaction mixture was added 80 mL of ethyl acetate and the reaction mixture was poured into a 250 mL separatory funnel. The aqueous layer was removed and the organic layer was washed with diluted aqueous sodium bicarbonate (10% wt, 50 mL), and saturated aqueous brine (50 mL), dried over magnesium sulfate, filtered and concentrated. Purification by silica gel flash chromatography (Isco®, Redi-Sep® column, 30-100% ethyl acetate/hexane, linear gradient) afforded the title compound.

EXAMPLE 136C 6-(2-chloro-6-hydroxyphenyl)-2-[(1,1-dimethyl-2,3-dihydro-1H-isoindol-5-yl)amino]-8-methylpyrido[4,3-d]pyrimidin-5(6H)-one The title compound was prepared as described in Example 98C, substituting Example 98B with Example 136B and substituting tert-butyl 7-amino-3,4-dihydroisoquinoline-2 (1H)-carboxylate with tert-butyl 5-amino-1,1-dimethyl-isoindoline-2-carboxylate. Purification by silica gel flash chromatography (Isco®, Redi-Sep® column, 20-100% ethyl acetate/hexane, linear gradient) afforded the Boc protected intermediate. The product was dissolved in a mixture of 0.5 mL of dichloromethane, and 1 mL of ethyl acetate. Hydrochloric acid (2M diethylether, ~5 mL) was added and the reaction mixture was stirred at 50° C. for 3 hours. The solid was filtered and washed with diethyl ether to afford the title compound as an HCl salt. $^1$H NMR (300 MHz, dimethylsulfoxide-$d_6$) δ 10.45 (brs, 2H), 9.52 (brs, 2H), 9.18 (s, 1H), 8.03-7.86 (m, 2H), 7.55 (s, 1H), 7.41-7.27 (m, 2H), 7.13-6.93 (m, 2H), 4.60-4.52 (m, 2H), 2.23 (d, J=1.0, 3H), 1.63 (s, 6H). MS (ESI) m/z 448 (M+H)$^+$.

EXAMPLE 137

6-(2,6-dichlorophenyl)-8-methyl-2-{[2-(1-methylpiperidin-4-yl)-2,3-dihydro-1H-isoindol-5-yl]amino}pyrido[4,3-d]pyrimidin-5(6H)-one Example 28D (70 mg, 0.199 mmol) was dissolved in dichloroethane (1987 μl) and 3-chlorobenzoperoxoic acid (53.4 mg, 0.238 mmol) was added. The reaction mixture was stirred at ambient temperature for 30 minutes then trifluoroacetic acid (30.6 μl, 0.397 mmol) and 1-(5-amino-2,3-dihydro-1H-inden-2-yl)-N,N-dimethylpiperidin-4-amine (55.2 mg, 0.238 mmol) were added and the reaction mixture was concentrated. After addition of 1.5 mL of acetonitrile, the reaction mixture was stirred at 90° C. for 16 hours. The reaction mixture was then diluted with ethyl acetate (30 mL) and washed with saturated aqueous sodium bicarbonate (20 mL), and saturated aqueous brine (20 mL), dried over magnesium sulfate, filtered and concentrated. Purification by silica gel flash chromatography (Isco®, Redi-Sep® column, 2-50% 2:1 methanol:$H_2O$ in ethyl acetate with 5% triethylamine, linear gradient) followed by reverse-phase preparative HPLC on a Phenomenex Luna C8(2) 5 um 100 Å AXIA column (30 mm×75 mm) using a gradient of acetonitrile (A) and 0.1% trifluoroacetic acid in water (B) at a flow rate of 50 mL/min (0-0.5 min 10% A, 0.5-7.0 min linear gradient 10-95% A, 7.0-10.0 min 95% A, 10.0-12.0 min linear gradient 95-10% A) afforded the title compound as a bis TFA salt. $^1$H NMR (300 MHz, dimethylsulfoxide-$d_6$) δ 11.03 (brs, 1H), 10.57 (s, 1H), 9.63 (brs, 1H), 9.22 (s, 1H), 8.07 (s, 1H), 7.87 (d, J=8.1, 1H), 7.78-7.67 (m, 3H), 7.60 (dd, J=8.9, 7.4, 1H), 7.41 (d, J=8.4, 1H), 4.97-4.49 (m, 4H), 3.10-2.92 (m, 2H), 2.81 (s, 3H), 2.45-2.31 (m, 2H), 2.25 (s, 3H), 1.98-1.75 (m, 2H). MS (ESI) m/z 535 (M+H)$^+$.

EXAMPLE 138

6-(2,6-dichlorophenyl)-2-[(4-{4-[2-(dimethylamino)ethyl]piperazin-1-yl}phenyl)amino]-8-methylpyrido[4,3-d]pyrimidin-5(6H)-one The title compound was prepared as described in Example 125, substituting $N^1$-(1-methylpyrrolidin-3-yl)benzene-1,4-diamine with 4-(4-(2-(dimethylamino)ethyl)piperazin-1-yl)aniline. Purification of the residue by reverse-phase preparative HPLC on a Phenomenex Luna C8(2) 5 um 100 Å AXIA column (30 mm×75 mm) using a gradient of acetonitrile (A) and 0.1% ammonium acetate in water (B) at a flow rate of 50 mL/min (0-0.5 min 10% A, 0.5-7.0 min linear gradient 10-95% A, 7.0-10.0 min 95% A, 10.0-12.0 min linear gradient 95-10% A) afforded the title compound. $^1$H NMR (500 MHz, dimethylsulfoxide-$d_6$) δ 9.85 (s, 1H), 9.10 (s, 1H), 7.72 (d, J=8.8, 2H), 7.69-7.65 (m, 2H), 7.55 (dd, J=8.7, 7.7, 1H), 7.49 (s, 1H), 6.91 (d, J=9.1, 2H), 3.13-3.06 (m, 4H), 2.59-2.53 (m, 4H), 2.50-2.38 (m, 4H), 2.21 (s, 3H), 2.19 (s, 6H). MS (ESI) m/z 552 (M+H)$^+$.

EXAMPLE 139

2-[(4-{4-[3-(dimethylamino)propyl]piperazin-1-yl}phenyl)amino]-6-(2,6-dimethylphenyl)-8-methyl-pyrido[4,3-d]pyrimidin-5(6H)-one The title compound was prepared as described in Example 125, substituting $N^1$-(1-methylpyrrolidin-3-yl)benzene-1,4-diamine with 4-(4-(3-(dimethylamino)propyl)piperazin-1-yl)aniline and substituting Example 28D with Example 88B. Purification of the residue by reverse-phase preparative HPLC on a Phenomenex Luna C8(2) 5 um 100 Å AXIA column (30 mm×75 mm) using a gradient of acetonitrile (A) and 0.1% ammonium acetate in water (B) at a flow rate of 50 mL/min (0-0.5 min 10% A, 0.5-7.0 min linear gradient 10-95% A, 7.0-10.0 min 95% A, 10.0-12.0 min linear gradient 95-10% A) afforded the title compound. $^1$H NMR (400 MHz, dimethylsulfoxide-$d_6$) δ 9.65 (s, 1H), 9.12 (s, 1H), 7.73 (d, J=9.0, 2H), 7.35 (d, J=1.1, 1H), 7.29-7.15 (m, 3H), 6.91 (d, J=9.1, 2H), 3.14-3.09 (m, 4H), 2.55-2.50 (m, 5H), 2.39-2.33 (m, 2H), 2.28-2.24 (m, 2H), 2.22 (d, J=1.0, 3H), 2.14 (s, 6H), 2.05 (s, 6H), 1.64-1.51 (m, 2H). MS (ESI) m/z 526 (M+H)$^+$.

EXAMPLE 140

6-(2,6-dichlorophenyl)-2-[(4-{4-[3-(dimethylamino)propyl]piperazin-1-yl}phenyl)amino]-8-(fluoromethyl)pyrido[4,3-d]pyrimidin-5(6H)-one The title compound was prepared as described in Example 125, substituting $N^1$-(1-methylpyrrolidin-3-yl)benzene-1,4-diamine with 4-(4-(3-(dimethylamino)propyl)piperazin-1-yl)aniline and substituting Example 28D with Example 37B. Purification of the residue by reverse-phase preparative HPLC on a Phenomenex Luna C8(2) 5 um 100 Å AXIA column (30 mm×75 mm) using a gradient of acetonitrile (A) and 0.1% ammonium acetate in water (B) at a flow rate of 50 mL/min (0-0.5 min 10% A, 0.5-7.0 min linear gradient 10-95% A, 7.0-10.0 min 95% A, 10.0-12.0 min linear gradient 95-10% A) afforded the title compound. $^1$H NMR (400 MHz, dimethylsulfoxide-$d_6$) δ 9.87 (s, 1H), 9.13 (s, 1H), 7.93 (d, J=4.0, 1H), 7.74-7.65 (m, 4H), 7.58 (dd, J=8.9, 7.4, 1H), 6.95-6.86 (m, 2H), 5.49 (d, J=48.4, 2H), 3.16-3.11 (m, 4H), 2.55-2.50 (m, 4H), 2.40-2.33 (m, 2H), 2.29-2.23 (m, 2H), 2.14 (s, 6H), 1.63-1.53 (m, 2H). MS (ESI) m/z 584 (M+H)$^+$.

EXAMPLE 141

6-(2,6-dichlorophenyl)-2-({2-[2-(dimethylamino)ethyl]-2,3-dihydro-1H-isoindol-5-yl}amino)-8-methylpyrido[4,3-d]pyrimidin-5(6H)-one The title compound was prepared as described in Example 137, substituting 1-(5-amino-2,3-dihydro-1H-inden-2-yl)-N,N-dimethylpiperidin-4-amine with 2-(2-(dimethylamino)ethyl)isoindolin-5-amine. Purification by silica gel flash chromatography (Isco®, Redi-Sep® column, 2-50% 2:1 methanol:$H_2O$ in ethyl acetate with 5% triethylamine, linear gradient) followed by reverse-phase preparative HPLC on a Phenomenex Luna C8(2) 5 um 100 Å AXIA column (30 mm×75 mm) using a gradient of acetonitrile (A) and 0.1% trifluoroacetic acid in water (B) at a flow rate of 50 mL/min (0-0.5 min 10% A, 0.5-7.0 min linear gradient 10-95% A, 7.0-10.0 min 95% A, 10.0-12.0 min linear gradient 95-10% A) afforded the title compound as a bis TFA salt. $^1$H NMR (300 MHz, dimethylsulfoxide-$d_6$) δ 10.49 (s, 1H), 9.20 (s, 1H), 8.02 (s, 1H), 7.80 (d, J=8.4, 1H), 7.77-7.72 (m, 2H), 7.69 (d, J=1.2, 1H), 7.59 (dd, J=8.9, 7.3, 1H), 7.36 (d, J=8.2, 1H), 4.57-4.24 (m, 4H), 3.60-3.28 (m, 4H), 2.85 (s, 6H), 2.23 (d, J=1.1, 3H). MS (ESI) m/z 509 (M+H)$^+$.

EXAMPLE 142

Wee1 Assay

Wee1 kinase was assayed using a time-resolved fluorescence equilibrium binding assay monitoring displacement of a rapidly reversible Oregon Green-labeled ATP-competitive kinase probe (N-(2-(2-(2-(4-(4-(5-chloro-4-(2-(1-hydroxycyclobutyl)thiazol-5-yl)-1H-pyrrolo[2,3-b]pyridin-2-yl)phenyl)piperazin-1-yl)ethoxy)ethoxy)ethyl)-2',7'-difluoro-3',6'-dihydroxy-3-oxo-3H-spiro[isobenzofuran-1,9'-xanthene]-5-carboxamide) by competitive Wee1 inhibitors. GST-tagged-Wee1 kinase (Carnabio #05-177, 2 nM final concentration), was mixed with fluorescent probe (300 nM final concentration, $K_d$=137 nM) and terbium-labeled anti-GST antibody (1 nM final concentration, Invitrogen #PV3551) and then inhibitor (0.003 to 10 micromolar) in final volume of 18 μl kinase buffer (20 mM HEPES, pH 7.5, 10 mM MgCl$_2$, 100 μM Na$_3$VO$_4$, 0.0075% Triton X-100, 1 mM DTT, 2% DMSO), incubated (1 hour) to allow attainment of equilibrium and time-resolved fluorescence measured using an Envision plate reader (Perkin Elmer; ex=337 nM, em=495/520 nM).

Table 1 depicts enzyme binding data ($K_i$) for exemplary compounds.

| Example | Wee-1 binding ($K_i$ nM) |
|---|---|
| 1 | 0.071 |
| 2 | 0.011 |
| 3 | 0.14 |
| 4 | 0.125 |
| 5 | 0.018 |
| 6 | 0.002 |
| 7 | 0.9 |
| 8 | 0.042 |
| 9 | 0.15 |
| 10 | 0.094 |
| 11 | 0.11 |
| 12 | 0.92 |
| 13 | 0.084 |
| 14 | 0.32 |
| 15 | 1.3 |
| 16 | 0.91 |
| 17 | >3 |
| 18 | 1.7 |
| 19 | >3 |
| 20 | 0.5 |
| 21 | 0.003 |
| 22 | 0.002 |
| 23 | 0.003 |
| 24 | <0.001 |
| 25 | 0.001 |
| 26 | <0.001 |
| 27 | <0.001 |
| 28 | <0.001 |
| 29 | <0.001 |
| 30 | <0.001 |
| 31 | <0.001 |
| 32 | <0.001 |
| 33 | 0.48 |
| 34 | <0.001 |
| 35 | <0.001 |
| 36 | <0.001 |
| 37 | <0.001 |
| 38 | <0.001 |
| 39 | 0.12 |
| 40 | 0.19 |
| 41 | 0.11 |
| 42 | 0.058 |
| 43 | 0.021 |
| 44 | 0.016 |
| 45 | 0.002 |
| 46 | 0.048 |
| 47 | 0.008 |
| 48 | 0.004 |
| 49 | 0.3 |
| 50 | 0.5 |
| 51 | 0.4 |
| 52 | 1.8 |
| 53 | 0.3 |
| 54 | 0.4 |
| 55 | 0.6 |
| 56 | 0.5 |
| 57 | 0.1 |
| 58 | 0.1 |
| 59 | 0.1 |
| 60 | 0.5 |
| 61 | 0.3 |
| 62 | 0.3 |
| 63 | 0.9 |
| 64 | 0.5 |
| 65 | 127 |
| 66 | 0.9 |
| 67 | 0.8 |
| 68 | 0.9 |
| 69 | 2.4 |
| 70 | 1.6 |
| 71 | 1.2 |
| 72 | 5.1 |
| 73 | 1.5 |
| 74 | 0.6 |
| 75 | 0.8 |
| 76 | 0.5 |
| 77 | 0.3 |
| 78 | 0.2 |
| 79 | 0.4 |
| 80 | 0.5 |
| 81 | 0.4 |
| 82 | 0.1 |
| 83 | 0.2 |
| 84 | 0.328 |
| 85 | 0.265 |
| 86 | 0.305 |
| 87 | 0.254 |
| 88 | 0.544 |
| 89 | 0.897 |
| 90 | 0.193 |
| 91 | 0.22 |
| 92 | 0.378 |
| 93 | 0.358 |
| 94 | 0.568 |
| 95 | 0.38 |
| 96 | 1.8 |
| 97 | 28.2 |
| 98 | 0.5 |
| 99 | 0.9 |
| 100 | 4.3 |
| 101 | 2.8 |
| 102 | 17.8 |
| 103 | 0.9 |
| 104 | 0.9 |
| 105 | 122 |
| 106 | 115 |
| 107 | 321 |
| 108 | 242 |

-continued

| Example | Wee-1 binding (K$_i$ nM) |
|---|---|
| 109 | 0.3 |
| 110 | 0.4 |
| 111 | 0.2 |
| 112 | 0.4 |
| 113 | 0.4 |
| 114 | 0.8 |
| 115 | 0.2 |
| 116 | 0.1 |
| 117 | 2.0 |
| 118 | 0.6 |
| 119 | 1.6 |
| 120 | 0.3 |
| 121 | 0.1 |
| 122 | 0.4 |
| 123 | 1.3 |
| 124 | 1.6 |
| 125 | 0.3 |
| 126 | 0.4 |
| 127 | 0.3 |
| 128 | 2.0 |
| 129 | 0.2 |
| 130 | 0.3 |
| 131 | 0.2 |
| 132 | 0.4 |
| 133 | 0.5 |
| 134 | 6.5 |
| 135 | 5.7 |
| 136 | 0.2 |
| 137 | 0.4 |
| 138 | 0.2 |
| 139 | 2.1 |
| 140 | 0.2 |
| 141 | 1.0 |

All publication and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

We claim:
1. The compound, or a pharmaceutically acceptable salt or solvate thereof, which is
    ethyl 2-{[4-(4-methylpiperazin-1-yl)phenyl]amino}-5-oxo-6-(prop-2-en-1-yl)-5,6-dihydropyrido[4,3-d]pyrimidine-8-carboxylate;
    ethyl 2-{[4-(4-methylpiperazin-1-yl)phenyl]amino}-5-oxo-6-phenyl-5,6-dihydropyrido[4,3-d]pyrimidine-8-carboxylate;
    6-benzyl-N-methyl-2-{[4-(4-methylpiperazin-1-yl)phenyl]amino}-5-oxo-5,6-dihydropyrido[4,3-d]pyrimidine-8-carboxamide;
    ethyl 6-benzyl-2-{[4-(4-methylpiperazin-1-yl)phenyl]amino}-5-oxo-5,6-dihydropyrido[4,3-d]pyrimidine-8-carboxylate;
    ethyl 6-(2-chlorophenyl)-2-{[4-(4-methylpiperazin-1-yl)phenyl]amino}-5-oxo-5,6-dihydropyrido[4,3-d]pyrimidine-8-carboxylate;
    ethyl 2-{[4-(4-methylpiperazin-1-yl)phenyl]amino}-5-oxo-5,6-dihydropyrido[4,3-d]pyrimidine-8-carboxylate;
    6-benzyl-2-{[4-(4-methylpiperazin-1-yl)phenyl]amino}1-8-phenylpyrido[4,3-d]pyrimidin-5(6H)-one;
    6-(2-methylbenzyl)-2-{[4-(4-methylpiperazin-1-yl)phenyl]amino}-8-phenylpyrido[4,3-d]pyrimidin-5(6H)-one;
    8-bromo-6-(2,6-difluorobenzyl)-2-{[4-(4-methylpiperazin-1-yl)phenyl]amino}pyrido[4,3-d]pyrimidin-5(6H)-one;
    6-(3-methylbenzyl)-2-{[4-(4-methylpiperazin-1-yl)phenyl]amino}-8-phenylpyrido[4,3-d]pyrimidin-5(6H)-one;
    6-[2-fluoro-6-(trifluoromethyl)benzyl]-2-{[4-(4-methylpiperazin-1-yl)phenyl]amino}-8-phenylpyrido[4,3-d]pyrimidin-5(6H)-one;
    6-(2-fluorobenzyl)-2-{[4-(4-methylpiperazin-1-yl)phenyl]amino}-8-phenylpyrido[4,3-d]pyrimidin-5(6H)-one;
    2-{[2-{[4-(4-methylpiperazin-1-yl)phenyl]amino}-5-oxo-8-phenylpyrido[4,3-d]pyrimidin-6(5H)-yl]methyl}benzonitrile;
    6-(2-chlorobenzyl)-2-{[4-(4-methylpiperazin-1-yl)phenyl]amino}-8-phenylpyrido[4,3-d]pyrimidin-5(6H)-one;
    6-(2,6-dichlorobenzyl)-2-{[4-(4-methylpiperazin-1-yl)phenyl]amino}-8-phenylpyrido[4,3-d]pyrimidin-5(6H)-one;
    6-(4-tert-butylbenzyl)-2-{[4-(4-methylpiperazin-1-yl)phenyl]amino}-8-phenylpyrido[4,3-d]pyrimidin-5(6H)-one;
    6[2-fluoro-5-(trifluoromethyl)benzyl]-2-{[4-(4-methylpiperazin-1-yl)phenyl]amino}-8-phenylpyrido[4,3-d]pyrimidin-5(6H)-one;
    ethyl [2-{[4-(4-methylpiperazin-1-yl)phenyl]amino}-5-oxo-8-phenylpyrido[4,3-d]pyrimidin-6(5H)-yl]acetate;
    6-(2,6-dichlorophenyl)-2-{[4-(4-methylpiperazin-1-yl)phenyl]amino}-8-[(phenylamino)methyl]pyrido[4,3-d]pyrimidin-5(6H)-one;
    6-(2,6-dichlorophenyl)-2-{[4-(4-methylpiperazin-1-yl)phenyl]amino}-8-{[(2,2,2-trifluoroethyl)amino]methyl}pyrido[4,3-d]pyrimidin-5(6H)-one;
    8(1,3-benzothiazol-2-yl)-6-(2,6-dichlorophenyl)-2-{[4-(4-methylpiperazin-1-yl)phenyl]amino}pyrido[4,3-d]pyrimidin-5(6H)-one;
    8-(1H-benzimidazol-2-yl)-6-(2,6-dichlorophenyl)-2-{[4-(4-methylpiperazin-1-yl)phenyl]amino}pyrido[4,3-d]pyrimidin-5(6H)-one;
    6-(2,6-dichlorophenyl)-8-ethenyl-2-{[4-(4-methylpiperazin-1-yl)phenyl]amino}pyrido[4,3-d]pyrimidin-5(6H)-one;
    6-(2,6-dichlorophenyl)-8-ethyl-2-{[4-(4-methylpiperazin-1-yl)phenyl]amino}pyrido[4,3-d]pyrimidin-5(6H)-one;
    6-(2,6-dichlorophenyl)-2-{[4-(4-methylpiperazin-1-yl)phenyl]amino}-5-oxo-5,6-dihydropyrido[4,3-d]pyrimidine-8-carbaldehyde;
    6-(2,6-dichlorophenyl)-8-methyl-2-{[4-(4-methylpiperazin-1-yl)phenyl]amino}pyrido[4,3-d]pyrimidin-5(6H)-one;
    6-(2,6-dichlorophenyl)-8-methyl-2-[(2'-methyl-2',3'-dihydro-1'H-spiro[cyclopropane-1,4'-isoquinolin]-7'-yl)amino]pyrido[4,3-d]pyrimidin-5(6H)-one;
    6-(2,6-dichlorophenyl)-2-(2',3'-dihydro-1'H-spiro[cyclopropane-1,4'-isoquinolin]-7'-ylamino)-8-methylpyrido[4,3-d]pyrimidin-5(6H)-one;
    6-(2,6-dichlorophenyl)-2-{[2-(dimethylamino)-2,3-dihydro-1H-inden-5-yl]amino}-8-methylpyrido[4,3-d]pyrimidin-5(6H)-one;

6-(2,6-dichlorophenyl)-8-ethenyl-2-[(2'-methyl-2',3'-dihydro-1'H-spiro[cyclopropane-1,4'-isoquinolin]-7'-yl)amino]pyrido[4,3-d]pyrimidin-5(6H)-one;

6,8-dimethyl-2-{[4-(4-methylpiperazin-1-yl)phenyl]amino}pyrido[4,3-d]pyrimidin-5(6H)-one;

6-(2,6-dichlorophenyl)-8-(1H-imidazol-2-yl)-2-{[4-(4-methylpiperazin-1-yl)phenyl]amino}pyrido[4,3-d]pyrimidin-5(6H)-one;

6-(2,6-dichlorophenyl)-2-({4-[4-(dimethylamino)piperidin-1-yl]phenyl}amino)-8-methylpyrido[4,3-d]pyrimidin-5(6H)-one;

6-(2,6-dichlorophenyl)-8-(difluoromethyl)-2-{[4-(4-methylpiperazin-1-yl)phenyl]amino}pyrido[4,3-d]pyrimidin-5(6H)-one;

6-(2,6-dichlorophenyl)-8-(fluoromethyl)-2-{[4-(4-methylpiperazin-1-yl)phenyl]amino}pyrido[4,3-d]pyrimidin-5(6H)-one;

6-(2,6-dichlorophenyl)-8-(hydroxymethyl)-2-{[4-(4-methylpiperazin-1-yl)phenyl]amino}pyrido[4,3-d]pyrimidin-5(6H)-one;

8-bromo-6-(cyclopropylmethyl)-2-{[4-(4-methylpiperazin-1-yl)phenyl]amino}pyrido[4,3-d]pyrimidin-5(6H)-one;

8-(cyclohex-1-en-1-yl)-6-(cyclopropylmethyl)-2-{[4-(4-methylpiperazin-1-yl)phenyl]amino}pyrido[4,3-d]pyrimidin-5(6H)-one;

8-(cyclopent-1-en-1-yl)-6-(cyclopropylmethyl)-2-{[4-(4-methylpiperazin-1-yl)phenyl]amino}pyrido[4,3-d]pyrimidin-5(6H)-one;

8-bromo-6-ethyl-2-{[4-(4-methylpiperazin-1-yl)phenyl]amino}pyrido[4,3-d]pyrimidin-5(6H)-one;

8-(cyclohex-1-en-1-yl)-6-ethyl-2-{[4-(4-methylpiperazin-1-yl)phenyl]amino}pyrido[4,3-d]pyrimidin-5(6H)-one;

6-(2,6-dichlorophenyl)-2-{[2-(dimethylamino)-2,3-dihydro-1H-inden-5-yl]amino}-8-ethenylpyrido[4,3-d]pyrimidin-5(6H)-one;

6-(2,6-dichlorophenyl)-2-({4-[4-(dimethylamino)piperidin-1-yl]phenyl}amino)-8-ethenylpyrido[4,3-d]pyrimidin-5(6H)-one;

6-(2,6-dichlorophenyl)-2-(2',3'-dihydro-1'H-spiro[cyclopropane-1,4'-isoquinolin]-7'-ylamino)-8-ethenylpyrido[4,3-d]pyrimidin-5(6H)-one;

6-(2,6-dichlorophenyl)-8-ethenyl-2-{[4-(hexahydropyrrolo[3,4-c]pyrrol-2(1H)-yl)phenyl]amino}pyrido[4,3-d]pyrimidin-5(6H)-one;

6-(2,6-dichlorophenyl)-8-(hydroxymethyl)-2-[(2'-methyl-2',3'-dihydro-1'H-spiro[cyclopropane-1,4'-isoquinolin]-7'-yl)amino]pyrido[4,3-d]pyrimidin-5(6H)-one;

6-(2,6-dichlorophenyl)-2-{[2-(dimethylamino)-2,3-dihydro-1H-inden-5-yl]amino}-8-(hydroxymethyl)pyrido[4,3-d]pyrimidin-5(6H)-one;

6-(2,6-dichlorophenyl)-2-({4-[4-(dimethylamino)piperidin-1-yl]phenyl}amino)-8-(hydroxymethyl)pyrido[4,3-d]pyrimidin-5(6H)-one;

6-(2,6-dichlorophenyl)-2-[(4,4-dimethyl-1,2,3,4-tetrahydroisoquinolin-7-yl)amino]-8-ethenylpyrido[4,3-d]pyrimidin-5(6H)-one;

6-(2,6-dichlorophenyl)-2-(2',3'-dihydro-1'H-spiro[cyclopropane-1,4'-isoquinolin]-7'-ylamino)-8-(hydroxymethy)pyrido[4,3-d]pyrimidin-5(6H)-one;

6-(2,6-dichlorophenyl)-2-[(4,4-dimethyl-1,2,3,4-tetrahydroisoquinolin-7-yl)amino]-8-(hydroxymethyl)pyrido[4,3-d]pyrimidin-5(6H)-one;

6-(2,6-dichlorophenyl)-8-ethenyl-2-(1,2,3,4-tetrahydroisoquinolin-6-ylamino)pyrido[4,3-d]pyrimidin-5(6H)-one;

6-(2-chloro-6-fluorophenyl)-2-({4-[4-(dimethylamino)piperidin-1-yl]phenyl}amino)-8-ethenylpyrido[4,3-d]pyrimidin-5(6H)-one;

6-(2-chloro-6-fluorophenyl)-8-ethenyl-2-{[4-(4-methylpiperidin-4-yl)phenyl]amino}pyrido[4,3-d]pyrimidin-5(6H)-one;

6-(2-chloro-6-fluorophenyl)-8-ethenyl-2-{[4-(4-methylpiperazin-1-yl)phenyl]amino}pyrido[4,3-d]pyrimidin-5(6H)-one;

6-(2-chloro-6-fluorophenyl)-8-ethenyl-2-[(2'-methyl-2',3'-dihydro-1'H-spiro[cyclopropane-1,4'-isoquinolin]-7'-yl)amino]pyrido[4,3-d]pyrimidin-5(6H)-one;

6-(2-chloro-6-fluorophenyl)-2-{[2-(dimethylamino)-2,3-dihydro-1H-inden-5-yl]amino}-8-ethenylpyrido[4,3-d]pyrimidin-5(6H)-one;

6-(2-chloro-6-fluorophenyl)-8-methyl-2-{[4-(4-methylpiperazin-1-yl)phenyl]amino}pyrido[4,3-d]pyrimidin-5(6H)-one;

6-(2-chloro-6-fluorophenyl)-8-methyl-2-[(2'-methyl-2',3'-dihydro-1'H-spiro[cyclopropane-1,4'-isoquinolin]-7'-yl)amino]pyrido[4,3-d]pyrimidin-5(6H)-one;

6-(2-chloro-6-fluorophenyl)-2-{[2-(dimethylamino)-2,3-dihydro-1H-inden-5-yl]amino}-8-methylpyrido[4,3-d]pyrimidin-5(6H)-one;

6-(2-chloro-6-fluorophenyl)-2-({4-[4-(dimethylamino)piperidin-1-yl]phenyl}amino)-8-methylpyrido[4,3-d]pyrimidin-5(6H)-one;

6-(2-chloro-6-fluorophenyl)-8-methyl-2{-[4-(1-methylpiperidin-4-yl)phenyl]amino}pyrido[4,3-d]pyrimidin-5(6H)-one;

6-(2-chloro-6-fluorophenyl)-8-methyl-2-(1,2,3,4-tetrahydroisoquinolin-6-ylamino)pyrido[4,3-d]pyrimidin-5(6H)-one;

6-(2-chloro-6-fluorophenyl)-2-[(4,4-dimethyl-1,2,3,4-tetrahydroisoquinolin-7-yl)amino]-8-methylpyrido[4,3-d]pyrimidin-5(6H)-one;

6-(2-chloro-6-fluorophenyl)-2-(2',3'-dihydro-1'H-spiro[cyclopropane-1,4'-isoquinolin]-7'-ylamino)-8-methylpyrido[4,3-d]pyrimidin-5(6H)-one;

6-(2-chloro-6-fluorophenyl)-8-methyl-2-(1,2,3,4-tetrahydroisoquinolin-7-ylamino)pyrido[4,3-d]pyrimidin-5(6H)-one;

6-(2,6-dichlorophenyl)-8-methyl-2-(1,2,3,4-tetrahydroisoquinolin-6-ylamino)pyrido[4,3-d]pyrimidin-5(6H)-one;

6-(2,6-dichlorophenyl)-2-[(4,4-dimethyl-1,2,3,4-tetrahydroisoquinolin-7-yl)amino]-8-methylpyrido[4,3-d]pyrimidin-5(6H)-one;

6-(2,6-dichlorophenyl)-8-methyl-2-[(2,4,4-trimethyl-1,2,3,4-tetrahydroisoquinolin-7-yl)amino]pyrido[4,3-d]pyrimidin-5(6H)-one;

6-(2,6-dichlorophenyl)-8-methyl-2-(1,2,3,4-tetrahydroisoquinolin-7-ylamino)pyrido[4,3-d]pyrimidin-5(6H)-one;

6-(2,6-dichlorophenyl)-8-(1H-imidazol-2-yl)-2-(1,2,3,4-tetrahydroisoquinolin-6-ylamino)pyrido[4,3-d]pyrimidin-5(6H)-one;

6-(2,6-dichlorophenyl)-8-(difluoromethyl)-2-{[4-(1-methylpiperidin-4-yl)phenyl]amino}pyrido[4,3-d]pyrimidin-5(6H)-one;

6-(2,6-dichlorophenyl)-8-(difluoromethyl)-2-{[2-(dimethylamino)-2,3-dihydro-1H-inden-5-yl]amino}pyrido[4,3-d]pyrimidin-5(6H)-one;

6-(2,6-dichlorophenyl)-8-(difluoromethyl)-2-({4-[4-(dimethylamino)piperidin-1-yl]phenyl}amino)pyrido[4,3-d]pyrimidin-5(6H)-one;

6-(2,6-dichlorophenyl)-8-(difluoromethyl)-2-[(4,4-dimethyl-1,2,3,4-tetrahydroisoquinolin-7-yl)amino]pyrido[4,3-d]pyrimidin-5(6H)-one;

6-(2,6-dichlorophenyl)-8-(difluoromethyl)-2-(2',3'-dihydro-1'H-spiro[cyclopropane-1,4'-isoquinolin]-7'-ylamino)pyrido[4,3-d]pyrimidin-5(6H)-one;

6-(2,6-dichlorophenyl)-8-(difluoromethyl)-2-(1,2,3,4-tetrahydroisoquinolin-7-ylamino)pyrido[4,3-d]pyrimidin-5(6H)-one;

6-(2,6-dimethylphenyl)-8-methyl-2-[(2'-methyl-2',3'-dihydro-1'H-spiro[cyclopropane-1,4'-isoquinolin]-7'-yl)amino]pyrido[4,3-d]pyrimidin-5(6H)-one;

2-({4-[4-(dimethylamino)piperidin-1-yl]phenyl}amino)-6-(2,6-dimethylphenyl)-8-methylpyrido[4,3-d]pyrimidin-5(6H)-one;

6-(2-chloro-6-methylphenyl)-8-methyl-2-[(2'-methyl-2',3'-dihydro-1'H-spiro[cyclopropane-1,4'-isoquinolin]-7'-yl)amino]pyrido[4,3-d]pyrimidin-5(6H)-one;

6-(2-chloro-6-methylphenyl)-2-({4-[4-(dimethylamino)piperidin-1-yl]phenyl}amino)-8-methylpyrido[4,3-d]pyrimidin-5(6H)-one;

6-(2,6-dichlorophenyl)-2-[(4-{[2-(dimethylamino)ethyl]sulfanyl}phenyl)amino]-8-methylpyrido[4,3-d]pyrimidin-5(6H)-one;

6-(2,6-dichlorophenyl)-8-(difluoromethyl)-2-(1,2,3,4-tetrahydroisoquinolin-6-ylamino)pyrido[4,3-d]pyrimidin-5(6H)-one;

6-(2,6-dichlorophenyl)-8-(difluoromethyl)-2-[(2'-methyl-2',3'-dihydro-1'H-spiro[cyclopropane-1,4'-isoquinolin]-7'-yl)amino]pyrido[4,3-d]pyrimidin-5(6H)-one;

6-(2,6-dichlorophenyl)-8-(difluoromethyl)-2-{[2-(pyrrolidin-1-yl)-2,3-dihydro-1H-inden-5-yl]amino}pyrido[4,3-d]pyrimidin-5(6H)-one;

6-(2,6-dichlorophenyl)-2-[(4-{[2-(dimethylamino)ethyl]sulfonyl}phenyl)amino]-8-methylpyrido[4,3-d]pyrimidin-5(6H)-one;

6-(2-chlorophenyl)-8-methyl-2-(1,2,3,4-tetrahydroisoquinolin-7-ylamino)pyrido[4,3-d]pyrimidin-5(6H)-one;

6-(2-chlorophenyl)-2-({4-[4-(dimethylamino)piperidin-1-yl]phenyl}amino)-8-methylpyrido[4,3-d]pyrimidin-5(6H)-one;

6-(2-fluoro-6-methylphenyl)-8-methyl-2-(1,2,3,4-tetrahydroisoquinolin-7-ylamino)pyrido[4,3-d]pyrimidin-5(6H)-one;

2-({4-[4-(dimethylamino)piperidin-1-yl]phenyl}amino)-6-(2-fluoro-6-methylphenyl)-8-methylpyrido[4,3-d]pyrimidin-5(6H)-one;

6-(2,6-dichlorophenyl)-8-(fluoromethyl)-2-(1,2,3,4-tetrahydroisoquinolin-7-ylamino)pyrido[4,3-d]pyrimidin-5(6H)-one;

6-(2,6-dichlorophenyl)-8-(fluoromethyl)-2-(1,2,3,4-tetrahydroisoquinolin-6-ylamino)pyrido[4,3-d]pyrimidin-5(6H)-one;

6-(2,6-dichlorophenyl)-2-({4-[4-(dimethylamino)piperidin-1-yl]phenyl}amino)-8-(fluoromethyl)pyrido[4,3-d]pyrimidin-5(6H)-one;

6-(2,6-dichlorophenyl)-2-{[2-(dimethylamino)-2,3-dihydro-1H-inden-5-yl]amino}-8-(fluoromethyl)pyrido[4,3-d]pyrimidin-5(6H)-one;

6-(2,6-dichlorophenyl)-8-(fluoromethyl)-2-[(2'-methyl-2',3'-dihydro-1'H-spiro[cyclopropane-1,4'-isoquinolin]-7'-yl)amino]pyrido[4,3-d]pyrimidin-5(6H)-one;

6-(2,6-dichlorophenyl)-8-methyl-2[(1,1,2-trimethyl-2,3-dihydro-1H-isoindol-5-yl)amino]pyrido[4,3-d]pyrimidin-5(6H)-one;

6-(2,6-dichlorophenyl)-8-methyl-2-({4-[(1-methylpiperidin-4-yl)amino]phenyl}amino)pyrido[4,3-d]pyrimidin-5(6H)-one;

6-(2-hydroxyphenyl)-8-methyl-2-(1,2,3,4-tetrahydroisoquinolin-7-ylamino)pyrido[4,3-d]pyrimidin-5(6H)-one;

6-(2-hydroxy-6-methylphenyl)-8-methyl-2-(1,2,3,4-tetrahydroisoquinolin-7-ylamino)pyrido[4,3-d]pyrimidin-5(6H)-one;

8-methyl-2-(1,2,3,4-tetrahydroisoquinolin-7-ylamino)-6-(1,3,5-trimethyl-1H-pyrazol-4-yl)pyrido[4,3-d]pyrimidin-5(6H)-one;

6-(2,6-dichlorophenyl)-2-[(1,1-dimethyl-2,3-dihydro-1H-isoindol-5-yl)amino]-8-methylpyrido[4,3-d]pyrimidin-5(6H)-one;

6-(2,6-dichlorophenyl)-8-methyl-2-({4[(1-methylpiperidin-4-yl)oxy]phenyl}amino)pyrido[4,3-d]pyrimidin-5(6H)-one;

6-(2-hydroxyphenyl)-8-methyl-2-(1,2,3,4-tetrahydroisoquinolin-7-ylamino)pyrido[4,3-d]pyrimidin-5(6H)-one;

6-(2-hydroxy-6-methylphenyl)-8-methyl-2-(1,2,3,4-tetrahydroisoquinolin-7-ylamino)pyrido[4,3-d]pyrimidin-5(6H)-one;

8-methyl-2-(1,2,3,4-tetrahydroisoquinolin-7-ylamino)-6-(1,3,5-trimethyl-1H-pyrazol-4-yl)pyrido[4,3-d]pyrimidin-5(6H)-one;

2-[(4-{[6-(2,6-dichlorophenyl)-8-methyl-5-oxo-5,6-dihydropyrido[4,3-d]pyrimidin-2-yl]amino}phenyl)sulfonyl]-N-methylacetamide;

6-(2,6-dichlorophenyl)-2-[(1,1-dimethyl-2,3-dihydro-1H-isoindol-5-yl)amino]-8-methylpyrido[4,3-d]pyrimidin-5(6H)-one;

6-(2,6-dichlorophenyl)-8-methyl-2-({4[(1-methylpiperidin-4-yl)oxy]phenyl}amino)pyrido[4,3-d]pyrimidin-5(6H)-one;

6-(3,5-dimethyl-1H-pyrazol-4-yl)-8-methyl-2-(1,2,3,4-tetrahydroisoquinolin-7-ylamino)pyrido[4,3-d]pyrimidin-5(6H)-one;

6-(3,5-dimethyl-1,2-oxazol-4-yl)-8-methyl-2-(1,2,3,4-tetrahydroisoquinolin-7-ylamino)pyrido[4,3-d]pyrimidin-5(6H)-one;

6-(2,6-dichlorophenyl)-8-methyl-2-({4[(1-methylpyrrolidin-3-yl)amino]phenyl}amino)pyrido[4,3-d]pyrimidin-5(6H)-one;

6-(2,6-dimethylphenyl)-8-methyl-2-(1,2,3,4-tetrahydroisoquinolin-7-ylamino)pyrido[4,3-d]pyrimidin-5(6H)-one;

6-(2-chloro-6-methylphenyl)-8-methyl-2-(1,2,3,4-tetrahydroisoquinolin-7-ylamino)pyrido[4,3-d]pyrimidin-5(6H)-one;

6-(2,6-dichlorophenyl)-8-(1-hydroxyethyl)-2-[4-({4-methylpiperazin-1-yl)phenyl]amino}pyrido[4,3-d]pyrimidin-5(6H)-one;

methyl 5-{[6-(2,6-dichlorophenyl)-8-methyl-5-oxo-5,6-dihydropyrido[4,3-d]pyrimidin-2-yl]amino}-2-(4-methylpiperazin-1-yl)benzoate;

6-(2,6-dichlorophenyl)-2-[(4-{[2-(dimethylamino)ethyl]amino}phenyl)amino]-8-methylpyrido[4,3-d]pyrimidin-5(6H)-one;

6-(2,6-dichlorophenyl)-2-[(4-{[trans-4-(dimethylamino)cyclohexyl]amino}phenyl)amino]-8-methylpyrido[4,3-d]pyrimidin-5(6H)-one;

6-(2,6-dichlorophenyl)-2-[(4-{[cis-4-(dimethylamino)cyclohexyl]amino}phenyl)amino]-8-methylpyrido[4,3-d]pyrimidin-5(6H)-one;

6-(2-chloro-6-hydroxyphenyl)-2-[(1,1-dimethyl-2,3-dihydro-1H-isoindol-5-yl)amino]-8-methylpyrido[4,3-d]pyrimidin-5(6H)-one;

6-(2,6-dichlorophenyl)-8-methyl-2-{[2-(1-methylpiperidin-4-yl)-2,3-dihydro-1H-isoindol-5-yl]amino}pyrido[4,3-d]pyrimidin-5(6H)-one; or 6-(2,6-dichlorophenyl)-2-({2-[2-(dimethylamino)ethyl]-2,3-dihydro-1H-isoindol-5-yl}amino)-8-methylpyrido[4,3-d]pyrimidin-5(6H)-one.

* * * * *